US010301336B2

(12) United States Patent
Wiles et al.

(10) Patent No.: US 10,301,336 B2
(45) Date of Patent: May 28, 2019

(54) PHOSPHONATE COMPOUNDS FOR TREATMENT OF COMPLEMENT MEDIATED DISORDERS

(71) Applicant: Achillion Pharmaceuticals, Inc., New Haven, CT (US)

(72) Inventors: Jason Allan Wiles, Madison, CT (US); Akihiro Hashimoto, Branford, CT (US); Venkat Rao Gadhachanda, Hamden, CT (US); Godwin Pais, Hamden, CT (US); Qiuping Wang, Bethany, CT (US); Dawei Chen, Guilford, CT (US); Xiangzhu Wang, Branford, CT (US); Atul Agarwal, Hamden, CT (US); Milind Deshpande, Madison, CT (US); Avinash Phadke, Branford, CT (US)

(73) Assignee: Achillion Pharmaceuticals, Inc., New Haven, CT (US)

( * ) Notice: Subject to any disclaimer, the term of this patent is extended or adjusted under 35 U.S.C. 154(b) by 0 days.

(21) Appl. No.: 16/162,162

(22) Filed: Oct. 16, 2018

(65) Prior Publication Data

US 2019/0085005 A1 Mar. 21, 2019

Related U.S. Application Data

(63) Continuation of application No. 15/607,120, filed on May 26, 2017, now Pat. No. 10,100,072, which is a (Continued)

(51) Int. Cl.
*A61K 31/444* (2006.01)
*C07F 9/572* (2006.01)
(Continued)

(52) U.S. Cl.
CPC .......... *C07F 9/5728* (2013.01); *A61K 9/0014* (2013.01); *A61K 9/0019* (2013.01); *A61K 9/0048* (2013.01); *A61K 9/0053* (2013.01); *A61K 31/404* (2013.01); *A61K 31/407* (2013.01); *A61K 31/4045* (2013.01); *A61K 31/4162* (2013.01); *A61K 31/4178* (2013.01); *A61K 31/4184* (2013.01); *A61K 31/4188* (2013.01); *A61K 31/4192* (2013.01); *A61K 31/437* (2013.01); *A61K 31/444* (2013.01); *A61K 31/4439* (2013.01); *A61K 31/4709* (2013.01); *A61K 31/496* (2013.01); *A61K 31/501* (2013.01); *A61K 31/506* (2013.01); *A61K 31/519* (2013.01); *A61K 31/549* (2013.01); *A61K 31/55* (2013.01); *A61K 31/675* (2013.01); *A61K 31/683* (2013.01); *C07B 59/002* (2013.01); *C07D 209/12* (2013.01); *C07D 209/14* (2013.01); *C07D 209/30* (2013.01); *C07D 209/40* (2013.01); *C07D 209/42* (2013.01); *C07D 209/44* (2013.01); *C07D 209/88* (2013.01); *C07D 401/14* (2013.01); *C07D 403/06* (2013.01); *C07D 403/08* (2013.01); *C07D 403/12* (2013.01); *C07D 403/14* (2013.01); *C07D 405/12* (2013.01); *C07D 405/14* (2013.01); *C07D 413/06* (2013.01); *C07D 413/14* (2013.01); *C07D 417/06* (2013.01); *C07D 417/12* (2013.01); *C07D 417/14* (2013.01); *C07D 471/04* (2013.01); *C07D 471/08* (2013.01); *C07D 487/04* (2013.01); *C07D 487/14* (2013.01); *C07D 491/113* (2013.01); *C07D 495/04* (2013.01); *C07D 513/04* (2013.01); *C07F 5/025* (2013.01); *C07F 5/027* (2013.01);
(Continued)

(58) Field of Classification Search
None
See application file for complete search history.

(56) References Cited

U.S. PATENT DOCUMENTS 6,489,476 B1 12/2002 Dang et al.
6,653,340 B1 11/2003 Babu et al.
(Continued)

FOREIGN PATENT DOCUMENTS

WO WO 1993/020099 A2 10/1993
WO WO 1995/029697 A1 11/1995
(Continued)

OTHER PUBLICATIONS

Airey et al. "A Convenient Preparation of Thieno[3,2-c]pyrazole" Synthesis, 2014; 46: 96-100.
(Continued)

*Primary Examiner* — Heidi Reese
(74) *Attorney, Agent, or Firm* — Knowles Intellectal Property Strategies, LLC

(57) ABSTRACT

Compounds, methods of use, and processes for making inhibitors of complement factor D comprising Formula I, or a pharmaceutically acceptable salt or composition thereof wherein $R^{12}$ or $R^{13}$ on the A group is a phosphonate ($R^{32}$) are provided. The inhibitors described herein target factor D and inhibit or regulate the complement cascade at an early and essential point in the alternative complement pathway, and reduce factor D's ability to modulate the classical and lectin complement pathways. The inhibitors of factor D described herein are capable of reducing the excessive activation of complement, which has been linked to certain autoimmune, inflammatory, and neurodegenerative diseases, as well as ischemia-reperfusion injury and cancer.

20 Claims, No Drawings

Related U.S. Application Data continuation of application No. 14/631,785, filed on Feb. 25, 2015, now Pat. No. 9,663,543.

(60) Provisional application No. 62/046,783, filed on Sep. 5, 2014, provisional application No. 62/022,916, filed on Jul. 10, 2014, provisional application No. 61/944,189, filed on Feb. 25, 2014.

(51) Int. Cl.

| | |
|---|---|
| ***A61K 31/4045*** | (2006.01) |
| ***A61K 31/404*** | (2006.01) |
| ***A61K 31/407*** | (2006.01) |
| ***A61K 31/4162*** | (2006.01) |
| ***A61K 31/4178*** | (2006.01) |
| ***A61K 31/4184*** | (2006.01) |
| ***A61K 31/4188*** | (2006.01) |
| ***A61K 31/4192*** | (2006.01) |
| ***A61K 31/437*** | (2006.01) |
| ***A61K 31/4439*** | (2006.01) |
| ***A61K 31/4709*** | (2006.01) |
| ***A61K 31/496*** | (2006.01) |
| ***A61K 31/506*** | (2006.01) |
| ***A61K 31/549*** | (2006.01) |
| ***A61K 31/55*** | (2006.01) |
| ***A61K 31/683*** | (2006.01) |
| ***C07F 9/6558*** | (2006.01) |
| ***C07F 9/6561*** | (2006.01) |
| ***C07D 513/04*** | (2006.01) |
| ***C07B 59/00*** | (2006.01) |
| ***C07D 209/14*** | (2006.01) |
| ***C07D 209/40*** | (2006.01) |
| ***C07D 405/12*** | (2006.01) |
| ***C07D 417/12*** | (2006.01) |
| ***C07D 487/14*** | (2006.01) |
| ***C07D 491/113*** | (2006.01) |
| ***C07D 495/04*** | (2006.01) |
| ***C07D 413/06*** | (2006.01) |
| ***C07D 403/08*** | (2006.01) |
| ***C07D 405/14*** | (2006.01) |
| ***C07D 487/04*** | (2006.01) |
| ***C07D 413/14*** | (2006.01) |
| ***C07D 417/14*** | (2006.01) |
| ***C07D 403/06*** | (2006.01) |
| ***C07F 5/02*** | (2006.01) |
| ***C07D 471/04*** | (2006.01) |
| ***C07D 417/06*** | (2006.01) |
| ***C07F 7/08*** | (2006.01) |
| ***C07D 401/14*** | (2006.01) |
| ***C07D 403/14*** | (2006.01) |
| ***C07D 403/12*** | (2006.01) |
| ***C07D 209/42*** | (2006.01) |
| ***C07D 471/08*** | (2006.01) |
| ***C07D 209/30*** | (2006.01) |
| ***C07D 209/44*** | (2006.01) |
| ***C07D 209/88*** | (2006.01) |
| ***C07D 209/12*** | (2006.01) |
| ***A61K 31/519*** | (2006.01) |
| ***A61K 31/501*** | (2006.01) |
| ***A61K 9/00*** | (2006.01) |
| ***A61K 31/675*** | (2006.01) |

(52) U.S. Cl.

CPC .......... *C07F 7/0812* (2013.01); *C07F 9/6561* (2013.01); *C07F 9/65583* (2013.01); *C07F 9/65616* (2013.01); *C07B 2200/05* (2013.01)

(56) References Cited

U.S. PATENT DOCUMENTS

| | | | |
|---|---|---|---|
| 2002/0133004 | A1 | 9/2002 | Takaaki et al. |
| 2005/0228000 | A1 | 10/2005 | Smallheer et al. |
| 2005/0267108 | A1 | 12/2005 | Hsieh et al. |
| 2007/0155712 | A1 | 7/2007 | Zahn et al. |
| 2008/0075720 | A1 | 3/2008 | Holers et al. |
| 2008/0075728 | A1 | 3/2008 | Newman et al. |
| 2008/0108691 | A1 | 5/2008 | Hamann et al. |
| 2010/0041628 | A1 | 2/2010 | Enomoto et al. |
| 2011/0280808 | A1 | 11/2011 | Kroth et al. |
| 2012/0231471 | A1 | 9/2012 | Sato et al. |
| 2012/0295884 | A1 | 11/2012 | Altmann et al. |
| 2013/0296377 | A1 | 11/2013 | Adams et al. |
| 2014/0371133 | A1 | 12/2014 | Francois et al. |
| 2015/0141455 | A1 | 5/2015 | Altmann et al. |
| 2015/0148374 | A1 | 5/2015 | Hommel et al. |
| 2015/0239837 | A1 | 8/2015 | Wiles et al. |
| 2015/0239868 | A1 | 8/2015 | Pais et al. |
| 2015/0239893 | A1 | 8/2015 | Wang et al. |
| 2015/0239894 | A1 | 8/2015 | Gadhachanda et al. |
| 2015/0239895 | A1 | 8/2015 | Gadhachanda et al. |
| 2015/0239919 | A1 | 8/2015 | Gadhachanda et al. |
| 2015/0239920 | A1 | 8/2015 | Gadhachanda et al. |
| 2015/0239921 | A1 | 8/2015 | Wiles et al. |

FOREIGN PATENT DOCUMENTS

| | | | |
|---|---|---|---|
| WO | WO 1999/048492 | A1 | 9/1999 |
| WO | WO 2004/007501 | A1 | 1/2004 |
| WO | WO 2004/045518 | A2 | 6/2004 |
| WO | WO 2004/111041 | A1 | 12/2004 |
| WO | WO 2008/047831 | A1 | 4/2008 |
| WO | WO 2009/091826 | A2 | 7/2009 |
| WO | WO 2012/093101 | A1 | 7/2012 |
| WO | WO 2012/177782 | A1 | 12/2012 |
| WO | WO 2013/166436 | A1 | 11/2013 |
| WO | WO 2014/002051 | A2 | 1/2014 |
| WO | WO 2014/002052 | A1 | 1/2014 |
| WO | WO 2014/002053 | A1 | 1/2014 |
| WO | WO 2014/002054 | A1 | 1/2014 |
| WO | WO 2014/002057 | A1 | 1/2014 |
| WO | WO 2014/002058 | A2 | 1/2014 |
| WO | WO 2014/002059 | A1 | 1/2014 |
| WO | WO 2014/005150 | A1 | 1/2014 |
| WO | WO 2014/009833 | A2 | 1/2014 |
| WO | WO 2014/037480 | A1 | 3/2014 |
| WO | WO 2014/116880 | A1 | 7/2014 |
| WO | WO 2015/008861 | A1 | 1/2015 |
| WO | WO 2015/130784 | A1 | 9/2015 |
| WO | WO 2015/130795 | A1 | 9/2015 |
| WO | WO 2015/130806 | A1 | 9/2015 |
| WO | WO 2015/130830 | A1 | 9/2015 |
| WO | WO 2015/130838 | A1 | 9/2015 |
| WO | WO 2015/130842 | A2 | 9/2015 |
| WO | WO 2015/130845 | A1 | 9/2015 |
| WO | WO 2017/035348 | A1 | 3/2017 |
| WO | WO 2017/035349 | A1 | 3/2017 |
| WO | WO 2017/035351 | A1 | 3/2017 |
| WO | WO 2017/035352 | A1 | 3/2017 |
| WO | WO 2017/035353 | A1 | 3/2017 |
| WO | WO 2017/035355 | A1 | 3/2017 |
| WO | WO 2017/035357 | A1 | 3/2017 |
| WO | WO 2017/035360 | A1 | 3/2017 |
| WO | WO 2017/035361 | A1 | 3/2017 |
| WO | WO 2017/035362 | A1 | 3/2017 |
| WO | WO 2017/035401 | A1 | 3/2017 |
| WO | WO 2017/035405 | A1 | 3/2017 |
| WO | WO 2017/035408 | A1 | 3/2017 |
| WO | WO 2017/035409 | A1 | 3/2017 |
| WO | WO 2017/035411 | A1 | 3/2017 |
| WO | WO 2017/035413 | A1 | 3/2017 |
| WO | WO 2017/035415 | A1 | 3/2017 |
| WO | WO 2017/035417 | A1 | 3/2017 |

(56) References Cited

FOREIGN PATENT DOCUMENTS

WO WO 2017/035418 A1 3/2017
WO WO 2017/098328 A2 6/2017

OTHER PUBLICATIONS

Barraclough et al. "Synthesis of (2S,3R)- and (@S,3S)-[3-2H1]-proline via highly selective hydrolysis of a silyl enol ether" Tetrahedron Letters, 2005; 46: 4653-4655.
Barraclough et al. "Two separate and distinct syntheses of stereospecifically deuteriated samples of (2S)-proline" Organic & Biomolecular Chemistry, 2006; 4: 1483-1491.
Cole et al. "Structure of 3,4-Dichloroisocoumarin-Inhibited Factor D" Acta Crystallographica, 1998; D54: 711-717.
Database Registry Chemical Abstracts Service, Columbus, Ohio, Accession No. RN1236248-20-6, Entered STN: Aug. 16, 2010.
Database Registry Chemical Abstracts Service, Columbus, Ohio, Accession No. RN1380849-41-1, Entered STN: Jul. 3, 2012.
De Luca et al. "HIV-1 integrase strand-transfer inhibitors: Design, synthesis and molecular modeling investigation" European Journal of Medicinal Chemistry, 2011; 46: 756-764.
Donthiri et al. "Copper-Catalyzed C—H Functionalization of Pyridines and Isoquinolines with Vinyl Azides: Synthesis of Imidazo Heterocycles" Journal of Organic Chemistry, 2014; 79: 11277-11284.
Dormoy et al. "Synthesis of N-t-Butoxycarbonyl-4,4-dideuterio-L-proline" Synthesis, 1986; 1: 81-82.
Hecker et al. "Liver-Targeted Prodrugs of 2'-C-Methyladenosine for Therapy of Hepatitis C Virus Infection" Journal of Medicinal Chemistry, 2007; 50(16): 3891-3896.
Hruby et al. "Carbon-13 NMR studies of the Peptide hormones oxytocin, arginine vasopressin, isotocin, mesotocin, glumitocin, aspartocin, related analogs, and diastereoisomers. Use of specifically deuterated hormone derivatives for assignments and effects of structural changes on carbon-13 NMR chemical shifts in peptides" Journal of the American Chemical Society, 1979; 101(1): 202-212.
International Search Report and Written Opinion for PCT/US2015/017523 dated May 14, 2015.
International Search Report and Written Opinion for PCT/US2015/017538 dated May 14, 2015.
International Search Report and Written Opinion for PCT/US2015/017554 dated May 14, 2015.
International Search Report and Written Opinion for PCT/US2015/017583 dated May 27, 2015.
International Search Report and Written Opinion for PCT/US2015/017593 dated Jun. 16, 2015.
International Search Report and Written Opinion for PCT/US2015/017597 dated Jan. 29, 2016.
International Search Report and Written Opinion for PCT/US2015/17600 dated May 27, 2015.
International Search Report and Written Opinion for PCT/US2015/017609 dated May 29, 2015.
International Search Report and Written Opinion for PCT/US2016/048688 dated Dec. 28, 2016.
International Search Report and Written Opinion for PCT/US2016/048690 dated Dec. 28, 2016.
International Search Report and Written Opinion for PCT/US2016/048693 dated Jan. 13, 2017.
International Search Report and Written Opinion for PCT/US2016/048695 dated Dec. 30, 2016.
International Search Report and Written Opinion for PCT/US2016/048696 dated Jan. 5, 2017.
International Search Report and Written Opinion for PCT/US2016/048701 dated Jan. 10, 2017.
International Search Report and Written Opinion for PCT/US2016/048704 dated Dec. 27, 2016.
International Search Report and Written Opinion for PCT/ US2016/048707 dated Jan. 5, 2017.
International Search Report and Written Opinion for PCT/ US2016/048709 dated Jan. 17, 2017.
International Search Report and Written Opinion for PCT/ US2016/048797 dated Jan. 5, 2017.
International Search Report and Written Opinion for PCT/ US2016/048779 dated Dec. 27, 2016.
International Search Report and Written Opinion for PCT/ US2016/048783 dated Feb. 3, 2017.
International Search Report and Written Opinion for PCT/ US2016/048795 dated Feb. 17, 2017.
International Search Report and Written Opinion for PCT/ US2016/048788 dated Jan. 5, 2017.
International Search Report and Written Opinion for PCT/ US2016/048793 dated Dec. 28, 2016.
International Search Report and Written Opinion for PCT/ US2016/048799 dated Dec. 28, 2016.
International Search Report and Written Opinion for PCT/ US2016/048787 dated Jan. 5, 2017.
International Search Report and Written Opinion for PCT/ US2016/048800 dated Jan. 5, 2017.
International Search Report and Written Opinion for PCT/ US2016/048710 dated Jan. 5, 2017.
Kobayashi et al. "Carboxylation of alkynylsilanes with carbon dioxide mediated by cesium fluoride in DMSO" Organic & Biomolecular Chemistry, 2013; 11: 3773-3775.
Komiya et al., 2015, caplus an 2015:126147.
Kuang et al. "Synthesis of (Z)-1-bromo-1-alkenes and terminal alkynes from anti-2,3-dibromoalkanoic acids by microwave-induced reaction" Tetrahedron, 2006; 61(16): 4043-4052.
Mackay et al. "Rapid Synthesis of the N-Methylwelwitindolinone Skeleton" Organic Letters, 2005; 7: 3421-3424.
Okutani et al. "Conversion of Bromoalkenes into Alkynes by Wet Tetra-n-butylammonium Fluoride" Journal of Organic Chemistry, 2009; 74: 442-444.
Peifer et al. "Design, Synthesis, and Biological Evaluation of Novel 3-Aryl-4-(1H-indole-3yl)-1,5-dihydro-2H-pyrrole-2-ones as Vascular Endothelial Growth Factor Receptor (VEGF-R) Inhibitors", J. Med. Chem. 2008, vol. 51, pp. 3814-3824.
PubChem CID 1129904 entered Jul. 10, 2005.
PubChem CID 59912842 entered Aug. 20, 2012.
Qu et al. "Recent Developments in Low Molecular Weight Complement Inhibitors", Mol. Immunol. 2009. vol. 47 (2-3). pp. 185-195.
Quesada et al. "One-pot co nversion of activated alcohols into terminal alkynes using manganese dioxide in combination with the Bestmann-Ohira reagent" Tetrahedron Letters, 2005; 46: 6473-6476.
Roth et al. "Further Improvements of the Synthesis of Alkynes from Aldehydes" Synthesis, 2004; 1: 59-62.
Ruiz-Gomez et al. "Structure—Activity Relationships for Substrate-Based Inhibitors of Human Complement Factor B" Journal of Medicinal Chemistry, 2009; 52: 6042-6052.
Tandon et al. "Substrate specificity of human prolyl-4-hydroxylase" Bioorganic and Medicinal Chemistry Letters, 1998; 8(10): 1139-1144.
Tang et al. "Palladium-Catalyzed Carbonylative Sonogashira Coupling of Aryl Bromides via tert-Butyl Isocyanide Insertion" Journal of Organic Chemistry, 2013; 78(7): 3170-3175.

PHOSPHONATE COMPOUNDS FOR TREATMENT OF COMPLEMENT MEDIATED DISORDERS

CROSS-REFERENCE TO RELATED APPLICATIONS

This application is a continuation of U.S. patent application Ser. No. 15/607,120, filed May 26, 2017, which is a continuation of U.S. patent application Ser. No. 14/631,785, filed Feb. 25, 2015, now U.S. Pat. No. 9,664,543, issued May 30, 2017, which claims the benefit of provisional U.S. Application No. 61/944,189, filed Feb. 25, 2014, provisional U.S. Application No. 62/022,916, filed Jul. 10, 2014, and provisional U.S. Application 62/046,783, filed Sep. 5, 2014. The entirety of each of these applications is hereby incorporated by reference for all purposes.

BACKGROUND

The complement system is a part of the innate immune system which does not adapt to changes over the course of the host's life, but is recruited and used by the adaptive immune system. For example, it assists, or complements, the ability of antibodies and phagocytic cells to clear pathogens. This sophisticated regulatory pathway allows rapid reaction to pathogenic organisms while protecting host cells from destruction. Over thirty proteins and protein fragments make up the complement system. These proteins act through opsonization (enhancing phaogytosis of antigens), chemotaxis (attracting macrophages and neutrophils), cell lysis (rupturing membranes of foreign cells) and agglutination (clustering and binding of pathogens together).

The complement system has three pathways: classical, alternative and lectin. Complement factor D plays an early and central role in activation of the alternative pathway of the complement cascade. Activation of the alternative complement pathway is initiated by spontaneous hydrolysis of a thioester bond within C3 to produce C3($H_2O$), which associates with factor B to form the C3($H_2O$)B complex. Complement factor D acts to cleave factor B within the C3($H_2O$)B complex to form Ba and Bb. The Bb fragment remains associated with C3($H_2O$) to form the alternative pathway C3 convertase C3($H_2O$)Bb. Additionally, C3b generated by any of the C3 convertases also associates with factor B to form C3bB, which factor D cleaves to generate the later stage alternative pathway C3 convertase C3bBb. This latter form of the alternative pathway C3 convertase may provide important downstream amplification within all three of the defined complement pathways, leading ultimately to the recruitment and assembly of additional factors in the complement cascade pathway, including the cleavage of C5 to C5a and C5b. C5b acts in the assembly of factors C6, C7, C8, and C9 into the membrane attack complex, which can destroy pathogenic cells by lysing the cell.

The dysfunction of or excessive activation of complement has been linked to certain autoimmune, inflammatory, and neurodegenerative diseases, as well as ischemia-reperfusion injury and cancer. For example, activation of the alternative pathway of the complement cascade contributes to the production of C3a and C5a, both potent anaphylatoxins, which also have roles in a number of inflammatory disorders. Therefore, in some instances, it is desirable to decrease the response of the complement pathway, including the alternative complement pathway. Some examples of disorders mediated by the complement pathway include age-related macular degeneration (AMD), paroxysmal nocturnal hemoglobinuria (PNH), multiple sclerosis, and rheumatoid arthritis.

Age-related macular degeneration (AMD) is a leading cause of vision loss in industrialized countries. Based on a number of genetic studies, there is evidence of the link between the complement cascade and macular degeneration. Individuals with mutations in the gene encoding complement factor H have a fivefold increased risk of macular degeneration and individuals with mutations in other complement factor genes also have an increased risk of AMD. Individuals with mutant factor H also have increased levels of C-reactive protein, a marker of inflammation. Without adequate functioning factor H, the alternative pathway of the complement cascade is overly activated leading to cellular damage. Inhibition of the alternative pathway is thus desired.

Paroxysmal nocturnal hemoglobinuria (PNH) is a non-malignant, hematological disorder characterized by the expansion of hematopoietic stem cells and progeny mature blood cells which are deficient in some surface proteins. PNH erythrocytes are not capable of modulating their surface complement activation, which leads to the typical hallmark of PNH—the chronic activation of complement mediated intravascular anemia. Currently, only one product, the anti-C5 monoclonal antibody eculizumab, has been approved in the U.S. for treatment of PNH. However, many of the patients treated with eculizumab remain anemic, and many patients continue to require blood transfusions. In addition, treatment with eculizumab requires life-long intravenous injections. Thus, there is an unmet need to develop novel inhibitors of the complement pathway.

Factor D is an attractive target for inhibition or regulation of the complement cascade due to its early and essential role in the alternative complement pathway, and its potential role in signal amplification within the classical and lectin complement pathways. Inhibition of factor D effectively interrupts the pathway and attenuates the formation of the membrane attack complex.

While initial attempts have been made to develop inhibitors of factor D, there are currently no small molecule factor D inhibitors in clinical trials. Examples of factor D inhibitors or prolyl compounds are described in the following disclosures.

Biocryst Pharmaceuticals U.S. Pat. No. 6,653,340 titled "Compounds useful in the complement, coagulat and kallikrein pathways and method for their preparation" describes fused bicyclic ring compounds that are potent inhibitors of factor D. Development of the factor D inhibitor BCX1470 was discontinued due to lack of specificity and short half-life of the compound.

Novartis PCT patent publication WO2012/093101 titled "Indole compounds or analogues thereof useful for the treatment of age-related macular degeneration" describes certain factor D inhibitors.

Novartis PCT patent publications WO2014/002057 titled "Pyrrolidine derivatives and their use as complement pathway modulators" and WO2014/009833 titled "Complement pathway modulators and uses thereof" describe additional factor D inhibitors with heterocyclic substituents. Additional factor D inhibitors are described in Novartis PCT patent publications WO2014/002051, WO2014/002052, WO2014/002053, WO2014/002054, WO2014/002058, WO2014/002059, and WO2014/005150.

Bristol-Myers Squibb PCT patent publication WO2004/045518 titled "Open chain prolyl urea-related modulators of androgen receptor function" describes open chain prolyl urea and thiourea related compounds for the treatment of androgen receptor-associated conditions, such as age-related diseases, for example, sarcopenia.

Japan Tobacco Inc. PCT patent publication WO1999/048492 titled “Amide derivatives and nociceptin antagonists” describes compounds with a proline-like core and aromatic substituents connected to the proline core through amide linkages useful for the treatment of pain.

Ferring B. V. and Yamanouchi Pharmaceutical Co. ITD. PCT patent publication WO1993/020099 titled “CCK and/or gastrin receptor ligands” describes compounds with a proline-like core and heterocyclic substituents connected to the proline core through amide linkages for the treatment of, for example, gastric disorders or pain.

Alexion Pharmaceuticals PCT patent publication WO1995/029697 titled “Methods and compositions for the treatment of glomerulonephritis and other inflammatory diseases” discloses antibodies directed to C5 of the complement pathway for the treatment of glomerulonephritis and inflammatory conditions involving pathologic activation of the complement system. Alexion Pharmaceutical’s anti-C5 antibody eculizumab (Soliris®) is currently the only complement-specific antibody on the market, and is the first and only approved treatment for paroxysmal nocturnal hemoglobinuria (PNH).

Compounds which mediate the complement pathway, and for example, act as factor D inhibitors are needed for treatment of disorders in a host, including a human, associated with misregulation of the complement cascade.

SUMMARY

It has been discovered that a compound of Formula I, or a pharmaceutically acceptable salt or composition thereof, wherein $R^{12}$ or $R^{13}$ on the A group is a phosphonate, is a superior inhibitor of complement factor D.

In one embodiment, a method for the treatment of a disorder associated with a dysfunction, including increased activity, of the complement pathway is provided that includes the administration of an effective amount of a compound of Formula I, or a pharmaceutically acceptable salt thereof, optionally in a pharmaceutically acceptable carrier, as described in more detail below.

In one embodiment, the disorder is associated with the alternative complement cascade pathway. In yet another embodiment, the disorder is associated with the complement classical pathway. In a further embodiment, the disorder is associated with the complement lectin pathway. The factor D inhibitors provided herein can thus dampen or inhibit detrimental complement activity in a host, by administration of an effective amount in a suitable manner to a host in need thereof.

Specific embodiments of this invention are directed to certain disease indications. In one embodiment, a method for the treatment of paroxysmal nocturnal hemoglobinuria (PNH) is provided that includes the administration of an effective amount of a compound of Formula I, or a pharmaceutically acceptable salt thereof, optionally in a pharmaceutically acceptable carrier. In another embodiment, a method for the treatment of age-related macular degeneration (AMD) is provided that includes the administration of an effective amount of a compound of Formula I, or a pharmaceutically acceptable salt thereof, optionally in a pharmaceutically acceptable carrier. In another embodiment, a method for the treatment of rheumatoid arthritis is provided that includes the administration of an effective amount of a compound of Formula I, or a pharmaceutically acceptable salt thereof, optionally in a pharmaceutically acceptable carrier. In another embodiment, a method for the treatment of multiple sclerosis is provided that includes the administration of an effective amount of a compound of Formula I, or a pharmaceutically acceptable salt thereof, optionally in a pharmaceutically acceptable carrier.

In other embodiments of the invention, an active compound provided herein can be used to treat or prevent a disorder in a host mediated by complement factor D, or by an excessive or detrimental amount of the C3 amplification loop of the complement pathway. As examples, the invention includes methods to treat or prevent complement associated disorders that are induced by antibody-antigen interactions, a component of an immune or autoimmune disorder or by ischemic injury. The invention also provides methods to decrease inflammation or an immune response, including an autoimmune response, where mediated or affected by factor D.

The disclosure provides compounds of Formula I (I)

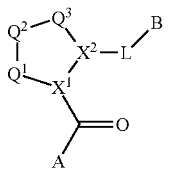

and the pharmaceutically acceptable salts and compositions thereof, wherein:

$Q^1$ is $N(R^1)$ or $C(R^1R^{1'})$;

$Q^2$ is $C(R^2R^{2'})$, $C(R^2R^{2'})$—$C(R^2R^{2'})$, S, O, $N(R^2)$ or $C(R^2R^{2'})O$;

$Q^3$ is $N(R^3)$, S, or $C(R^3R^{3'})$;

$X^1$ and $X^2$ are independently N, CH, or CZ, or $X^1$ and $X^2$ together are C═C; and wherein $Q^1$, $Q^2$, $Q^3$, $X^1$, and $X^2$ are selected such that a stable compound results.

Non-limiting examples of the

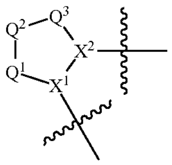

ring are illustrated below (any of which can be otherwise substituted with $R^1$, $R^{1'}$, $R^2$, $R^{2'}$, $R^3$, and $R^{3'}$) as described in more detail below.

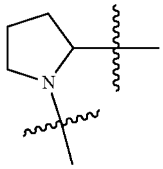
,
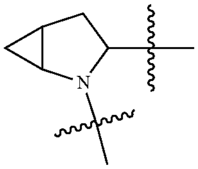
,

-continued
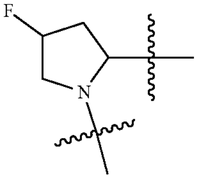,
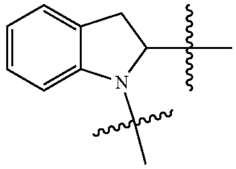,
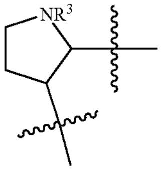,
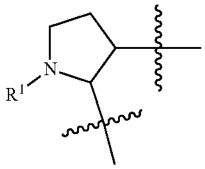,
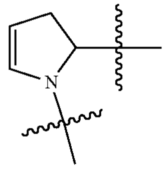,
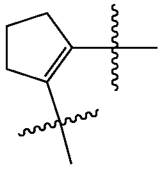,
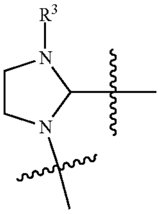,
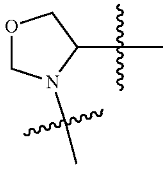,
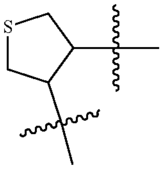,
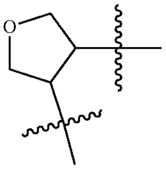,
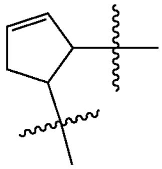,
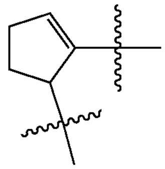,
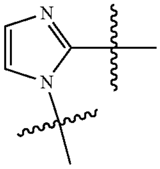,
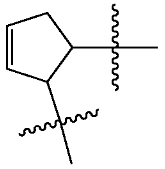,
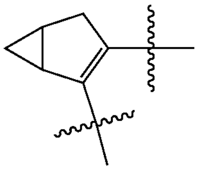,
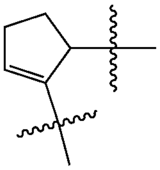,
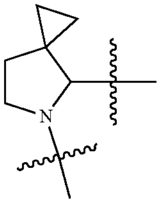,
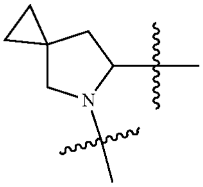,
-continued
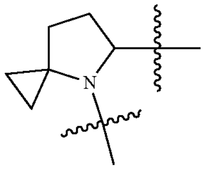,
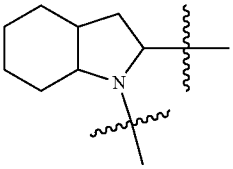,
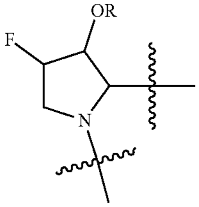,
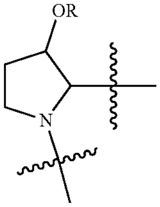,
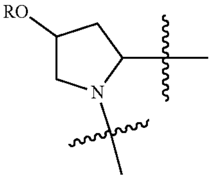,
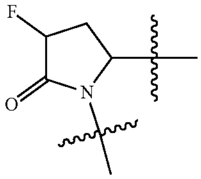,
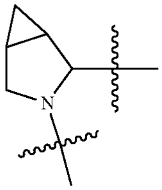,
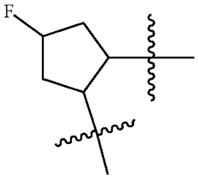,
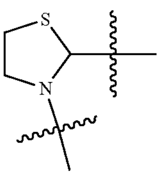,
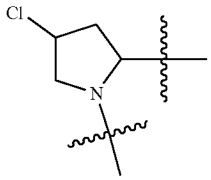,
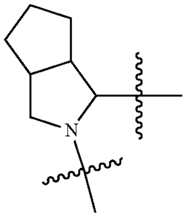,
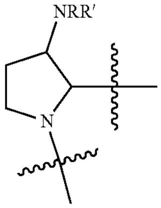,
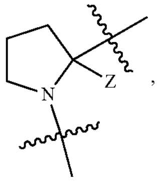,
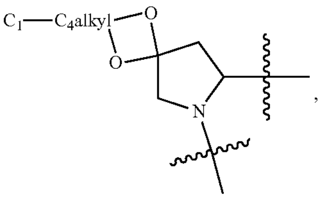,
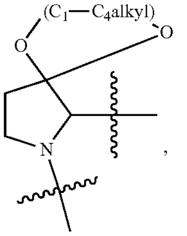,
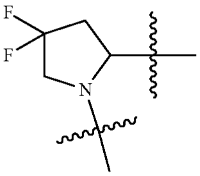, -continued

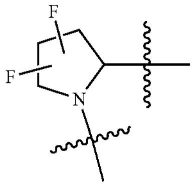 ,

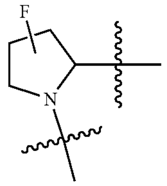 ,

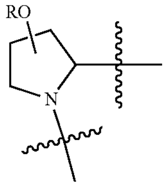 ,

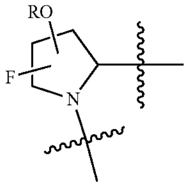 ,

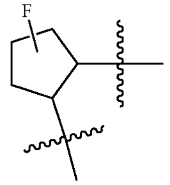 ,

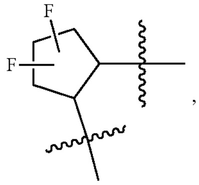 ,

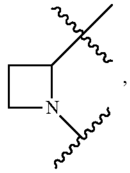 ,

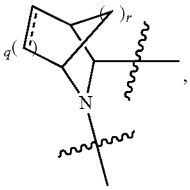 , and

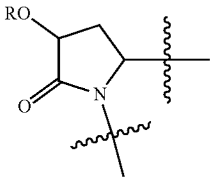 ;

wherein q is 0, 1, 2 or 3 and r is 1, 2 or 3.

R and R' are independently chosen from H, alkyl, cycloalkyl, cycloalkylalkyl, heterocycle, heterocycloalkyl, aryl, arylalkyl, heteroaryl, heteroarylalkyl wherein each group can be optionally substituted or any other substituent group herein that provides the desired properties. In some embodiments, the ring includes one or more chiral carbon atoms. The invention includes embodiments in which the chiral carbon can be provided as an enantiomer, or mixtures of enantiomers, including a racemic mixture. Where the ring includes more than one stereocenter, all of the enantiomers and diastereomers are included in the invention as individual species.

Z is F, Cl, $NH_2$, $CH_3$, $CH_2D$, $CHD_2$, or $CD_3$.

$R^1$, $R^{1'}$, $R^2$, $R^{2'}$, $R^3$, and $R^{3'}$ are independently chosen at each occurrence, as appropriate, and only where a stable compound results, from hydrogen, halogen, hydroxyl, nitro, cyano, amino, $C_1$-$C_6$alkyl, $C_2$-$C_6$alkenyl, $C_2$-$C_6$alkynyl, $C_1$-$C_6$alkoxy, $C_2$-$C_6$alkynyl, $C_2$-$C_6$alkanoyl, $C_1$-$C_6$thioalkyl, hydroxy$C_1$-$C_6$alkyl, amino$C_1$-$C_6$alkyl, —$C_0$-$C_4$alkyl$NR^9R^{10}$, —C(O)$OR^9$, —OC(O)$R^9$, —$NR^9$C(O)$R^{10}$, —C(O)$NR^9R^{10}$, —OC(O)$NR^9R^{10}$, —$NR^9$C(O)$OR^{10}$, $C_1$-$C_2$haloalkyl, and $C_1$-$C_2$haloalkoxy, where $R^9$ and $R^{10}$ are independently chosen at each occurrence from hydrogen, $C_1$-$C_6$alkyl, ($C_3$-$C_7$cycloalkyl)$C_0$-$C_4$alkyl, —$C_0$-$C_4$alkyl($C_3$-$C_7$cycloalkyl), and —O—$C_0$-$C_4$alkyl($C_3$-$C_7$cycloalkyl).

In alternative embodiments, $R^1$ and $R^{1'}$ or $R^3$ and $R^{3'}$ may be taken together to form a 3- to 6-membered carbocyclic spiro ring or a 3- to 6-membered heterocyclic spiro ring containing 1 or 2 heteroatoms independently chosen from N, O, or S; $R^2$ and $R^{2'}$ may be taken together to form a 3- to 6-membered carbocyclic spiro ring; or $R^2$ and $R^{2'}$ may be taken together to form a 3- to 6-membered heterocyclic spiro ring; each of which spiro ring each of which ring may be unsubstituted or substituted with 1 or more substituents independently chosen from halogen (and in particular F), hydroxyl, cyano, —COOH, $C_1$-$C_4$alkyl (including in particular methyl), $C_2$-$C_4$alkenyl, $C_2$-$C_4$alkynyl, $C_1$-$C_4$alkoxy, $C_2$-$C_4$alkanoyl, hydroxy$C_1$-$C_4$alkyl, (mono- and di-$C_1$-$C_4$alkylamino)$C_0$-$C_4$alkyl, —$C_0$-$C_4$alkyl($C_3$-$C_7$cycloalkyl), —O—$C_0$-$C_4$alkyl($C_3$-$C_7$cycloalkyl), $C_1$-$C_2$haloalkyl, and $C_1$-$C_2$haloalkoxy.

In alternative embodiments, $R^1$ and $R^2$ may be taken together to form a 3-membered carbocyclic ring; $R^1$ and $R^2$ may be taken together to form a 4- to 6-membered carbocyclic or aryl ring or a 4- to 6-membered heterocyclic or heteroaryl ring containing 1 or 2 heteroatoms independently chosen from N, O, and S; or $R^2$ and $R^3$, if bound to adjacent carbon atoms, may be taken together to form a 3- to 6-membered carbocyclic or aryl ring or a 3- to 6-membered heterocyclic or heteroaryl ring; each of which ring may be unsubstituted or substituted with 1 or more substituents independently chosen from halogen (and in particular F), hydroxyl, cyano, —COOH, $C_1$-$C_4$alkyl (including in particular methyl), $C_2$-$C_4$alkenyl, $C_2$-$C_4$alkynyl, $C_1$-$C_4$alkoxy, $C_2$-$C_4$alkanoyl, hydroxy$C_1$-$C_4$alkyl, (mono- and di-$C_1$-$C_4$alkylamino)$C_0$-$C_4$alkyl, —$C_0$-$C_4$alkyl($C_3$-$C_7$cycloalkyl), —O—$C_0$-$C_4$alkyl($C_3$-$C_7$cycloalkyl), $C_1$-$C_2$haloalkyl, and $C_1$-$C_2$haloalkoxy.

In alternative embodiments, $R^1$ and $R^{1'}$, $R^2$ and $R^{2'}$, or $R^3$ and $R^{3'}$ can be taken together to form a carbonyl group. In alternative embodiments, $R^1$ and $R^2$ or $R^2$ and $R^3$ can be taken together to form a carbon-carbon double bond.

A is a group chosen from:

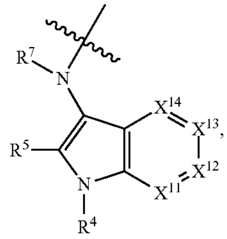 ,

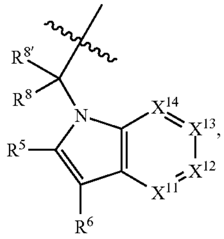 ,

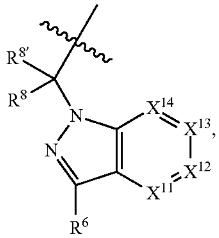 ,

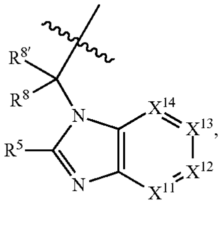 ,

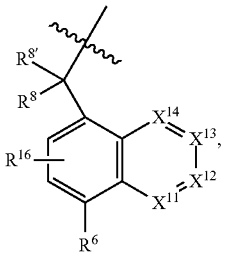 ,

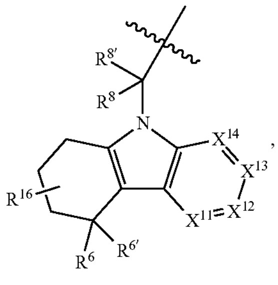 ,

-continued

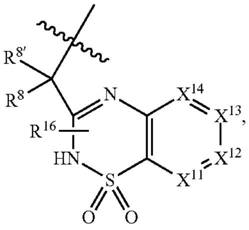

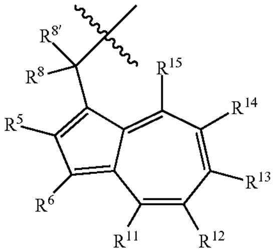

,

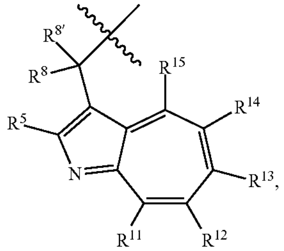

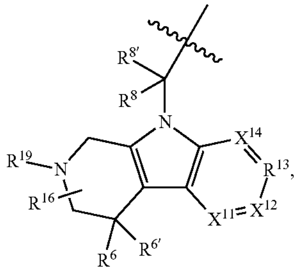

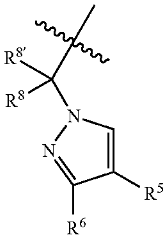

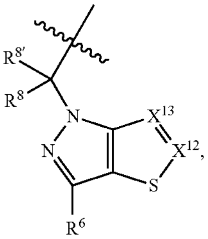

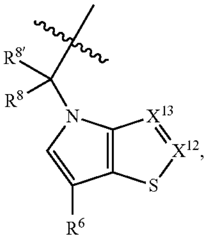

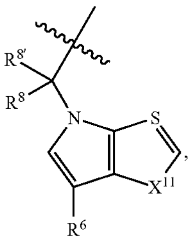

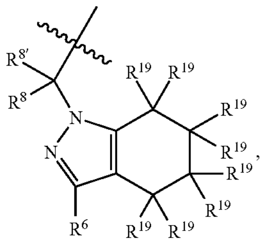

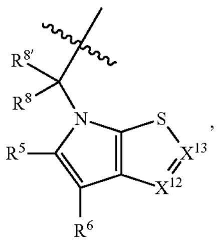

, or

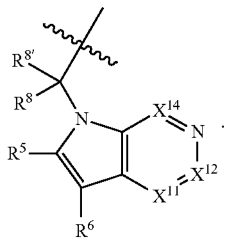

.

$R^4$ is chosen from —CHO, —$CONH_2$, $C_2$-$C_6$alkanoyl, hydrogen, —$SO_2NH_2$, —$C(CH_2)_2F$, —$CH(CF_3)NH_2$, $C_1$-$C_6$alkyl, —$C_0$-$C_4$alkyl($C_3$-$C_7$cycloalkyl), —C(O)$C_0$-$C_2$alkyl($C_3$-$C_7$cycloalkyl),

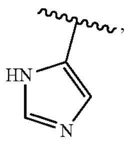

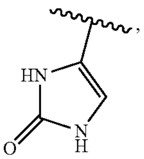

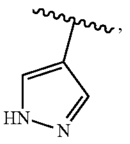

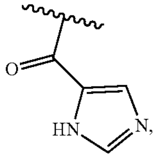

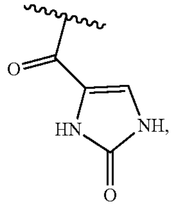

or

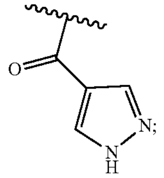

each of which $R^4$ other than hydrogen, —CHO, and —$CONH_2$, is unsubstituted or substituted with one or more of amino, imino, halogen, hydroxyl, cyano, cyanoimino, $C_1$-$C_2$alkyl, $C_1$-$C_2$alkoxy, —$C_0$-$C_2$alkyl(mono- and di-$C_1$-$C_4$alkylamino), $C_1$-$C_2$haloalkyl, and $C_1$-$C_2$haloalkoxy.

$R^5$ and $R^6$ are independently chosen from —CHO, —C(O)$NH_2$, —C(O)NH($CH_3$), $C_2$-$C_6$alkanoyl, hydrogen, hydroxyl, halogen, cyano, nitro, —COOH, —$SO_2NH_2$, vinyl, $C_1$-$C_6$alkyl (including methyl), $C_2$-$C_6$alkenyl, $C_1$-$C_6$alkoxy, —$C_0$-$C_4$alkyl($C_3$-$C_7$cycloalkyl), —C(O)$C_0$-$C_4$alkyl($C_3$-$C_7$cycloalkyl), —P(O)($OR^9$)$_2$, —OC(O)$R^9$, —C(O)$OR^9$, —C(O)N($CH_2CH_2R^9$)($R^{10}$), —$NR^9$C(O)$R^{10}$, phenyl, or 5- to 6-membered heteroaryl.

Each $R^5$ and $R^6$ other than hydrogen, hydroxyl, cyano, and —COOH is unsubstituted or optionally substituted. For example, $R^5$ and $R^6$ other than hydrogen, hydroxyl, cyano, and —COOH may be substituted with one or more substituents independently chosen from halogen, hydroxyl, amino, imino, cyano, cyanoimino, $C_1$-$C_2$alkyl, $C_1$-$C_4$alkoxy, —$C_0$-$C_2$alkyl(mono- and di-$C_1$-$C_4$alkylamino), $C_1$-$C_2$haloalkyl, and $C_1$-$C_2$haloalkoxy.

$R^{6'}$ is hydrogen, halogen, hydroxyl, $C_1$-$C_4$alkyl, —$C_0$-$C_4$alkyl($C_3$-$C_7$cycloalkyl), or $C_1$-$C_4$alkoxy; or $R^6$ and $R^{6'}$ may be taken together to form an oxo, vinyl, or imino group.

$R^7$ is hydrogen, $C_1$-$C_6$alkyl, or —$C_0$-$C_4$alkyl($C_3$-$C_7$cycloalkyl).

$R^8$ and $R^{8'}$ are independently chosen from hydrogen, halogen, hydroxyl, $C_1$-$C_6$alkyl, —$C_0$-$C_4$alkyl($C_3$-$C_7$cycloalkyl), $C_1$-$C_6$alkoxy, and ($C_1$-$C_4$alkylamino)$C_0$-$C_2$alkyl; or $R^8$ and $R^{8'}$ are taken together to form an oxo group; or $R^8$ and $R^{8'}$ can be taken together with the carbon that they are bonded to form a 3-membered carbocyclic ring.

$R^{16}$ is absent or may include one or more substituents independently chosen from halogen, hydroxyl, nitro, cyano, $C_1$-$C_6$alkyl, $C_2$-$C_6$alkenyl, $C_2$-$C_6$alkanoyl, $C_1$-$C_6$alkoxy, —$C_0$-$C_4$alkyl(mono- and di-$C_1$-$C_6$alkylamino), —$C_0$-$C_4$alkyl($C_3$-$C_7$cycloalkyl), $C_1$-$C_2$haloalkyl, and $C_1$-$C_2$haloalkoxy.

$R^{19}$ is hydrogen, $C_1$-$C_6$alkyl, $C_2$-$C_6$alkenyl, $C_2$-$C_6$alkanoyl, —$SO_2C_1$-$C_6$alkyl, (mono- and di-$C_1$-$C_6$alkylamino)$C_1$-$C_4$alkyl, —$C_0$-$C_4$alkyl($C_3$-$C_7$cycloalkyl), —$C_0$-$C_4$alkyl($C_3$-$C_7$heterocycloalkyl), —$C_0$-$C_4$alkyl(aryl), $C_0$-$C_4$alkyl(heteroaryl), and wherein $R^{19}$ other than hydrogen is unsubstituted or substituted with one or more substituents independently chosen from halogen, hydroxyl, amino, —COOH, and —C(O)O$C_1$-$C_4$alkyl.

$X^{11}$ is N or $CR^{11}$.

$X^{12}$ is N or $CR^{12}$.

$X^{13}$ is N or $CR^{13}$.

$X^{14}$ is N or $CR^{14}$.

No more than 2 of $X^{11}$, $X^{12}$, $X^{13}$, and $X^{14}$ are N.

One of $R^{12}$ and $R^{13}$ is chosen from $R^{31}$ and the other of $R^{12}$ and $R^{13}$ is chosen from $R^{32}$. In an alternative embodiment, $R^{12}$ and $R^{13}$ are each independently selected from an $R^{32}$ moiety.

$R^{31}$ is chosen from hydrogen, halogen, hydroxyl, nitro, cyano, amino, —COOH, $C_1$-$C_2$haloalkyl, $C_1$-$C_2$haloalkoxy, $C_1$-$C_6$alkyl, —$C_0$-$C_4$alkyl($C_3$-$C_7$cycloalkyl), $C_2$-$C_6$alkenyl, $C_2$-$C_6$alkanoyl, $C_1$-$C_6$alkoxy, $C_2$-$C_6$alkenyloxy, —C(O)O$R^9$, $C_1$-$C_6$thioalkyl, —$C_0$-$C_4$alkylN$R^9R^{10}$, —C(O)N$R^9R^{10}$, —$SO_2R^9$, —$SO_2NR^9R^{10}$, —OC(O)$R^9$, and —C($NR^9$)$NR^9R^{10}$, each of which $R^{31}$ other than hydrogen, halogen, hydroxyl, nitro, cyano, $C_1$-$C_2$haloalkyl, and $C_1$-$C_2$haloalkoxy is unsubstituted or substituted with one or more substituents independently selected from halogen, hydroxyl, nitro, cyano, amino, —COOH, —$CONH_2C_1$-$C_2$haloalkyl, and $C_1$-$C_2$haloalkoxy, and each of which $R^{31}$ is also optionally substituted with one substituent chosen from phenyl and 4- to 7-membered heterocycle containing 1, 2, or 3 heteroatoms independently chosen from N, O, and S; which phenyl or 4- to 7-membered heterocycle is unsubstituted or substituted with one or more substituents independently chosen from halogen, hydroxyl, nitro, cyano, $C_1$-$C_6$alkyl, $C_2$-$C_6$alkenyl, $C_2$-$C_6$alkanoyl, $C_1$-$C_6$alkoxy, (mono- and di-$C_1$-$C_6$alkylamino)$C_0$-$C_4$alkyl, $C_1$-$C_6$alkylester, —$C_0$-$C_4$alkyl)($C_3$-$C_7$cycloalkyl), $C_1$-$C_2$haloalkyl, and $C_1$-$C_2$haloalkoxy;

$R^{32}$ is —P(O)$R^{20}R^{20}$.

$R^{20}$ is independently chosen at each occurrence from hydroxyl, $C_1$-$C_6$alkoxy, $C_1$-$C_6$haloalkoxy, $C_1$-$C_6$alkyl, ($C_3$-$C_7$cycloalkyl)$C_0$-$C_4$alkyl-, (aryl)$C_0$-$C_4$alkyl-, —O—$C_0$-$C_4$alkyl(aryl), —O—$C_0$-$C_4$alkyl($C_3$-$C_7$cycloalkyl), (4- to 7-membered heterocycloalkyl)$C_0$-$C_4$alkyl-O—having 1, 2, or 3 heteroatoms independently chosen from N, O, and S; (5- or 6-membered unsaturated or aromatic heterocycle)$C_0$-$C_4$alkyl-O— having 1, 2, or 3 heteroatoms independently chosen from N, O, and S; —O$(CH_2)_{2\text{-}4}$O$(CH_2)_{8\text{-}18}$, —OC$(R^{20a})_2$OC(O)O$R^{20b}$, —OC$(R^{20a})_2$OC(O)$R^{20b}$, —$NR^9R^{10}$, an N-linked amino acid or an N-linked amino acid ester and each $R^{20}$ can be optionally substituted;

$R^{20a}$ is independently chosen at each occurrence from hydrogen, $C_1$-$C_8$alkyl, $C_2$-$C_8$alkenyl, $C_2$-$C_8$alkynyl, (aryl)$C_0$-$C_4$alkyl-, (aryl)$C_2$-$C_8$alkenyl- or (aryl)$C_2$-$C_8$alkynyl-; or two $R^{20a}$ groups can be taken together with the carbon that they are bonded to form a 3-6 membered heterocycloalkyl having 1, 2, or 3 heteroatoms independently chosen from N, O, and S, or a 3-6 membered carbocyclic ring.

$R^{20b}$ is independently chosen at each occurrence from $C_1$-$C_8$alkyl, $C_2$-$C_8$alkenyl, $C_2$-$C_8$alkynyl, (aryl)$C_0$-$C_4$alkyl, (aryl)$C_2$-$C_8$alkenyl or (aryl)$C_2$-$C_8$alkynyl.

$R^{11}$, $R^{14}$, and $R^{15}$ are independently chosen at each occurrence from hydrogen, halogen, hydroxyl, nitro, cyano, —O(PO)$(OR^9)_2$, —(PO)$(OR^9)_2$, $C_1$-$C_6$alkyl, $C_2$-$C_6$alkenyl, $C_2$-$C_6$alkynyl, $C_2$-$C_6$alkenyl(aryl), $C_2$-$C_6$alkenyl(cycloalkyl), $C_2$-$C_6$alkenyl(heterocycle), $C_2$-$C_6$alkenyl(heteroaryl), $C_2$-$C_6$alkynyl, $C_2$-$C_6$alkynyl(aryl), $C_2$-$C_6$alkynyl(cycloalkyl), $C_2$-$C_6$alkynyl(heterocycle), $C_2$-$C_6$alkynyl(heteroaryl), $C_2$-$C_6$alkanoyl, $C_1$-$C_6$alkoxy, $C_1$-$C_6$thioalkyl, —$C_0$-$C_4$alkyl(mono- and di-$C_1$-$C_6$alkylamino), —$C_0$-$C_4$alkyl($C_3$-$C_7$cycloalkyl), —$C_0$-$C_4$alkoxy($C_3$-$C_7$cycloalkyl), $C_1$-$C_2$haloalkyl, and $C_1$-$C_2$haloalkoxy.

L is a bond or is chosen from the formulas

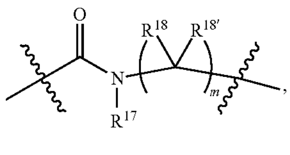,

-continued

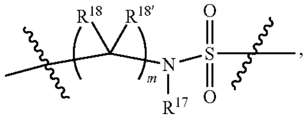,

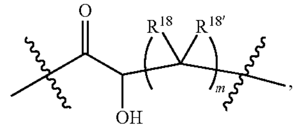, 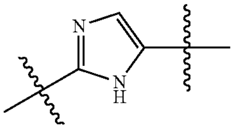 and

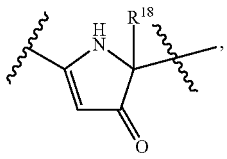, where $R^{17}$ is hydrogen, $C_1$-$C_6$alkyl, or —$C_0$-$C_4$alkyl($C_3$-$C_7$cycloalkyl) and $R^{18}$ and $R^{18'}$ are independently chosen from hydrogen, halogen, hydroxymethyl, and methyl; and m is 0, 1, 2, or 3.

B is a monocyclic or bicyclic carbocyclic; a monocyclic or bicyclic carbocyclic-oxy group; a monocyclic, bicyclic, or tricyclic heterocyclic group having 1, 2, 3, or 4 heteroatoms independently selected from N, O, and S and from 4 to 7 ring atoms per ring; $C_2$-$C_6$alkenyl; $C_2$-$C_6$alkynyl; —($C_0$-$C_4$alkyl)(aryl); —($C_0$-$C_4$alkyl)(heteroaryl); or —($C_0$-$C_4$alkyl)(biphenyl).

Each of which B is unsubstituted or substituted with one or more substituents independently chosen from $R^{33}$ and $R^{34}$, and 0 or 1 substituents chosen from $R^{35}$ and $R^{36}$.

$R^{33}$ is independently chosen from halogen, hydroxyl, —COOH, cyano, $C_1$-$C_6$alkyl, $C_2$-$C_6$alkanoyl, $C_1$-$C_6$alkoxy, —$C_0$-$C_4$alkylN$R^9R^{10}$, —$SO_2R^9$, $C_1$-$C_2$haloalkyl, and $C_1$-$C_2$haloalkoxy;

$R^{34}$ is independently chosen from nitro, $C_2$-$C_6$alkenyl, $C_2$-$C_6$alkynyl, $C_1$-$C_6$thioalkyl, -J$C_3$-$C_7$cycloalkyl, —$B(OH)_2$, -JC(O)$NR^9R^{23}$, -J$OSO_2OR^{21}$, —C(O)$(CH_2)_{1\text{-}4}$S(O)$R^{21}$, —O$(CH_2)_{1\text{-}4}$S(O)$NR^{21}R^{22}$, -JOP(O)$(OR^{21})(OR^{22})$, -JP(O)$(OR^{21})(OR^{22})$, -JOP(O)$(OR^{21})R^{22}$, -JP(O)$(OR^{21})R^{22}$, -JOP(O)$R^{21}R^{22}$, -JP(O)$R^{21}R^{22}$, -JSP(O)$(OR^{21})(OR^{22})$, -JSP(O)$(OR^{21})(R^{22})$, -JSP(O)$(R^{21})(R^{22})$, -J$NR^9$P(O)$(NHR^{21})(NHR^{22})$, -J$NR^9$P(O)$(OR^{21})(NHR^{22})$, -J$NR^9$P(O)$(OR^{21})(OR^{22})$, -JC(S)$R^{21}$, -J$NR^{21}SO_2R^{22}$, -J$NR^9$S(O)$NR^{10}R^{22}$, -J$NR^9SO_2NR^{10}R^{22}$, -J$SO_2NR^9COR^{22}$, -J$SO_2NR^9CONR^{21}R^{22}$, -J$NR^{21}SO_2R^{22}$, -JC(O)$NR^{21}SO_2R^{22}$, -JC($NH_2$)$NR^{22}$, -JC($NH_2$)$NR^9S(O)_2R^{22}$, -JOC(O)$NR^{21}R^{22}$, -J$NR^{21}$C(O)O$R^{22}$, -J$NR^{21}$OC(O)$R^{22}$, —$(CH_2)_{1\text{-}4}$C(O)$NR^{21}R^{22}$, -JC(O)$R^{24}R^{25}$, -J$NR^9$C(O)$R^{21}$, -JC(O)$R^{21}$, -J$NR^9$C(O)$NR^{10}R^{22}$, —CC$R^{21}$, —$(CH_2)_{1\text{-}4}$OC(O)$R^{21}$, and -JC(O)O$R^{23}$; each of which $R^{34}$ may be unsubstituted or substituted with one or more substituents independently chosen from halogen, hydroxyl, nitro, cyano, amino, oxo, —$B(OH)_2$, —$Si(CH_3)_3$, —COOH, —$CONH_2$, —P(O)$(OH)_2$, $C_1$-$C_6$alkyl, —$C_0$-$C_4$alkyl($C_3$-$C_7$cycloalkyl), $C_1$-$C_6$alkoxy, —$C_0$-$C_2$alkyl(mono- and di-$C_1$-$C_4$alkylamino), $C_1$-$C_6$alkylester, $C_1$-$C_4$alkylamino, $C_1$-$C_4$hydroxylalkyl, $C_1$-$C_2$haloalkyl, and $C_1$-$C_2$haloalkoxy.

$R^{35}$ is independently chosen from naphthyl, naphthyloxy, indanyl, (4- to 7-membered heterocycloalkyl)$C_0$-$C_4$alkyl containing 1 or 2 heteroatoms chosen from N, O, and S, and bicyclic heterocycle containing 1, 2, or 3 heteroatoms independently chosen from N, O, and S, and containing 4- to 7-ring atoms in each ring; each of which $R^{35}$ is unsubstituted or substituted with one or more substituents independently chosen from halogen, hydroxyl, nitro, cyano, $C_1$-$C_6$alkyl, $C_2$-$C_6$alkenyl, $C_2$-$C_6$alkanoyl, $C_1$-$C_6$alkoxy, (mono- and di-$C_1$-$C_6$alkylamino)$C_0$-$C_4$alkyl, $C_1$-$C_6$alkylester, —$C_0$-$C_4$alkyl($C_3$-$C_7$cycloalkyl), —$SO_2R^9$, $C_1$-$C_2$haloalkyl, and $C_1$-$C_2$haloalkoxy.

$R^{36}$ is independently chosen from tetrazolyl, (phenyl)$C_0$-$C_2$alkyl, (phenyl)$C_1$-$C_2$alkoxy, phenoxy, and 5- or 6-membered heteroaryl containing 1, 2, or 3 heteroatoms independently chosen from N, O, B, and S, each of which $R^{36}$ is unsubstituted or substituted with one or more substituents independently chosen from halogen, hydroxyl, nitro, cyano, $C_1$-$C_6$alkyl, $C_2$-$C_6$alkenyl, $C_2$-$C_6$alkanoyl, $C_1$-$C_6$alkoxy, (mono- and di-$C_1$-$C_6$alkylamino)$C_0$-$C_4$alkyl, $C_1$-$C_6$alkylester, —$C_0$-$C_4$alkyl($C_3$-$C_7$cycloalkyl), —$SO_2R^9$, —$OSi(CH_3)_2C(CH_3)_3$, —$Si(CH_3)_2C(CH_3)_3$, $C_1$-$C_2$haloalkyl, and $C_1$-$C_2$haloalkoxy.

$R^{21}$ and $R^{22}$ are independently chosen at each occurrence from hydrogen, hydroxyl, cyano, amino, $C_1$-$C_6$alkyl, $C_1$-$C_6$haloalkyl, $C_1$-$C_6$alkoxy, ($C_3$-$C_7$cycloalkyl)$C_0$-$C_4$alkyl, (phenyl)$C_0$-$C_4$alkyl, —$C_1$-$C_4$alkylOC(O)OC$_1$-$C_6$alkyl, —$C_1$-$C_4$alkylOC(O)C$_1$-$C_6$alkyl, —$C_1$-$C_4$alkylC(O)OC$_1$-$C_6$alkyl, (4- to 7-membered heterocycloalkyl)$C_0$-$C_4$alkyl having 1, 2, or 3 heteroatoms independently chosen from N, O, and S, and (5- or 6-membered unsaturated or aromatic heterocycle)$C_0$-$C_4$alkyl having 1, 2, or 3 heteroatoms independently chosen from N, O, and S, and each $R^{21}$ and $R^{22}$ can be optionally substituted.

$R^{23}$ is independently chosen at each occurrence from $C_1$-$C_6$alkyl, $C_1$-$C_6$haloalkyl, (aryl)$C_0$-$C_4$alkyl, ($C_3$-$C_7$cycloalkyl)$C_0$-$C_4$alkyl, (phenyl)$C_0$-$C_4$alkyl, (4- to 7-membered heterocycloalkyl)$C_0$-$C_4$alkyl having 1, 2, or 3 heteroatoms independently chosen from N, O, and S, and (5- or 6-membered unsaturated or aromatic heterocycle)$C_0$-$C_4$alkyl having 1, 2, or 3 heteroatoms independently chosen from N, O, and S, and each $R^{23}$ can be optionally substituted.

$R^{24}$ and $R^{25}$ are taken together with the nitrogen to which they are attached to form a 4- to 7-membered monocyclic heterocycloalkyl group, or a 6- to 10-membered bicyclic heterocyclic group having fused, spiro, or bridged rings, and each $R^{24}$ and $R^{25}$ can be optionally substituted.

J is independently chosen at each occurrence from a covalent bond, $C_1$-$C_4$alkylene, —$OC_1$-$C_4$alkylene, $C_2$-$C_4$alkenylene, and $C_2$-$C_4$alkynylene.

Pharmaceutical compositions comprising a compound or salt of Formula I together with a pharmaceutically acceptable carrier are also disclosed.

Methods of treating or preventing disorders mediated by complement cascade factor D, including but not limited to age-related macular degeneration (AMD), retinal degeneration, other ophthalmic diseases (e.g., geographic atrophy), paroxysymal nocturnal hemoglobinuria (PNH), multiple sclerosis (MS), arthritis including rheumatoid arthritis (RA), a respiratory disease or a cardiovascular disease, are provided, comprising administering a therapeutically effective amount of a compound or salt of Formula I to a host, including a human, in need of such treatment are also disclosed.

In another embodiment, an effective amount of an active factor D inhibiting compound is provided to treat an inflammatory or immune disorder, including an autoimmune disorder, that is mediated or affected by factor D. In an alternative embodiment, the compound of Formula I can be used to treat a disorder mediated by the complement pathway, regardless whether it is acting through Factor D.

The present invention includes at least the following features:

(a) a compound of Formula I as described herein, and pharmaceutically acceptable salts and prodrugs thereof (each of which and all subgenuses and species thereof considered individually and specifically described);

(b) Formula I as described herein, and pharmaceutically acceptable salts and prodrugs thereof, for use in treating or preventing disorders mediated by the complement pathway, and for example, cascade factor D, including age-related macular degeneration (AMD), retinal degeneration, paroxysymal nocturnal hemoglobinuria (PNH), multiple sclerosis (MS), and rheumatoid arthritis (RA) and other disorders described further herein;

(c) use of Formula I, and pharmaceutically acceptable salts and prodrugs thereof in the manufacture of a medicament for use in treating or preventing disorders mediated by complement cascade factor D, including age-related macular degeneration (AMD), retinal degeneration, paroxysymal nocturnal hemoglobinuria (PNH), multiple sclerosis (MS), and rheumatoid arthritis (RA) and other disorders described further herein;

(d) a process for manufacturing a medicament intended for the therapeutic use for treating or preventing treating or preventing disorders mediated by complement cascade factor D, including age-related macular degeneration (AMD), retinal degeneration, paroxysymal nocturnal hemoglobinuria (PNH), multiple sclerosis (MS), and rheumatoid arthritis (RA) and other disorders described further herein characterized in that Formula I as described herein is used in the manufacture;

(e) a pharmaceutical formulation comprising an effective host-treating amount of the Formula I or a pharmaceutically acceptable salt or prodrug thereof together with a pharmaceutically acceptable carrier or diluent;

(f) Formula I as described herein in substantially pure form, including substantially isolated from other chemical entities (e.g., at least 90 or 95%);

(g) processes for the manufacture of the compounds of Formula I and salts, compositions, dosage forms thereof; and (h) processes for the preparation of therapeutic products that contain an effective amount of Formula I, as described herein.

DETAILED DESCRIPTION

I. Terminology

Compounds are described using standard nomenclature. Unless defined otherwise, all technical and scientific terms used herein have the same meaning as is commonly understood by one of skill in the art to which this invention belongs.

The compounds in any of the Formulas described herein include enantiomers, mixtures of enantiomers, diastereomers, tautomers, racemates and other isomers, such as rotamers, as if each is specifically described. "Formula I" includes all subgeneric groups of Formula I, such as Formula IA and Formula IB and also includes pharmaceutically acceptable salts of a compound of Formula I, unless clearly contraindicated by the context in which this phrase is used. "Formula I" also includes all subgeneric groups of Formula I, such as Formulas IC-ID, and Formulas II-XXX, and also includes pharmaceutically acceptable salts of all subgeneric groups of Formula I, such as Formulas IA-ID, and Formulas II-XXX, unless contraindicated by the context in which this phrase is used.

The terms "a" and "an" do not denote a limitation of quantity, but rather denote the presence of at least one of the referenced item. The term "or" means "and/or". Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of examples, or exemplary language (e.g., "such as"), is intended merely to better illustrate the invention and does not pose a limitation on the scope of the invention unless otherwise claimed. Unless defined otherwise, technical and scientific terms used herein have the same meaning as is commonly understood by one of skill in the art to which this invention belongs.

The present invention includes compounds of Formula I and the use of compounds with at least one desired isotopic substitution of an atom, at an amount above the natural abundance of the isotope, i.e., enriched. Isotopes are atoms having the same atomic number but different mass numbers, i.e., the same number of protons but a different number of neutrons.

Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes isotopically modified compounds of Formula I. In one embodiment, isotopically labelled compounds can be used in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

By way of general example and without limitation, isotopes of hydrogen, for example, deuterium ($^{2}H$) and tritium ($^{3}H$) may be used anywhere in described structures that achieves the desired result. Alternatively or in addition, isotopes of carbon, e.g., $^{13}C$ and $^{14}C$, may be used. In one embodiment, the isotopic substitution is deuterium for hydrogen at one or more locations on the molecule to improve the performance of the drug, for example, the pharmacodynamics, pharmacokinetics, biodistribution, half-life, stability, AUC, Tmax, Cmax, etc. For example, the deuterium can be bound to carbon in a location of bond breakage during metabolism (an α-deuterium kinetic isotope effect) or next to or near the site of bond breakage (a β-deuterium kinetic isotope effect).

Isotopic substitutions, for example deuterium substitutions, can be partial or complete. Partial deuterium substitution means that at least one hydrogen is substituted with deuterium. In certain embodiments, the isotope is 90, 95 or 99% or more enriched in an isotope at any location of interest. In one embodiments deuterium is 90, 95 or 99% enriched at a desired location. Unless otherwise stated, the enrichment at any point is above natural abundance and enough to alter a detectable property of the drug in a human.

In one embodiment, the substitution of a hydrogen atom for a deuterium atom occurs within an R group substituent on the L-B moiety region. In one embodiment, the substitution of a hydrogen atom for a deuterium atom occurs within an R group selected from any of $R^{18}$, $R^{18'}$, $R^{33}$, $R^{34}$, $R^{35}$, and/or $R^{36}$. In one embodiment, the substitution of a hydrogen atom for a deuterium atom occurs within an R group substituent within the A-carbonyl moiety region. In one embodiment, the substitution of a hydrogen atom for a deuterium atom occurs at $R^{4'}$ $R^{5}$, $R^{6}$, $R^{6'}$, $R^{7}$, $R^{8}$, $R^{8'}$, $R^{11}$, $R^{12}$, $R^{13}$, $R^{14}$, $R^{15}$, $R^{16}$, $R^{19}$, $R^{20}$, $R^{20a}$, $R^{20b}$, $R^{21}$, $R^{22}$, $R^{23}$, $R^{31}$, and $R^{32}$. In other embodiments, certain substituents on the proline ring are selectively deuterated. For example, in one embodiment, the substitution of a hydrogen atom for a deuterium atom occurs at R, R', $R^{1}$, $R^{1'}$, $R^{2}$, $R^{2'}$, $R^{3}$, and/or $R^{3'}$. In one embodiment, for example, when any of the R substituents of the proline ring are methyl or methoxy, the alkyl residue is optionally deuterated, e.g., $CD_3$ or $OCD_3$. In certain other embodiments, when two substituents of the proline ring are combined to form a cyclopropyl ring, the unsubstituted methylene carbon is deuterated.

The substitution of a hydrogen atom for a deuterium atom occurs within an R group when at least one of the variables within the R group is hydrogen (e.g., $^{2}H$ or D) or alkyl (e.g., $CD_3$). For example, when any of R groups are, or contain for example through substitution, methyl or ethyl, the alkyl residue is typically deuterated, e.g., $CD_3$, $CH_2CD_3$ or $CD_2CD_3$.

The compound of the present invention may form a solvate with solvents (including water). Therefore, in one embodiment, the invention includes a solvated form of the active compound. The term "solvate" refers to a molecular complex of a compound of the present invention (including salts thereof) with one or more solvent molecules. Examples of solvents are water, ethanol, dimethyl sulfoxide, acetone and other common organic solvents. The term "hydrate" refers to a molecular complex comprising a compound of the invention and water. Pharmaceutically acceptable solvates in accordance with the invention include those wherein the solvent of crystallization may be isotopically substituted, e.g. $D_2O$, $d_6$-acetone, $d_6$-DMSO. A solvate can be in a liquid or solid form.

A dash ("-") that is not between two letters or symbols is used to indicate a point of attachment for a substituent. For example, $-(C{=}O)NH_2$ is attached through carbon of the keto ($C{=}O$) group.

The term "substituted", as used herein, means that any one or more hydrogens on the designated atom or group is replaced with a moiety selected from the indicated group, provided that the designated atom's normal valence is not exceeded. For example, when the substituent is oxo (i.e., $=O$) then two hydrogens on the atom are replaced. When an oxo group replaces two hydrogens in an aromatic moiety, the corresponding partially unsaturated ring replaces the aromatic ring. For example a pyridyl group substituted by oxo is a pyridone. Combinations of substituents and/or variables are permissible only if such combinations result in stable compounds or useful synthetic intermediates.

A stable compound or stable structure refers to a compound leading to a compound that can be isolated and can be formulated into a dosage form with a shelf life of at least one month.

Any suitable group may be present on a "substituted" or "optionally substituted" position that forms a stable molecule and advances the desired purpose of the invention and includes, but is not limited to, e.g., halogen (which can independently be F, Cl, Br or I); cyano; hydroxyl; nitro;

azido; alkanoyl (such as a $C_2$-$C_6$ alkanoyl group); carboxamide; alkyl, cycloalkyl, alkenyl, alkynyl, alkoxy, aryloxy such as phenoxy; alkylthio including those having one or more thioether linkages; alkylsulfinyl; alkylsulfonyl groups including those having one or more sulfonyl linkages; aminoalkyl groups including groups having one or more N atoms; aryl (e.g., phenyl, biphenyl, naphthyl, or the like, each ring either substituted or unsubstituted aromatic); arylalkyl having for example, 1 to 3 separate or fused rings and from 6 to about 14 or 18 ring carbon atoms, with benzyl being an exemplary arylalkyl group; arylalkoxy, for example, having 1 to 3 separate or fused rings with benzyloxy being an exemplary arylalkoxy group; or a saturated, unsaturated, or aromatic heterocyclic group having 1 to 3 separate or fused rings with one or more N, O or S atoms, e.g. coumarinyl, quinolinyl, isoquinolinyl, quinazolinyl, pyridyl, pyrazinyl, pyrimidinyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such heterocyclic groups may be further substituted, e.g. with hydroxy, alkyl, alkoxy, halogen and amino. In certain embodiments "optionally substituted" includes one or more substituents independently chosen from halogen, hydroxyl, amino, cyano, —CHO, —COOH, —$CONH_2$, $C_1$-$C_6$alkyl, $C_2$-$C_6$alkenyl, $C_2$-$C_6$alkynyl, —$C_1$-$C_6$alkoxy, $C_2$-$C_6$alkanoyl, $C_1$-$C_6$alkylester, (mono- and di-$C_1$-$C_6$alkylamino)$C_0$-$C_2$alkyl, $C_1$-$C_2$haloalkyl, hydroxy$C_1$-$C_6$alkyl, ester, carbamate, urea, sulfonamide, —$C_1$-$C_6$alkyl (heterocyclo), $C_1$-$C_6$alkyl(heteroaryl), —$C_1$-$C_6$alkyl($C_3$-$C_7$cycloalkyl), O—$C_1$-$C_6$alkyl($C_3$-$C_7$cycloalkyl), $B(OH)_2$, phosphate, phosphonate and $C_1$-$C_2$haloalkoxy.

"Alkyl" is a branched or straight chain saturated aliphatic hydrocarbon group. In one embodiment, the alkyl contains from 1 to about 18 carbon atoms, more generally from 1 to about 6 carbon atoms or from 1 to about 4 carbon atoms. In one embodiment, the alkyl contains from 1 to about 8 carbon atoms. In certain embodiments, the alkyl is $C_1$-$C_2$, $C_1$-$C_3$, or $C_1$-$C_6$. The specified ranges as used herein indicate an alkyl group having each member of the range described as an independent species. For example, the term $C_1$-$C_6$ alkyl as used herein indicates a straight or branched alkyl group having from 1, 2, 3, 4, 5, or 6 carbon atoms and is intended to mean that each of these is described as an independent species. For example, the term $C_1$-$C_4$alkyl as used herein indicates a straight or branched alkyl group having from 1, 2, 3, or 4 carbon atoms and is intended to mean that each of these is described as an independent species. When $C_0$-$C_n$ alkyl is used herein in conjunction with another group, for example, ($C_3$-$C_7$cycloalkyl)$C_0$-$C_4$ alkyl, or —$C_0$-$C_4$alkyl ($C_3$-$C_7$cycloalkyl), the indicated group, in this case cycloalkyl, is either directly bound by a single covalent bond ($C_0$alkyl), or attached by an alkyl chain in this case 1, 2, 3, or 4 carbon atoms. Alkyls can also be attached via other groups such as heteroatoms as in —O—$C_0$-$C_4$alkyl($C_3$-$C_7$cycloalkyl). Examples of alkyl include, but are not limited to, methyl, ethyl, n-propyl, isopropyl, n-butyl, isobutyl, sec-butyl, t-butyl, n-pentyl, isopentyl, tert-pentyl, neopentyl, n-hexyl, 2-methylpentane, 3-methylpentane, 2,2-dimethylbutane and 2,3-dimethylbutane. In one embodiment, the alkyl group is optionally substituted as described above.

"Alkenyl" is a branched or straight chain aliphatic hydrocarbon group having one or more carbon-carbon double bonds that may occur at a stable point along the chain. Nonlimiting examples are $C_2$-$C_8$alkenyl, $C_2$-$C_6$alkenyl and $C_2$-$C_4$alkenyl. The specified ranges as used herein indicate an alkenyl group having each member of the range described as an independent species, as described above for the alkyl moiety. Examples of alkenyl include, but are not limited to, ethenyl and propenyl. In one embodiment, the alkenyl group is optionally substituted as described above.

"Alkynyl" is a branched or straight chain aliphatic hydrocarbon group having one or more carbon-carbon triple bonds that may occur at any stable point along the chain, for example, $C_2$-$C_8$alkynyl or $C_2$-$C_6$alkynyl. The specified ranges as used herein indicate an alkynyl group having each member of the range described as an independent species, as described above for the alkyl moiety. Examples of alkynyl include, but are not limited to, ethynyl, propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl. In one embodiment, the alkynyl group is optionally substituted as described above.

"Alkylene" is a bivalent saturated hydrocarbon. Alkylenes, for example, can be a 1 to 8 carbon moiety, 1 to 6 carbon moiety, or an indicated number of carbon atoms, for example $C_1$-$C_4$alkylene, C1-C3alkylene, or $C_1$-$C_2$alkylene.

"Alkenylene" is a bivalent hydrocarbon having at least one carbon-carbon double bond. Alkenylenes, for example, can be a 2 to 8 carbon moiety, 2 to 6 carbon moiety, or an indicated number of carbon atoms, for example $C_2$-$C_4$alkenylene.

"Alkynylene" is a bivalent hydrocarbon having at least one carbon-carbon triple bond. Alkynylenes, for example, can be a 2 to 8 carbon moiety, 2 to 6 carbon moiety, or an indicated number of carbon atoms, for example $C_2$-$C_4$alkynylene.

"Alkoxy" is an alkyl group as defined above covalently bound through an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. Similarly an "alkylthio" or a "thioalkyl" group is an alkyl group as defined above with the indicated number of carbon atoms covalently bound through a sulfur bridge (—S—). In one embodiment, the alkoxy group is optionally substituted as described above.

"Alkenyloxy" is an alkenyl group as defined covalently bound to the group it substitutes by an oxygen bridge (—O—).

"Alkanoyl" is an alkyl group as defined above covalently bound through a carbonyl (C═O) bridge. The carbonyl carbon is included in the number of carbons, that is C2alkanoyl is a $CH_3$(C═O)— group. In one embodiment, the alkanoyl group is optionally substituted as described above.

"Alkylester" is an alkyl group as defined herein covalently bound through an ester linkage. The ester linkage may be in either orientation, e.g., a group of the formula —O(C═O)alkyl or a group of the formula —(C═O)Oalkyl.

"Amide" or "carboxamide" is —C(O)N$R^aR^b$ wherein $R^a$ and $R^b$ are each independently selected from hydrogen, alkyl, for example, $C_1$-$C_6$alkyl, alkenyl, for example, $C_2$-$C_6$alkenyl, alkynyl, for example, $C_2$-$C_6$alkynyl, —$C_0$-$C_4$alkyl($C_3$-$C_7$cycloalkyl), —$C_0$-$C_4$alkyl($C_3$-$C_7$heterocycloalkyl), —$C_0$-$C_4$alkyl(aryl), and —$C_0$-$C_4$alkyl (heteroaryl); or together with the nitrogen to which they are bonded, $R^a$ and $R^b$ can form a $C_3$-$C_7$heterocyclic ring. In one embodiment, the $R^a$ and $R^b$ groups are each independently optionally substituted as described above.

"Carbocyclic group", "carbocyclic ring", or "cycloalkyl" is a saturated or partially unsaturated (i.e., not aromatic)

group containing all carbon ring atoms. A carbocyclic group typically contains 1 ring of 3 to 7 carbon atoms or 2 fused rings each containing 3 to 7 carbon atoms. Cycloalkyl substituents may be pendant from a substituted nitrogen or carbon atom, or a substituted carbon atom that may have two substituents can have a cycloalkyl group, which is attached as a spiro group. Examples of carbocyclic rings include cyclohexenyl, cyclohexyl, cyclopentenyl, cyclopentyl, cyclobutenyl, cyclobutyl and cyclopropyl rings. In one embodiment, the carbocyclic ring is optionally substituted as described above. In one embodiment, the cycloalkyl is a partially unsaturated (i.e., not aromatic) group containing all carbon ring atoms. In another embodiment, the cycloalkyl is a saturated group containing all carbon ring atoms.

"Carbocyclic-oxy group" is a monocyclic carbocyclic ring or a mono- or bi-cyclic carbocyclic group as defined above attached to the group it substitutes via an oxygen, —O—, linker.

"Haloalkyl" indicates both branched and straight-chain alkyl groups substituted with 1 or more halogen atoms, up to the maximum allowable number of halogen atoms. Examples of haloalkyl include, but are not limited to, trifluoromethyl, monofluoromethyl, difluoromethyl, 2-fluoroethyl, and penta-fluoroethyl.

"Haloalkoxy" indicates a haloalkyl group as defined herein attached through an oxygen bridge (oxygen of an alcohol radical).

"Hydroxyalkyl" is an alkyl group as previously described, substituted with at least one hydroxyl substitutent.

"Aminoalkyl" is an alkyl group as previously described, substituted with at least one amino substituent.

"Halo" or "halogen" indicates independently any of fluoro, chloro, bromo, and iodo.

"Aryl" indicates aromatic groups containing only carbon in the aromatic ring or rings. In one embodiment, the aryl groups contain 1 to 3 separate or fused rings and is 6 to about 14 or 18 ring atoms, without heteroatoms as ring members. When indicated, such aryl groups may be further substituted with carbon or non-carbon atoms or groups. Such substitution may include fusion to a 5 to 7-membered saturated cyclic group that optionally contains 1 or 2 heteroatoms independently chosen from N, O, and S, to form, for example, a 3,4-methylenedioxyphenyl group. Aryl groups include, for example, phenyl and naphthyl, including 1-naphthyl and 2-naphthyl. In one embodiment, aryl groups are pendant. An example of a pendant ring is a phenyl group substituted with a phenyl group. In one embodiment, the aryl group is optionally substituted as described above.

The term "heterocycle," or "heterocyclic ring" as used herein refers to a saturated or a partially unsaturated (i.e., having one or more double and/or triple bonds within the ring without aromaticity) carbocyclic radical of 3 to about 12, and more typically 3, 5, 6, 7 to 10 ring atoms in which at least one ring atom is a heteroatom selected from nitrogen, oxygen, phosphorus and sulfur, the remaining ring atoms being C, where one or more ring atoms is optionally substituted independently with one or more substituents described above. A heterocycle may be a monocycle having 3 to 7 ring members (2 to 6 carbon atoms and 1 to 4 heteroatoms selected from N, O, P, and S) or a bicycle having 6 to 10 ring members (4 to 9 carbon atoms and 1 to 6 heteroatoms selected from N, O, P, and S), for example: a bicyclo [4,5], [5,5], [5,6], or [6,6]system. In one embodiment, the only heteroatom is nitrogen. In one embodiment, the only heteroatom is oxygen. In one embodiment, the only heteroatom is sulfur. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. Examples of heterocyclic rings include, but are not limited to, pyrrolidinyl, dihydrofuranyl, tetrahydrothienyl, tetrahydropyranyl, dihydropyranyl, tetrahydrothiopyranyl, piperidino, piperidonyl, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, dihydroisoquinolinyl, tetrahydroisoquinolinyl, pyrazolidinylimidazolinyl, imidazolidinyl, 2-oxa-5-azabicyclo[2.2.2]octane, 3-oxa-8-azabicyclo[3.2.1]octane, 8-oxa-3-azabicyclo[3.2.1]octane, 6-oxa-3-azabicyclo[3.1.1]heptane, 2-oxa-5-azabicyclo[2.2.1]heptane, 3-azabicyclo[3.1.0]hexanyl, 3-azabicyclo[4.1.0]heptanyl, azabicyclo[2.2.2]hexanyl, 3H-indolyl, quinolizinyl, N-pyridyl ureas, and pyrrolopyrimidine. Spiro moieties are also included within the scope of this definition. Examples of a heterocyclic group wherein 1 or 2 ring carbon atoms are substituted with oxo (═O) moieties are pyrimidinonyl and 1,1-dioxo-thiomorpholinyl. The heterocycle groups herein are optionally substituted independently with one or more substituents described herein.

"Heterocyclicoxy group" is a monocyclic heterocyclic ring or a bicyclic heterocyclic group as described previously linked to the group it substitutes via an oxygen, —O—, linker.

"Heteroaryl" indicates a stable monocyclic aromatic ring which contains from 1 to 3, or in some embodiments from 1 to 2, heteroatoms chosen from N, O, and S, with remaining ring atoms being carbon, or a stable bicyclic or tricyclic system containing at least one 5- to 7-membered aromatic ring which contains from 1 to 3, or in some embodiments from 1 to 2, heteroatoms chosen from N, O, and S, with remaining ring atoms being carbon. In one embodiment, the only heteroatom is nitrogen. In one embodiment, the only heteroatom is oxygen. In one embodiment, the only heteroatom is sulfur. Monocyclic heteroaryl groups typically have from 5 to 7 ring atoms. In some embodiments bicyclic heteroaryl groups are 9- to 10-membered heteroaryl groups, that is, groups containing 9 or 10 ring atoms in which one 5- to 7-member aromatic ring is fused to a second aromatic or non-aromatic ring. When the total number of S and O atoms in the heteroaryl group exceeds 1, these heteroatoms are not adjacent to one another. In one embodiment, the total number of S and O atoms in the heteroaryl group is not more than 2. In another embodiment, the total number of S and O atoms in the aromatic heterocycle is not more than 1. Examples of heteroaryl groups include, but are not limited to, pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, tetrahydrofuranyl, and furopyridinyl. Heteroaryl groups are optionally substituted independently with one or more substituents described herein. "Heteroaryloxy" is a heteroaryl group as described bound to the group it substituted via an oxygen, —O—, linker.

"Heterocycloalkyl" is a saturated ring group. It may have, for example, 1, 2, 3, or 4 heteroatoms independently chosen from N, S, and O, with remaining ring atoms being carbon. In a typical embodiment, nitrogen is the heteroatom. Monocyclic heterocycloalkyl groups typically have from 3 to about 8 ring atoms or from 4 to 6 ring atoms. Examples of heterocycloalkyl groups include morpholinyl, piperazinyl, piperidinyl, and pyrrolinyl.

The term "mono- and/or di-alkylamino" indicates secondary or tertiary alkylamino groups, wherein the alkyl groups are independently chosen alkyl groups, as defined herein. The point of attachment of the alkylamino group is on the nitrogen. Examples of mono- and di-alkylamino groups include ethylamino, dimethylamino, and methyl-propylamino.

A "dosage form" means a unit of administration of an active agent. Examples of dosage forms include tablets, capsules, injections, suspensions, liquids, emulsions, implants, particles, spheres, creams, ointments, suppositories, inhalable forms, transdermal forms, buccal, sublingual, topical, gel, mucosal, and the like. A "dosage form" can also include an implant, for example an optical implant.

"Pharmaceutical compositions" are compositions comprising at least one active agent, such as a compound or salt of Formula I, and at least one other substance, such as a carrier. "Pharmaceutical combinations" are combinations of at least two active agents which may be combined in a single dosage form or provided together in separate dosage forms with instructions that the active agents are to be used together to treat any disorder described herein.

"Pharmaceutically acceptable salts" includes derivatives of the disclosed compounds in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are typical, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, $HOOC—(CH_2)_n—COOH$ where n is 0-4, and the like. Lists of additional suitable salts may be found, e.g., in *Remington's Pharmaceutical Sciences,* 17th ed., Mack Publishing Company, Easton, Pa., p. 1418 (1985).

The term "carrier" applied to pharmaceutical compositions/combinations of the invention refers to a diluent, excipient, or vehicle with which an active compound is provided.

A "pharmaceutically acceptable excipient" means an excipient that is useful in preparing a pharmaceutical composition/combination that is generally safe, non-toxic and neither biologically nor otherwise inappropriate for administration to a host, and includes, in one embodiment, an excipient that is acceptable for veterinary use as well as human pharmaceutical use. A "pharmaceutically acceptable excipient" as used in the present application includes both one and more than one such excipient.

A "patient" or "host" or "subject" is a human or non-human animal in need of modulation of the complement factor D pathway. Typically the host is a human. A "patient" or "host" or "subject" also refers to for example, mammals, primates (e.g., humans), cows, sheep, goats, horses, dogs, cats, rabbits, rats, mice, fish, birds and the like.

A "prodrug" as used herein, means a compound which when administered to a host in vivo is converted into a parent drug. As used herein, the term "parent drug" means any of the presently described chemical compounds that are useful to treat any of the disorders described herein, or to control or improve the underlying cause or symptoms associated with any physiological or pathological disorder described herein in a host, typically a human. Prodrugs can be used to achieve any desired effect, including to enhance properties of the parent drug or to improve the pharmaceutic or pharmacokinetic properties of the parent. Prodrug strategies exist which provide choices in modulating the conditions for in vivo generation of the parent drug, all of which are deemed included herein. Nonlimiting examples of prodrug strategies include covalent attachment of removable groups, or removable portions of groups, for example, but not limited to acylation, phosphorylation, phosphonylation, phosphoramidate derivatives, amidation, reduction, oxidation, esterification, alkylation, other carboxy derivatives, sulfoxy or sulfone derivatives, carbonylation or anhydride, among others.

"Providing a compound of Formula I with at least one additional active agent" means the compound of Formula I and the additional active agent(s) are provided simultaneously in a single dosage form, provided concomitantly in separate dosage forms, or provided in separate dosage forms for administration separated by some amount of time that is within the time in which both the compound of Formula I and the at least one additional active agent are within the blood stream of a patient. In certain embodiments the compound of Formula I and the additional active agent need not be prescribed for a patient by the same medical care worker. In certain embodiments the additional active agent or agents need not require a prescription. Administration of the compound of Formula I or the at least one additional active agent can occur via any appropriate route, for example, oral tablets, oral capsules, oral liquids, inhalation, injection, suppositories or topical contact.

A "therapeutically effective amount" of a pharmaceutical composition/combination of this invention means an amount effective, when administered to a patient, to provide a therapeutic benefit such as an amelioration of symptoms, e.g., an amount effective to decrease the symptoms of a macular degeneration. In one embodiment, a therapeutically effective amount is an amount sufficient to prevent a significant increase or will significantly reduce the detectable level of complement factor D in the patient's blood, serum, or tissues.

II. Detailed Description of the Active Compounds

According to the present invention, a compound of Formula I is provided:

(I)

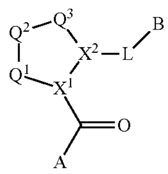

as well as the pharmaceutically acceptable salts and compositions thereof. Formula I can be considered to have a central core, an L-B substituent, and a (C═O)A substituent. It has been discovered that a compound of Formula I, or a pharmaceutically acceptable salt or composition thereof, wherein $R^{12}$ or $R^{13}$ on the A group is a phosphonate, is a superior inhibitor of complement factor D, and therefore can be used as an effective amount to treat a host in need of complement factor D modulation.

Non-limiting examples of compounds falling within Formula I with variations in the variables e.g., A, B, $R^1$—$R^{3'}$, and L, are illustrated below. The disclosure includes all combinations of these definitions so long as a stable compound results.

Formulas II-XXX

In one aspect, the disclosure includes compounds and salts of Formula II, III, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, XXIX and XXX which are within the scope of Formula I. The variables shown in Formula II-XXX carry the definitions set forth in the SUMMARY section for Formula I or any of the definitions set forth in this disclosure.

Formula II

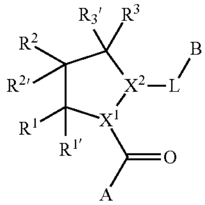

Formula III

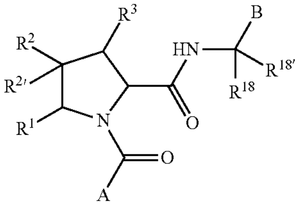

-continued

Formula IV

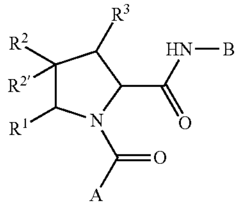

Formula V

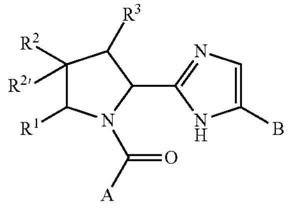

Formula VI

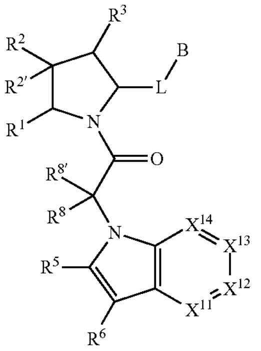

Formula VII

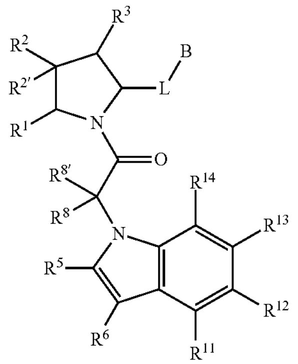

Formula VIII

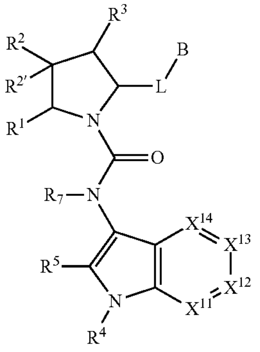

-continued
Formula IX
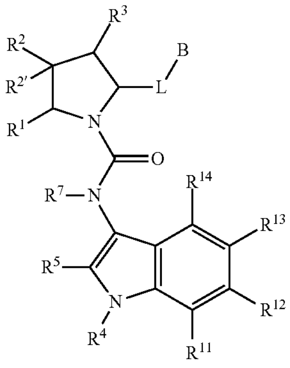
Formula X
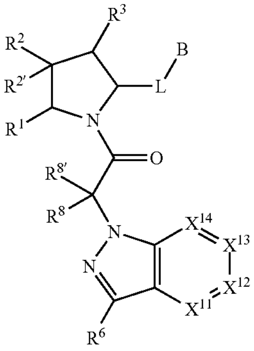
Formula XI
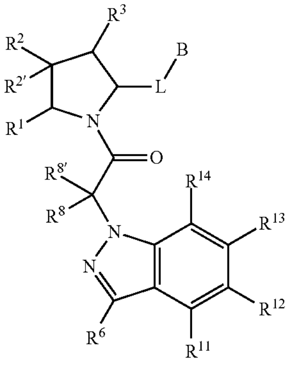
Formula XII
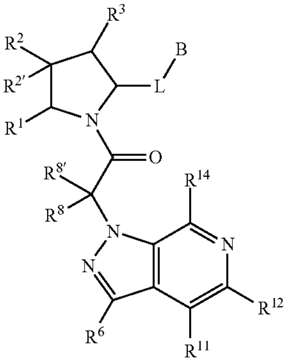
-continued
Formula XIII
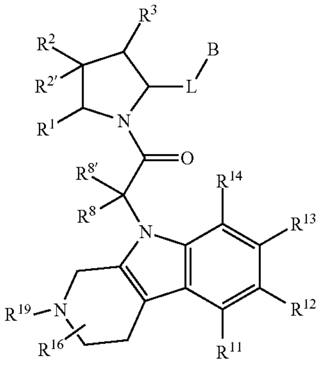
Formula XIV
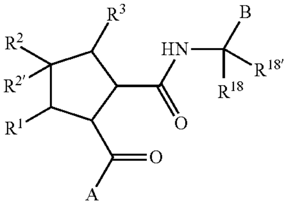
Formula XV
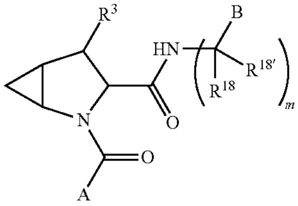
m is 0 or 1.
Formula XVI
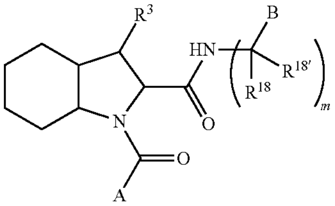
m is 0 or 1.
Formula XVII
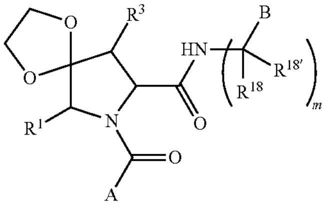
m is 0 or 1.
Formula XVIII
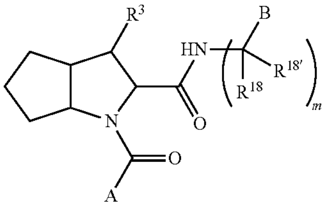
m is 0 or 1.

-continued
Formula XIX
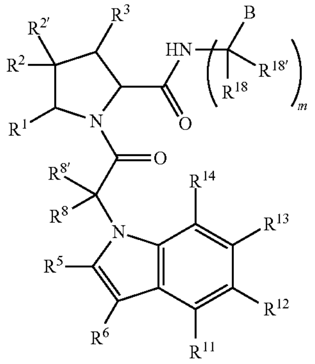
m is 0 or 1.
Formula XX
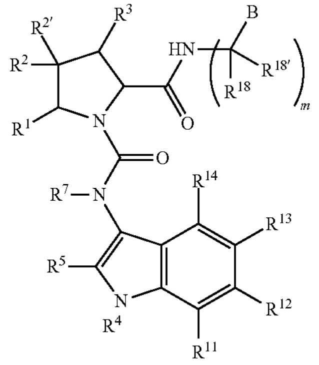
m is 0 or 1.
Formula XXI
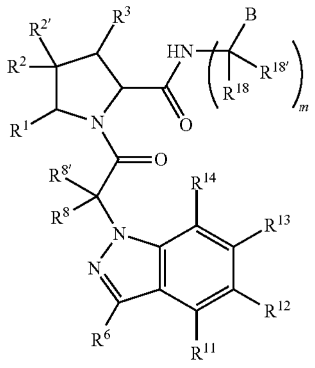
m is 0 or 1.
Formula XXII
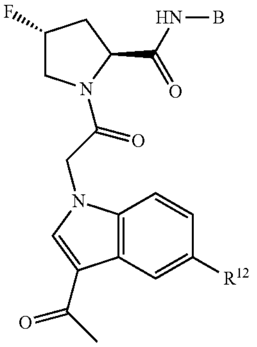
-continued
Formula XXIII
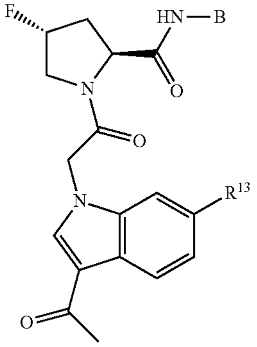
Formula XXIV
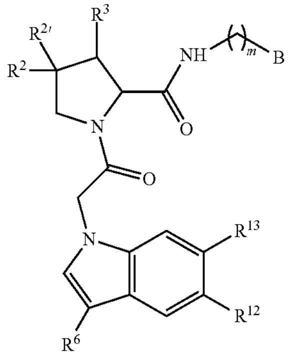
Formula XXV
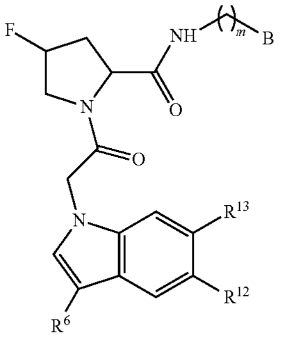
m is 0 or 1.
Formula XXVI
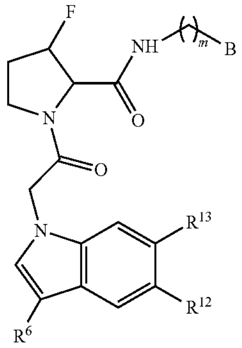
m is 0 or 1.

-continued

Formula XXVII

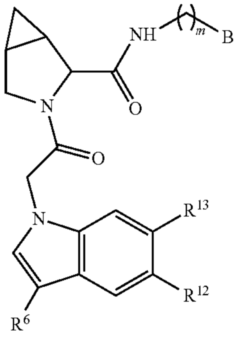

m is 0 or 1.

Formula XXVIII

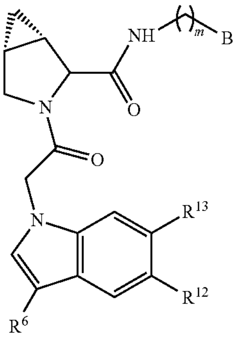

m is 0 or 1.

Formula XXIX

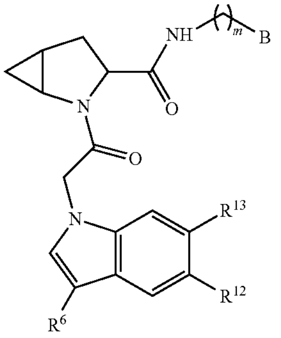

m is 0 or 1.

Formula XXX

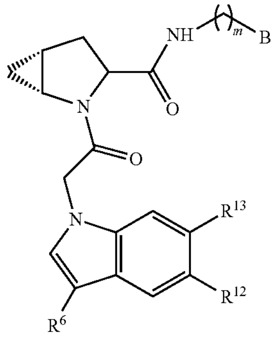

m is 0 or 1.

In these embodiments, it should be understood that where $R^1$ or $R^3$ is attached to a carbon, there can be two independent attachments as in $R^2/R^{2'}$ and these formulas should be considered to include all such variations.

Additionally, the disclosure includes compounds and salts of Formula I and pharmaceutically acceptable compositions thereof, and any of its subformulae (II-XXX) in which at least one of the following conditions is met in the embodiments described below.

The $R^{12}$ and $R^{13}$ Phosphonate Substituents

It has been discovered that a compound of Formula I, a pharmaceutically acceptable salt or composition thereof, wherein $R^{12}$ or $R^{13}$ on the A group is a phosphonate, is a superior inhibitor of complement factor D.

One of $R^{12}$ and $R^{13}$ is chosen from $R^{31}$ and the other of $R^{12}$ and $R^{13}$ is chosen from $R^{32}$. In another embodiment, each of $R^{12}$ and $R^{13}$ can be independently selected from $R^{32}$.

$R^{31}$ is chosen from hydrogen, halogen, hydroxyl, nitro, cyano, amino, —COOH, $C_1$-$C_2$haloalkyl, $C_1$-$C_2$haloalkoxy, $C_1$-$C_6$alkyl, —$C_0$-$C_4$alkyl($C_3$-$C_7$cycloalkyl), $C_2$-$C_6$alkenyl, $C_2$-$C_6$alkanoyl, $C_1$-$C_6$alkoxy, $C_2$-$C_6$alkenyloxy, —C(O)$OR^9$, $C_1$-$C_6$thioalkyl, —$C_0$-$C_4$alkyl$NR^9R^{10}$, —C(O)$NR^9R^{10}$, —$SO_2R^9$, —$SO_2NR^9R^{10}$, —OC(O)$R^9$, and —C($NR^9$)$NR^9R^{10}$, each of which $R^{31}$ other than hydrogen, halogen, hydroxyl, nitro, cyano, $C_1$-$C_2$haloalkyl, and $C_1$-$C_2$haloalkoxy is unsubstituted or substituted with one or more substituents independently selected from halogen, hydroxyl, nitro, cyano, amino, —COOH, —$CONH_2C_1$-$C_2$haloalkyl, and $C_1$-$C_2$haloalkoxy, and each of which $R^{31}$ is also optionally substituted with one substituent chosen from phenyl and 4- to 7-membered heterocycle containing 1, 2, or 3 heteroatoms independently chosen from N, O, and S; which phenyl or 4- to 7-membered heterocycle is unsubstituted or substituted with one or more substituents independently chosen from halogen, hydroxyl, nitro, cyano, $C_1$-$C_6$alkyl, $C_2$-$C_6$alkenyl, $C_2$-$C_6$alkanoyl, $C_1$-$C_6$alkoxy, (mono- and di-$C_1$-$C_6$alkylamino)$C_0$-$C_4$alkyl, $C_1$-$C_6$alkylester, —$C_0$-$C_4$alkyl)($C_3$-$C_7$cycloalkyl), $C_1$-$C_2$haloalkyl, and $C_1$-$C_2$haloalkoxy;

$R^{32}$ is —P(O)$R^{20}R^{20}$.

$R^{20}$ is independently chosen at each occurrence from hydroxyl, $C_1$-$C_6$alkoxy, $C_1$-$C_6$haloalkoxy, $C_1$-$C_6$alkyl, ($C_3$-$C_7$cycloalkyl)$C_0$-$C_4$alkyl-, (aryl)$C_0$-$C_4$alkyl-, —O—$C_0$-$C_4$alkyl(aryl), —O—$C_0$-$C_4$alkyl($C_3$-$C_7$cycloalkyl), (4- to 7-membered heterocycloalkyl)$C_0$-$C_4$alkyl-O—having 1, 2, or 3 heteroatoms independently chosen from N, O, and S; (5- or 6-membered unsaturated or aromatic heterocycle)$C_0$-$C_4$alkyl-O— having 1, 2, or 3 heteroatoms independently chosen from N, O, and S; —O$(CH_2)_{2\text{-}4}$O$(CH_2)_{8\text{-}18}$, —OC$(R^{20a})_2$OC(O)O$R^{20b}$, —OC$(R^{20a})_2$OC(O)$R^{20b}$ an N-linked amino acid or an N-linked amino acid ester and each $R^{20}$ can be optionally substituted;

$R^{20a}$ is independently chosen at each occurrence from hydrogen, $C_1$-$C_8$alkyl, $C_2$-$C_8$alkenyl, $C_2$-$C_8$alkynyl, (aryl)$C_0$-$C_4$alkyl-, (aryl)$C_2$-$C_8$alkenyl- or (aryl)$C_2$-$C_8$alkynyl-; or two $R^{20a}$ groups can be taken together with the carbon that they are bonded to form a 3-6 membered heterocycloalkyl having 1, 2, or 3 heteroatoms independently chosen from N, O, and S, or a 3-6 membered carbocyclic ring.

$R^{20b}$ is independently chosen at each occurrence from $C_1$-$C_8$alkyl, $C_2$-$C_8$alkenyl, $C_2$-$C_8$alkynyl, (aryl)$C_0$-$C_4$alkyl, (aryl)$C_2$-$C_8$alkenyl or (aryl)$C_2$-$C_8$alkynyl.

In certain embodiments, $R^{32}$ is selected from:

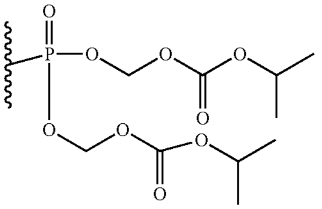

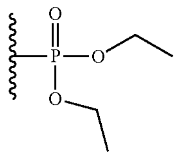

-continued
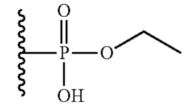
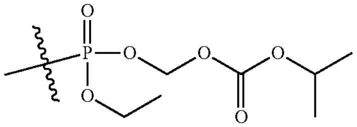
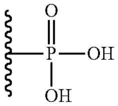
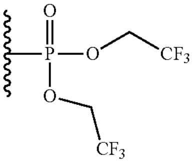
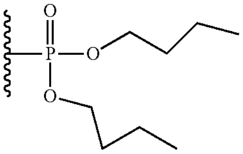
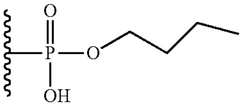
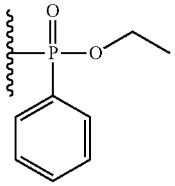
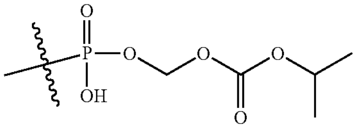
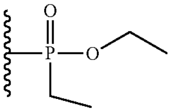
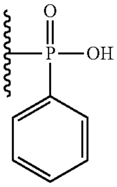
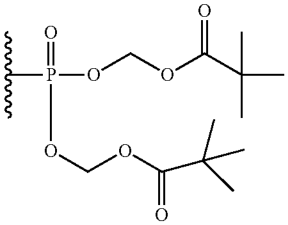
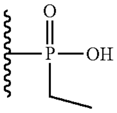
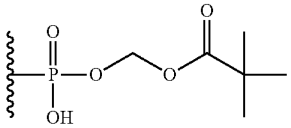
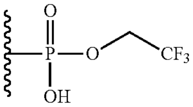
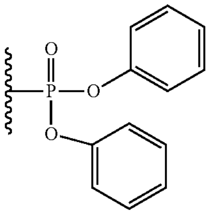
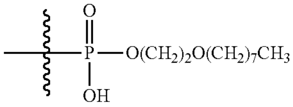
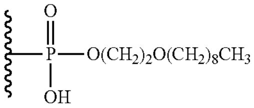
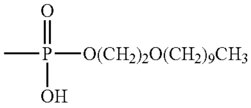
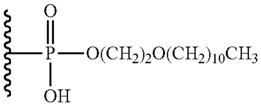
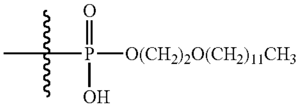
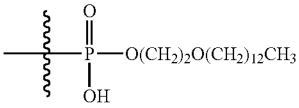
-continued
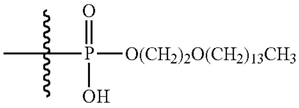
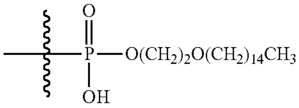
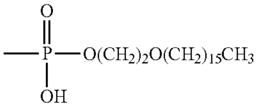
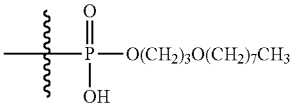
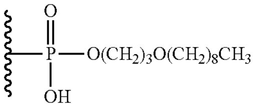
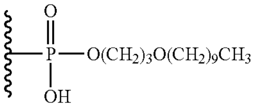
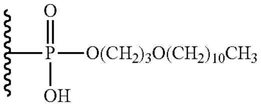
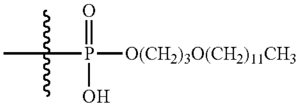
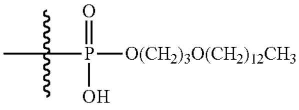
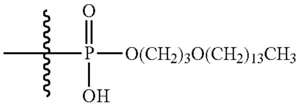
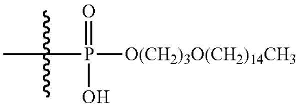
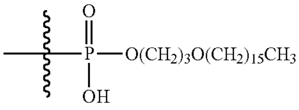
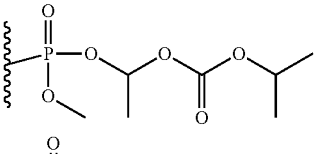
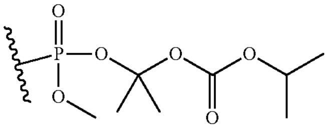
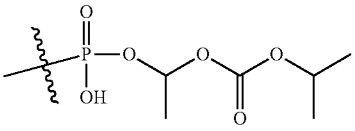

-continued

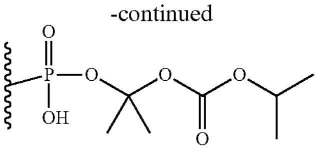

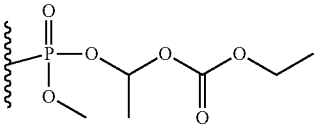

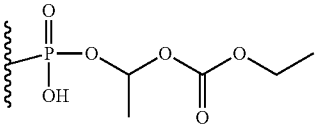

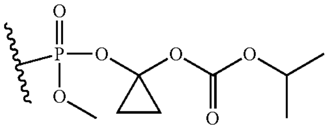

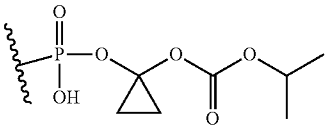

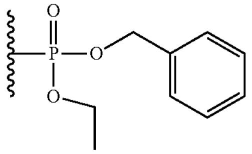

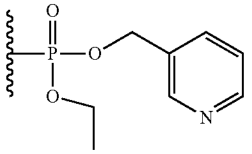

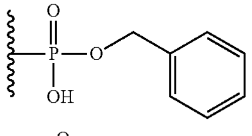

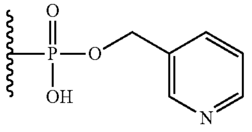

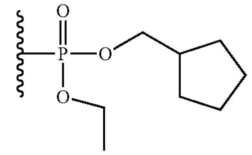

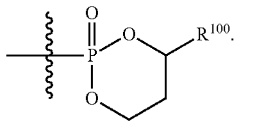

In one embodiment, two $R^{20}$ groups in a $P(O)R^{20}R^{20}$ phosphonate can come together to form a heterocyclic ring that can be optionally substituted with an $R^{100}$ group, wherein $R^{100}$ is aryl, heteroaryl, heterocycle, alkyl, alkenyl, alkynyl and cycloalkyl. See for example: HepDirect (Cyclic 1-aryl-1,3-propanyl esters) Prodrugs: Activation via CYP-mediated oxidation of the benzylic carbon. See Hecker, S. J. et al. *J. Med. Chem.* 2007, 50, 3891-3896.

Non-Limiting $R^{12}/R^{13}$ Embodiments

In one embodiment, $R^{12}$ is —$P(O)R^{20}R^{20}$.

In one embodiment, $R^{13}$ is —$P(O)R^{20}R^{20}$.

In one embodiment, the disclosure provides compounds of Formula I, wherein;

one of $R^{12}$ and $R^{13}$ is H and the other of $R^{12}$ and $R^{13}$ is $R^{32}$, where $R^{32}$ is —$P(O)R^{20}R^{20}$;

wherein $R^{20}$ is as defined in the summary section above.

In another embodiment, the disclosure provides compounds of Formula I, wherein;

$R^1$, $R^{1'}$, $R^2$, and $R^{3'}$ are all hydrogen;

$R^2$ is fluoro and $R^3$ is hydrogen, —$C_0$-$C_4$alkyl($C_3$-$C_7$cycloalkyl), or —O—$C_0$-$C_4$alkyl($C_3$-$C_7$cycloalkyl);

$R^5$ is hydrogen, halogen, or $C_1$-$C_2$alkyl;

$R^{11}$, $R^{13}$, $R^{14}$, and $R^{15}$ if present, are independently chosen at each occurrence from hydrogen, halogen, hydroxyl, amino, $C_1$-$C_4$alkyl, $C_1$-$C_4$alkoxy, —$C_0$-$C_2$alkyl (mono- and di-$C_1$-$C_2$alkylamino), trifluoromethyl, and trifluoromethoxy;

$X^{12}$ is $CR^{12}$; and $R^{12}$ is —$P(O)R^{20}R^{20}$;

wherein $R^{20}$ is as defined in the summary section above.

In one embodiment, the disclosure provides compounds of Formula I, wherein;

m is 0 or 1;

$R^2$ is halogen, $R^{2'}$ is hydrogen or halogen, and $R^3$ is hydrogen, halogen, —$C_0$-$C_4$alkyl($C_3$-$C_7$cycloalkyl), or —O—$C_0$-$C_4$alkyl($C_3$-$C_7$cycloalkyl);

$R^6$ is —C(O)$C_1$-$C_4$alkyl, —C(O)$NH_2$, —C(O)$CF_3$, —C(O)($C_3$-$C_7$cycloalkyl), or -ethyl(cyanoimino);

one of $R^{12}$ and $R^{13}$ is selected from hydrogen, halogen, $C_1$-$C_4$alkyl, $C_1$-$C_4$alkoxy, trifluoromethyl, and trifluoromethoxy; the other of $R^{12}$ and $R^{13}$ is $R^{32}$, where $R^{32}$ is —$P(O)R^{20}R^{20}$;

wherein $R^{20}$ is as defined in the summary section above.

In one embodiment, the disclosure provides compounds of Formula I, wherein;

one of $R^{12}$ and $R^{13}$ is hydrogen, hydroxyl, halogen, methyl, or methoxy; and the other of $R^{12}$ and $R^{13}$ is $R^{32}$, where $R^{32}$ is —$P(O)R^{20}R^{20}$;

wherein $R^{20}$ is as defined in the summary section above.

In one embodiment, $R^{32}$ may be unsubstituted or substituted with one or more substituents independently chosen from halogen, hydroxyl, nitro, cyano, amino, oxo, —$B(OH)_2$, —$Si(CH_3)_3$, —COOH, —$CONH_2$, —$P(O)(OH)_2$, $C_1$-$C_6$alkyl, $C_1$-$C_6$alkoxy, —$C_0$-$C_2$alkyl(mono- and di-$C_1$-$C_4$alkylamino), $C_1$-$C_6$alkylester, $C_1$-$C_4$alkylamino, $C_1$-$C_4$hydroxylalkyl, $C_1$-$C_2$haloalkyl, and $C_1$-$C_2$haloalkoxy.

Central Core Moiety

The central core moiety in Formula I is illustrated below:

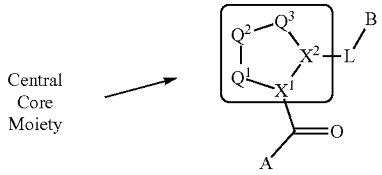

wherein:

$Q^1$ is $N(R^1)$ or $C(R^1R^{1'})$;

$Q^2$ is $C(R^2R^{2'})$, $C(R^2R^{2'})$—$C(R^2R^{2'})$, S, O, $N(R^2)$ or $C(R^2R^{2'})O$;

$Q^3$ is $N(R^3)$, S, or $C(R^3R^{3'})$;

$X^1$ and $X^2$ are independently N, CH, or CZ, or $X^1$ and $X^2$ together are C═C; and wherein $Q^1$, $Q^2$, $Q^3$, $X^1$, and $X^2$ are selected such that a stable compound results.

Non-limiting examples of the

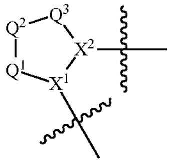

ring are illustrated below (any of which can be otherwise substituted with $R^1$, $R^{1'}$, $R^2$, $R^{2'}$, $R^3$, and $R^{3'}$) as described in more detail below.
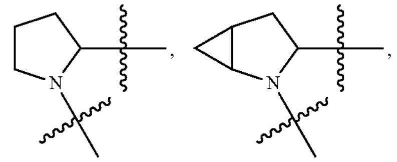
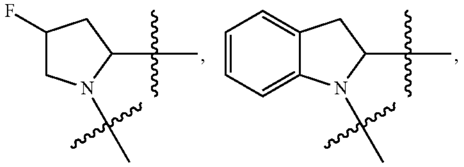
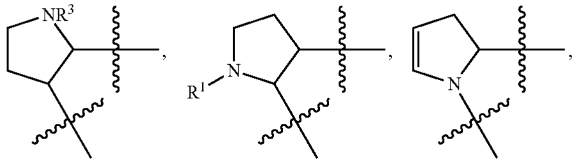
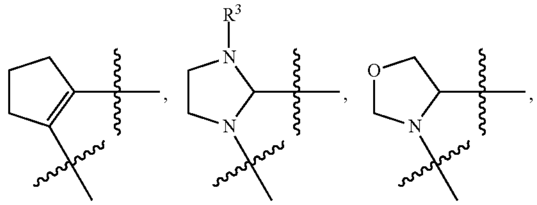
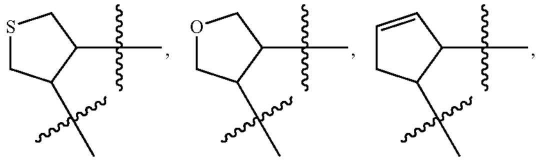
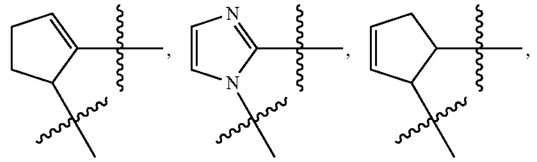
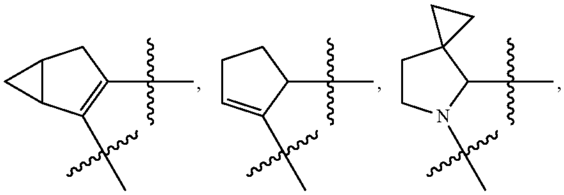
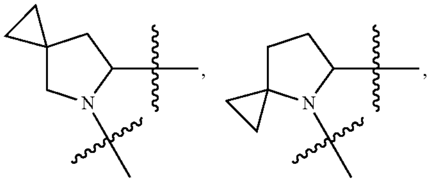
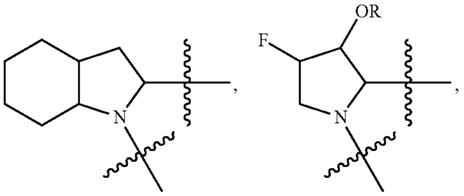
-continued
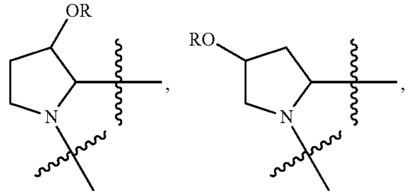
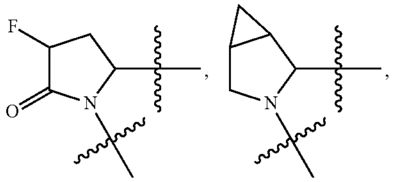
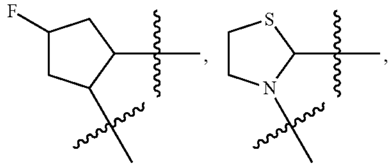
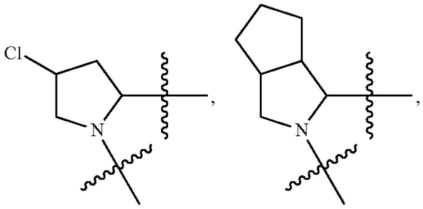
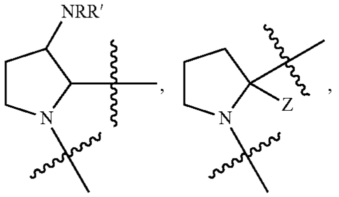
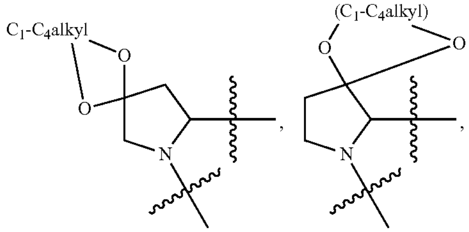
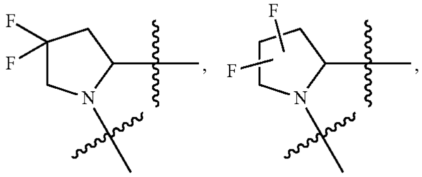
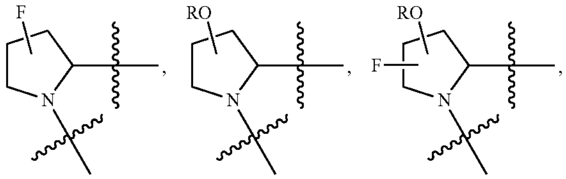
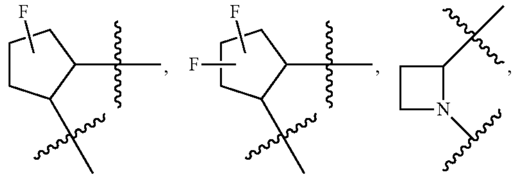

-continued

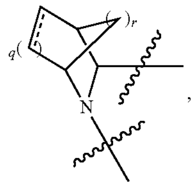

, and

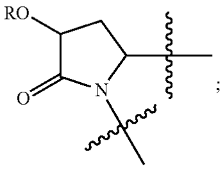

;

wherein q is 0, 1, 2 or 3 and r is 1, 2 or 3.

R and R' are independently chosen from H, alkyl, cycloalkyl, cycloalkylalkyl, heterocycle, heterocycloalkyl, aryl, aralkyl, heteroaryl, heteroarylalkyl wherein each group can be optionally substituted or any other substituent group herein that provides the desired properties. In some embodiments, the ring includes one or more chiral carbon atoms. The invention includes embodiments in which the chiral carbon can be provided as an enantiomer, or mixtures of enantiomers, including a racemic mixture. Where the ring includes more than one stereocenter, all of the enantiomers and diastereomers are included in the invention as individual species.

Z is F, Cl, $NH_2$, $CH_3$, $CH_2D$, $CHD_2$, or $CD_3$.

$R^1$, $R^{1'}$, $R^2$, $R^{2'}$, $R^3$, and $R^{3'}$ are independently chosen at each occurrence, as appropriate, and only where a stable compound results, from hydrogen, halogen, hydroxyl, nitro, cyano, amino, $C_1$-$C_6$alkyl, $C_2$-$C_6$alkenyl, $C_2$-$C_6$alkynyl, $C_1$-$C_6$alkoxy, $C_2$-$C_6$alkynyl, $C_2$-$C_6$alkanoyl, $C_1$-$C_6$thioalkyl, hydroxy$C_1$-$C_6$alkyl, amino$C_1$-$C_6$alkyl, —$C_0$-$C_4$alkyl$NR^9R^{10}$, —C(O)$OR^9$, —OC(O)$R^9$, —$NR^9$C(O)$R^{10}$, —C(O)$NR^9R^{10}$, —OC(O)$NR^9R^{10}$, —$NR^9$C(O)$OR^{10}$, $C_1$-$C_2$haloalkyl, and $C_1$-$C_2$haloalkoxy, where $R^9$ and $R^{10}$ are independently chosen at each occurrence from hydrogen, $C_1$-$C_6$alkyl, ($C_3$-$C_7$cycloalkyl)$C_0$-$C_4$alkyl, —$C_0$-$C_4$alkyl($C_3$-$C_7$cycloalkyl), and —O—$C_0$-$C_4$alkyl($C_3$-$C_7$cycloalkyl).

Non-Limiting Central Core Embodiments

In alternative embodiments, $R^1$ and $R^{1'}$ or $R^3$ and $R^{3'}$ may be taken together to form a 3- to 6-membered carbocyclic spiro ring or a 3- to 6-membered heterocyclic spiro ring containing 1 or 2 heteroatoms independently chosen from N, O, or S; $R^2$ and $R^{2'}$ may be taken together to form a 3- to 6-membered carbocyclic spiro ring; or $R^2$ and $R^{2'}$ may be taken together to form a 3- to 6-membered heterocyclic spiro ring;

each of which ring may be unsubstituted or substituted with one or more substituents independently chosen from halogen (and in particular F), hydroxyl, cyano, —COOH, $C_1$-$C_4$alkyl (including in particular methyl), $C_2$-$C_4$alkenyl, $C_2$-$C_4$alkynyl, $C_1$-$C_4$alkoxy, $C_2$-$C_4$alkanoyl, hydroxy$C_1$-$C_4$alkyl, (mono- and di-$C_1$-$C_4$alkylamino)$C_0$-$C_4$alkyl, —$C_0$-$C_4$alkyl($C_3$-$C_7$cycloalkyl), —O—$C_0$-$C_4$alkyl($C_3$-$C_7$cycloalkyl), $C_1$-$C_2$haloalkyl, and $C_1$-$C_2$haloalkoxy.

In alternative embodiments, $R^1$ and $R^2$ may be taken together to form a 3-membered carbocyclic ring; $R^1$ and $R^2$ may be taken together to form a 4- to 6-membered carbocyclic or aryl ring or a 4- to 6-membered heterocyclic or heteroaryl ring containing 1 or 2 heteroatoms independently chosen from N, O, and S; or $R^2$ and $R^3$, if bound to adjacent carbon atoms, may be taken together to form a 3- to 6-membered carbocyclic or aryl ring or a 3- to 6-membered heterocyclic or heteroaryl ring;

each of which ring may be unsubstituted or substituted with one or more substituents independently chosen from halogen (and in particular F), hydroxyl, cyano, —COOH, $C_1$-$C_4$alkyl (including in particular methyl), $C_2$-$C_4$alkenyl, $C_2$-$C_4$alkynyl, $C_1$-$C_4$alkoxy, $C_2$-$C_4$alkanoyl, hydroxy$C_1$-$C_4$alkyl, (mono- and di-$C_1$-$C_4$alkylamino)$C_0$-$C_4$alkyl, —$C_0$-$C_4$alkyl($C_3$-$C_7$cycloalkyl), —O—$C_0$-$C_4$alkyl($C_3$-$C_7$cycloalkyl), $C_1$-$C_2$haloalkyl, and $C_1$-$C_2$haloalkoxy.

In one embodiment, the central core moiety is proline.

In one embodiment, the central core moiety is 4-fluoropyrroline.

In one embodiment, $R^1$, $R^{1'}$, $R^{2'}$, $R^3$, and $R^{3'}$, if present, are all hydrogen; and $R^2$ is fluoro.

In one embodiment, $R^1$, $R^{1'}$, $R^{2'}$, and $R^{3'}$, if present, are all hydrogen; and $R^2$ is fluoro and $R^3$ is —$C_0$-$C_4$alkyl($C_3$-$C_7$cycloalkyl) or —O—$C_0$-$C_4$alkyl($C_3$-$C_7$cycloalkyl).

In one embodiment, $R^1$ and $R^2$ are taken together to form a 3- to 6-membered cycloalkyl group, and $R^{1'}$, $R^{2'}$, $R^3$, and $R^{3'}$, where present, are all hydrogen.

In one embodiment, $R^1$, $R^{1'}$, $R^3$, and $R^{3'}$, if present, are all hydrogen, and $R^2$ and $R^{2'}$ are taken together to form a 5- or 6-membered heterocycloalkyl group having 1 or 2 oxygen atoms.

In one embodiment, $R^1$ is hydrogen and $R^2$ is fluoro.

In one embodiment, $R^1$ and $R^2$ are joined to form a 3 membered ring.

The disclosure includes compounds of Formula I in which the central pyrrolidine is vinyl substituted, for example:

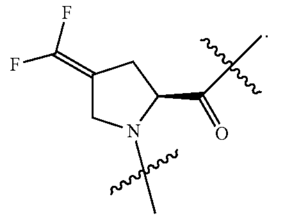 [SMILES: *C(=O)[C@@H]1CC(=C(F)F)CN1*]

In one embodiment, the compound of Formula I has the structure:

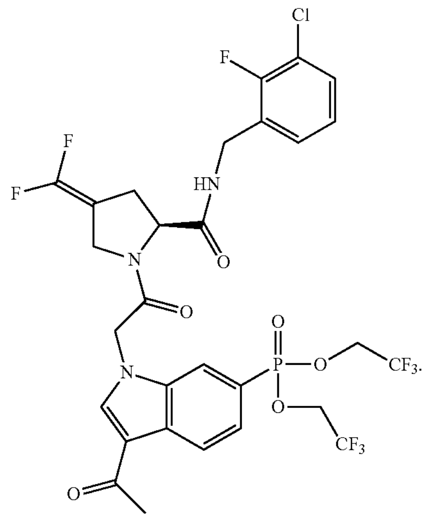 [SMILES: CC(=O)c1cn(CC(=O)N2CC(=C(F)F)C[C@H]2C(=O)NCc2cccc(Cl)c2F)c2cc(P(=O)(OCC(F)(F)F)OCC(F)(F)F)ccc12]

In one embodiment, the central pyrrolidine is modified by addition of a second heteroatom to a pyrrolidine ring, such as N, O, S, or Si, for example:

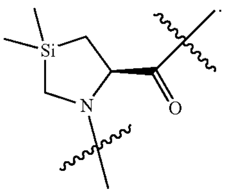 [SMILES: *C(=O)[C@@H]1C[Si](C)(C)CN1*]

Another modification within the scope of the disclosure is joining a substituent on the central pyrrolidine ring to $R^7$ or $R^8$ to form a 5- to 6-membered heterocyclic ring, for example:

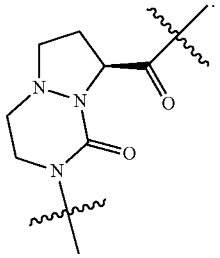 [SMILES: *C(=O)[C@@H]1CCN2CCN(*)C(=O)N12]

Example compounds having the modifications disclosed above include:

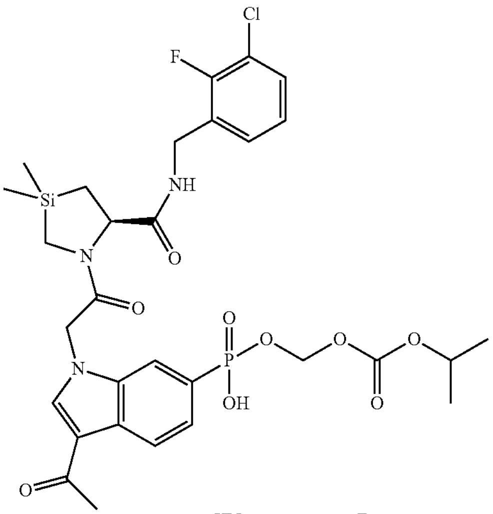

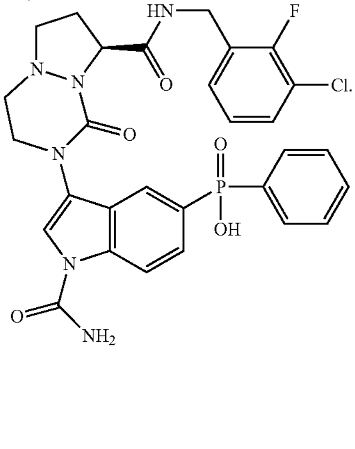

Central Core L-B Substituents

The central core L-B substituents in Formula I are illustrated below:

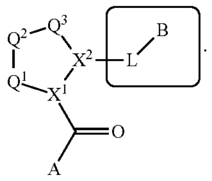

L is a bond or is chosen from the formulas:

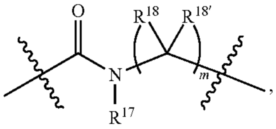
,
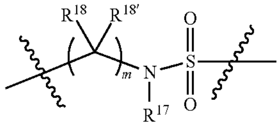
,
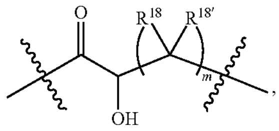
,
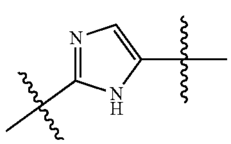
and
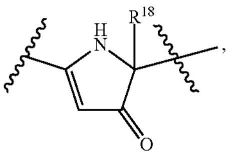
, where $R^{17}$ is hydrogen, $C_1$-$C_6$alkyl, or —$C_0$-$C_4$alkyl($C_3$-$C_7$cycloalkyl) and $R^{18}$ and $R^{18'}$ are independently chosen from hydrogen, halogen, hydroxymethyl, and methyl; and m is 0, 1, 2, or 3.

B is a monocyclic or bicyclic carbocyclic; a monocyclic or bicyclic carbocyclic-oxy group; a monocyclic, bicyclic, or tricyclic heterocyclic group having 1, 2, 3, or 4 heteroatoms independently selected from N, O, and S and from 4 to 7 ring atoms per ring; $C_2$-$C_6$alkenyl; $C_2$-$C_6$alkynyl; —($C_0$-$C_4$alkyl)(aryl); —($C_0$-$C_4$alkyl)(heteroaryl); or —($C_0$-$C_4$alkyl)(biphenyl).

Each of which B is unsubstituted or substituted with one or more substituents independently chosen from $R^{33}$ and $R^{34}$, and 0 or 1 substituents chosen from $R^{35}$ and $R^{36}$:

$R^{33}$ is independently chosen from halogen, hydroxyl, —COOH, cyano, $C_1$-$C_6$alkyl, $C_2$-$C_6$alkanoyl, $C_1$-$C_6$alkoxy, —$C_0$-$C_4$alkylNR$^9$R$^{10}$, —SO$_2$R$^9$, $C_1$-$C_2$haloalkyl, and $C_1$-$C_2$haloalkoxy;

$R^{34}$ is independently chosen from nitro, $C_2$-$C_6$alkenyl, $C_2$-$C_6$alkynyl, $C_1$-$C_6$thioalkyl, -J$C_3$-$C_7$cycloalkyl, —B(OH)$_2$, -JC(O)NR$^9$R$^{23}$, -JOSO$_2$OR$^{21}$, —C(O)(CH$_2$)$_{1-4}$S(O)R$^{21}$, —O(CH$_2$)$_{1-4}$S(O)NR$^{21}$R$^{22}$, -JOP(O)(OR$^{21}$)(OR$^{22}$), -JP(O)(OR$^{21}$)(OR$^{22}$), -JOP(O)(OR$^{21}$)R$^{22}$, -JP(O)(OR$^{21}$)R$^{22}$, -JOP(O)R$^{21}$R$^{22}$, -JP(O)R$^{21}$R$^{22}$, -JSP(O)(OR$^{21}$)(OR$^{22}$), -JSP(O)(OR$^{21}$)(R$^{22}$), -JSP(O)(R$^{21}$)(R$^{22}$), -JNR$^9$P(O)(NHR$^{21}$)(NHR$^{22}$), -JNR$^9$P(O)(OR$^{21}$)(NHR$^{22}$) -JNR$^9$P(O)(OR$^{21}$)(OR$^{22}$), -JC(S)R$^{21}$, -JNR$^{21}$SO$_2$R$^{22}$, -JNR$^9$S(O)NR$^{10}$R$^{22}$, -JNR$^9$SO$_2$NR$^{10}$R$^{22}$, -JSO$_2$NR$^9$COR$^{22}$, -JSO$_2$NR$^9$CONR$^{21}$R$^{22}$, -JNR$^{21}$SO$_2$R$^{22}$, -JC(O)NR$^{21}$SO$_2$R$^{22}$, -JC(NH$_2$)NR$^{22}$, -JC(NH$_2$)NR$^9$S(O)$_2$R$^{22}$, -JOC(O)NR$^{21}$R$^{21}$R$^{22}$, -JNR$^{21}$C(O)OR$^{22}$, -JNR$^{21}$OC(O)R$^{22}$, —(CH$_2$)$_{1-4}$C(O)NR$^{21}$R$^{22}$, -JC(O)R$^{24}$R$^{25}$, -JNR$^9$C(O)R$^{21}$, -JC(O)R$^{21}$, -JNR$^9$C(O)NR$^{10}$R$^{22}$, —CCR$^{21}$, —(CH$_2$)$_{1-4}$OC (O)$R^{21}$, and -JC(O)O$R^{23}$; each of which $R^{34}$ may be unsubstituted or substituted with one or more substituents independently chosen from halogen, hydroxyl, nitro, cyano, amino, oxo, —$B(OH)_2$, —$Si(CH_3)_3$, —COOH, —$CONH_2$, —$P(O)(OH)_2$, $C_1$-$C_6$alkyl, —$C_0$-$C_4$alkyl($C_3$-$C_7$cycloalkyl), $C_1$-$C_6$alkoxy, —$C_0$-$C_2$alkyl(mono- and di-$C_1$-$C_4$alkylamino), $C_1$-$C_6$alkylester, $C_1$-$C_4$alkylamino, $C_1$-$C_4$hydroxylalkyl, $C_1$-$C_2$haloalkyl, and $C_1$-$C_2$haloalkoxy;

$R^{35}$ is independently chosen from naphthyl, naphthyloxy, indanyl, (4- to 7-membered heterocycloalkyl)$C_0$-$C_4$alkyl containing 1 or 2 heteroatoms chosen from N, O, and S, and bicyclic heterocycle containing 1, 2, or 3 heteroatoms independently chosen from N, O, and S, and containing 4- to 7-ring atoms in each ring; each of which $R^{35}$ is unsubstituted or substituted with one or more substituents independently chosen from halogen, hydroxyl, nitro, cyano, $C_1$-$C_6$alkyl, $C_2$-$C_6$alkenyl, $C_2$-$C_6$alkanoyl, $C_1$-$C_6$alkoxy, (mono- and di-$C_1$-$C_6$alkylamino)$C_0$-$C_4$alkyl, $C_1$-$C_6$alkylester, —$C_0$-$C_4$alkyl($C_3$-$C_7$cycloalkyl), —$SO_2R^9$, $C_1$-$C_2$haloalkyl, and $C_1$-$C_2$haloalkoxy; and $R^{36}$ is independently chosen from tetrazolyl, (phenyl)$C_0$-$C_2$alkyl, (phenyl)$C_1$-$C_2$alkoxy, phenoxy, and 5- or 6-membered heteroaryl containing 1, 2, or 3 heteroatoms independently chosen from N, O, B, and S, each of which $R^{36}$ is unsubstituted or substituted with one or more substituents independently chosen from halogen, hydroxyl, nitro, cyano, $C_1$-$C_6$alkyl, $C_2$-$C_6$alkenyl, $C_2$-$C_6$alkanoyl, $C_1$-$C_6$alkoxy, (mono- and di-$C_1$-$C_6$alkylamino)$C_0$-$C_4$alkyl, $C_1$-$C_6$alkylester, —$C_0$-$C_4$alkyl($C_3$-$C_7$cycloalkyl), —$SO_2R^9$, —$OSi(CH_3)_2C(CH_3)_3$, —$Si(CH_3)_2C(CH_3)_3$, $C_1$-$C_2$haloalkyl, and $C_1$-$C_2$haloalkoxy.

J is independently chosen at each occurrence from a covalent bond, $C_1$-$C_4$alkylene, —O$C_1$-$C_4$alkylene, $C_2$-$C_4$alkenylene, and $C_2$-$C_4$alkynylene.

In one embodiment, -L-B— is

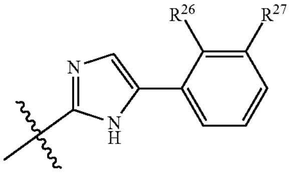

or

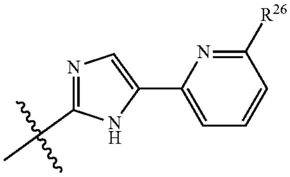

where $R^{26}$ and $R^{27}$ are independently chosen from hydrogen, halogen, hydroxyl, nitro, cyano, $C_1$-$C_6$alkyl, $C_2$-$C_6$alkenyl, $C_2$-$C_6$alkanoyl, $C_1$-$C_6$alkoxy, $C_1$-$C_6$thioalkyl, —$C_0$-$C_4$alkyl (mono- and di-$C_1$-$C_6$alkylamino), —$C_0$-$C_4$alkyl($C_3$-$C_7$cycloalkyl), —$C_0$-$C_4$alkoxy($C_3$-$C_7$cycloalkyl), $C_1$-$C_2$haloalkyl, $C_1$-$C_2$haloalkoxy, and $C_1$-$C_2$haloalkylthio.

Non-Limiting L-B Embodiments

In another embodiment, -L-B— is

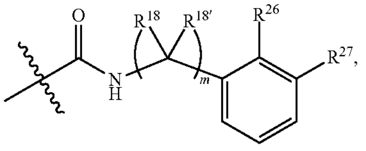

-continued

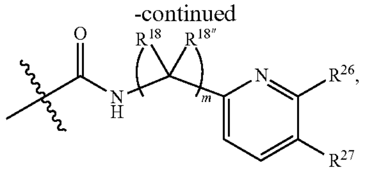

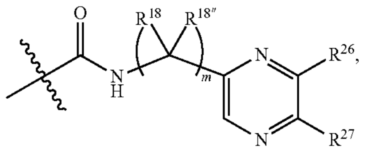

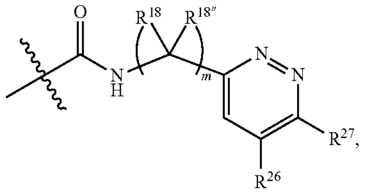

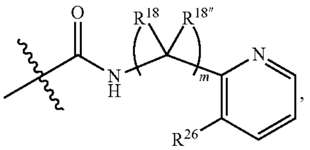

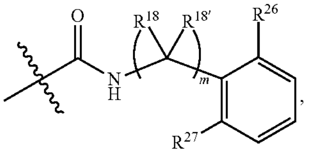

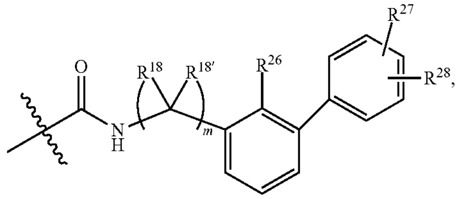

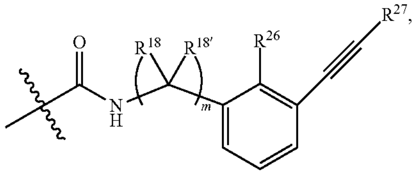

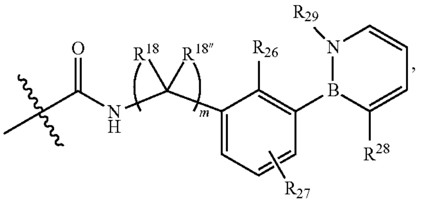

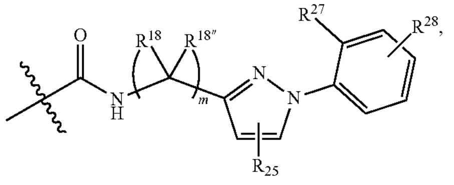

or

-continued

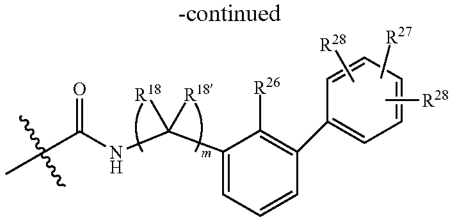

wherein $R^{18}$ and $R^{18'}$ are independently chosen from hydrogen, halogen, hydroxymethyl, and methyl; and m is 0 or 1; and $R^{26}$, $R^{27}$, and $R^{28}$ are independently chosen from hydrogen, halogen, hydroxyl, nitro, cyano, $C_1$-$C_6$alkyl, $C_2$-$C_6$alkenyl, $C_2$-$C_6$alkanoyl, $C_1$-$C_6$alkoxy, $C_1$-$C_6$thioalkyl, (mono- and di-$C_1$-$C_6$alkylamino)$C_0$-$C_4$alkyl, ($C_3$-$C_7$cycloalkyl)$C_0$-$C_4$alkyl, (aryl)$C_0$-$C_4$alkyl-, (heteroaryl)$C_0$-$C_4$alkyl-, and —$C_0$-$C_4$alkoxy($C_3$-$C_7$cycloalkyl); each of which $R^{26}$, $R^{27}$, and $R^{28}$ other than hydrogen, halogen, hydroxyl, nitro, cyano, is unsubstituted or substituted with one or more substituents independently chosen from halogen, hydroxyl, amino, $C_1$-$C_2$alkoxy, $C_1$-$C_2$haloalkyl, ($C_3$-$C_7$cycloalkyl)$C_0$-$C_4$alkyl-, and $C_1$-$C_2$haloalkoxy; and $R^{29}$ is hydrogen, $C_1$-$C_2$alkyl, $C_1C_2$haloalkyl or —$Si(CH_3)_2C(CH_3)_3$.

In one embodiment, m is 0.

In one embodiment, the disclosure further includes compounds and salts of Formula I in which B is 2-fluoro-3-chlorophenyl. In another embodiment, another carbocyclic, aryl, heterocyclic, or heteroaryl group such as 2-bromo-pyridin-6-yl, 1-(2,2,2-trifluoroethyl)-1H-pyrazol-3-yl, 2,2-dichlorocyclopropylmethyl, or 2-fluoro-3-trimethylsilylphenyl is used.

In another embodiment, B is phenyl, pyridyl, or indanyl each of which is unsubstituted or substituted with one or more substituents independently chosen from hydrogen, halogen, hydroxyl, nitro, cyano, $C_1$-$C_6$alkyl, $C_2$-$C_6$alkenyl, $C_2$-$C_6$alkanoyl, $C_1$-$C_6$alkoxy, $C_1$-$C_6$thioalkyl, (mono- and di-$C_1$-$C_6$alkylamino)$C_0$-$C_4$alkyl, ($C_3$-$C_7$cycloalkyl)$C_0$-$C_4$alkyl, —$C_0$-$C_4$alkoxy($C_3$-$C_7$cycloalkyl), (phenyl)$C_0$-$C_2$alkyl, (pyridyl)$C_0$-$C_2$alkyl; each of which substituents other than hydrogen, halogen, hydroxyl, nitro, cyano, is unsubstituted or substituted with one or more substituents independently chosen from halogen, hydroxyl, amino, $C_1$-$C_2$alkyl, $C_1$-$C_2$alkoxy, —$OSi(CH_3)_2C(CH_3)_3$, —$Si(CH_3)_2C(CH_3)_3$, $C_1$-$C_2$haloalkyl, and $C_1$-$C_2$haloalkoxy.

In another embodiment, B is phenyl or pyridyl substituted with 1, 2, or 3 substituents chosen from chloro, bromo, hydroxyl, —$SCF_3$, $C_1$-$C_2$alkyl, $C_1$-$C_2$alkoxy, trifluoromethyl, phenyl and trifluoromethoxy each of which substituents other than chloro, bromo, hydroxyl, —$SCF_3$, can be optionally substituted.

In certain embodiments, B is a 2-fluoro-3-chlorophenyl or a 2-fluoro-3-trifluoromethoxyphenyl group.

In one embodiment, B is pyridyl, optionally substituted with halogen, $C_1$-$C_2$alkoxy, and trifluoromethyl.

In one embodiment, B is phenyl, substituted with 1, 2, or 3 substituents independently selected from halogen, $C_1$-$C_2$alkyl, $C_1$-$C_2$alkoxy, trifluoromethyl, and optionally substituted phenyl.

In one embodiment, $R^{23}$ is independently chosen at each occurrence from ($C_3$-$C_7$cycloalkyl)$C_0$-$C_4$alkyl, (phenyl)$C_0$-$C_4$alkyl, (4- to 7-membered heterocycloalkyl)$C_0$-$C_4$alkyl having 1, 2, or 3 heteroatoms independently chosen from N, O, and S, and (5- or 6-membered unsaturated or aromatic heterocycle)$C_0$-$C_4$alkyl having 1, 2, or 3 heteroatoms independently chosen from N, O, and S.

In one embodiment, B is selected from

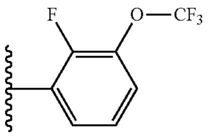
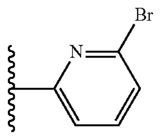
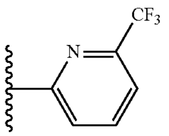
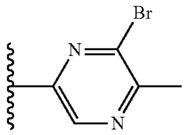
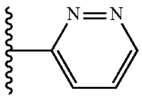
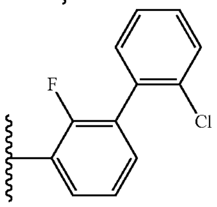
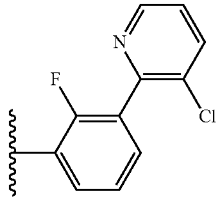
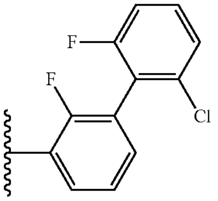
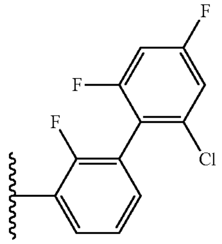
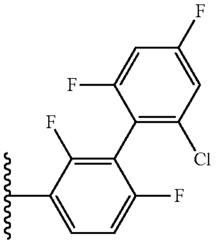
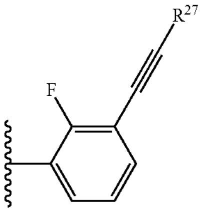
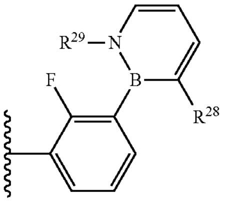
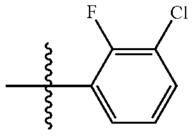
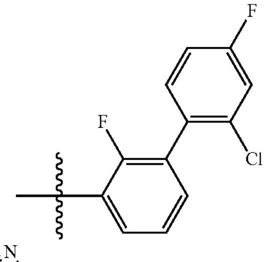
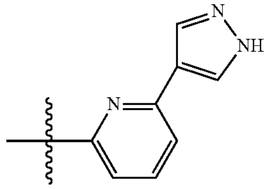
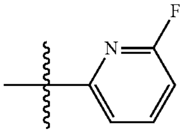
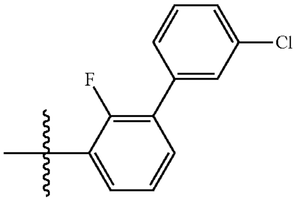
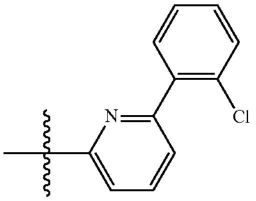

-continued
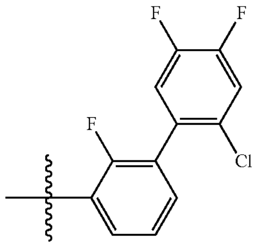
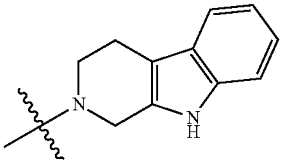
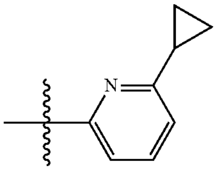
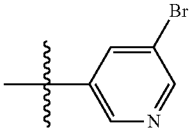
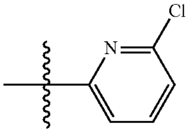
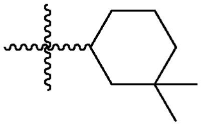
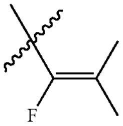
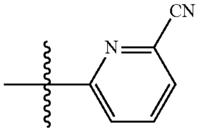
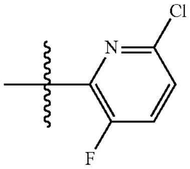
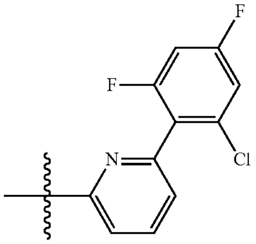
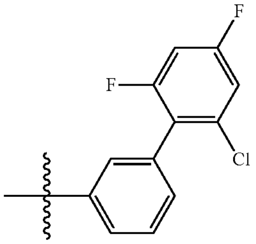
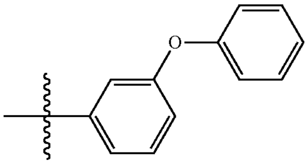
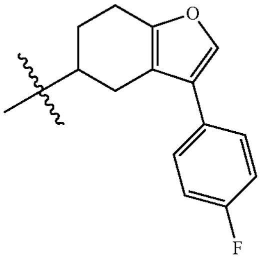
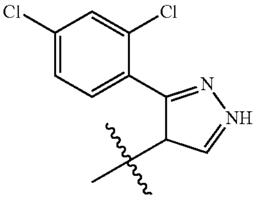
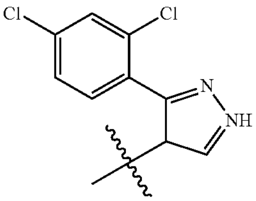 [SMILES: *C1C=NN=C1c1ccc(Cl)cc1Cl]
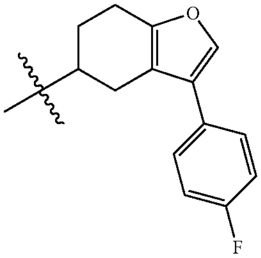
-continued
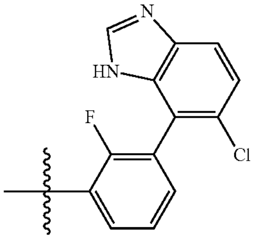
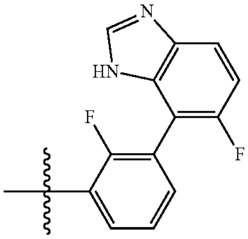
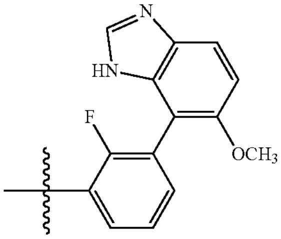
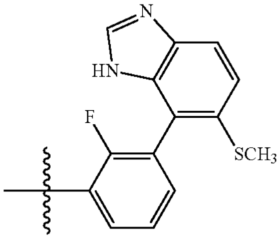
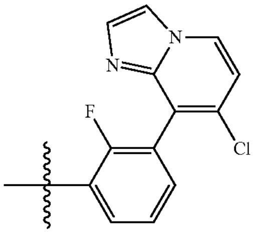
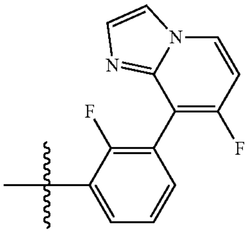
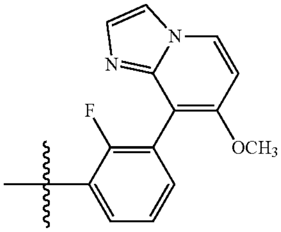
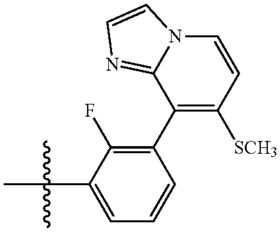
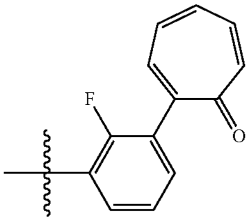
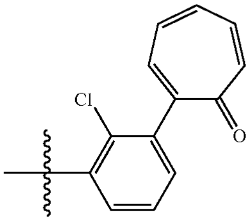
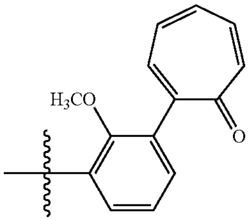
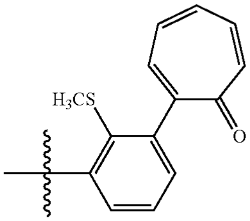
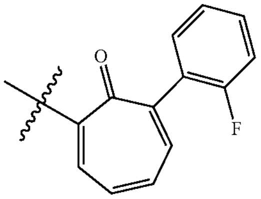
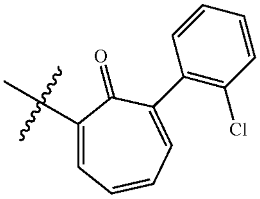

-continued
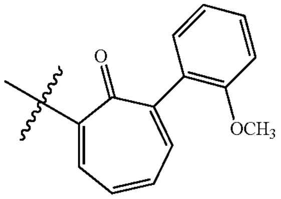
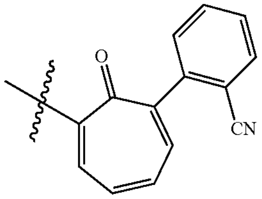
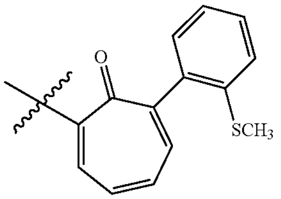
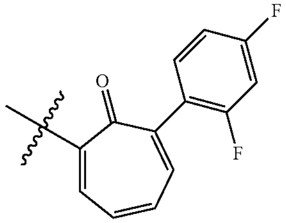
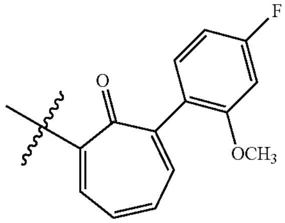
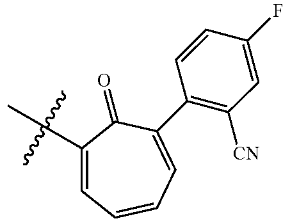
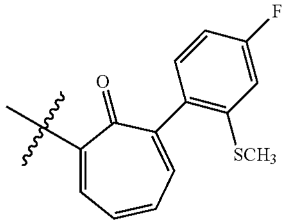
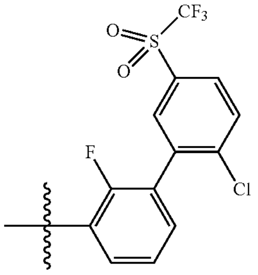
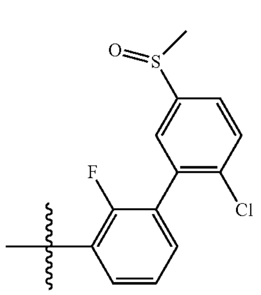
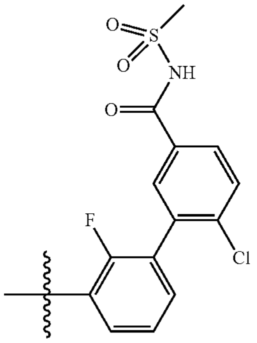
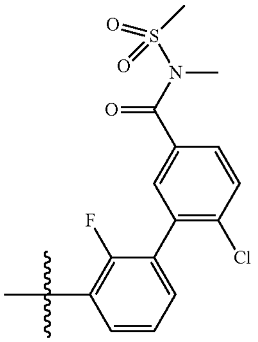
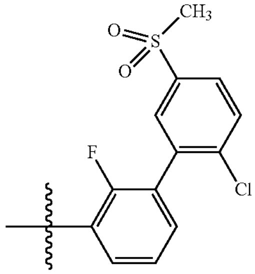
-continued
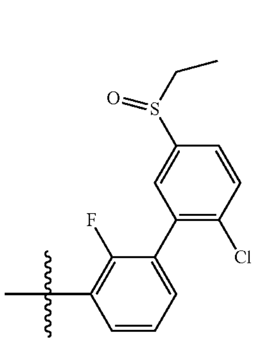
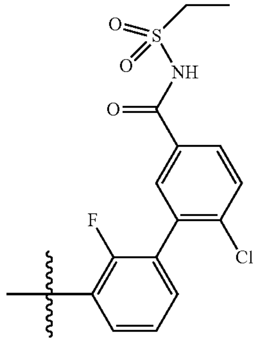
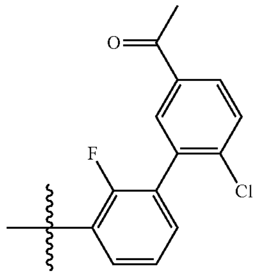
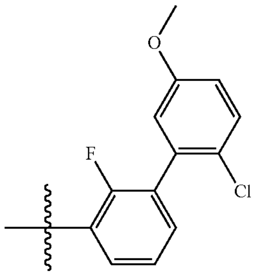
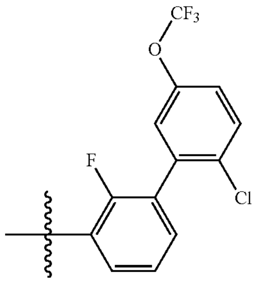
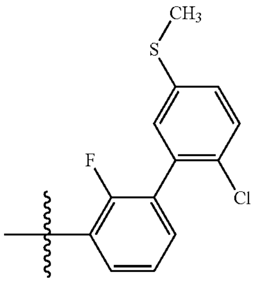
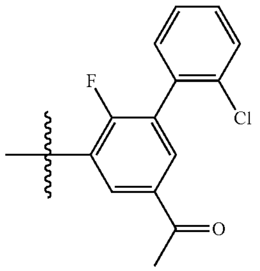
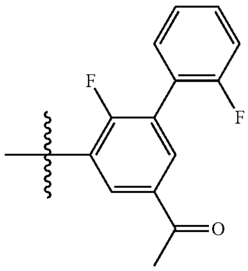
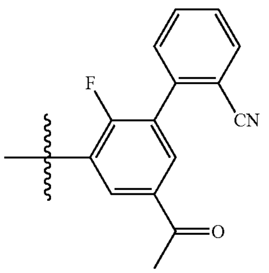
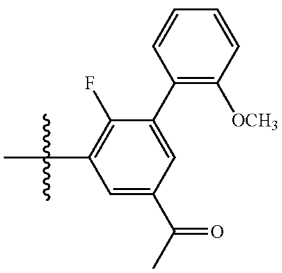
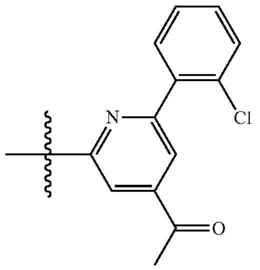
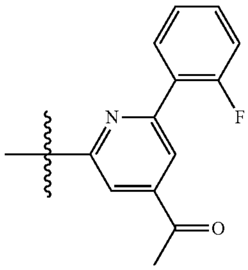

-continued
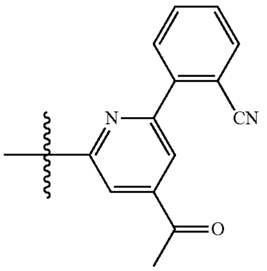
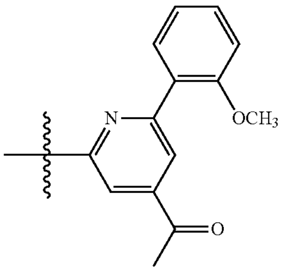
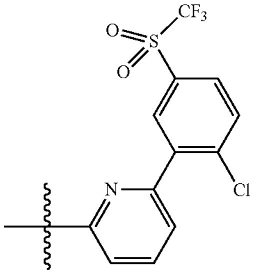
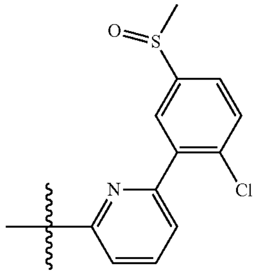
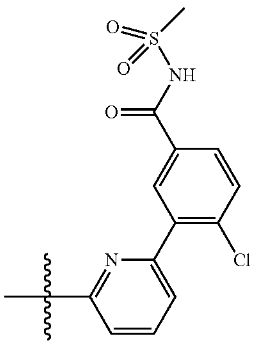
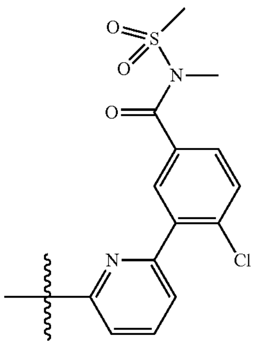
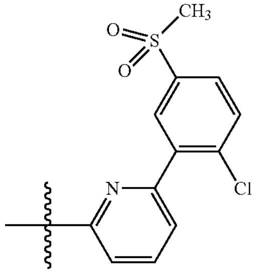
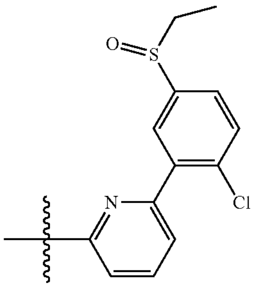
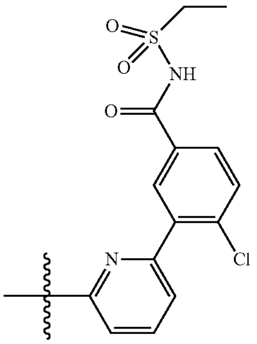
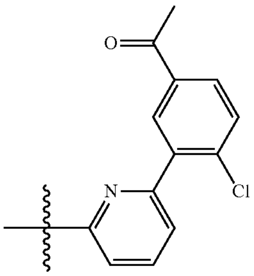
-continued
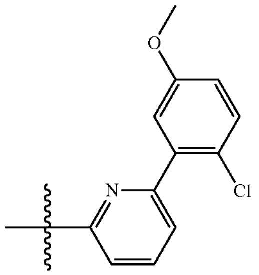
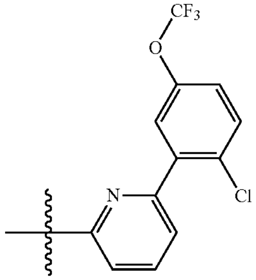
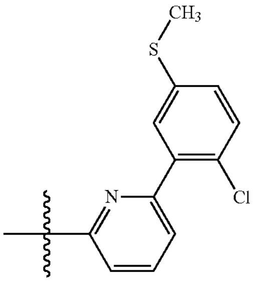
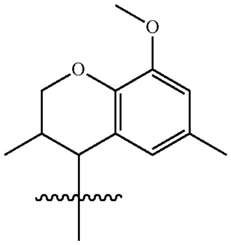
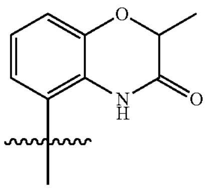
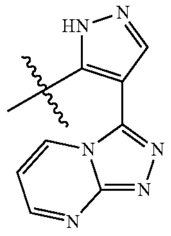
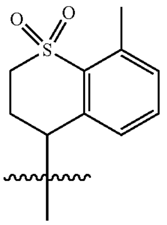
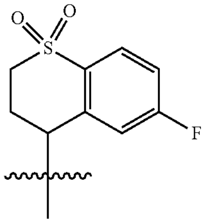
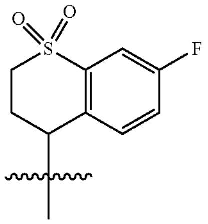
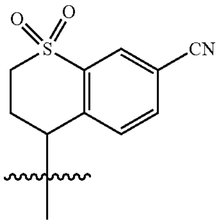
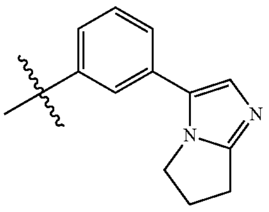
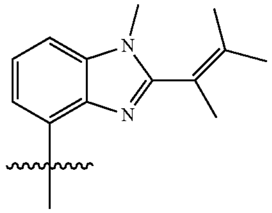
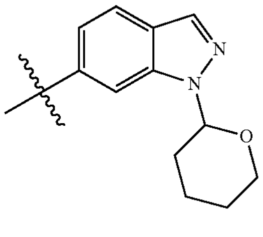
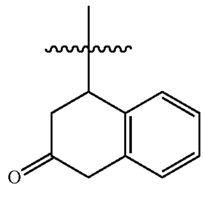

-continued
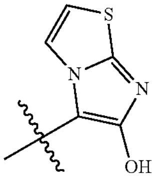
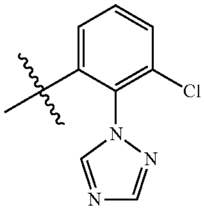
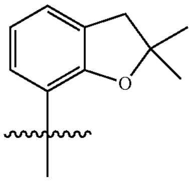
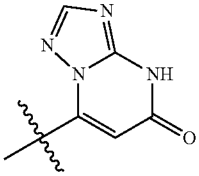
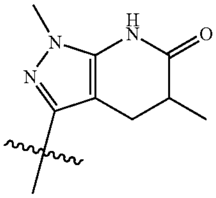
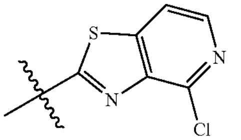
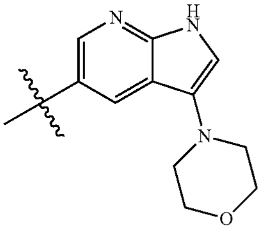
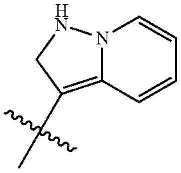
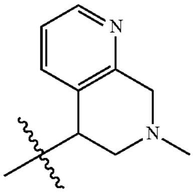
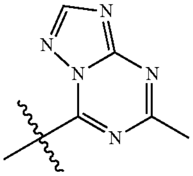
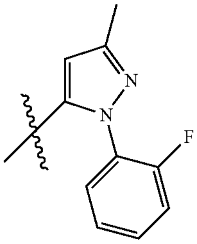
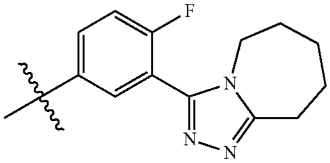
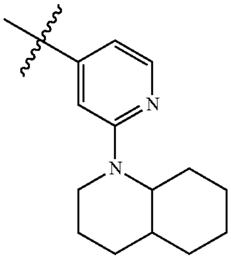
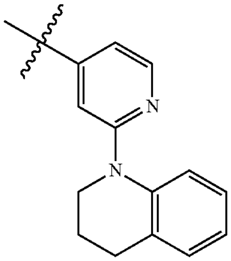
-continued
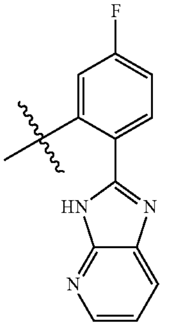
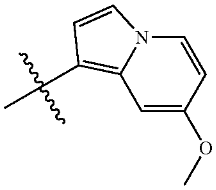
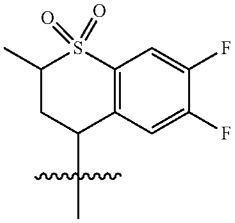
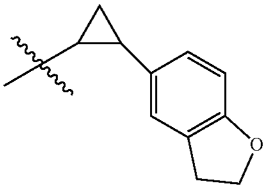
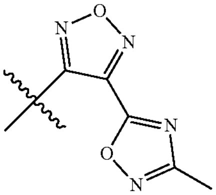
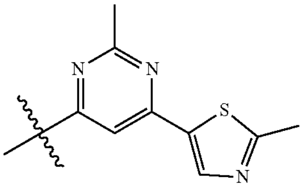
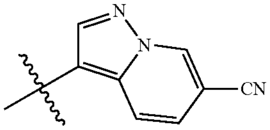
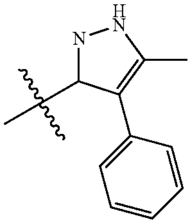
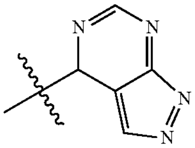
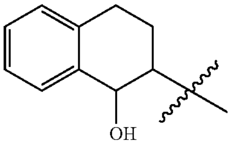
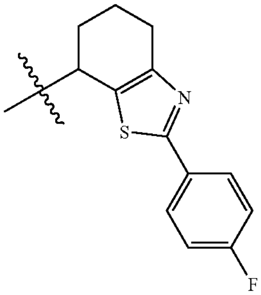
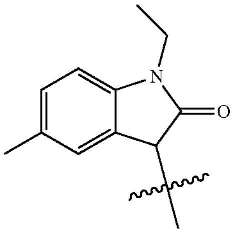
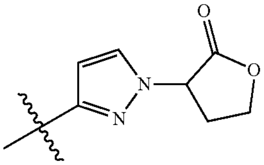

-continued
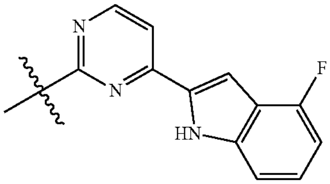
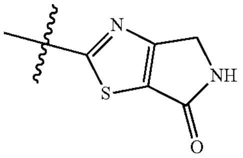
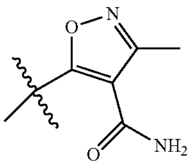
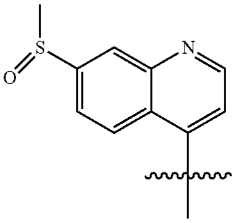
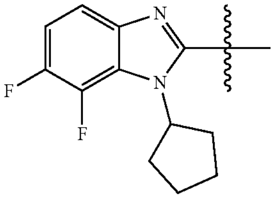
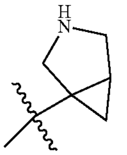
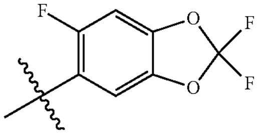
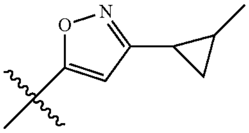
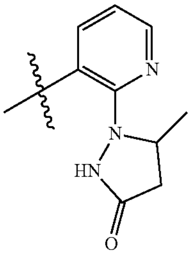
where $R^{27}$ is hydrogen, methyl, or trifluoromethyl; $R^{28}$ is hydrogen or halogen; and $R^{29}$ is hydrogen, methyl, trifluoromethyl, or $—Si(CH_3)_2C(CH_3)_3$.
Central Core (C═O)A Substituent
The central core (C═O)A substituent in Formula I is illustrated below:
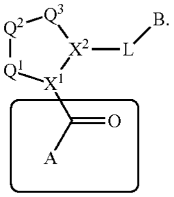
A is a group chosen from:
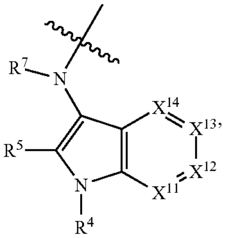
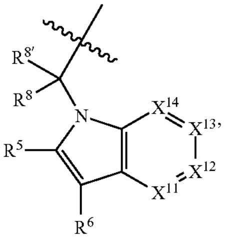
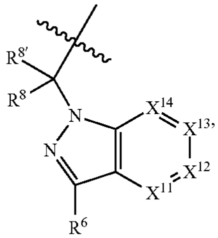
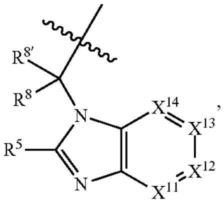
,
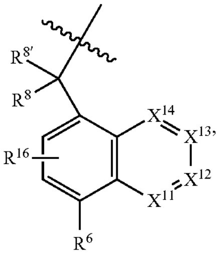
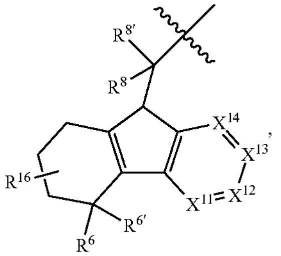
,
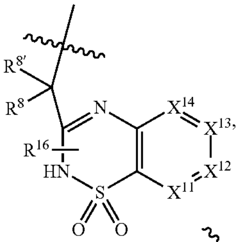
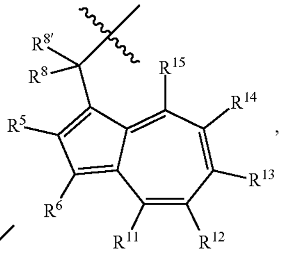
,
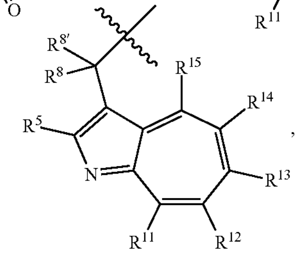
,
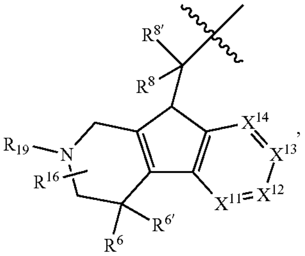
,
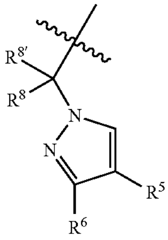
,
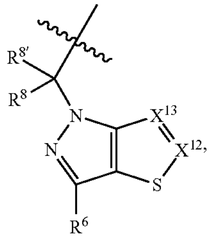
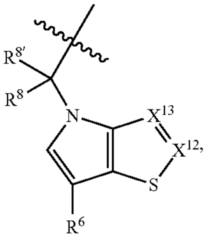

-continued

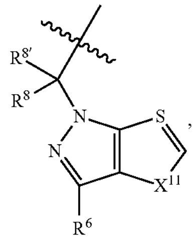,

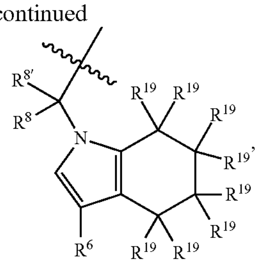

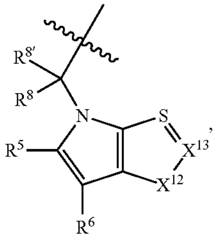, or

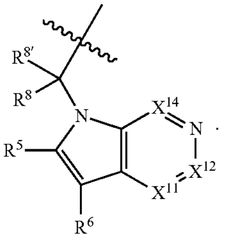.

$R^4$ is chosen from —CHO, —$CONH_2$, $C_2$-$C_6$alkanoyl, hydrogen, —$SO_2NH_2$, —$C(CH_2)_2F$, —$CH(CF_3)NH_2$, $C_1$-$C_6$alkyl, —$C_0$-$C_4$alkyl($C_3$-$C_7$cycloalkyl), —$C(O)C_0$-$C_2$alkyl($C_3$-$C_7$cycloalkyl),

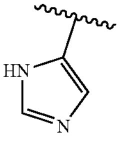,

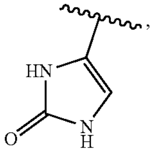,

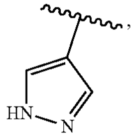,

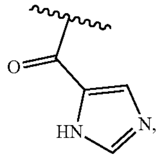,

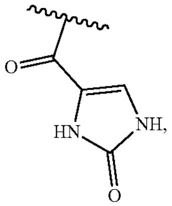, or

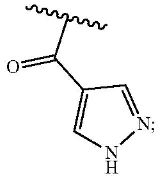;

each of which $R^4$ other than hydrogen, —CHO, and —$CONH_2$, is unsubstituted or substituted with one or more of amino, imino, halogen, hydroxyl, cyano, cyanoimino, $C_1$-$C_2$alkyl, $C_1$-$C_2$alkoxy, —$C_0$-$C_2$alkyl(mono- and di-$C_1$-$C_4$alkylamino), $C_1$-$C_2$haloalkyl, and $C_1$-$C_2$haloalkoxy.

$R^5$ and $R^6$ are independently chosen from —CHO, —$C(O)NH_2$, —$C(O)NH(CH_3)$, $C_2$-$C_6$alkanoyl, hydrogen, hydroxyl, halogen, cyano, nitro, —COOH, —$SO_2NH_2$, vinyl, $C_1$-$C_6$alkyl (including methyl), $C_2$-$C_6$alkenyl, $C_1$-$C_6$alkoxy, —$C_0$-$C_4$alkyl($C_3$-$C_7$cycloalkyl), —$C(O)C_0$-$C_4$alkyl($C_3$-$C_7$cycloalkyl), —$P(O)(OR^9)_2$, —$OC(O)R^9$, —$C(O)OR^9$, —$C(O)N(CH_2CH_2R^9)(R^{10})$, —$NR^9C(O)R^{10}$, phenyl, or 5- to 6-membered heteroaryl.

Each $R^5$ and $R^6$ other than hydrogen, hydroxyl, cyano, and —COOH is unsubstituted or optionally substituted. For example, $R^5$ and $R^6$ other than hydrogen, hydroxyl, cyano, and —COOH may be substituted with one or more substituents independently chosen from halogen, hydroxyl, amino, imino, cyano, cyanoimino, $C_1$-$C_2$alkyl, $C_1$-$C_4$alkoxy, —$C_0$-$C_2$alkyl(mono- and di-$C_1$-$C_4$alkylamino), $C_1$-$C_2$haloalkyl, and $C_1$-$C_2$haloalkoxy.

$R^{6'}$ is hydrogen, halogen, hydroxyl, $C_1$-$C_4$alkyl, —$C_0$-$C_4$alkyl($C_3$-$C_7$cycloalkyl), or $C_1$-$C_4$alkoxy; or $R^6$ and $R^{6'}$ may be taken together to form an oxo, vinyl, or imino group.

$R^7$ is hydrogen, $C_1$-$C_6$alkyl, or —$C_0$-$C_4$alkyl($C_3$-$C_7$cycloalkyl).

$R^8$ and $R^{8'}$ are independently chosen from hydrogen, halogen, hydroxyl, $C_1$-$C_6$alkyl, —$C_0$-$C_4$alkyl($C_3$-$C_7$cycloalkyl), $C_1$-$C_6$alkoxy, and ($C_1$-$C_4$alkylamino)$C_0$-$C_2$alkyl; or $R^8$ and $R^{8'}$ are taken together to form an oxo group; or $R^8$ and $R^{8'}$ can be taken together with the carbon that they are bonded to form a 3-membered carbocyclic ring.

$R^{16}$ is absent or may include one or more substituents independently chosen from halogen, hydroxyl, nitro, cyano, $C_1$-$C_6$alkyl, $C_2$-$C_6$alkenyl, $C_2$-$C_6$alkanoyl, $C_1$-$C_6$alkoxy, —$C_0$-$C_4$alkyl(mono- and di-$C_1$-$C_6$alkylamino), —$C_0$-$C_4$alkyl($C_3$-$C_7$cycloalkyl), $C_1$-$C_2$haloalkyl, and $C_1$-$C_2$haloalkoxy.

$R^{19}$ is hydrogen, $C_1$-$C_6$alkyl, $C_2$-$C_6$alkenyl, $C_2$-$C_6$alkanoyl, —$SO_2C_1$-$C_6$alkyl, (mono- and di-$C_1$-$C_6$alkylamino)$C_1$-$C_4$alkyl, —$C_0$-$C_4$alkyl($C_3$-$C_7$cycloalkyl), —$C_0$-$C_4$alkyl($C_3$-$C_7$heterocycloalkyl), —$C_0$-$C_4$alkyl(aryl), $C_0$-$C_4$alkyl(heteroaryl), and wherein $R^{19}$ other than hydrogen is unsubstituted or substituted with one or more substituents independently chosen from halogen, hydroxyl, amino, —COOH, and —$C(O)OC_1$-$C_4$alkyl.

$X^{11}$ is N or $CR^{11}$.

$X^{12}$ is N or $CR^{12}$.

$X^{13}$ is N or $CR^{13}$.

$X^{14}$ is N or $CR^{14}$.

No more than 2 of $X^{11}$, $X^{12}$, $X^{13}$, and $X^{14}$ are N.

$R^{11}$, $R^{14}$, and $R^{15}$ are independently chosen at each occurrence from hydrogen, halogen, hydroxyl, nitro, cyano, —$O(PO)(OR^9)_2$, —$(PO)(OR^9)_2$, $C_1$-$C_6$alkyl, $C_2$-$C_6$alkenyl, $C_2$-$C_6$alkynyl, $C_2$-$C_6$alkenyl(aryl), $C_2$-$C_6$alkenyl(cycloalkyl), $C_2$-$C_6$alkenyl(heterocycle), $C_2$-$C_6$alkenyl(heteroaryl), $C_2$-$C_6$alkynyl, $C_2$-$C_6$alkynyl(aryl), $C_2$-$C_6$alkynyl(cycloalkyl), $C_2$-$C_6$alkynyl(heterocycle), $C_2$-$C_6$alkynyl(heteroaryl), $C_2$-$C_6$alkanoyl, $C_1$-$C_6$alkoxy, $C_1$-$C_6$thioalkyl, —$C_0$-$C_4$alkyl(mono- and di-$C_1$-$C_6$alkylamino), —$C_0$-$C_4$alkyl($C_3$-$C_7$cycloalkyl), —$C_0$-$C_4$alkoxy($C_3$-$C_7$cycloalkyl), $C_1$-$C_2$haloalkyl, and $C_1$-$C_2$haloalkoxy.

In one embodiment, $R^5$ and $R^6$ are independently chosen from —CHO, —$C(O)NH_2$, —$C(O)NH(CH_3)$, $C_2$-$C_6$alkanoyl, and hydrogen.

In one embodiment, each $R^5$ and $R^6$ other than hydrogen, hydroxyl, cyano, and —COOH is unsubstituted or substituted with one or more substituents independently chosen from halogen, hydroxyl, amino, imino, cyano, cyanoimino, $C_1$-$C_2$alkyl, $C_1$-$C_4$alkoxy, —$C_0$-$C_2$alkyl(mono- and di-$C_1$-$C_4$alkylamino), $C_1$-$C_2$haloalkyl, and $C_1$-$C_2$haloalkoxy.

In one embodiment, $R^8$ and $R^{8'}$ are independently hydrogen or methyl.

In one embodiment, $R^8$ and $R^{8'}$ are hydrogen.

In one embodiment, $R^7$ is hydrogen or methyl.

In one embodiment, $R^7$ is hydrogen.

Embodiments of Formulas IA, IB, IC, and ID

To further illustrate the invention, various embodiments of Formula IA, IB, IC and ID are provided. These are presented by way of example to show some of the variations among presented compounds within the invention and can be applied to any of the Formulas I-XXX.

In one aspect, this disclosure includes compounds and salts of Formula IA:

(IA)

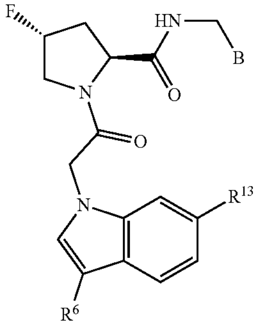

where
$R^6$, $R^{13}$, and B may carry any of the definitions set forth herein for this variable.

In another aspect, this disclosure includes compounds and salts of Formula IB, IC, and ID.

IB

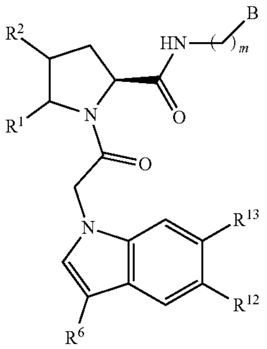

IC

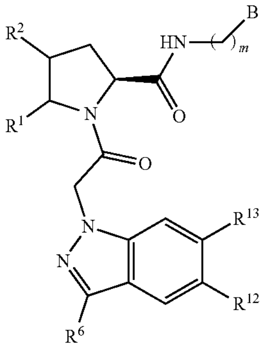

ID

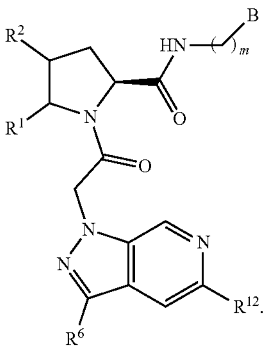

In Formulas IA, IB, IC, and ID, the variables may include any of the definitions set forth herein that results in a stable compound. In certain embodiments, the following conditions apply for Formula IB and IC.

In some embodiments, structures are provided including Formulas IB and IC, wherein m=0, $R^1$ is H, $R^2$ is F, $R^6$ is alkanoyl, $R^{12}$ is $R^{32}$, $R^{32}$ is —P(O)$R^{20}R^{20}$, $R^{13}$ is H, and B is heteroaryl.

In some embodiments, structures are provided including Formulas IB and IC, wherein m=0, $R^1$ and $R^2$ are joined to form a 3 membered ring, $R^6$ is alkanoyl, $R^{12}$ is $R^{32}$, $R^{32}$ is —P(O)$R^{20}R^{20}$, $R^{13}$ is H, and B is heteroaryl.

In some embodiments, structures are provided including Formulas IB and IC, wherein m=0, $R^1$ is H, $R^2$ is F, $R^6$ is amide, $R^{12}$ is $R^{32}$, $R^{32}$ is —P(O)$R^{20}R^{20}$, $R^{13}$ is H, and B is heteroaryl.

In some embodiments, structures are provided including Formulas IB and IC, wherein m=0, $R^1$ and $R^2$ are joined to form a 3 membered ring, $R^6$ is amide, $R^{12}$ is $R^{32}$, $R^{32}$ is —P(O)$R^{20}R^{20}$, $R^{13}$ is H, and B is heteroaryl.

In some embodiments, structures are provided including Formulas IB and IC, wherein m=0, $R^1$ is H, $R^2$ is F, $R^6$ is alkanoyl, $R^{12}$ is H, $R^{13}$ is $R^{32}$, $R^{32}$ is —P(O)$R^{20}R^{20}$, and B is heteroaryl.

In some embodiments, structures are provided including Formulas IB and IC, wherein m=0, $R^1$ and $R^2$ are joined to form a 3 membered ring, $R^6$ is alkanoyl, $R^{12}$ is H, $R^{13}$ is $R^{32}$, $R^{32}$ is —P(O)$R^{20}R^{20}$, and B is heteroaryl.

In some embodiments, structures are provided including Formulas IB and IC, wherein m=0, $R^1$ is H, $R^2$ is F, $R^6$ is amide, $R^{12}$ is H, $R^{13}$ is $R^{32}$, $R^{32}$ is —P(O)$R^{20}R^{20}$, and B is heteroaryl.

In some embodiments, structures are provided including Formulas IB and IC, wherein m=0, $R^1$ and $R^2$ are joined to form a 3 membered ring, $R^6$ is amide, $R^{12}$ is H, $R^{13}$ is $R^{32}$, $R^{32}$ is —P(O)$R^{20}R^{20}$, and B is heteroaryl.

In some embodiments, structures are provided including Formulas IB and IC, wherein m=0, $R^1$ is H, $R^2$ is F, $R^6$ is alkanoyl, $R^{12}$ is $R^{32}$, $R^{32}$ is —P(O)$R^{20}R^{20}$, $R^{13}$ is H, and B is phenyl.

In some embodiments, structures are provided including Formulas IB and IC, wherein m=0, $R^1$ and $R^2$ are joined to form a 3 membered ring, $R^6$ is alkanoyl, $R^{12}$ is $R^{32}$, $R^{32}$ is —P(O)$R^{20}R^{20}$, $R^{13}$ is H, and B is phenyl.

In some embodiments, structures are provided including Formulas IB and IC, wherein m=0, $R^1$ is H, $R^2$ is F, $R^6$ is amide, $R^{12}$ is $R^{32}$, $R^{32}$ is —P(O)$R^{20}R^{20}$, $R^{13}$ is H, and B is phenyl.

In some embodiments, structures are provided including Formulas IB and IC, wherein m=0, $R^1$ and $R^2$ are joined to form a 3 membered ring, $R^6$ is amide, $R^{12}$ is $R^{32}$, $R^{32}$ is —P(O)$R^{20}R^{20}$, $R^{13}$ is H, and B is phenyl.

In some embodiments, structures are provided including Formulas IB and IC, wherein m=0, $R^1$ is H, $R^2$ is F, $R^6$ is alkanoyl, $R^{12}$ is H, $R^{13}$ is $R^{32}$, $R^{32}$ is —P(O)$R^{20}R^{20}$, and B is phenyl.

In some embodiments, structures are provided including Formulas IB and IC, wherein m=0, $R^1$ and $R^2$ are joined to form a 3 membered ring, $R^6$ is alkanoyl, $R^{12}$ is H, $R^{13}$ is $R^{32}$, $R^{32}$ is —P(O)$R^{20}R^{20}$, and B is phenyl.

In some embodiments, structures are provided including Formulas IB and IC, wherein m=0, $R^1$ is H, $R^2$ is F, $R^6$ is amide, $R^{12}$ is H, $R^{13}$ is $R^{32}$, $R^{32}$ is —P(O)$R^{20}R^{20}$, and B is phenyl.

In some embodiments, structures are provided including Formulas IB and IC, wherein m=0, $R^1$ and $R^2$ are joined to form a 3 membered ring, $R^6$ is amide, $R^{12}$ is H, $R^{13}$ is $R^{32}$, $R^{32}$ is —P(O)$R^{20}R^{20}$, and B is phenyl.

In some embodiments, structures are provided including Formulas IB and IC, wherein m=1, $R^1$ is H, $R^2$ is F, $R^6$ is alkanoyl, $R^{12}$ is $R^{32}$, $R^{32}$ is —P(O)$R^{20}R^{20}$, $R^{13}$ is H, and B is heteroaryl.

In some embodiments, structures are provided including Formulas IB and IC, wherein m=1, $R^1$ and $R^2$ are joined to form a 3 membered ring, $R^6$ is alkanoyl, $R^{12}$ is $R^{32}$, $R^{32}$ is —P(O)$R^{20}R^{20}$, $R^{13}$ is H, and B is heteroaryl.

In some embodiments, structures are provided including Formulas IB and IC, wherein m=1, $R^1$ is H, $R^2$ is F, $R^6$ is amide, $R^{12}$ is $R^{32}$, $R^{32}$ is —P(O)$R^{20}R^{20}$, $R^{13}$ is H, and B is heteroaryl.

In some embodiments, structures are provided including Formulas IB and IC, wherein m=1, $R^1$ and $R^2$ are joined to form a 3 membered ring, $R^6$ is amide, $R^{12}$ is $R^{32}$, $R^{32}$ is —P(O)$R^{20}R^{20}$, $R^{13}$ is H, and B is heteroaryl.

In some embodiments, structures are provided including Formulas IB and IC, wherein m=1, $R^1$ is H, $R^2$ is F, $R^6$ is alkanoyl, $R^{12}$ is H, $R^{13}$ is $R^{32}$, $R^{32}$ is —P(O)$R^{20}R^{20}$, and B is heteroaryl.

In some embodiments, structures are provided including Formulas IB and IC, wherein m=1, $R^1$ and $R^2$ are joined to form a 3 membered ring, $R^6$ is alkanoyl, $R^{12}$ is H, $R^{13}$ is $R^{32}$, $R^{32}$ is —P(O)$R^{20}R^{20}$, and B is heteroaryl.

In some embodiments, structures are provided including Formulas IB and IC, wherein m=1, $R^1$ is H, $R^2$ is F, $R^6$ is amide, $R^{12}$ is H, $R^{13}$ is $R^{32}$, $R^{32}$ is —P(O)$R^{20}R^{20}$, and B is heteroaryl.

In some embodiments, structures are provided including Formulas IB and IC, wherein m=1, $R^1$ and $R^2$ are joined to form a 3 membered ring, $R^6$ is amide, $R^{12}$ is H, $R^{13}$ is $R^{32}$, $R^{32}$ is —P(O)$R^{20}R^{20}$, and B is heteroaryl.

In some embodiments, structures are provided including Formulas IB and IC, wherein m=1, $R^1$ is H, $R^2$ is F, $R^6$ is alkanoyl, $R^{12}$ is $R^{32}$, $R^{32}$ is —P(O)$R^{20}R^{20}$, $R^{13}$ is H, and B is phenyl.

In some embodiments, structures are provided including Formulas IB and IC, wherein m=1, $R^1$ and $R^2$ are joined to form a 3 membered ring, $R^6$ is alkanoyl, $R^{12}$ is $R^{32}$, $R^{32}$ is —P(O)$R^{20}R^{20}$, $R^{13}$ is H, and B is phenyl.

In some embodiments, structures are provided including Formulas IB and IC, wherein m=1, $R^1$ is H, $R^2$ is F, $R^6$ is amide, $R^{12}$ is $R^{32}$, $R^{32}$ is —P(O)$R^{20}R^{20}$, $R^{13}$ is H, and B is phenyl.

In some embodiments, structures are provided including Formulas IB and IC, wherein m=1, $R^1$ and $R^2$ are joined to form a 3 membered ring, $R^6$ is amide, $R^{12}$ is $R^{32}$, $R^{32}$ is —P(O)$R^{20}R^{20}$, $R^{13}$ is H, and B is phenyl.

In some embodiments, structures are provided including Formulas IB and IC, wherein m=1, $R^1$ is H, $R^2$ is F, $R^6$ is alkanoyl, $R^{12}$ is H, $R^{13}$ is $R^{32}$, $R^{32}$ is —P(O)$R^{20}R^{20}$, and B is phenyl.

In some embodiments, structures are provided including Formulas IB and IC, wherein m=1, $R^1$ and $R^2$ are joined to form a 3 membered ring, $R^6$ is alkanoyl, $R^{12}$ is H, $R^{13}$ is $R^{32}$, $R^{32}$ is —P(O)$R^{20}R^{20}$, and B is phenyl.

In some embodiments, structures are provided including Formulas IB and IC, wherein m=1, $R^1$ is H, $R^2$ is F, $R^6$ is amide, $R^{12}$ is H, $R^{13}$ is $R^{32}$, $R^{32}$ is —P(O)$R^{20}R^{20}$, and B is phenyl.

In some embodiments, structures are provided including Formulas IB and IC, wherein m=1, $R^1$ and $R^2$ are joined to form a 3 membered ring, $R^6$ is amide, $R^{12}$ is H, $R^{13}$ is $R^{32}$, $R^{32}$ is —P(O)$R^{20}R^{20}$, and B is phenyl.

In the above embodiments, structures are provided including Formulas IB and IC, wherein $R^{20}$ is independently chosen at each occurrence from hydroxyl, $C_1$-$C_6$alkoxy, $C_1$-$C_6$haloalkoxy, $C_1$-$C_6$alkyl, ($C_3$-$C_7$cycloalkyl)$C_0$-$C_4$alkyl-, (aryl)$C_0$-$C_4$alkyl-, —O—$C_0$-$C_4$alkyl(aryl), —O—$C_0$-$C_4$alkyl($C_3$-$C_7$cycloalkyl), (4- to 7-membered heterocycloalkyl)$C_0$-$C_4$alkyl-O—having 1, 2, or 3 heteroatoms independently chosen from N, O, and S; (5- or 6-membered unsaturated or aromatic heterocycle)$C_0$-$C_4$alkyl-O—having 1, 2, or 3 heteroatoms independently chosen from N, O, and S; —O$(CH_2)_{2-4}$O$(CH_2)_{8-18}$, —OC$(R^{20a})_2$OC(O)O$R^{20b}$, —OC$(R^{20a})_2$OC(O)$R^{20b}$ an N-linked amino acid or an N-linked amino acid ester and each $R^{20}$ can be optionally substituted;

$R^{20a}$ is independently chosen at each occurrence from hydrogen, $C_1$-$C_8$alkyl, $C_2$-$C_8$alkenyl, $C_2$-$C_8$alkynyl, (aryl)$C_0$-$C_4$alkyl-, (aryl)$C_2$-$C_8$alkenyl- or (aryl)$C_2$-$C_8$alkynyl-; or two $R^{20a}$ groups can be taken together with the carbon that they are bonded to form a 3-6 membered heterocycloalkyl having 1, 2, or 3 heteroatoms independently chosen from N, O, and S, or a 3-6 membered carbocyclic ring.

$R^{20b}$ is independently chosen at each occurrence from $C_1$-$C_8$alkyl, $C_2$-$C_8$alkenyl, $C_2$-$C_8$alkynyl, (aryl)$C_0$-$C_4$alkyl, (aryl)$C_2$-$C_8$alkenyl or (aryl)$C_2$-$C_8$alkynyl.

Embodiments of Formula VII

To further illustrate the invention, various embodiments of Formula VII. In one aspect, the disclosure includes compounds and salts of Formula VII:

(VII)

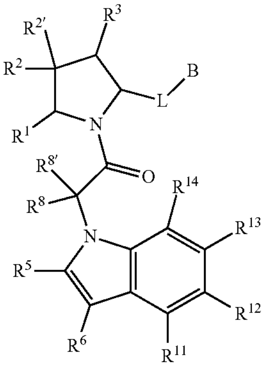

wherein:

$R^1$, $R^2$, $R^{2'}$, and $R^3$ are independently chosen from hydrogen, halogen, $C_1$-$C_4$alkyl, $C_1$-$C_4$alkoxy, —$C_0$-$C_2$alkylN$R^9R^{10}$, —$C_0$-$C_4$alkyl($C_3$-$C_7$cycloalkyl), —O—$C_0$-$C_4$alkyl($C_3$-$C_7$cycloalkyl), $C_1$-$C_2$haloalkyl, and $C_1$-$C_2$haloalkoxy;

$R^8$ and $R^{8'}$ are independently chosen from hydrogen, halogen, and methyl;

$R^5$ is hydrogen, hydroxyl, cyano, —COOH, $C_1$-$C_6$alkyl, $C_1$-$C_6$alkoxy, $C_2$-$C_6$alkanoyl —$C_0$-$C_4$alkyl($C_3$-$C_7$cycloalkyl), —C(O)$C_0$-$C_4$alkyl($C_3$-$C_7$cycloalkyl, $C_1$-$C_2$haloalkyl, or $C_1$-$C_2$haloalkoxy;

$R^6$ is —C(O)$CH_3$, —C(O)$NH_2$, —C(O)$CF_3$, —C(O)(cyclopropyl), or -ethyl(cyanoimino); and $R^{11}$ and $R^{14}$ are independently chosen from hydrogen, halogen, hydroxyl, amino, nitro, cyano, $C_1$-$C_6$alkyl, $C_2$-$C_6$alkenyl, $C_2$-$C_6$alkanoyl, $C_1$-$C_6$alkoxy, $C_1$-$C_6$thioalkyl, —$C_0$-$C_4$alkyl(mono- and di-$C_1$-$C_6$alkylamino), —$C_0$-$C_4$alkyl($C_3$-$C_7$cycloalkyl), —O$C_0$-$C_4$alkyl($C_3$-$C_7$cycloalkyl), $C_1$-$C_2$haloalkyl, and $C_1$-$C_2$haloalkoxy.

III. Pharmaceutical Preparations

Compounds disclosed herein can be administered as the neat chemical, but can also administered as a pharmaceutical composition, that includes an effective amount for a host in need of treatment of the selected compound of Formula I, as described herein. Accordingly, the disclosure provides pharmaceutical compositions comprising an effective amount of compound or pharmaceutically acceptable salt of Formula I, together with at least one pharmaceutically acceptable carrier. The pharmaceutical composition may contain a compound or salt of Formula I as the only active agent, or, in an alternative embodiment, Formula I and at least one additional active agent. In certain embodiments the pharmaceutical composition is in a dosage form that contains from about 0.1 mg to about 2000 mg, from about 10 mg to about 1000 mg, from about 100 mg to about 800 mg, or from about 200 mg to about 600 mg of a compound of Formula I and optionally from about 0.1 mg to about 2000 mg, from about 10 mg to about 1000 mg, from about 100 mg to about 800 mg, or from about 200 mg to about 600 mg of an additional active agent in a unit dosage form. Examples are dosage forms with at least 25, 50, 100, 200, 250, 300, 400, 500, 600, 700, or 750 mg of active compound, or its salt. The pharmaceutical composition may also include a molar ratio of a compound of Formula I and an additional active agent. For example the pharmaceutical composition may contain a molar ratio of about 0.5:1, about 1:1, about 2:1, about 3:1 or from about 1.5:1 to about 4:1 of an another anti-inflammatory agent.

Compounds disclosed herein may be administered orally, topically, parenterally, by inhalation or spray, sublingually, via implant, including ocular implant, transdermally, via buccal administration, rectally, as an ophthalmic solution, injection, including ocular injection, intraveneous, intra-aortal, intracranial, or by other means, in dosage unit formulations containing conventional pharmaceutically acceptable carriers. The pharmaceutical composition may be formulated as any pharmaceutically useful form, e.g., as an aerosol, a cream, a gel, a pill, a capsule, a tablet, a syrup, a transdermal patch, or an ophthalmic solution. Some dosage forms, such as tablets and capsules, are subdivided into suitably sized unit doses containing appropriate quantities of the active components, e.g., an effective amount to achieve the desired purpose.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorants, glidents, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the compound of the present invention.

The pharmaceutical compositions/combinations can be formulated for oral administration. These compositions can contain any amount of active compound for Formula I that achieves the desired result, for example between 0.1 and 99 weight % (wt. %) of a compound of Formula I and usually at least about 5 wt. % of a compound of Formula I. Some embodiments contain from about 25 wt. % to about 50 wt. % or from about 5 wt. % to about 75 wt. % of the compound of Formula I.

The complement factor D inhibitors of the present invention can be administered, for example, either systemically or locally. Systemic administration includes, for example, oral, transdermal, subdermal, intraperitioneal, subcutaneous, transnasal, sublingual, or rectal. Local administration for ocular administration includes: topical, intravitreal, periocular, transscleral, retrobulbar, juxtascleral, sub-tenon, or via an intraocular device. The inhibitors may be delivered via a sustained delivery device implanted intravitreally or transsclerally, or by other known means of local ocular delivery.

IV. Methods of Treatment

The compounds and pharmaceutical compositions disclosed herein are useful for treating or preventing a disorder that is mediated by the complement pathway, and in particular, a pathway that is modulated by complement factor D. In certain embodiments, the disorder is an inflammatory disorder, an immune disorder, an autoimmune disorder, or complement factor D related disorders in a host. In one embodiment, the disorder is an ocular disorder. Complement mediated disorders that may be treated or prevented by the compounds and compositions of this disclosure include, but are not limited to, inflammatory effects of sepsis, systemic inflammatory response syndrome (SIRS), ischemia/reperfusion injury (I/R injury), psoriasis, myasthenia gravis, system lupus erythematosus (SLE), paroxysmal nocturnal hemoglobinuria (PNH), hereditary angioedema, multiple sclerosis, trauma, burn injury, capillary leak syndrome, obesity, diabetes, Alzheimer's dementia, stroke, schizophrenia, epilepsy, age-related macular degeneration, glaucoma, diabetic retinopathy, asthma, allergy, acute respiratory distress syndrome (ARDS), atypical hemolytic uremic syndrome (aHUS), hemolytic uremic syndrome (HUS), cystic fibrosis, myocardial infarction, lupus nephritides, Crohn's disease, rheumatoid arthritis, atherosclerosis, transplant rejection, prevention of fetal loss, biomaterial reactions (e.g. in hemodialysis, inplants), C3 glomerulonephritis, abdominal aortic aneurysm, neuromyelitis optica (NMO), vasculitis, neurological disorders, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during I L-2 therapy, inflammatory disorders, inflammation of autoimmune diseases, adult respiratory distress syndrome, thermal injury including burns or frostbite, myocarditis, post-ischemic reperfusion conditions, balloon angioplasty, post-pump syndrome in cardiopulmonary bypass or renal bypass, hemodialysis, renal ischemia, mesenteric artery reperfusion after aortic reconstruction, immune complex disorders and autoimmune diseases, SLE nephritis, proliferative nephritis, liver fibrosis, hemolytic anemia, tissue regeneration and neural regeneration. In addition, other known complement related disease are lung disease and disorders such as dyspnea, hemoptysis, chronic obstructive pulmonary disease (COPD), emphysema, pulmonary embolisms and infarcts, pneumonia, fibrogenic dust diseases, inert dusts and minerals (e.g., silicon, coal dust, beryllium, and asbestos), pulmonary fibrosis, organic dust diseases, chemical injury (due to irritant gases and chemicals, e.g., chlorine, phosgene, sulfur dioxide, hydrogen sulfide, nitrogen dioxide, ammonia, and hydrochloric acid), smoke injury, thermal injury (e.g., burn, freeze), bronchoconstriction, hypersensitivity pneumonitis, parasitic diseases, Goodpasture's Syndrome, pulmonary vasculitis, Pauci-immune vasculitis, immune complex-associated inflammation, uveitis (including Behcet's disease and other sub-types of uveitis), antiphospholipid syndrome, arthritis, autoimmune heart disease, inflammatory bowel disease, ischemia-reperfusion injuries, Barraquer-Simons Syndrome, hemodialysis, systemic lupus, lupus erythematosus, transplantation, diseases of the central nervous system and other neurodegenerative conditions, glomerulonephritis (including membrane proliferative glomerulonephritis), blistering cutaneous diseases (including bullous pemphigoid, pemphigus, and epidermolysis bullosa), ocular cicatrical pemphigoid, MPGN II, uveitis, adult macular degeneration, diabetic retinopathy, retinitis pigmentosa, macular edema, Behcet's uveitis, multifocal choroiditis, Vogt-Koyangi-Harada syndrome, imtermediate uveitis, birdshot retino-chorioditis, sympathetic ophthalmia, ocular dicatricial pemphigoid, ocular pemphigus, nonartertic ischemic optic neuropathy, postoperative inflammation, and retinal vein occlusion.

In some embodiments, complement mediated diseases include ophthalmic diseases (including early or neovascular age-related macular degeneration and geographic atrophy), autoimmune diseases (including arthritis, rheumatoid arthritis), respiratory diseases, cardiovascular diseases. In other embodiments, the compounds of the invention are suitable for use in the treatment of diseases and disorders associated with fatty acid metabolism, including obesity and other metabolic disorders.

In one embodiment, a method for the treatment of paroxysmal nocturnal hemoglobinuria (PNH) is provided that includes the administration of an effective amount of a compound of Formula I, or a pharmaceutically acceptable salt thereof, optionally in a pharmaceutically acceptable carrier. In another embodiment, a method for the treatment of age-related macular degeneration (AMD) is provided that includes the administration of an effective amount of a compound of Formula I, or a pharmaceutically acceptable salt thereof, optionally in a pharmaceutically acceptable carrier. In another embodiment, a method for the treatment of rheumatoid arthritis is provided that includes the administration of an effective amount of a compound of Formula I, or a pharmaceutically acceptable salt thereof, optionally in a pharmaceutically acceptable carrier. In another embodiment, a method for the treatment of multiple sclerosis is provided that includes the administration of an effective amount of a compound of Formula I, or a pharmaceutically acceptable salt thereof, optionally in a pharmaceutically acceptable carrier. In another embodiment, a method for the treatment of myasthenia gravis is provided that includes the administration of an effective amount of a compound of Formula I, or a pharmaceutically acceptable salt thereof, optionally in a pharmaceutically acceptable carrier. In another embodiment, a method for the treatment of atypical hemolytic uremic syndrome (aHUS) is provided that includes the administration of an effective amount of a compound of Formula I, or a pharmaceutically acceptable salt thereof, optionally in a pharmaceutically acceptable carrier. In another embodiment, a method for the treatment of C3 glomerulonephritis is provided that includes the administration of an effective amount of a compound of Formula I, or a pharmaceutically acceptable salt thereof, optionally in a pharmaceutically acceptable carrier. In another embodiment, a method for the treatment of abdominal aortic aneurysm is provided that includes the administration of an effective amount of a compound of Formula I, or a pharmaceutically acceptable salt thereof, optionally in a pharmaceutically acceptable carrier. In another embodiment, a method for the treatment of neuromyelitis optica (NMO) is provided that includes the administration of an effective amount of a compound of Formula I, or a pharmaceutically acceptable salt thereof, optionally in a pharmaceutically acceptable carrier.

In some embodiments, the present invention provides methods of treating or preventing an inflammatory disorder or a complement related disease, by administering to a host in need thereof an effective amount of a compound of Formula I of the invention. In some embodiments, the present invention provides methods of treating or preventing an inflammatory disorder more generally, an immune disorder, autoimmune disorder, or complement factor D related disease, by providing an effective amount of a compound or pharmaceutically acceptable salt of Formula I to patient with a factor D mediated inflammatory disorder. A compound or salt of Formula I may be provided as the only active agent or may be provided together with one or more additional active agents.

In one embodiment, a method for the treatment of a disorder associated with a dysfunction in the complement cascade is provided that includes the administration of an effective amount of a compound of Formula I, or a pharmaceutically acceptable salt thereof, optionally in a pharmaceutically acceptable carrier. In one embodiment, a method of inhibiting activation of the alternative complement pathway in a subject is provided that includes the administration of an effective amount of a compound of Formula I, or a pharmaceutically acceptable salt thereof, optionally in a pharmaceutically acceptable carrier. In one embodiment, a method of modulating factor D activity in a subject is provided that includes the administration of an effective amount of a compound of Formula I, or a pharmaceutically acceptable salt thereof, optionally in a pharmaceutically acceptable carrier.

"Prevention" as used in this disclosure means decreasing the likelihood of the appearance of symptoms in a patient administered the compound prophylactically as compared to the likelihood of the appearance of symptoms in patients not administered the compound or decreasing the severity of symptoms in a patient administered the compound prophylactically as compared to the severity of symptoms experienced by patients with the disorder or condition who were not administered the compound. In an alternative embodiment, an effective amount of a compound of Formula I is used to prevent or prophylaxis of a complement factor D related disorder.

An effective amount of a pharmaceutical composition/combination of the invention may be an amount sufficient to (a) inhibit the progression of a disorder mediated by the complement pathway, including an inflammatory, immune, including an autoimmune, disorder or complement factor D related disease; (b) cause a regression of an inflammatory, immune, including an autoimmune, disorder or complement factor D related disease; or (c) cause a cure of an inflammatory, immune, including an autoimmune, disorder or complement factor D related disease.

An effective amount of a compound or pharmaceutical composition described herein will also provide a sufficient amount of the active agent when administered to a patient to provide a clinical benefit. Such an amount may be ascertained experimentally, for example by assaying blood concentration of the agent, or theoretically, by calculating bioavailability.

V. Combination Therapy

In one embodiment, a compound or salt of Formula I may be provided in combination or alternation with at least one additional inhibitor of the complement system or a second active compound with a different biological mechanism of action. In one embodiment, a compound or salt of Formula I may be provided in combination with a complement C5 inhibitor or C5 convertase inhibitor. In another embodiment, a compound or salt of Formula I may be provided in combination with eculizumab. In one embodiment, a compound or salt of Formula I may be provided in combination with additional inhibitors of factor D.

In one embodiment, a compound or salt of Formula I may be provided together with a compound that inhibits an enzyme that metabolizes protease inhibitors. In one embodiment, a compound or salt of Formula I may be provided together with ritonavir.

In nonlimiting embodiments, a compound or salt of Formula I may be provided together with a protease inhibitor, a soluble complement regulator, a therapeutic antibody (monoclonal or polyclonal), complement component inhibitors, receptor agonists, or siRNAs.

Nonlimiting Examples of Active Agents in these Categories are:

Protease inhibitors: plasma-derived C1-INH concentrates, for example Cetor® (Sanquin), Berinert-P® (CSL Behring, Lev Pharma), and Cinryze®; and recombinant human C1-inhibitors, for example Rhucin®;

Soluble complement regulators: Soluble complement receptor 1 (TP10) (Avant Immunotherapeutics); sCR1-sLe$^x$/TP-20 (Avant Immunotherapeutics); MLN-2222/CAB-2 (Millenium Pharmaceuticals); Mirococept (Inflazyme Pharmaceuticals);

Therapeutic antibodies: Eculizumab/Soliris (Alexion Pharmaceuticals); Pexelizumab (Alexion Pharmaceuticals); Ofatumumab (Genmab A/S); TNX-234 (Tanox); TNX-558 (Tanox); TA106 (Taligen Therapeutics); Neutrazumab (G2 Therapies); Anti-properdin (Novelmed Therapeutics); HuMax-$CD_{38}$ (Genmab A/S);

Complement component inhibitors: Compstatin/POT-4 (Potentia Pharmaceuticals); ARC1905 (Archemix);

Receptor agonists: PMX-53 (Peptech Ltd.); JPE-137 (Jerini); JSM-7717 (Jerini);

Others: Recombinant human MBL (rhMBL; Enzon Pharmaceuticals).

In an embodiment, the present invention provides a method of treating or preventing age-related macular degeneration (AMD) by administering to a subject in need thereof an effective amount of a composition comprising a compound of the current invention. In one embodiment, the compositions of the present invention are administered in combination with an anti-VEGF agent. Nonlimiting examples of anti-VEGF agents include, but are not limited to, aflibercept (Eylea®; Regeneron Pharmaceuticals); ranibizumab (Lucentis®: Genentech and Novartis); and pegaptanib (Macugen®; OSI Pharmaceuticals and Pfizer); Bevacizumab (Avastin; Genentech/Roche); anecortane acetate, squalamine lactate, and corticosteroids, including, but not limited to, triamcinolone acetonide.

In another embodiment, a compound of Formula I can be combined with a second agent in order to treat a disorder of the eye.

Examples of types of therapeutic agents that can be used in combination for ocular applications include anti-inflammatory drugs, antimicrobial agents, anti-angiogenesis agents, immunosuppressants, antibodies, steroids, ocular antihypertensive drugs and combinations thereof. Examples of therapeutic agents include amikacin, anecortane acetate, anthracenedione, anthracycline, an azole, amphotericin B, bevacizumab, camptothecin, cefuroxime, chloramphenicol, chlorhexidine, chlorhexidine digluconate, clortrimazole, a clotrimazole cephalosporin, corticosteroids, dexamethasone, desamethazone, econazole, eftazidime, epipodophyllotoxin, fluconazole, flucytosine, fluoropyrimidines, fluoroquinolines, gatifloxacin, glycopeptides, imidazoles, itraconazole, ivermectin, ketoconazole, levofloxacin, macrolides, miconazole, miconazole nitrate, moxifloxacin, natamycin, neomycin, nystatin, ofloxacin, polyhexamethylene biguanide, prednisolone, prednisolone acetate, pegaptanib, platinum analogues, polymicin B, propamidine isethionate, pyrimidine nucleoside, ranibizumab, squalamine lactate, sulfonamides, triamcinolone, triamcinolone acetonide, triazoles, vancomycin, anti-vascular endothelial growth factor (VEGF) agents, VEGF antibodies, VEGF antibody fragments, vinca alkaloid, timolol, betaxolol, travoprost, latanoprost, bimatoprost, brimonidine, dorzolamide, acetazolamide, pilocarpine, ciprofloxacin, azithromycin, gentamycin, tobramycin, cefazolin, voriconazole, gancyclovir, cidofovir, foscarnet, diclofenac, nepafenac, ketorolac, ibuprofen, indomethacin, fluoromethalone, rimexolone, anecortave, cyclosporine, methotrexate, tacrolimus and combinations thereof. Examples of eye disorders that may be treated according to the compositions and methods disclosed herein include amoebic keratitis, fungal keratitis, bacterial keratitis, viral keratitis, onchorcercal keratitis, bacterial keratoconjunctivitis, viral keratoconjunctivitis, corneal dystrophic diseases, Fuchs' endothelial dystrophy, Sjogren's syndrome, Stevens-Johnson syndrome, autoimmune dry eye diseases, environmental dry eye diseases, corneal neovascularization diseases, post-corneal transplant rejection prophylaxis and treatment, autoimmune uveitis, infectious uveitis, anterior uveitis, posterior uveitis (including toxoplasmosis), pan-uveitis, an inflammatory disease of the vitreous or retina, endophthalmitis prophylaxis and treatment, macular edema, macular degeneration, age related macular degeneration, proliferative and non-proliferative diabetic retinopathy, hypertensive retinopathy, an autoimmune disease of the retina, primary and metastatic intraocular melanoma, other intraocular metastatic tumors, open angle glaucoma, closed angle glaucoma, pigmentary glaucoma and combinations thereof.

A compound of Formula I, or a combination of Formula I and another active agent, can be administered into an eye compartment of via injection into the vitreous chamber, subretinal space, subchoroidal space, the episclera, the conjunctiva, the sclera, the anterior chamber, and the cornea and compartments therein (e.g., subepithelial, intrastromal, endothelial).

In an alternative embodiment, a compound of Formula I, or a combination of Formula I and another active agent, can be administered into an eye compartment via binding to a mucosal penetrating particle to treat a condition located in the vitreous chamber, subretinal space, subchoroidal space, the episclera, the conjunctiva, the sclera or the anterior chamber, and the cornea and compartments therein (e.g., subepithelial, intrastromal, endothelial). Mucosal penetrating particles are known in the art, and are described in, for example, PCT published application WO 2013166436 to Kala Pharmaceuticals, incorporated in its entirety herein.

In other embodiments, a composition comprising compound of Formula I suitable for topical administration to an eye is provided. The pharmaceutical composition comprises a plurality of coated particles, comprising a core particle comprising a compound of Formula I, wherein Formula I constitutes at least about 80 wt % of the core particle, and a coating comprising one or more surface-altering agents, wherein the one or more surface-altering agents comprise at least one of a poloxamer, a poly(vinyl alcohol), or a polysorbate. The one or more surface-altering agents is present on the outer surface of the core particle at a density of at least 0.01 molecules/nm. The one or more surface-altering agents is present in the pharmaceutical composition in an amount of between about 0.001% to about 5% by weight. The plurality of coated particles have an average smallest cross-sectional dimension of less than about 1 micron. The pharmaceutical composition also includes one or more ophthalmically acceptable carriers, additives, and/or diluents.

It will be appreciated by one of ordinary skill in the art that particles suitable for use with the presently disclosed methods can exist in a variety of shapes, including, but not limited to, spheroids, rods, disks, pyramids, cubes, cylinders, nanohelixes, nanosprings, nanorings, rod-shaped particles, arrow-shaped particles, teardrop-shaped particles, tetrapod-shaped particles, prism-shaped particles, and a plurality of other geometric and non-geometric shapes. In some embodiments, the presently disclosed particles have a spherical shape.

In one embodiment, the present invention provides a method of treating or preventing paroxysmal nocturnal hemoglobinuria (PNH) by administering to a subject in need thereof an effective amount of a composition comprising a compound of the current invention. In one embodiment, the present invention provides a method of treating or preventing paroxysmal nocturnal hemoglobinuria (PNH) by administering to a subject in need thereof an effective amount of a composition comprising a compound of the current invention in combination or alternation with additional inhibitors of the complement system or another active compound with a different biological mechanism of action. In another embodiment, the present invention provides a method of treating or preventing paroxysmal nocturnal hemoglobinuria (PNH) by administering to a subject in need thereof an effective amount of a composition comprising a compound of the current invention in combination or alternation with eculizumab.

In one embodiment, the present invention provides a method of treating or preventing rheumatoid arthritis by administering to a subject in need thereof an effective amount of a composition comprising a compound of the current invention. In one embodiment, the present invention provides a method of treating or preventing rheumatoid arthritis by administering to a subject in need thereof an effective amount of a composition comprising a compound of the current invention in combination or alternation with an additional inhibitor of the complement system. In another embodiment, the present invention provides a method of treating or preventing rheumatoid arthritis by administering to a subject in need thereof an effective amount of a composition comprising a compound of the current invention in combination or alternation with methotrexate.

In certain embodiments, a compound of Formula I is administered in combination or alternation with at least one anti-rhuematoid arthritis drug selected from: salicylates including aspirin (Anacin, Ascriptin, Bayer Aspirin, Ecotrin) and salsalate (Mono-Gesic, Salgesic); nonsteroidal anti-inflammatory drugs (NSAIDs); nonselective inhibitors of the cyclo-oxygenase (COX-1 and COX-2) enzymes, including diclofenac (Cataflam, Voltaren), ibuprofen (Advil, Motrin), ketoprofen (Orudis), naproxen (Aleve, Naprosyn), piroxicam (Feldene), etodolac (Lodine), indomethacin, oxaprozin (Daypro), nabumetone (Relafen), and meloxicam (Mobic); selective cyclo-oxygenase-2 (COX-2) inhibitors including Celecoxib (Celebrex); disease-modifying anti-rheumatic drugs (DMARDs), including azathioprine (Imuran), cyclosporine (Sandimmune, Neoral), gold salts (Ridaura, Solganal, Aurolate, Myochrysine), hydroxychloroquine (Plaquenil), leflunomide (Arava), methotrexate (Rheumatrex), penicillamine (Cuprimine), and sulfasalazine (Azulfidine); biologic drugs including abatacept (Orencia), etanercept (Enbrel), infliximab (Remicade), adalimumab (Humira), and anakinra (Kineret); corticosteroids including betamethasone (Celestone Soluspan), cortisone (Cortone), dexamethasone (Decadron), methylprednisolone (SoluMedrol, DepoMedrol), prednisolone (Delta-Cortef), prednisone (Deltasone, Orasone), and triamcinolone (Aristocort); gold salts, including Auranofin (Ridaura); Aurothioglucose (Solganal); Aurolate; Myochrysine; or any combination thereof.

In one embodiment, the present invention provides a method of treating or preventing multiple sclerosis by administering to a subject in need thereof an effective amount of a composition comprising a compound of the current invention. In one embodiment, the present invention provides a method of treating or preventing multiple sclerosis by administering to a subject in need thereof an effective amount of a composition comprising a compound of the current invention in combination or alternation with additional inhibitors of the complement system. In another embodiment, the present invention provides a method of treating or preventing multiple sclerosis by administering to a subject in need thereof an effective amount of a composition comprising a compound of the current invention in combination or alternation with a corticosteroid. Examples of corticosteroids include, but are not limited to, prednisone, dexamethasone, solumedrol, and methylprednisolone.

In one embodiment, a compound of Formula I is combined with at least one anti-multiple sclerosis drug selected from: Aubagio (teriflunomide), Avonex (interferon beta-la), Betaseron (interferon beta-lb), Copaxone (glatiramer acetate), Extavia (interferon beta-lb), Gilenya (fingolimod), Lemtrada (alemtuzumab), Novantrone (mitoxantrone), Plegridy (peginterferon beta-la), Rebif (interferon beta-la), Tecfidera (dimethyl fumarate), Tysabri (natalizumab), Solu-Medrol (methylpredni solone), High-dose oral Deltasone (prednisone), H.P. Acthar Gel (ACTH), and combinations thereof.

In one aspect, a compound or salt of Formula I may be provided in combination or alternation with an immunosuppressive agent or an anti-inflammatory agent.

In one embodiment of the present invention, a compound described herein can be administered in combination or alternation with at least one immunosuppressive agent. The immunosuppressive agent as nonlimiting examples, may be a calcineurin inhibitor, e.g. a cyclosporin or an ascomycin, e.g. Cyclosporin A (NEORAL®), FK506 (tacrolimus), pimecrolimus, a mTOR inhibitor, e.g. rapamycin or a derivative thereof, e.g. Sirolimus (RAPAMUNE®), Everolimus (Certican®), temsirolimus, zotarolimus, biolimus-7, biolimus-9, a rapalog, e.g.ridaforolimus, azathioprine, campath 1H, a S1P receptor modulator, e.g. fingolimod or an analogue thereof, an anti IL-8 antibody, mycophenolic acid or a salt thereof, e.g. sodium salt, or a prodrug thereof, e.g. Mycophenolate Mofetil (CELLCEPT®), OKT3 (ORTHOCLONE OKT3®), Prednisone, ATGAM®, THYMOGLOBULIN®, Brequinar Sodium, OKT4, T1OB9.A-3A, 33B3.1, 15-deoxyspergualin, tresperimus, Leflunomide ARAVA®, CTLAI-Ig, anti-$CD_{25}$, anti-IL2R, Basiliximab (SIMULECT®), Daclizumab (ZENAPAX®), mizorbine, methotrexate, dexamethasone, ISAtx-247, SDZ ASM 981 (pimecrolimus, Elidel®), CTLA4lg (Abatacept), belatacept, LFA3lg, etanercept (sold as Enbrel® by Immunex), adalimumab (Humira®), infliximab (Remicade®), an anti-LFA-1 antibody, natalizumab (Antegren®), Enlimomab, gavilimomab, antithymocyte immunoglobulin, siplizumab, Alefacept efalizumab, pentasa, mesalazine, asacol, codeine phosphate, benorylate, fenbufen, naprosyn, diclofenac, etodolac and indomethacin, aspirin and ibuprofen.

Examples of anti-inflammatory agents include methotrexate, dexamethasone, dexamethasone alcohol, dexamethasone sodium phosphate, fluromethalone acetate, fluromethalone alcohol, lotoprendol etabonate, medrysone, prednisolone acetate, prednisolone sodium phosphate, difluprednate, rimexolone, hydrocortisone, hydrocortisone acetate, lodoxamide tromethamine, aspirin, ibuprofen, suprofen, piroxicam, meloxicam, flubiprofen, naproxan, ketoprofen, tenoxicam, diclofenac sodium, ketotifen fumarate, diclofenac sodium, nepafenac, bromfenac, flurbiprofen sodium, suprofen, celecoxib, naproxen, rofecoxib, glucocorticoids, diclofenac, and any combination thereof. In one embodiment, a compound of Formula I is combined with one or more non-steroidal anti-inflammatory drugs (NSAIDs) selected from naproxen sodium (Anaprox), celecoxib (Celebrex), sulindac (Clinoril), oxaprozin (Daypro), salsalate (Disalcid), diflunisal (Dolobid), piroxicam (Feldene), indomethacin (Indocin), etodolac (Lodine), meloxicam (Mobic), naproxen (Naprosyn), nabumetone (Relafen), ketorolac tromethamine (Toradol), naproxen/esomeprazole (Vimovo), and diclofenac (Voltaren), and combinations thereof.

VI. Process of Preparation of Compounds of Formula I

Abbreviations $(Boc)_2O$ di-tert-butyl dicarbonate
AcCl acetyl chloride
ACN Acetonitrile
AcOEt, EtOAc ethyl acetate
AcOH acetic acid
$CH_3OH$, MeOH Methanol
CsF Cesium fluoride
CuI Cuprous iodide
DCM, $CH_2Cl_2$ Dichloromethane
DIEA, DIPEA N,N-diisopropylethylamine
DMA N,N-dimethylacetamide
DMF N,N-dimethylformamide
DMSO Dimethylsulfoxide
DPPA Diphenyl phosphoryl azide
Et3N, TEA Triethylamine
EtOAc Ethylacetate
EtOH Ethanol
FA formic acid
HATU 1-[Bis(dimethylamino)methylene]-1H-1,2,3-triazolo[4,5-b]pyridinium 3-oxide hexafluorophosphate
HCl Hydrochloric acid
$^iPr_2NEt$ N,N-diisopropylethylamine
$K_2CO_3$ Potassium carbonate
LiOH Lithium hydroxide
MTBE Methyl $^t$butylether
$Na_2SO_4$ Sodium sulfate
NaCl Sodium chloride
NaH Sodium hydride
$NaHCO_3$ Sodium bicarbonate
$NEt_3$ triethylamine
Pd $(OAc)_2$ Palladium acetate
Pd(dppf)$Cl_2$ [1,1'-Bis(diphenylphosphino) ferrocene]dichloropalladium(II)
$Pd(PPh_3)_2Cl_2$ Bis(triphenylphosphine)palladium(II) dichloride
$Pd(PPh_3)_4$ Tetrakis(triphenylphosphine)palladium(O)
$Pd_2(dba)_3$ Tris(dibenzylideneacetone)dipalladium(O)
$PPh_3$ Triphenylphosphine
RT Room temperature
tBuOK potassium tert-butoxide
TEA triethylamine
$Tf_2O$ trifluoromethanesulfonic anhydride
TFA Trifluoroacetic acid
THF Tetrahydrofuran
TMSBr bromotrimethylsilane
$t_R$ Retention time
$Zn(CN)_2$ Zinc cyanide

General Methods

All nonaqueous reactions were performed under an atmosphere of dry argon or nitrogen gas using anhydrous solvents. The progress of reactions and the purity of target compounds were determined using one of the two liquid chromatography (LC) methods listed below. The structure of starting materials, intermediates, and final products was confirmed by standard analytical techniques, including NMR spectroscopy and mass spectrometry.

LC Method A

Instrument: Waters Acquity Ultra Performance LC

Column: ACQUITY UPLC BEH C18 2.1×50 mm, 1.7 μm

Column Temperature: 40° C.

Mobile Phase: Solvent A: $H_2O$+0.05% FA; Solvent B: $CH_3CN$+0.05% FA

Flow Rate: 0.8 mL/min

Gradient: 0.24 min @ 15% B, 3.26 min gradient (15-85% B), then 0.5 min @ 85% B.

Detection: UV (PDA), ELS, and MS (SQ in EI mode)

LC Method B

Instrument: Shimadzu LC-2010A HT

Column: Athena, C18-WP, 50×4.6 mm, 5 m

Column Temperature: 40° C.

Mobile Phase: Solvent A: $H_2O/CH_3OH$/FA=90/10/0.1; Solvent B: $H_2O/CH_3OH$/FA=10/90/0.1

Flow Rate: 3 mL/min

Gradient: 0.4 min @ 30% B, 3.4 min gradient (30-100% B), then 0.8 min @ 100% B

Detection: UV (220/254 nm)

Example 1. General Route of Synthesis

A compound of the present invention can be prepared, for example, from a central core. In one embodiment, for example, the central core Structure 1 is an N-protected aminoacid where $X^1$ is nitrogen and PG=protecting group. In one embodiment, the central core is coupled to an amine to generate an amide of Structure 2 (wherein L-B includes a C(O)N moiety). Structure 2 can then be deprotected to generate Structure 3. Structure 3 is coupled to Structure 4 (A-COOH) to generate a second amide bond, forming a compound within Formula I. The chemistry is illustrated in Route 1.

Route 1

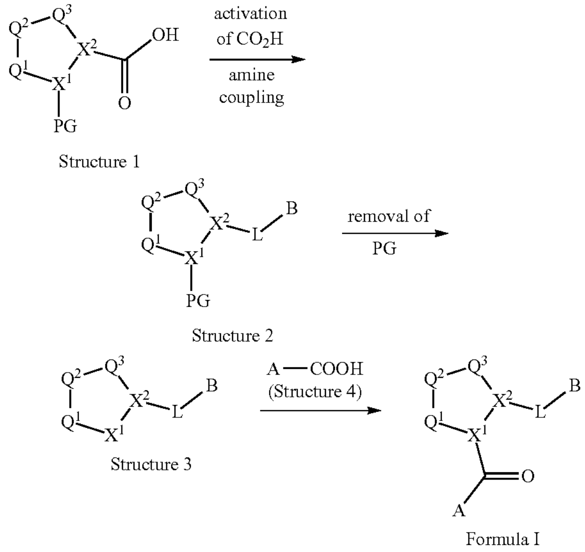

Structure 1
Structure 2
Structure 3
Formula I

In an alternative embodiment, central core Structure 5 is reacted with a heterocyclic or heteroaryl compound to generate a compound of Structure 6. In one embodiment, Structure 6 is deprotected to generate a carboxylic acid, Structure 7. In one embodiment, Structure 7 is coupled to an amine to generate a compound of Formula I. This chemistry is illustrated in Route 2.

Route 2

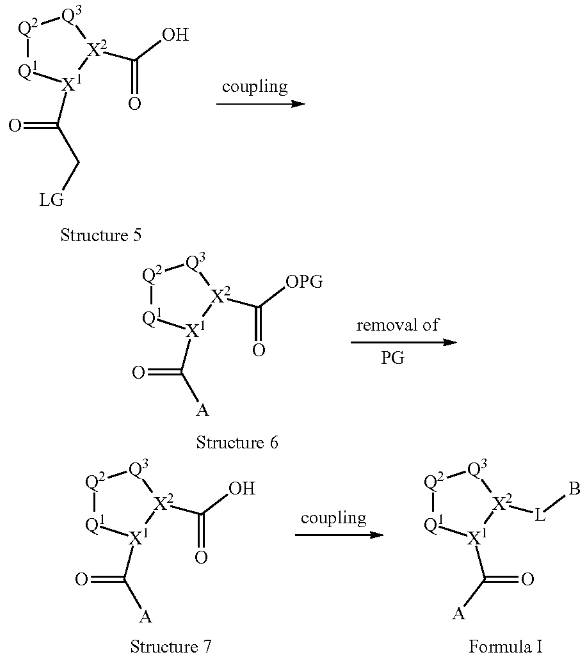

Structure 5
Structure 6
Structure 7
Formula I

In an alternative embodiment, Structure 8 is deprotected to generate an amine which is Structure 9. Structure 9 is then coupled to generate an amide which is Structure 6. Structure 6 is then deprotected to generate a carboxylic acid which is Structure 7. Structure 7 is then coupled to form the amide which falls within Formula I. The chemistry is illustrated in Route 3.

Route 3

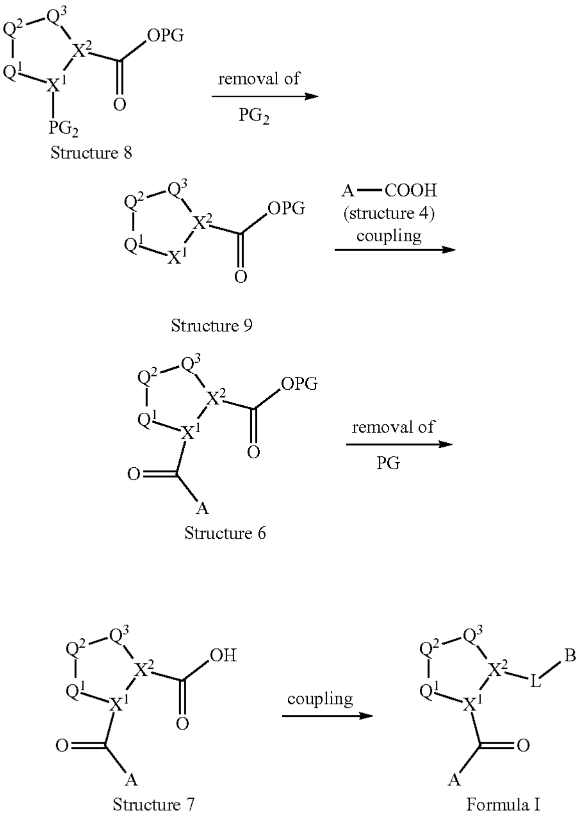

Structure 8
Structure 9
Structure 6
Structure 7
Formula I

In an alternate embodiment, a heteroaryl or aryl moiety, 4-1, is coupled to a central core to generate 4-2. The protected acid, 4-2 is deblocked to form the carboxylic acid, 4-3. The carboxylic acid is then coupled to form an amide (L-B) which is 4-4. The heteroaryl or aryl moiety, A', can then be further derivatized to add substitutents at the $X^{11}$, $X^{12}$, $X^{13}$ and $X^{14}$ positions to generate compounds of Formula I. This chemistry is illustrated in Route 4.

Route 4

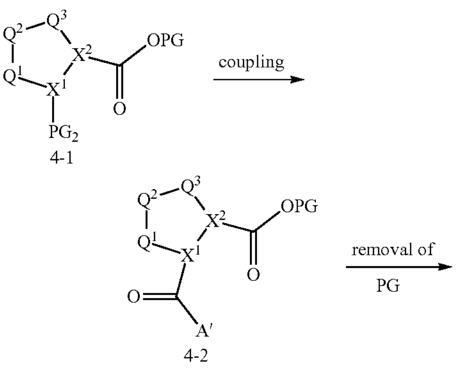

4-1
4-2

-continued

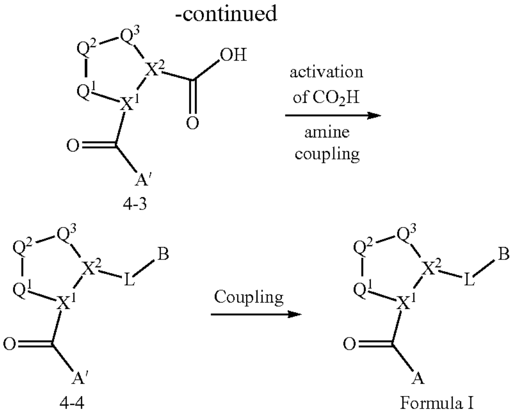

4-3

4-4

Formula I

In an alternate embodiment, Structure 5-1 is coupled to an acid, Structure 5-2, to generate Structure 5-3. The carboxylic acid, Structure 5-3, is deblocked to generate a carboxylic acid which is Structure 5-4. Carboxylic acid Structure 5-4 is coupled to an amine to form the product amide (L-B) which is a compound within Formula I. This chemistry is illustrated in Route 5.

Route 5

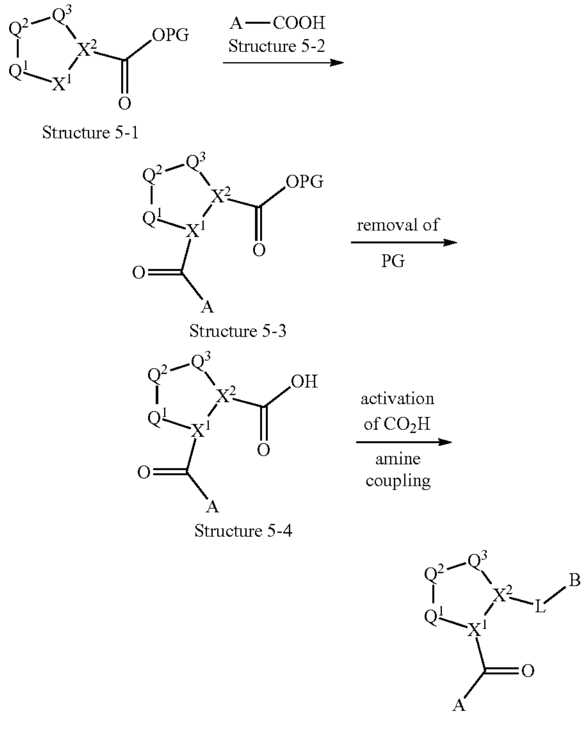

Structure 5-1

Structure 5-3

Structure 5-4

Formula I

In an alternate embodiment, the protected indole, Structure 6-1, is acylated to generate Structure 6-2. Structure 6-2 is treated with the activated ester, Structure 6-3 to generate Structure 6-4. Structure 6-4 is deprotected to generated Structure 6-5. Structure 6-5 is deprotected to generate the carboxylic acid 6-6. Structure 6-6 is coupled to Structure 3 from Route 1 to generate Structure 6-7. The alcohol is converted to a leaving group, LG; see, Structure 6-8. Structure 6-8 is treated with a phosphite, an organometallic reagent, a base and an organic solvent to generate a compound within Formula I. In some embodiments, the organometallic reagent is tetrakis(triphenylphosphine)palladium (O). In some embodiments, the base is triethylamine. In some embodiments, the organic solvent is tetrahydrofuran. The chemistry is illustrated in Route 6.

Route 6

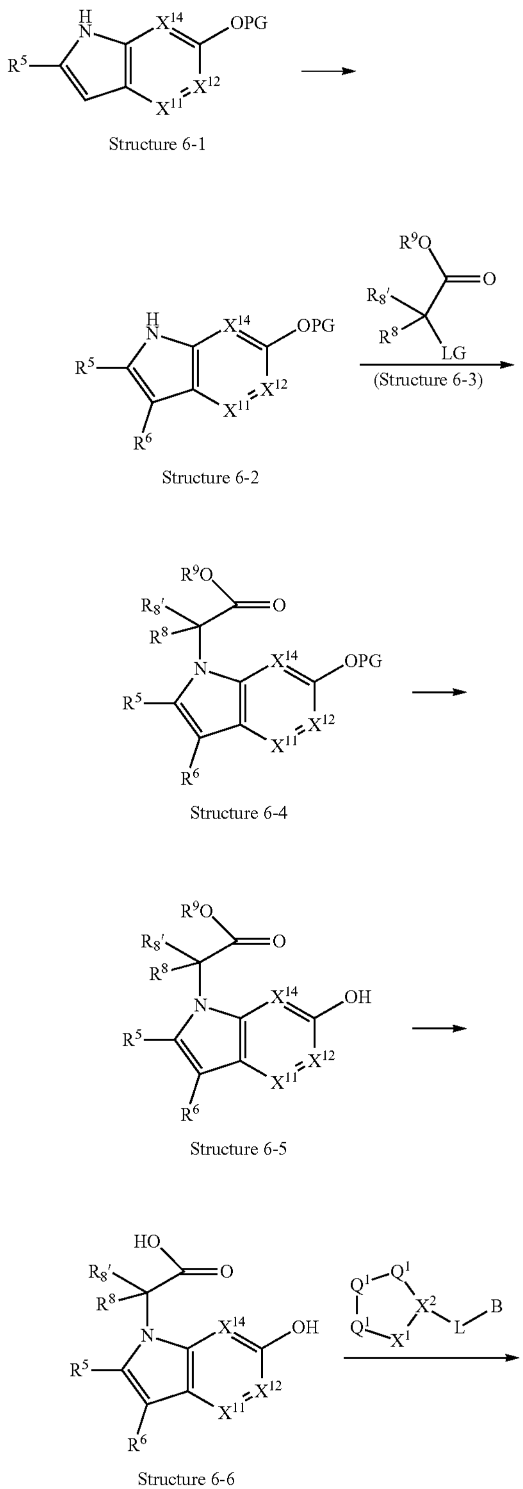

Structure 6-1

Structure 6-2

Structure 6-4

Structure 6-5

Structure 6-6

-continued

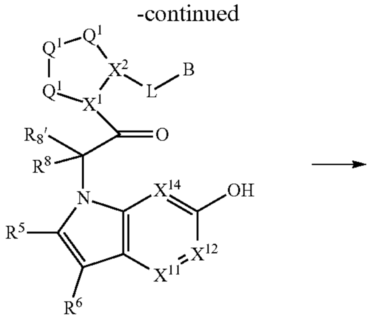

Structure 6-7

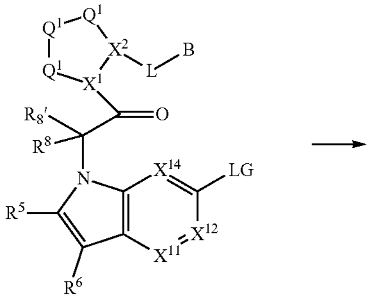

Structure 6-8

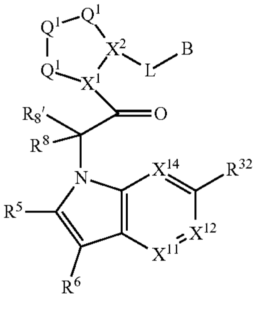

Formula I

In an alternate embodiment, the protected indole, Structure 7-1, is acylated to generate Structure 7-2. Structure 7-2 is treated with the activated ester, Structure 7-3, to generate Structure 7-4. Structure 7-4 is deprotected to generated Structure 7-5. Structure 7-5 is deprotected to generate the carboxylic acid 7-6. Structure 7-6 is coupled to Structure 3 from Route 1 to generate Structure 7-7. The alcohol is converted to a leaving group, LG; see, Structure 7-8. Structure 7-8 is treated with a phosphite, an organometallic reagent, a base and an organic solvent to generate a compound within Formula I. In some embodiments, the organometallic reagent is tetrakis(triphenylphosphine)palladium (O). In some embodiments, the base is triethylamine. In some embodiments, the organic solvent is tetrahydrofuran. This chemistry is illustrated in Route 7 below.

Route 7

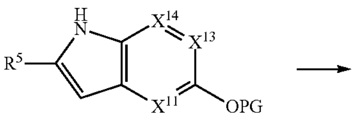

Structure 7-1

-continued

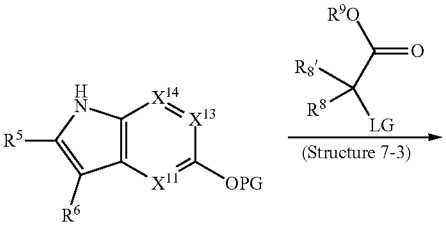

Structure 7-2

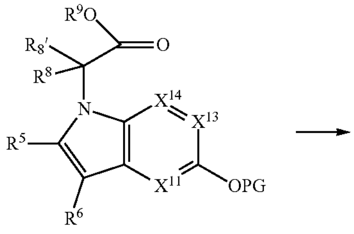

Structure 7-4

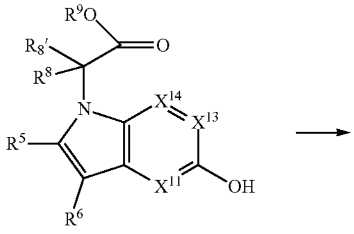

Structure 7-5

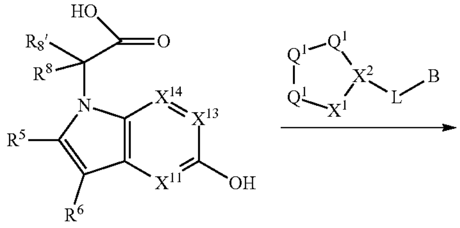

Structure 7-6

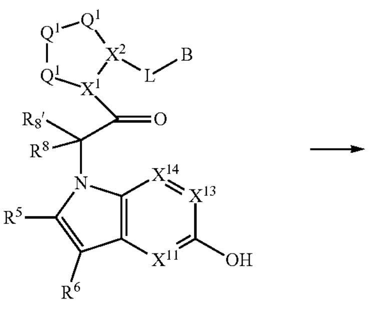

Structure 7-7

-continued

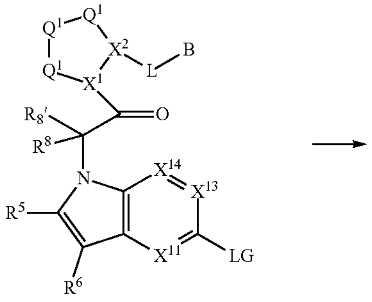

Structure 7-8

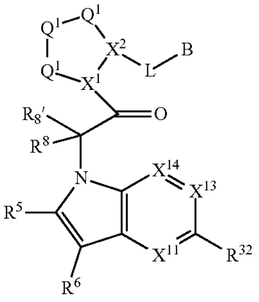

Formula I

In an alternate embodiment, a protected indazole, Structure 8-1, is acylated to generate Structure 8-2. Structure 8-2 is treated with the activated ester, Structure 8-3, to generate Structure 8-4. Structure 8-4 is deprotected to generated Structure 8-5. Structure 8-5 is deprotected to generate the carboxylic acid 8-6. Structure 8-6 is coupled to Structure 3 from Route 1 to generate Structure 8-7. The alcohol in Structure 8-7 is converted to a leaving group; see, Structure 8-8. Structure 8-8 is treated with a phosphite, an organometallic reagent, a base and an organic solvent to generate a compound within Formula I. In some embodiments, the organometallic reagent is tetrakis(triphenylphosphine)palladium(O). In some embodiments, the base is triethylamine. In some embodiments, the organic solvent is tetrahydrofuran. In some embodiments, the phosphite is diethyl phosphite. The chemistry is illustrated in Route 8 below.

Route 8

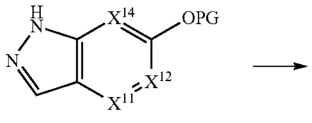

Structure 8-1

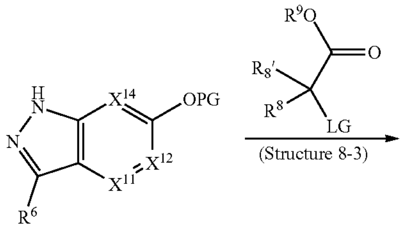

Structure 8-2

-continued

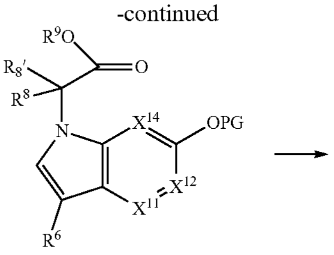

Structure 8-4

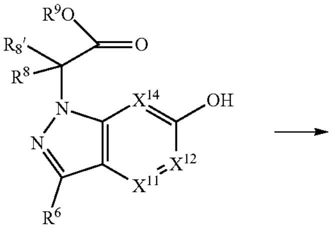

Structure 8-5

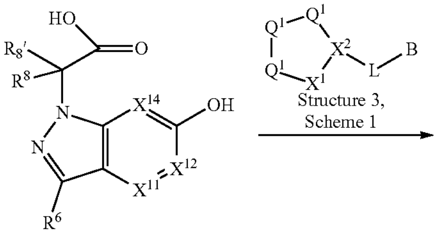

Structure 8-6

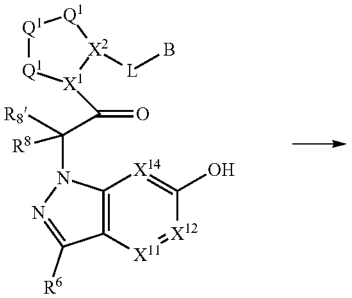

Structure 8-7

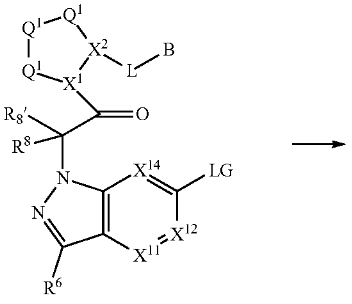

Structure 8-8

-continued

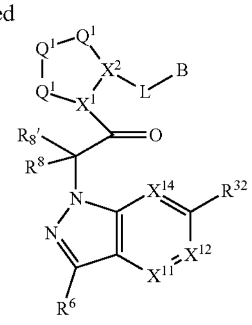

Formula I

In an alternate embodiment, a protected indazole, Structure 9-1, is acylated to generate Structure 9-2. Structure 9-2 is treated with the activated ester, Structure 9-3, to generate Structure 9-4. Structure 9-4 is deprotected to generated Structure 9-5. Structure 9-5 is deprotected to generate the carboxylic acid 9-6. Structure 9-6 is coupled to Structure 3 from Route 1 to generate Structure 9-7. The alcohol is converted to a leaving group; see, Structure 9-8. Structure 9-8 is treated with a phosphite, an organometallic reagent, a base and an organic solvent to generate a compound within Formula I. In some embodiments, the phosphite is diethyl phosphite. In some embodiments, the organometallic reagent is tetrakis(triphenylphosphine)palladium(O). In some embodiments, the base is triethylamine. In some embodiments, the organic solvent is tetrahydrofuran. The chemistry is illustrated in Route 9 below.

Route 9

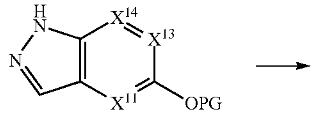

Structure 9-1

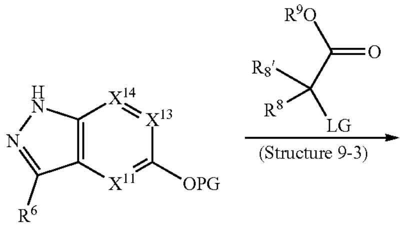

Structure 9-2

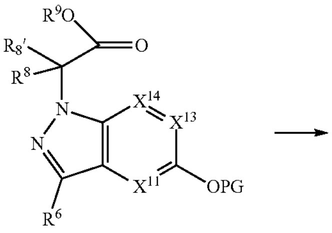

Structure 9-4

-continued

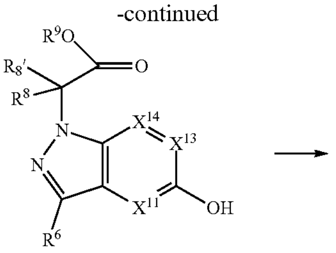

Structure 9-5

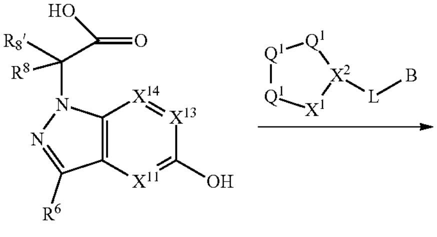

Structure 9-6

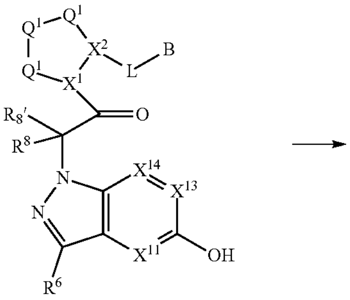

Structure 9-7

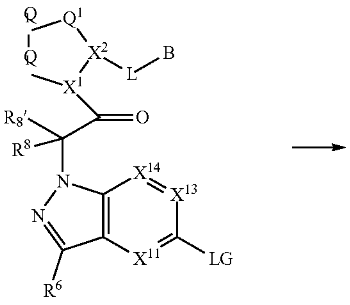

Structure 9-8

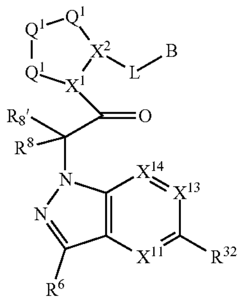

Formula I

In an alternate embodiment, a diethyl phosphonate from Route 9 is treated with TMSBr to generate a monoester, see, Structure 1, Route 10. In an alternate embodiment, a diethylphosphonate is treated with TMSBr to generate the phosphonic acid; Structure 2. The phosphonic acid Structure 2 can be used to generate phosphonate esters of the present invention, wherein the phosphonate is —P(O)$R^{20}R^{20}$. For example, Structure 2 can be treated with X—C($R^{20a}$)OC(O)$R^{20b}$ to form a mixture of mono and diesters that can be separated by chromatography, wherein X is a leaving group. In one embodiment the leaving group is a halide. This chemistry is illustrated in Route 10.

Route 10

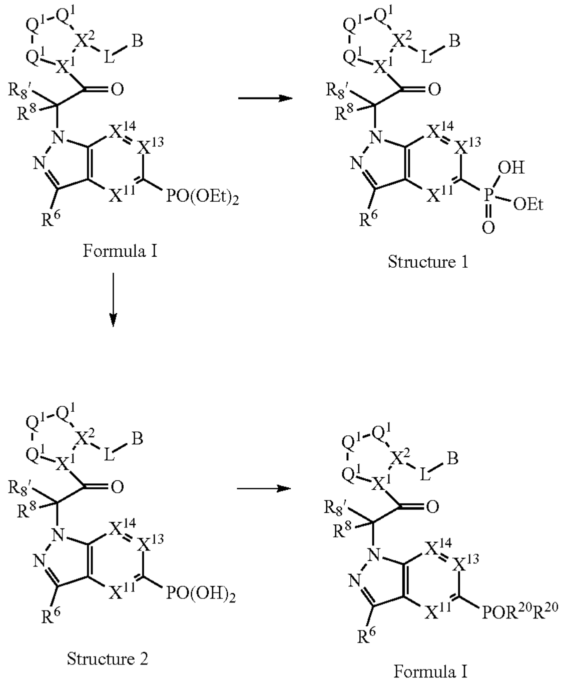

Formula I

Structure 1

Structure 2

Formula I

In an alternate embodiment, a diethyl phosphonate from Route 8 is treated with TMSBr to generate a monoester, see, Structure 1, Route 11. In an alternate embodiment, a diethyl phosphonate is treated with TMSBr to generate the phosphonic acid; Structure 2. The phosphonic acid Structure 2 can be used to generate phosphonate esters of the present invention, wherein the phosphonate is —P(O)$R^{20}R^{20}$. For example, Structure 2 can be treated with X—C($R^{20a}$)OC(O)$R^{20b}$ to form a mixture of mono and diesters that can be separated by chromatography, wherein X is a leaving group. In one embodiment the leaving group is a halide. This chemistry is illustrated in Route 11.

Route 11

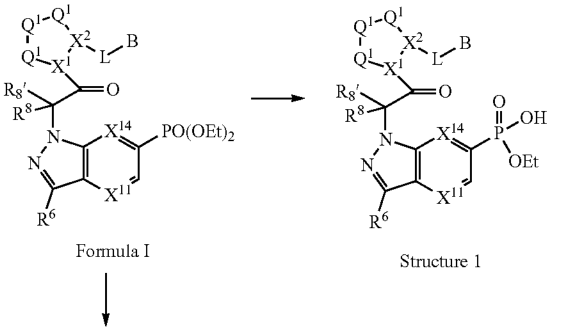

Formula I

Structure 1

-continued

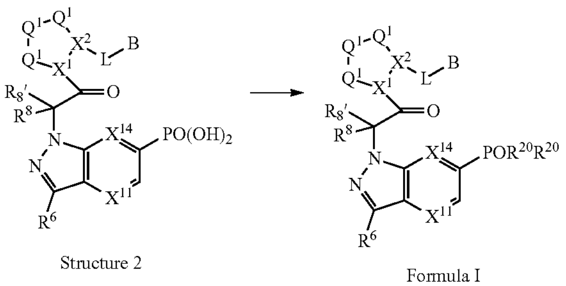

Structure 2

Formula I

In an alternate embodiment, Structure 12-1 is coupled to an amine to generate an amide (L-B), which is Structure 12-2. Structure 12-2, is coupled to an amine to generate compounds within Formula I. This chemistry is illustrated in Route 12.

Route 12

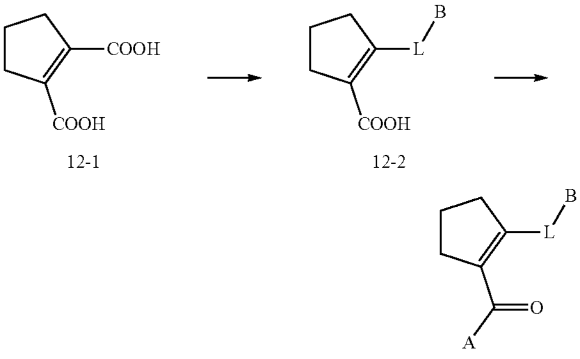

12-1

12-2

Formula I

Example 2. Examples of Central Synthons

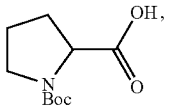

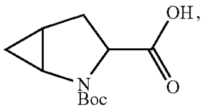

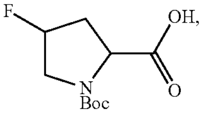

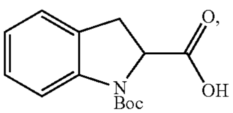

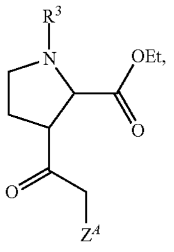

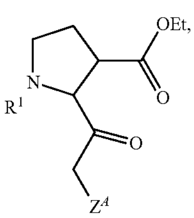

-continued
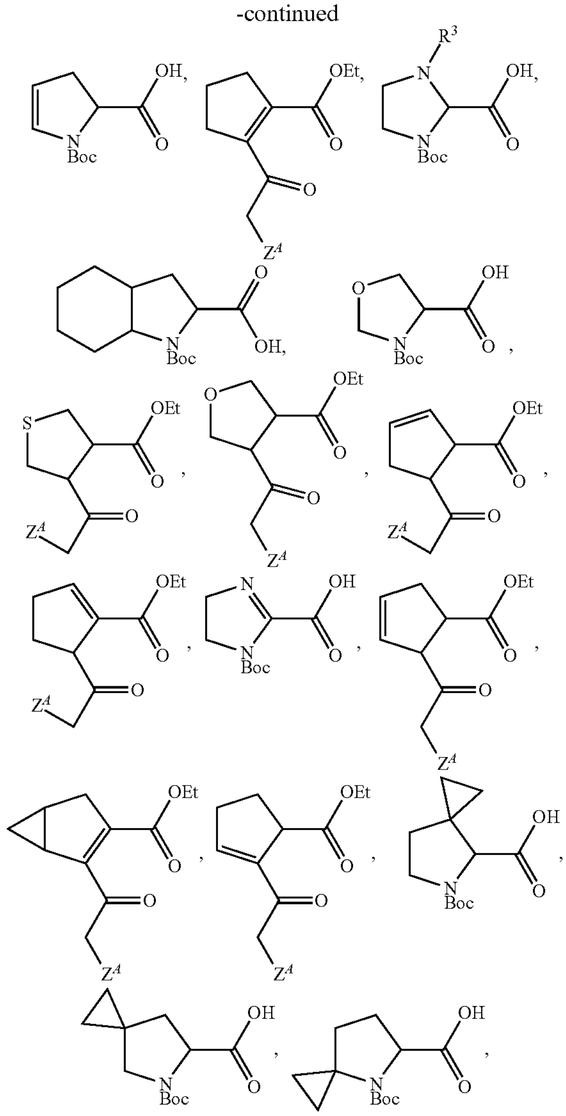
-continued
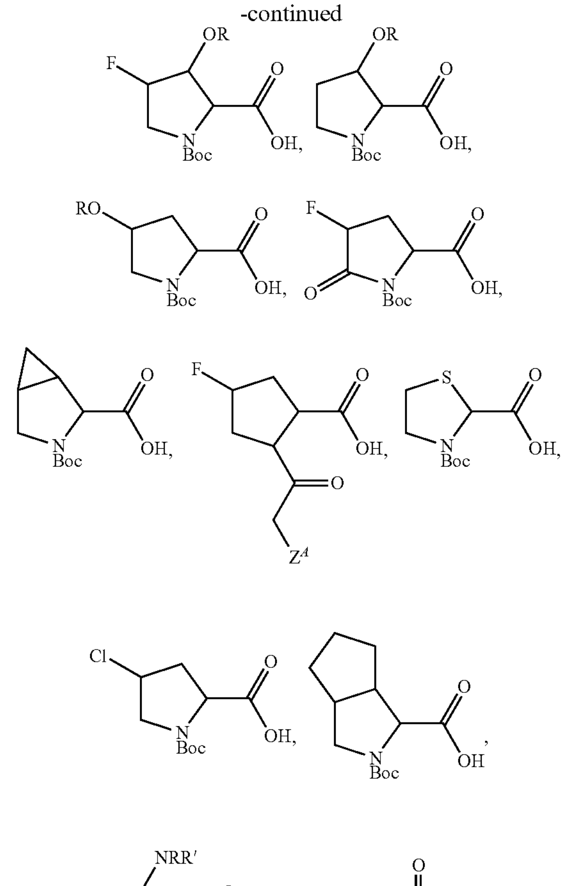
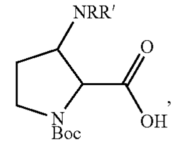
, and
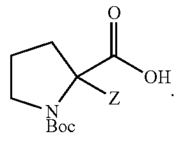
.
$Z^A$ is halogen.
In one embodiment, deuterated L-proline synthons are disclosed. Deuterated synthons include, but are not limited to, for example, the following compounds:
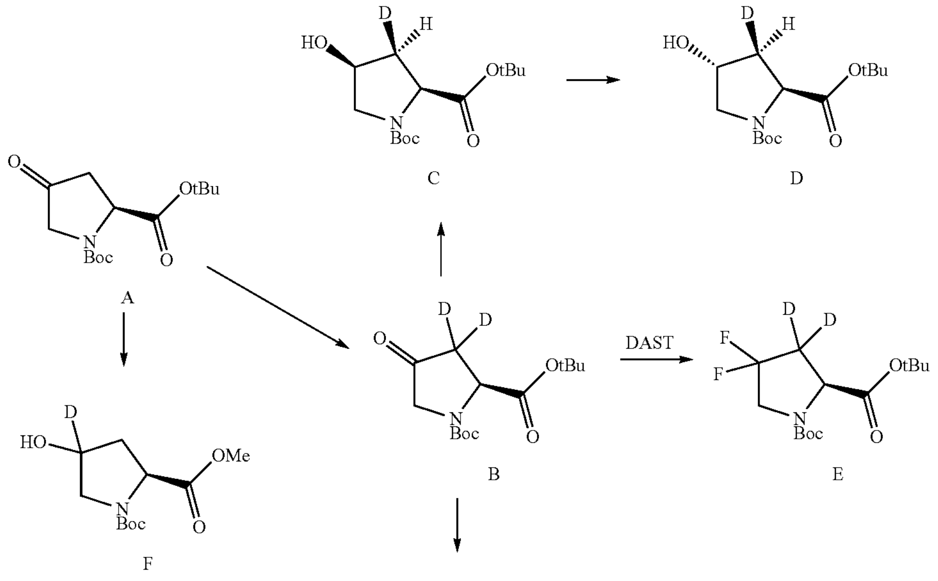

-continued

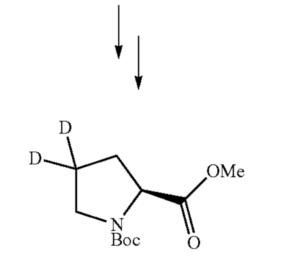

K

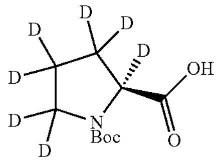

J

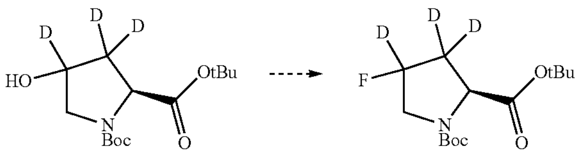

H H

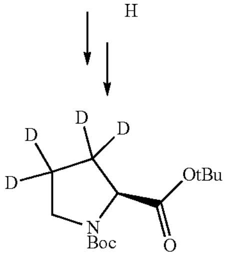

I

Structure A can be treated with deuterium oxide to generate Structure B. See, Barraclough, P. et al. Tetrahedron Lett. 2005, 46, 4653-4655; Barraclough, P. et al. Org. Biomol. Chem. 2006, 4, 1483-1491 and WO 2014/037480 (p. 103). Structure B can be reduced to generate Structure C. See, Barraclough, P. et al. Tetrahedron Lett. 2005, 46, 4653-4655; Barraclough, P. et al. Org. Biomol. Chem. 2006, 4, 1483-1491. Structure C can be treated with Mitsunobu reaction conditions to generate Structure D. Structure B can be treated with DAST to generate Structure E. See, WO 2014/037480. Structure A can be treated with sodium borodeuteride to generate Structure F. See, Dormoy, J.-R.; Castro, B. *Synthesis* 1986, 81-82. Compound F can be used to generate Structure K. See, Dormoy, J.-R.; Castro, B. *Synthesis* 1986, 81-82. Structure B can be treated with a deuterated reducing agent, for example sodium borodeuteride to generate Structure G. Structure G can be treated with DAST to generate Structure H. Structure F can be used to generate Structure K. See, Dormoy, J.-R.; Castro, B. *Synthesis* 1986, 81-82. Structure G can be used to generate Structure I. Structure J can be prepared according to Hruby, V. J. et al. *J. Am. Chem. Soc.* 1979, 101, 202-212. Structures A-J can be used to prepare compounds of Formula I.

Example 3. Preparation of Central-L-B Synthons

Routes 1a, 1b and 1c.

(1a)

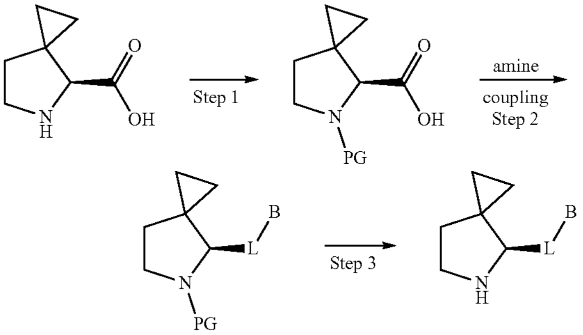

-continued (1b)

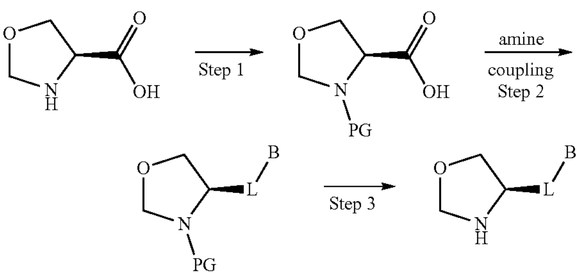

(1c)

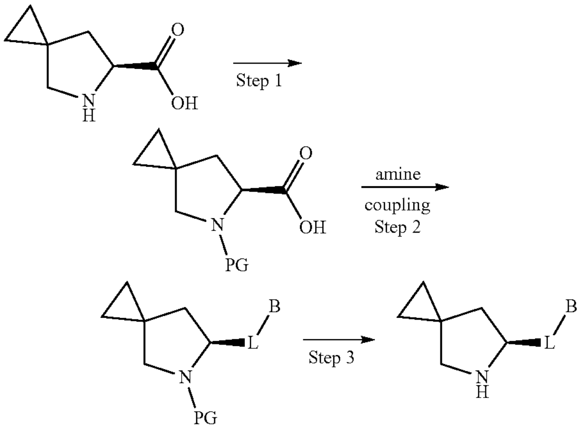

In Route 1a, 5-azaspiro[2.4]heptane-4,5-dicarboxylic acid, 5-(1,1-dimethylethyl) ester, (4S)-, CAS 209269-08-9, can be prepared as described in Tandon, M. et al. Bioorg. Med. Chem. Lett. 1998, 8, 1139-1144. In Step 2, the protected azaspiro[2.4]heptane is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 3, the protecting group is removed. In one embodiment, the starting material is reacted with an acid in the presence of an organic solvent. In one embodiment, the acid is 4N hydrochloric acid. In one embodiment, the organic solvent is dioxane.

In Route 1b, (4S) 4-oxazolidinecarboxylic acid, hydrochloride is treated with an amine protecting reagent. In one embodiment, the amine protecting reagent is di-tert-butyl dicarbonate. In another embodiment, 3,4-oxazolidinedicarboxylic acid, 3-(1,1-dimethylethyl) ester, (4S)-, is commercially available from JPM2 Pharmaceuticals. In one embodiment the reaction is carried out in an organic solvent in the presence of a base. In one embodiment, the organic solvent is acetonitrile. In one embodiment, the base is 4-dimentylaminopyridine (DMAP). In Step 2, the protected 4-oxazolidinecarboxylic acid is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 3, the protecting group is removed. In one embodiment, the starting material is reacted with an acid in the presence of an organic solvent. In one embodiment, the acid is 4N hydrochloric acid. In one embodiment, the organic solvent is dioxane.

In Route 1c, (S)-5-(tert-Butoxycarbonyl)-5-azaspiro[2.4]heptane-6-caboxylic acid, CAS 1129634-44-1, is commercially available from Ark Pharm. In Step 2, the carboxylic acid is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 3, the protecting group is removed. In one embodiment, the starting material is reacted with an acid in the presence of an organic solvent. In one embodiment, the acid is 4N hydrochloric acid. In one embodiment, the organic solvent is dioxane.

Routes 2a, 2b, 2c, and 2d.

2a

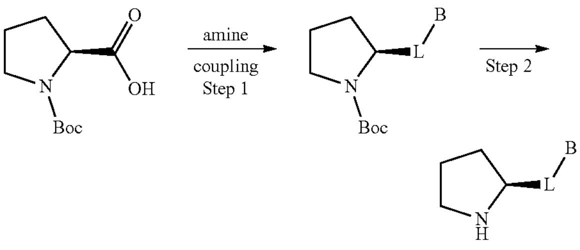

2b

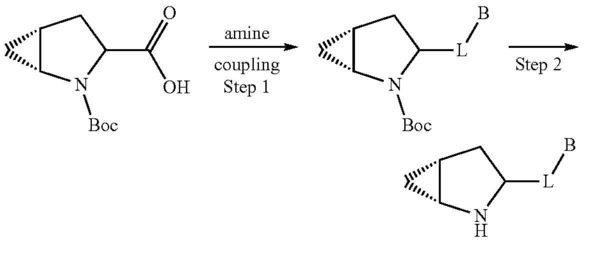

-continued

2c

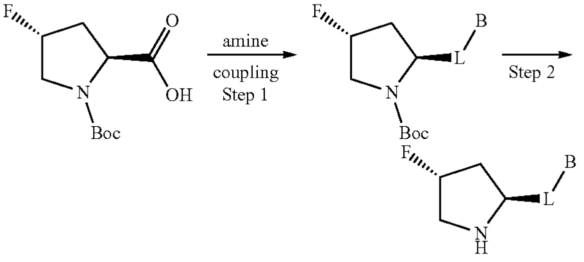

2d

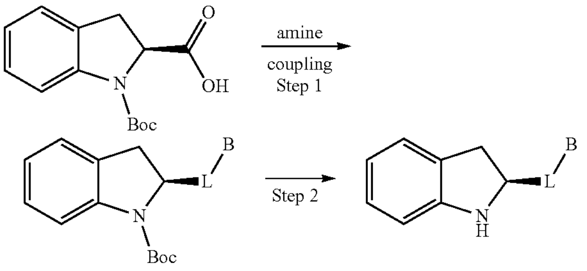

In Route 2a, commercially available Boc-L-proline is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 2, the Boc protecting group is removed. In one embodiment, the starting material is reacted with an acid in the presence of an organic solvent. In one embodiment, the acid is 4N hydrochloric acid. In one embodiment, the organic solvent is dioxane.

In Route 2b, commercially available (1R, 3S, 5R)-2-[(tert-butoxy)carbonyl]-2-azabicyclo[3.1.0]hexane-3-carboxylic acid, from Enamine, is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 2, the Boc protecting group is removed. In one embodiment, the starting material is reacted with an acid in the presence of an organic solvent. In one embodiment, the acid is 4N hydrochloric acid. In one embodiment, the organic solvent is dioxane.

In Route 2c, commercially available (2S,4R)-1-(tert-butoxycarbonyl)-4-fluoropyrrolidine-2-carboxylic acid, from Manchester Organics, is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 2, the Boc protecting group is removed. In one embodiment, the starting material is reacted with an acid in the presence of an organic solvent. In one embodiment, the acid is 4N hydrochloric acid. In one embodiment, the organic solvent is dioxane.

In Route 2d, commercially available (S)-1-(tert-butoxycarbonyl)indoline-2-carboxylic acid, from Chem-Impex, is coupled to an amine in the presence of an organic solvent, a base and a coupling reagent to generate an amide bond; the L-B moiety. In one embodiment, the amine is (3-chloro-2-fluorophenyl) methanamine. In one embodiment, the organic solvent is DMF. In one embodiment, the base is diisopropylethylamine. In one embodiment, the coupling reagent is HATU. In Step 2, the Boc protecting group is removed. In one embodiment, the starting material is reacted with an acid in the presence of an organic solvent. In one embodiment, the acid is 4N hydrochloric acid. In one embodiment, the organic solvent is dioxane. This chemistry is illustrated in Scheme 2.

Additional starting materials that can readily be converted to Central-L-B-Synthons include, but are not limited to: (S)-1-(tert-butoxycarbonyl)-2,3-dihydro-1H-pyrrole-2-carboxylic acid, CAS 90104-21-5, available from Ark Pharm; cyclopent-1-ene-1,2-dicarboxylic acid, CAS 3128-15-2, purchased from Ark Pharm; imidazole, 1H-imidazole-1,2-dicarboxylic acid, 1-(1,1-dimethylethyl) 2-ethyl ester, CAS 553650-00-3, commercially available from FCH Group; Boc-L-octahydroindole-2-carboxylic acid can be purchased from Chem Impex. The compound,

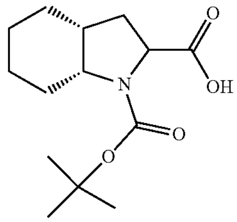 [SMILES: CC(C)(C)OC(=O)N1C(C(=O)O)C[C@H]2CCCC[C@H]21]

can be prepared according to the procedures disclosed in WO 2004/111041; (S)-Boc-5-oxopyrrolidine-2-carboxylic acid is available from the Aldrich Chemical Co.; (1S,2S,5R)-3-(tert-butoxycarbonyl)-3-azabicyclo[3.3.0]hexane-2-carboxylic acid is available from Ark Pharm; (S)-3-Boc-thiazolidine-2-carboxylic acid is available from Alfa Aesar; (2S,4R)-1-(tert-butoxycarbonyl)-4-chloropyrrolidine-2-carboxylic acid is available from Arch Bioscience; (1S,3aR,6aS)-2-(tert-butoxycarbonyl)octahydrocyclopenta[c]pyrrole-1-carboxylic acid is available from Ark Pharm; 1,2-pyrrolidinedicarboxylic acid, 3-[[(phenylmethoxy)carbonyl]amino]-, 1-(1,1-dimethylethyl) ester, (2S,3R) can be prepared as disclosed in WO 2004/007501. The Cbz group can be removed and the amino group can be alkylated to generate central core compounds of the present invention.

The compound

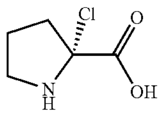

can be prepared as disclosed by Braun, J. V.; Heymons, Albrecht Berichte der Deutschen Chemischen Gesellschaft [Abteilung] B: Abhandlungen (1930) 63B, 502-7.

The compounds (2S,3S,4S)-4-fluoro-3-methoxy-pyrrolidine-1,2-dicarboxylic acid 1-tert-butyl ester and (2R,3R,4R)-3-fluoro-4-methoxy-pyrrolidine-1,2-dicarboxylic acid 1-tert-butyl ester can be prepared as a mixture according to WO 2012/093101 to Novartis and the regioisomers can be ultimately separated once coupled to generate the central core-L-B synthons. The compound (S)-Boc-5-oxopyrrolidine-2-carboxylic acid is available from the Aldrich Chemical Co.

Example 4. Preparation of A-C(O)-Moiety

Examples of the preparation of the A-C(O)-Moiety can be found in Example 1 and below.

In an alternate embodiment, an indole is acylated in Step 1. In Step 2, the indole is treated with an activated ester. In Step 3, a protecting group is removed. In Step 4, an ester is hydrolyzed to generate the A-C(O) moiety. This chemistry is illustrated in Scheme 4a.

Scheme 4a

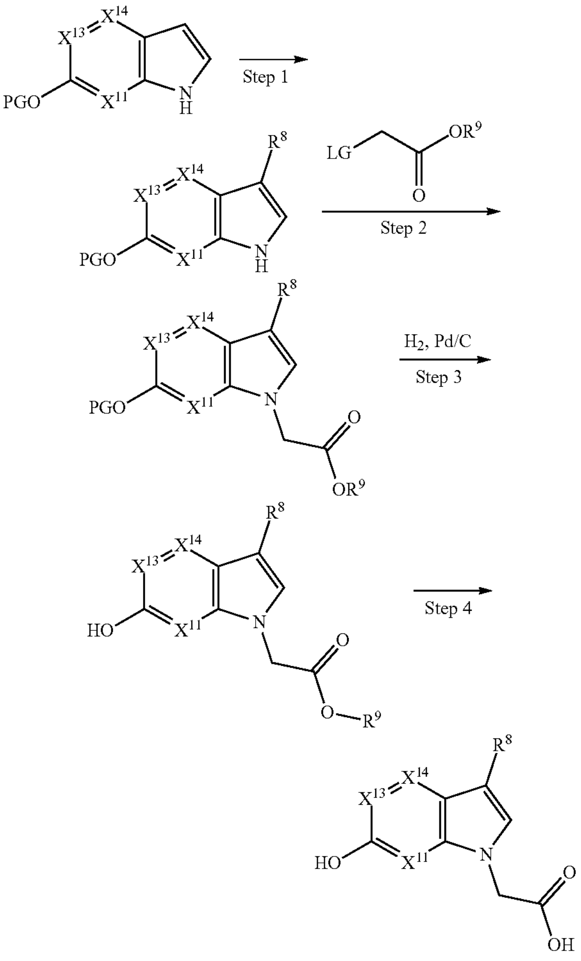

Example 5. Coupling of Central-L-B-Synthons to A-C(O)-Moieties

Examples of the coupling of central-L-B-synthons to A-C(O)-moieties can be found in Example 1.

Example 6. Synthesis of Phosphonates within Formula I

Examples of the synthesis of phosphonates within Formula I can be found in Example 1 and below.

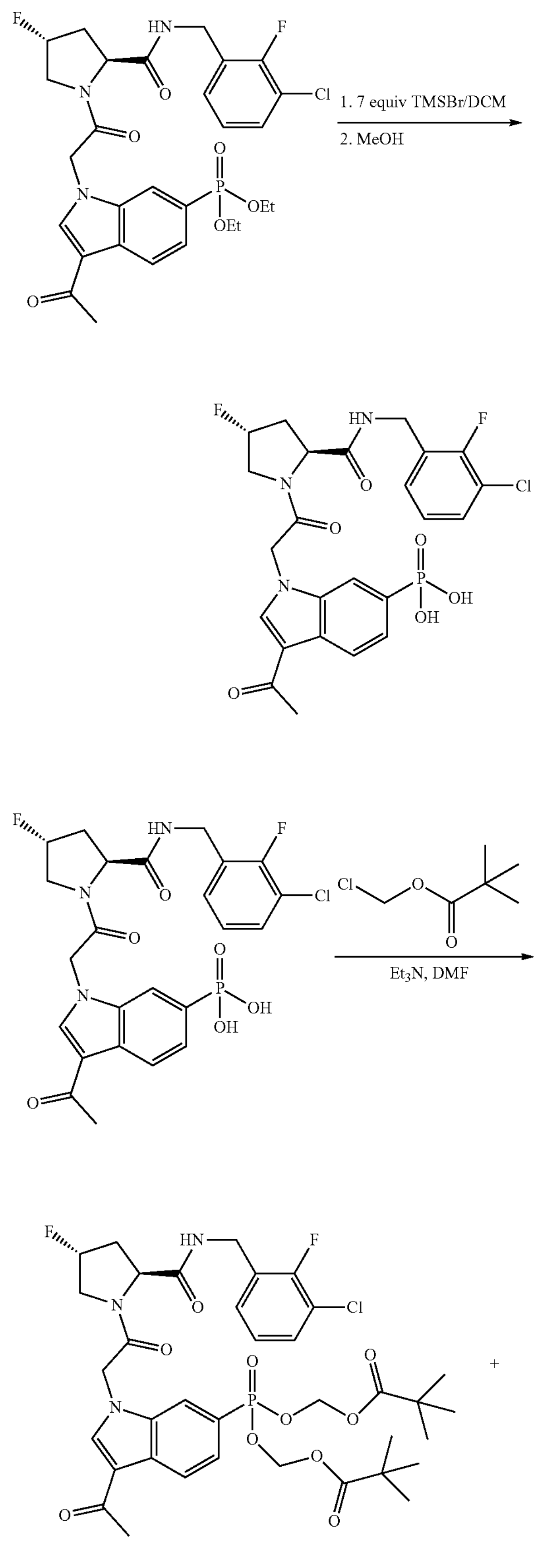

-continued

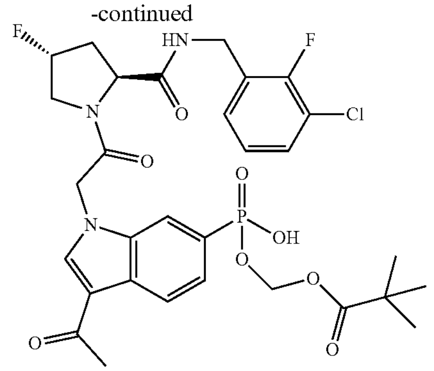

Example 7. Synthesis of 7A. (2S,4R)-tert-butyl 2-((3-chloro-2-fluoro-benzyl)carbamoyl)-4-fluoropyrrolidine-1-carboxylate

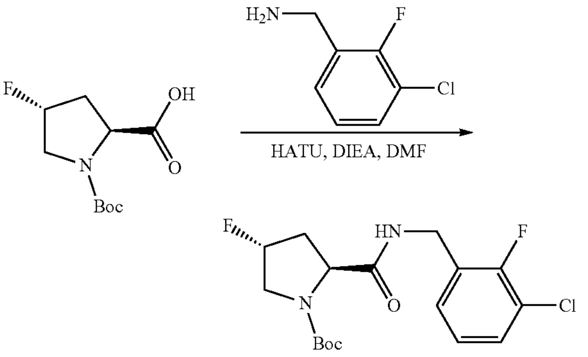

(2S,4R)-1-(tert-butoxycarbonyl)-4-fluoropyrrolidine-2-carboxylic acid (2.33 gm, 10 mmol) was dissolved in DMF (50 ml) and $^{i}$Pr2NEt (8.6 ml, 5 eq.) was added, followed by the addition of (3-chloro-2-fluorophenyl) methanamine (3.18 gm 20 mmol) at 5° C. Then HATU (8 gm, 2.1 eq) was added slowly at same temperature. The reaction mixture was then stirred for 18 h at RT. After completion of the reaction monitored by HPLC, The reaction mixture was diluted with 1M citric acid solution (200 ml+NaCl solid 20 gm) and extracted with DCM (150 mL×2), the organic layer was then washed with an aqueous solution of $NaHCO_3$ (100 ml) and washed with water (100 ml), brine (100 ml) and dried over $Na_2SO_4$ and concentrated under reduced pressure. The remaining residue was purified by column chromatography (eluted with DCM/EtOAc) to give (2S,4R)-tert-butyl 2-((3-chloro-2-fluorobenzyl)carbamoyl)-4-fluoropyrrolidine-1-carboxylate.

7B. (2S,4R)—N-(3-chloro-2-fluorobenzyl)-4-fluoropyrrolidine-2-carboxamide hydrochloride (A)

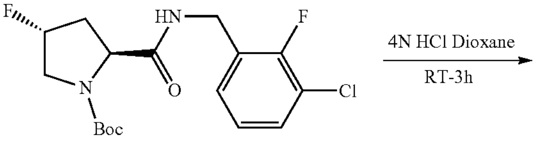

-continued

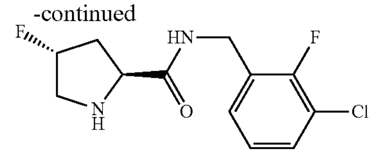

A (2S,4R)-tert-butyl 2-((3-chloro-2-fluorobenzyl)carbamoyl)-4-fluoropyrrolidine-1-carboxylate (500 mg,) was taken in 4N HCl dioxane (30 ml) and resulting reaction mixture was stirred at rt for 3 h. After completion of the reaction monitored by HPLC solvent was removed under reduced pressure. The residue, A, was used for next reaction.

Example 8. Synthesis of (2S,4R)-1-(2-(3-acetyl-6-hydroxy-1H-indol-1-yl)acetyl)-N-(3-chloro-2-fluorobenzyl)-4-fluoropyrrolidine-2-carboxamide

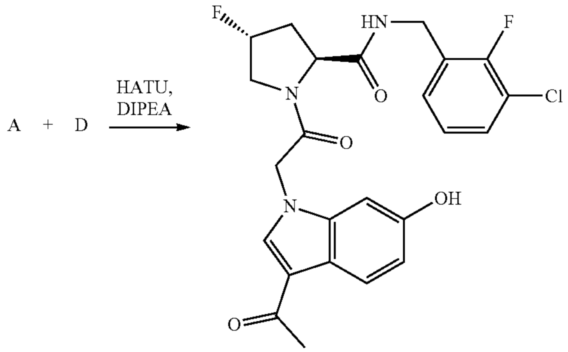

Compound D (2.5 g, 10.72 mmol) was dissolved in DMF (50 ml) and $^{i}$Pr2NEt (8.9 ml, 5 eq.) was added, followed by the addition of Compound A (3.6 g, 13.11 mmol) at 5° C. HATU (8.56 g, 2.1 eq) was added slowly at the same temperature. The reaction mixture was then stirred for 18 h at RT. After completion of the reaction, monitored by HPLC, the reaction mixture was diluted with 1M citric acid solution (200 ml+NaCl solid 20 gm) and extracted with DCM (150 mL×2). The organic layer was washed with an aqueous solution of $NaHCO_3$ (100 ml), water (100 ml), brine (100 ml), dried over $Na_2SO_4$ and concentrated under reduced pressure. The remaining residue was purified by column chromatography (eluted with DCM/EtOAc) to afford the product.

Example 9. Synthesis of Diethyl (3-acetyl-1-(2-((2S,4R)-2-((3-chloro-2-fluorobenzyl)carbamoyl)-4-fluoropyrrolidin-1-yl)-2-oxoethyl)-1H-indol-6-yl) phosphonate

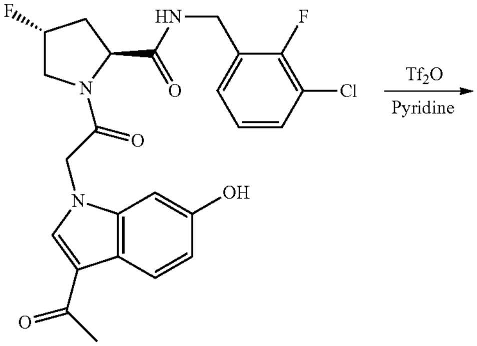

-continued

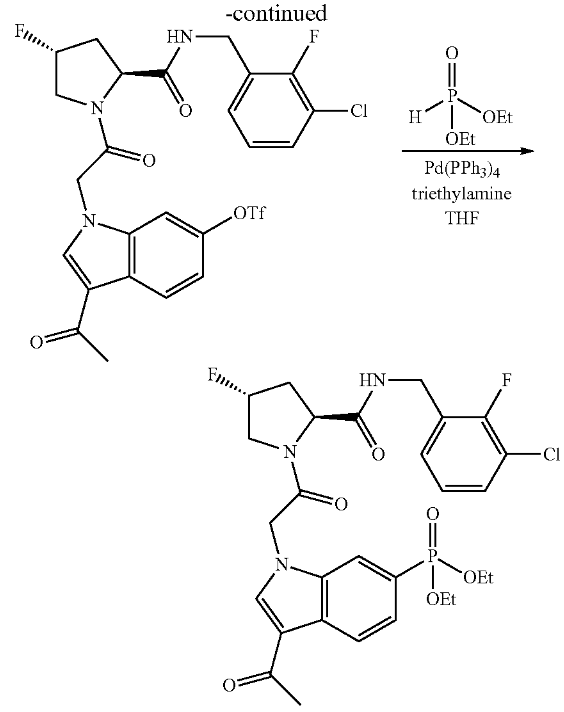

Under an atmosphere of argon gas, trifluoromethanesulfonic anhydride (250 μL) was added dropwise to a cooled (0° C.) solution of (2S,4R)-1-(2-(3-acetyl-6-hydroxy-1H-indol-1-yl)acetyl)-N-(3-chloro-2-fluorobenzyl)-4-fluoropyrrolidine-2-carboxamide (551 mg) in pyridine (10 mL). The resulting solution was stirred at 0° C. for 2.5 h, allowed to warm to rt, and concentrated under reduced pressure to afford an oil. This material was dissolved in ethyl acetate (75 mL), and the resulting solution was washed with a 1M aq. solution of citric acid (2×25 mL), and brine (25 mL). The organic layer was dried over sodium sulfate, and evaporated under reduce pressure to afford the crude product. This material was purified by flash column chromatography on silica (methanol/dichloromethane gradient, 0 to 5% v/v) to provide 3-acetyl-1-(2-((2S,4R)-2-((3-chloro-2-fluorobenzyl)carbamoyl)-4-fluoropyrrolidin-1-yl)-2-oxoethyl)-1H-indol-6-yl trifluoromethanesulfonate as a solid. LC-MS (method 1): $t_R$ 2.39 min, m/z found 622 ($[M+H]^+$).

Under an atmosphere of argon gas, a mixture of 3-acetyl-1-(2-((2S,4R)-2-((3-chloro-2-fluorobenzyl)carbamoyl)-4-fluoropyrrolidin-1-yl)-2-oxoethyl)-1H-indol-6-yl trifluoromethanesulfonate (526 mg), diethyl phosphite (1.2 mL), triethylamine (217 μL), and tetrakis(triphenylphosphine) palladium(O) (100 mg) in tetrahydrofuran (30 mL) was stirred at 100° C. in a sealed tube for 18 h. The reaction mixture was allowed to cool to room temperature and concentrated under reduced pressure. The remaining residue was purified by flash column chromatography on silica (methanol/dichloromethane gradient, 0 to 5% v/v) to afford diethyl (3-acetyl-1-(2-((2S,4R)-2-((3-chloro-2-fluorobenzyl)carbamoyl)-4-fluoropyrrolidin-1-yl)-2-oxoethyl)-1H-indol-6-yl)phosphonate as a solid. LC-MS (method 1): $t_R$ 1.84 min, m/z found 610 ($[M+H]^+$). LC-MS (method 2): $t_R$ 7.15 min, m/z found 610 ($[M+H]^+$).

Example 10. Synthesis of Ethyl Hydrogen (3-acetyl-1-(2-((2S,4R)-2-((3-chloro-2-fluorobenzyl) carbamoyl)-4-fluoropyrrolidin-1-yl)-2-oxoethyl)-1H-indol-6-yl)phosphonate

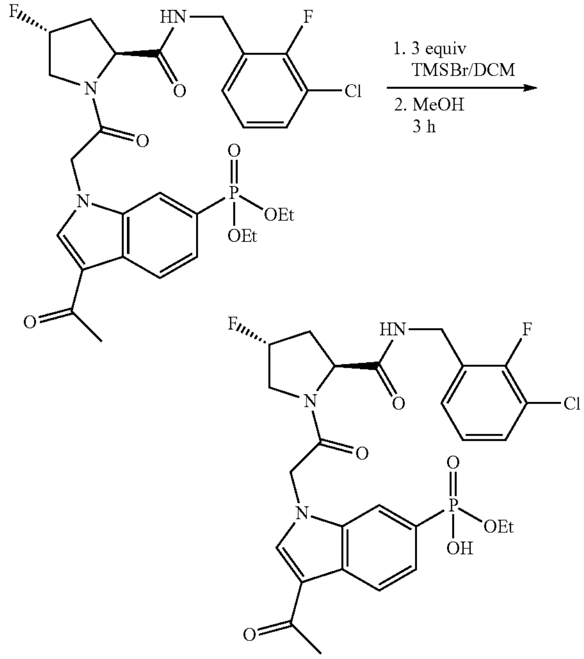

Under an atmosphere of argon gas at rt, bromotrimethylsilane (132 mg) was added to a solution of diethyl (3-acetyl-1-(2-((2S,4R)-2-((3-chloro-2-fluorobenzyl)carbamoyl)-4-fluoropyrrolidin-1-yl)-2-oxoethyl)-1H-indol-6-yl) phosphonate (200 mg) in dichloromethane (5 mL) at rt. The resulting solution was stirred for 3 h and evaporated to dryness under reduced pressure. The reaction was stopped at 3 h when the majority of the product was the monoethyl phosphonate. The residue was treated with a mixture of dichloromethane and methanol (3:1 v/v, 15 mL) and evaporated under reduced pressure. This treatment was repeated once, and the remaining solid was washed with ethyl acetate (15 mL), and dried in vacuo overnight. Ethyl hydrogen (3-acetyl-1-(2-((2S,4R)-2-((3-chloro-2-fluorobenzyl)carbamoyl)-4-fluoropyrrolidin-1-yl)-2-oxoethyl)-1H-indol-6-yl)phosphonate was purified by HPLC to provide 25 mg of solid. LC-MS: $t_R$ 1.20 min, m/z found 582 ([M+H]$^+$).

Example 11. Synthesis of (3-acetyl-1-(2-((2S,4R)-2-((3-chloro-2-fluorobenzyl)carbamoyl)-4-fluoropyrrolidin-1-yl)-2-oxoethyl)-1H-indol-6-yl)phosphonic Acid

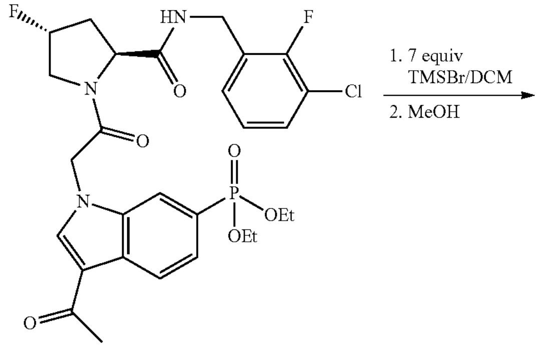

-continued

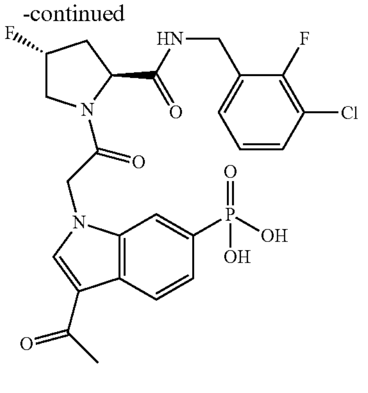

Under an atmosphere of argon gas at rt, bromotrimethylsilane (233 mg) was added to a solution of diethyl (3-acetyl-1-(2-((2S,4R)-2-((3-chloro-2-fluorobenzyl)carbamoyl)-4-fluoropyrrolidin-1-yl)-2-oxoethyl)-1H-indol-6-yl) phosphonate (150 mg) in dichloromethane (5 mL) at rt. The resulting solution was stirred for 18 h and evaporated to dryness under reduced pressure. The remaining residue was treated with a mixture of dichloromethane and methanol (3:1 v/v, 15 mL) and evaporated under reduced pressure. This treatment was repeated once, and the remaining solid was washed with ethyl acetate (15 mL), and dried in vacuo overnight to afford 132 mg of (3-acetyl-1-(2-((2S,4R)-2-((3-chloro-2-fluorobenzyl)carbamoyl)-4-fluoropyrrolidin-1-yl)-2-oxoethyl)-1H-indol-6-yl)phosphonic acid. LC-MS (method 1): $t_R$ 1.06 min, m/z found 554 ([M+H]$^+$). LC-MS (method 2): $t_R$ 5.40 min, m/z found 554 ([M+H]$^+$).

Example 12. Synthesis of (2S,4R)—N-(3-chloro-2-fluorobenzyl)-4-fluoropyrrolidine-2-carboxamide Hydrochloride (Int-1)

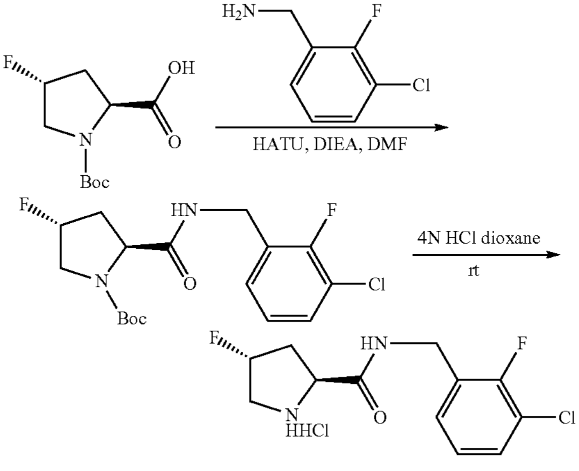

Int-1

(2S,4R)-1-(tert-Butoxycarbonyl)-4-fluoropyrrolidine-2-carboxylic acid (2.33 g, 10 mmol) was dissolved in DMF (50 mL) and DIEA (8.6 mL, 5 equiv) was added, followed by the addition of (3-chloro-2-fluorophenyl)methanamine (3.18 g, 20 mmol) at 5° C. Then HATU (8 g, 2.1 equiv) was added slowly at the same temperature. The reaction mixture was then stirred for 18 h at rt. After completion of the reaction monitored by HPLC, the reaction mixture was diluted with 1 M aqueous citric acid (200 mL+20 g solid NaCl) and extracted with DCM (2×150 mL). The organic layer was then washed successively with an aqueous solution of $NaHCO_3$ (100 mL), water (100 mL), and brine (100 mL), and then dried over $Na_2SO_4$ and concentrated under reduced pressure. The remaining residue was purified by column chromatography (eluted with DCM/EtOAc) to give (2S,4R)-tert-butyl 2-((3-chloro-2-fluorobenzyl)carbamoyl)-4-fluoropyrrolidine-1-carboxylate.

(2S,4R)-tert-Butyl 2-((3-chloro-2-fluorobenzyl)carbamoyl)-4-fluoropyrrolidine-1-carboxylate (500 mg) was taken in 4 N HCl in dioxane (30 mL) and the resulting reaction mixture was stirred at rt for 3 h. After completion of the reaction, which was monitored by HPLC, the solvent was removed under reduced pressure. The residue, Int-1, was used directly in the next step.

Example 13. Synthesis of (2S,4R)-1-(2-(3-acetyl-6-hydroxy-1H-indol-1-yl)acetyl)-N-(3-chloro-2-fluorobenzyl)-4-fluoropyrrolidine-2-carboxamide (Int-2)

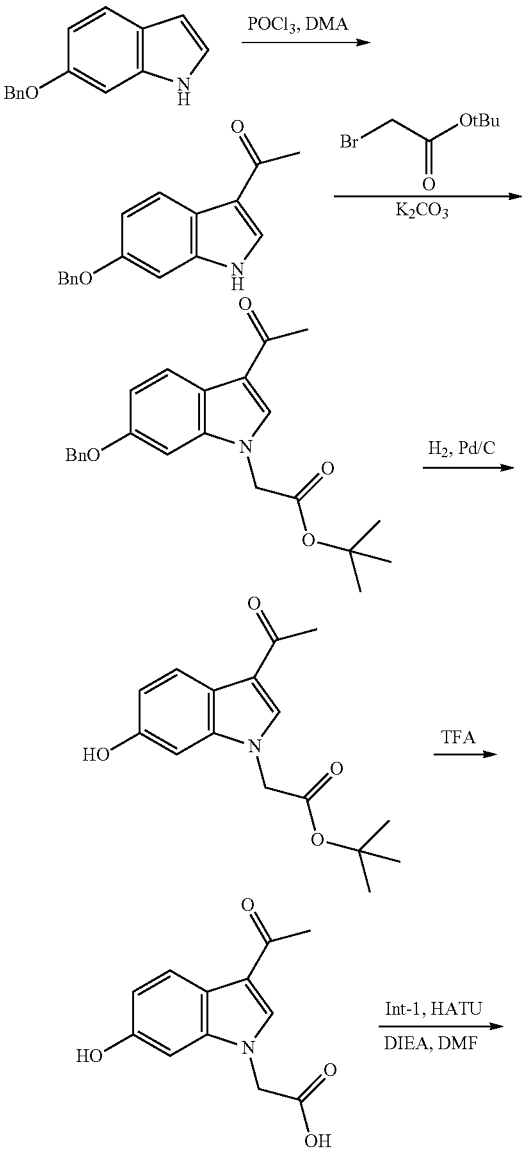

-continued

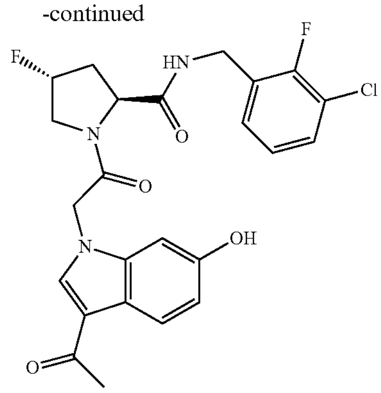

Int-2

Phosphoryl chloride (103 mL, 10 equiv) was added to ice-cold N,N-dimethylacetamide (311 mL, 30 equiv) with stirring and cooling in ice. 6-Benzyloxy indole (25 g, 1 equiv) was then added and the reaction mixture was stirred at rt for 12 h, then poured over ice and basified with a 4 N aqueous sodium hydroxide solution until a precipitate formed. The solid was collected by filtration, washed with water, and dried. The solid was then slurried with methanol, collected by filtration, and dried to give 1-(6-(benzyloxy)-1H-indol-3-yl)ethanone (20 g, 67%).

To a mixture of 1-(6-(benzyloxy)-1H-indol-3-yl)ethanone (25 g, 1 equiv) and potassium carbonate (11.6 g, 1.1 equiv) in acetonitrile (384 mL) was added tert-butyl bromoacetate (12.4 mL, 1.1 equiv) dropwise at rt. The resulting mixture was heated to reflux for 12 h, allowed to cool to rt, poured into water, and extracted with EtOAc. The combined organic extracts were concentrated under reduced pressure. The resulting solid was slurried with MTBE, collected by filtration, and dried to give tert-butyl 2-(3-acetyl-6-(benzyloxy)-1H-indol-1-yl)acetate (26 g, 72%).

A mixture of tert-butyl 2-(3-acetyl-6-(benzyloxy)-1H-indol-1-yl)acetate (22 g, 1 equiv), DCM/MeOH (600 mL), and Pd/C (2.2 g, 10%) was stirred at rt for 12 h under an atmosphere of $H_2$ (3.5 kg/$cm^2$). The reaction mixture was filtered through a pad of Celite® and washed with DCM and MeOH. The filtrate was evaporated under reduce pressure, and the remaining crude product was slurried with DCM, collected by filtration, and dried to give tert-butyl 2-(3-acetyl-6-hydroxy-1H-indol-1-yl)acetate (11.5 g, 69%).

tert-Butyl 2-(3-acetyl-6-hydroxy-1H-indol-1-yl)acetate (5 g) was treated with TFA (10 mL) in DCM (30 mL) for 2 h at rt. After evaporation of the volatiles under reduced pressure, 2-(3-acetyl-6-hydroxy-1H-indol-1-yl)acetic acid was obtained.

2-(3-Acetyl-6-hydroxy-1H-indol-1-yl)acetic acid (2.5 g) and Int-1 (3.6 g) were coupled in the presence of HATU and DIEA using a procedure similar to that described for the synthesis of Int-1 to give (2S,4R)-1-(2-(3-acetyl-6-hydroxy-1H-indol-1-yl)acetyl)-N-(3-chloro-2-fluorobenzyl)-4-fluoropyrrolidine-2-carboxamide Int-2.

Example 14. Synthesis of (2S,3aR,6aR)—N-(3-chloro-2-fluorobenzyl)octahydrocyclopenta[B]pyrrole-2-carboxamide TFA Salt (Int-3)

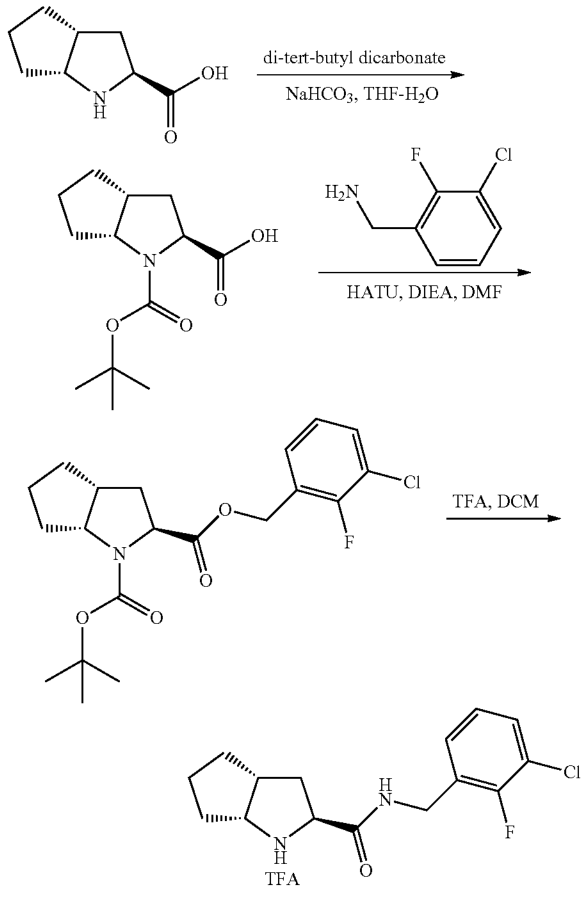

Int-3

(2S,3aR,6aR)-Octahydrocyclopenta[b]pyrrole-2-carboxylic acid (0.32 g) was dissolved in THF-$H_2O$ (1:1, 14 mL) in the presence of $NaHCO_3$ (0.52 g). Di-tert-butyl dicarbonate (0.95 mL) was added and the mixture was stirred at rt overnight. The reaction mixture was diluted with EtOAc and extracted with water. To the aqueous layer was added concentrated HCl to adjust the pH to 2, and then extracted with EtOAc. The combined organic extracts were dried over anhydrous $Na_2SO_4$ and evaporated to give (2S,3aR,6aR)-1-(tert-butoxycarbonyl)octahydrocyclopenta[b]pyrrole-2-carboxylic acid as a clear oil (0.532 g).

(2S,3aR,6aR)-1-(tert-Butoxycarbonyl)octahydrocyclopenta[b]pyrrole-2-carboxylic acid (2 mmol) and (3-chloro-2-fluorophenyl)methanamine (1.2 equiv) were dissolved in DMF (5 mL) and treated with HATU (1.2 equiv) followed by DIEA (1 mL). After stirring for 2h at rt, the reaction mixture was diluted with water and extracted with EtOAc. The extract was evaporated under reduced pressure and the remaining crude material was purified by column chromatography to give (2S,3aR,6aR)-1-tert-butyl 2-(3-chloro-2-fluorobenzyl) hexahydrocyclopenta[b]pyrrole-1,2(2H)-dicarboxylate as a white solid.

(2S,3aR,6aR)-1-tert-Butyl 2-(3-chloro-2-fluorobenzyl) hexahydrocyclopenta[b]pyrrole-1,2(2H)-dicarboxylate (159 mg) was treated with TFA (3 mL) in DCM (3 mL) for 1 h at rt. After evaporation of the volatiles, (2S,3aR,6aR)—N-(3-chloro-2-fluorobenzyl)octahydrocyclopenta[b]pyrrole-2-carboxamide TFA salt Int-3 was obtained.

Example 15. Synthesis of 2-(3-acetyl-6-(diethoxyphosphoryl)-1H-indol-1-yl)acetic Acid (Int-4)

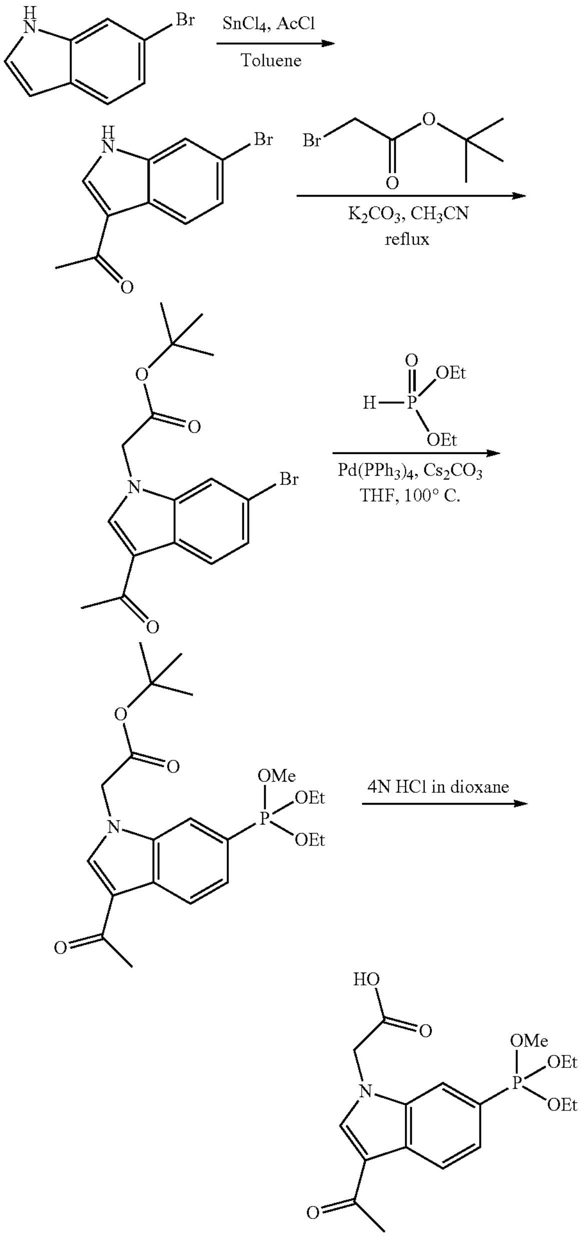

Int-4

1-(6-Bromo-1H-indol-3-yl)ethanone was prepared from 6-bromoindole according to the procedure of MacKay et al. (MacKay, J. A.; Bishop, R.; Rawal, V. H. *Org. Lett.* 2005, 7, 3421-3424.)

A mixture of 3.9 g (16.4 mmol) of 1-(6-bromo-1H-indol-3-yl)ethanone, 2.63 mL (18.02 mmol) of tert-butyl bromoacetate and 2.50 g (18.02 mmol) potassium carbonate in anhydrous acetonitrile (80 mL) was refluxed for 5 h. The reaction mixture was then cooled to rt and the solvent was removed under reduced pressure. The residue was taken in 1:1 mixture of DCM and water (100 mL: 100 mL). The two layers were separated and the organic layer was washed with water (2×100 mL). Finally, the organic layer was dried ($Na_2SO_4$) and concentrated. The resulting residue was stirred with 50 mL of heptane for 30 min, cooled in an ice bath and filtered, washing the solid with cold heptane (10 mL). This cream colored solid was dried under high vacuum to give 5.6 g of tert-butyl 2-(3-acetyl-6-bromo-1H-indol-1-yl)acetate.

tert-Butyl 2-(3-acetyl-6-bromo-1H-indol-1-yl)acetate (67 mg) was treated with 4 N HCl in dioxane (5 mL) at rt overnight. The volatiles were removed under reduced pressure to give 2-(3-acetyl-6-(diethoxyphosphoryl)-1H-indol-1-yl)acetic acid Int-4.

Example 16. Synthesis of Diethyl (3-acetyl-1-(2-((2S,4R)-2-((3-chloro-2-fluorobenzyl)carbamoyl)-4-fluoropyrrolidin-1-yl)-2-oxoethyl)-1H-indol-6-yl) phosphonate (1)

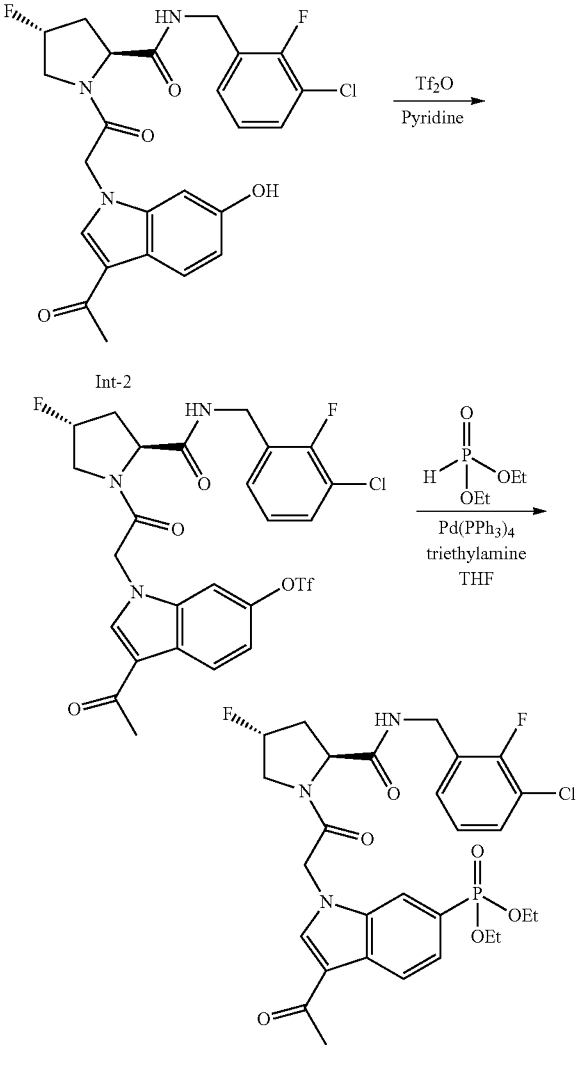

Int-2

1

Under an atmosphere of argon gas, trifluoromethanesulfonic anhydride (250 μL) was added dropwise to a cooled (0° C.) solution of (2S,4R)-1-(2-(3-acetyl-6-hydroxy-1H-indol-1-yl)acetyl)-N-(3-chloro-2-fluorobenzyl)-4-fluoropyrrolidine-2-carboxamide (551 mg) in pyridine (10 mL). The resulting solution was stirred at 0° C. for 2.5 h, allowed to warm to rt, and concentrated under reduced pressure to give an oil. This material was dissolved in ethyl acetate (75 mL), and the resulting solution was washed with a 1 M aqueous solution of citric acid (2×25 mL), washed with brine (25 mL), dried over sodium sulfate, and evaporated under reduce pressure to give the crude product. This material was purified by flash column chromatography on silica (methanol/dichloromethane gradient, 0 to 5% v/v) to give 3-acetyl-1-(2-((2S,4R)-2-((3-chloro-2-fluorobenzyl)carbamoyl)-4-fluoropyrrolidin-1-yl)-2-oxoethyl)-1H-indol-6-yl trifluoromethanesulfonate as a solid. LC-MS (method A): $t_R$ 2.24 min, m/z found 622 ($[M+H]^+$).

Under an atmosphere of argon gas, a mixture of 3-acetyl-1-(2-((2S,4R)-2-((3-chloro-2-fluorobenzyl)carbamoyl)-4-fluoropyrrolidin-1-yl)-2-oxoethyl)-1H-indol-6-yl trifluoromethanesulfonate (526 mg), diethyl phosphite (1.2 mL), triethylamine (217 μL), and tetrakis(triphenylphosphine) palladium(O) (100 mg) in tetrahydrofuran (30 mL) was stirred at 100° C. in a sealed tube for 18 h. The reaction mixture was allowed to cool to room temperature and concentrated under reduced pressure. The remaining residue was purified by flash column chromatography on silica (methanol/dichloromethane gradient, 0 to 5% v/v) to give diethyl (3-acetyl-1-(2-((2S,4R)-2-((3-chloro-2-fluorobenzyl)carbamoyl)-4-fluoropyrrolidin-1-yl)-2-oxoethyl)-1H-indol-6-yl)phosphonate 1 as a solid. H NMR (400 MHz, DMSO-$d_6$, 300 K): (major rotamer) δ 1.20 (2×t, J=7.2 Hz, 6H), 2.00-2.19 (m, 1H), 2.45 (s, 3H), 2.48-2.57 (m, 1H), 3.85-4.06 (m, 5H), 4.11-4.53 (m, 4H), 5.30 (d, J=17.0 Hz, 1H), 5.43-5.60 (m, 2H), 6.99 (m, 1H), 7.23 (m, 1H), 7.41 (m, 1H), 7.52 (m, 1H), 7.92 (m, 1H), 8.32 (m, 1H), 8.40 (s, 1H), 8.61 (t, J=5.9 Hz, 1H). $^{19}F$ NMR (376 MHz, DMSO-$d_6$, 300 K): (major rotamer) δ–176.1 (s, 1F), -121.8 (s, 1F). $^{31}P$ NMR (162 MHz, DMSO-$d_6$, 300 K): (major rotamer) δ 19.8 (s). LC-MS (method A): $t_R$ 1.83 min, m/z found 610 ($[M+H]^+$).

Example 17. Synthesis of Ethyl Hydrogen (3-acetyl-1-(2-((2S,4R)-2-((3-chloro-2-fluorobenzyl) carbamoyl)-4-fluoropyrrolidin-1-yl)-2-oxoethyl)-1H-indol-6-yl)phosphonate (2)

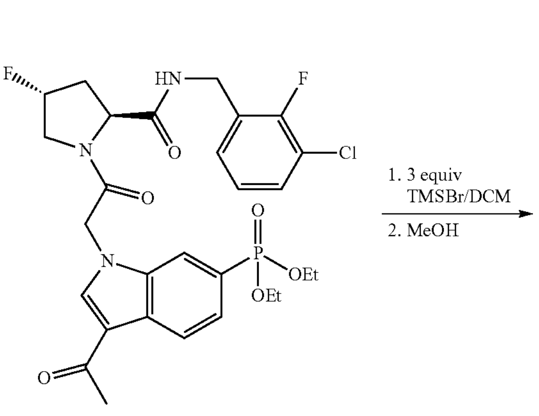

1

-continued

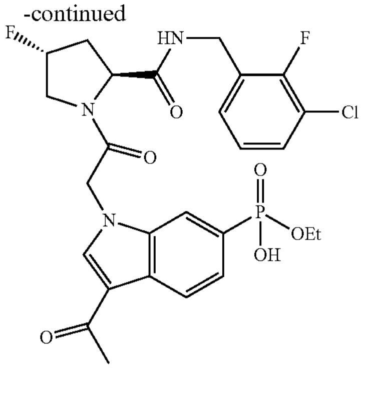

2

-continued

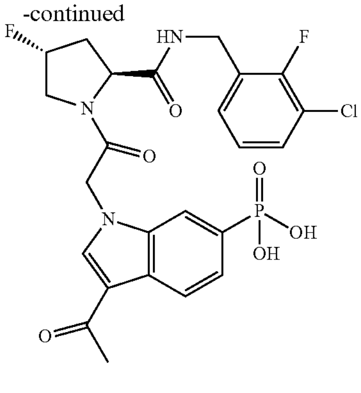

3

Under an atmosphere of argon gas at rt, bromotrimethylsilane (132 mg) was added to a solution of diethyl (3-acetyl-1-(2-((2S,4R)-2-((3-chloro-2-fluorobenzyl)carbamoyl)-4-fluoropyrrolidin-1-yl)-2-oxoethyl)-1H-indol-6-yl) phosphonate 1 (200 mg) in dichloromethane (5 mL) at rt. The resulting solution was stirred for 3 h (when, as judged by LC-MS analysis, the majority of the mixture was the desired monoethyl phosphonate) and evaporated to dryness under reduced pressure. The residue was treated with a mixture of dichloromethane and methanol (3:1 v/v, 15 mL) and evaporated under reduced pressure. This treatment was repeated once, and the remaining solid was washed with ethyl acetate (15 mL), and dried in vacuo overnight. Ethyl hydrogen (3-acetyl-1-(2-((2S,4R)-2-((3-chloro-2-fluorobenzyl)carbamoyl)-4-fluoropyrrolidin-1-yl)-2-oxoethyl)-1H-indol-6-yl)phosphonate 2 was purified by HPLC to give 25 mg of solid. $^{1}H$ NMR (400 MHz, DMSO-$d_6$, 300 K): (major rotamer) 1.15 (t, J=7.1 Hz, 3H), 2.00-2.19 (m, 1H), 2.45 (s, 3H), 2.46-2.56 (m, 1H), 3.80-4.01 (m, 3H), 4.13-4.54 (m, 4H), 5.29 (d, J=17.3 Hz, 1H), 5.44-5.61 (m, 2H), 7.04 (m, 1H), 7.25 (m, 1H), 7.43 (m, 1H), 7.52 (m, 1H), 7.90 (d, J=14.7 Hz, 1H), 8.29 (m, 1H), 8.37 (s, 1H), 8.64 (t, J=5.9 Hz, 1H). $^{19}F$ NMR (376 MHz, DMSO-$d_6$, 300 K): (major rotamer) δ–176.0 (s, 1F), –121.8 (s, 1F). $^{31}P$ NMR (162 MHz, DMSO-$d_6$, 300 K): (major rotamer) δ 16.8 (s). LC-MS (Method A): $t_R$ 1.20 min, m/z found 582 ([M+H]$^+$).

Example 18. Synthesis of (3-acetyl-1-(2-((2S,4R)-2-((3-chloro-2-fluorobenzyl)carbamoyl)-4-fluoropyrrolidin-1-yl)-2-oxoethyl)-1H-indol-6-yl)phosphonic Acid (3)

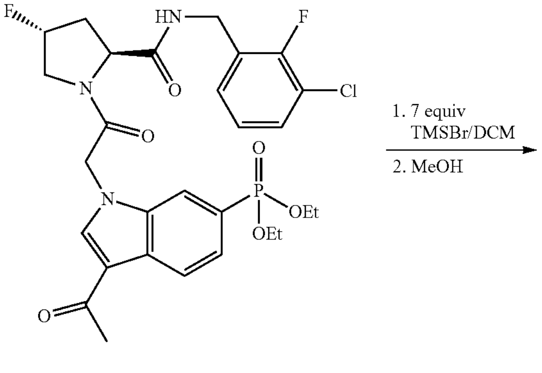

1

Under an atmosphere of argon gas at rt, bromotrimethylsilane (233 mg) was added to a solution of diethyl (3-acetyl-1-(2-((2S,4R)-2-((3-chloro-2-fluorobenzyl)carbamoyl)-4-fluoropyrrolidin-1-yl)-2-oxoethyl)-1H-indol-6-yl) phosphonate 1 (150 mg) in dichloromethane (5 mL) at rt. The resulting solution was stirred for 18 h and evaporated to dryness under reduced pressure. The remaining residue was treated with a mixture of dichloromethane and methanol (3:1 v/v, 15 mL) and evaporated under reduced pressure. This treatment was repeated once, and the remaining solid was washed with ethyl acetate (15 mL), and dried in vacuo overnight to give 132 mg of (3-acetyl-1-(2-((2S,4R)-2-((3-chloro-2-fluorobenzyl)carbamoyl)-4-fluoropyrrolidin-1-yl)-2-oxoethyl)-1H-indol-6-yl)phosphonic acid 3. $^{1}H$ NMR (400 MHz, DMSO-$d_6$, 300 K): (major rotamer) δ 2.01-2.20 (m, 1H), 2.44 (s, 3H), 2.38-2.49 (m, 1H), 3.84-4.01 (m, 1H), 4.14-4.56 (m, 4H), 5.28 (d, J=17.1 Hz, 1H), 5.43-5.62 (m, 2H), 7.07 (m, 1H), 7.26 (m, 1H), 7.44 (m, 1H), 7.55 (m, 1H), 7.89 (d, J=14.5 Hz, 1H), 8.26 (m, 1H), 8.35 (s, 1H), 8.66 (t, J=5.9 Hz, 1H). $^{19}F$ NMR (376 MHz, DMSO-$d_6$, 300 K): (major rotamer) δ–176.0 (s, 1F), -121.7 (s, 1F). $^{31}P$ NMR (162 MHz, DMSO-$d_6$, 300 K): (major rotamer) δ 14.2 (s). LC-MS (method A): $t_R$ 1.06 min, m/z found 554 ([M+H]$^+$).

Example 19. Synthesis of (3-acetyl-1-(2-((2S,3aR,6aR)-2-((3-chloro-2-fluorobenzyl)carbamoyl)hexahydrocyclopenta[b]pyrrol-1(2H)-yl)-2-oxoethyl)-1H-indol-6-yl)phosphonic Acid (7)

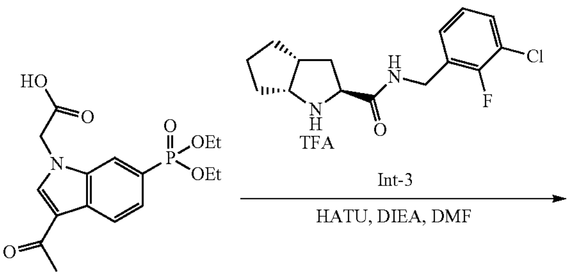

Int-4

-continued

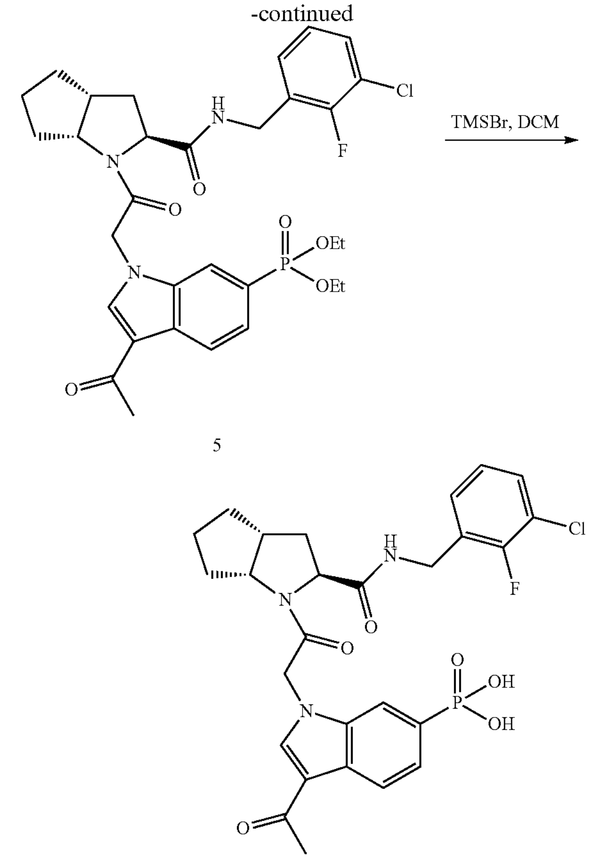

5

7

To a mixture of 2-(3-acetyl-6-(diethoxyphosphoryl)-1H-indol-1-yl)acetic acid Int-4 (0.164 mmol) and (2S,3aR,6aR)—N-(3-chloro-2-fluorobenzyl)octahydrocyclopenta[b]pyrrole-2-carboxamide TFA salt Int-3 (1.2 equiv) in DMF (2 mL), was added HATU (1.2 equiv) followed by DIEA (3.0 equiv). After stirring at rt for 1 h, the volatiles were removed under reduced pressure and the remaining residue was purified by column chromatography (7% MeOH in DCM as eluent) to give diethyl (3-acetyl-1-(2-((2S,3aR,6aR)-2-((3-chloro-2-fluorobenzyl)carbamoyl)hexahydrocyclopenta[b]pyrrol-1 (2H)-yl)-2-oxoethyl)-1H-indol-6-yl)phosphonate 5 (43 mg). LC-MS (method A): $t_R$ 2.13 min, m/z found 632 ($[M+H]^+$).

(3-Acetyl-1-(2-((2S,3aR,6aR)-2-((3-chloro-2-fluorobenzyl)carbamoyl)hexahydrocyclopenta[b]pyrrol-1 (2H)-yl)-2-oxoethyl)-1H-indol-6-yl)phosphonate was treated with TMSBr (7 equiv) in DCM at rt overnight. After evaporation under reduced pressure, the remaining residue was treated with a mixture of dichloromethane and methanol (3:1 v/v, 15 mL) and evaporated under reduced pressure. This treatment was repeated once, and the remaining solid was washed with ethyl acetate (15 mL), and dried in vacuo overnight to give (3-acetyl-1-(2-((2S,3aR,6aR)-2-((3-chloro-2-fluorobenzyl)carbamoyl)hexahydrocyclopenta[b]pyrrol-1 (2H)-yl)-2-oxoethyl)-1H-indol-6-yl)phosphonic acid 7 (17 mg). $^1$H NMR (400 MHz, methanol-$d_4$, 300 K): (major rotamer) δ 1.49-1.53 (m, 1H), 1.58-1.66 (m, 1H), 1.70-1.80 (m, 1H), 1.98-2.05 (m, 1H), 2.17-2.23 (m, 1H), 2.35-2.45 (m, 2H), 2.88-2.94 (m, 1H), 4.31-4.33 (m, 2H), 4.45-4.47 (m, 1H), 4.51-4.58 (m, 1H), 5.08 (d, J=18 Hz, 1H), 5.33 (d, J=17 Hz, 1H), 6.95 (t, J=8 Hz, 1H), 7.15-7.27 (m, 2H), 7.56 (t, J=8 Hz, 1H), 7.78 (d, J=15 Hz, 1H), 8.25 (s, 1H), 8.26-8.28 (m, 1H). $^{19}$F NMR (376 MHz, methanol-$d_4$, 300 K): (major rotamer) δ −123.3 (s). $^{31}$P NMR (162 MHz, methanol-$d_4$, 300 K): (major rotamer) δ 17.6 (s). LC-MS (method A): $t_R$ 1.44 min, m/z found 576 ($[M+H]^+$).

Example 20. Synthesis of (3-carbamoyl-1-(2-((2S,4R)-2-((3-chloro-2-fluorobenzyl)carbamoyl)-4-fluoropyrrolidin-1-yl)-2-oxoethyl)-1H-indazol-6-yl) phosphonic Acid (18)

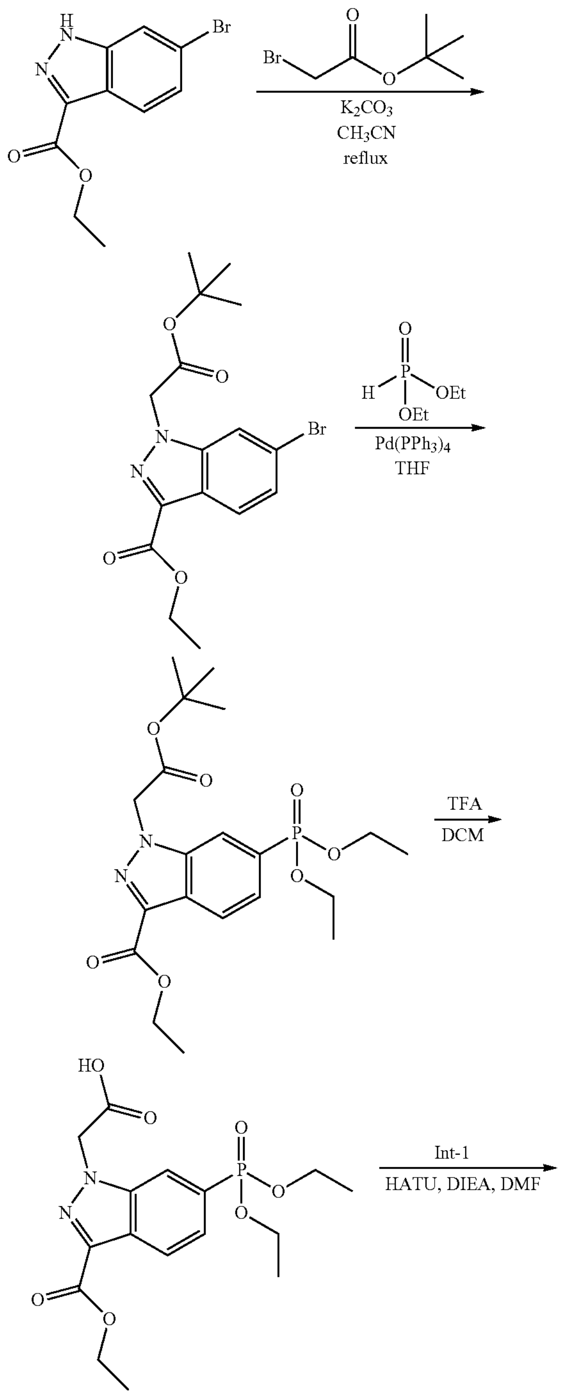

-continued

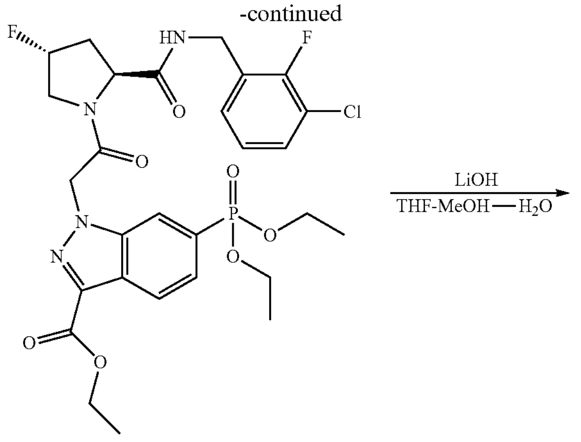

11

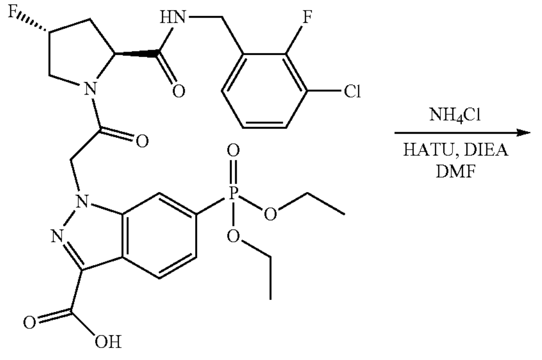

12

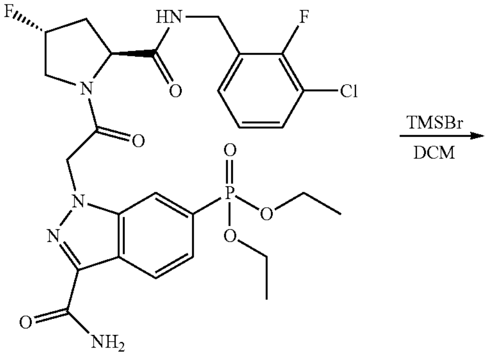

17

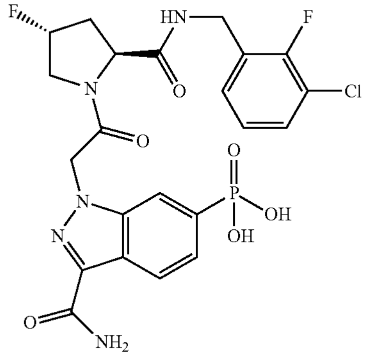

18

To a solution of ethyl 6-bromo-1H-indazole-3-carboxylate (2.69 g, 10 mmol) and tert-butyl 2-bromoacetate (2.73 g, 2.1 mL, 14.0 mmol) in $CH_3CN$ (70 mL), was added solid potassium carbonate (3.18 g, 23 mmol). The mixture was heated at reflux in an oil bath overnight under an atmosphere of argon gas. The reaction mixture was cooled to rt and filtered through a pad of Celite®. The solid cake was washed with $CH_3CN$ (20 mL), and the combined solution was concentrated under reduced pressure. The residue was purified by flash column chromatography on silica to afford ethyl 6-bromo-1-(2-(tert-butoxy)-2-oxoethyl)-1H-indazole-3-carboxylate (3.3 g). $^1H$ NMR (400 MHz, $CDCl_3$, 300 K): δ 1.45 (s, 9H), 1.48 (t, J=7.2 Hz, 3H), 4.52 (q, J=7.2 Hz, 2H), 5.11 (s, 2H), 7.42 (d, J=8.8 Hz, 1H), 7.56 (s, 1H), 8.08 (d, J=8.8 Hz, 1H).

Under an atmosphere of argon gas, a mixture of ethyl 6-bromo-1-(2-(tert-butoxy)-2-oxoethyl)-1H-indazole-3-carboxylate (3.3 g, 8.6 mmol), diethyl phosphite (1.45 mL, 11.2 mmol), triethylamine (1.78 mL, 12.9 mmol), and tetrakis (triphenylphosphine)palladium(O) (0.09 mmol) in tetrahydrofuran (100 mL) was heated at reflux overnight. The reaction mixture was allowed to cool to rt and concentrated under reduced pressure. The remaining residue was purified by flash column chromatography on silica to afford ethyl 1-(2-(tert-butoxy)-2-oxoethyl)-6-(diethoxyphosphoryl)-1H-indazole-3-carboxylate as an oil (3.98 g). $^1H$ NMR (400 MHz, $CDCl_3$, 300 K): δ 1.33 (t, J=7.2 Hz, 6H), 1.45 (s, 9H), 1.49 (t, J=7.2 Hz, 3H), 4.13-4.21 (m, 4H), 4.53 (q, J=7.2 Hz, 2H), 5.22 (s, 2H), 7.65 (dd, J=0.8, 8.4 Hz, 1H), 8.02 (d, J=15.2 Hz, 1H), 8.33 (dd, J=2.8, 8.4 Hz, 1H). $^{31}P$ NMR (162 MHz, DMSO-$d_6$, 300 K): δ 18.36.

Ethyl 1-(2-(tert-butoxy)-2-oxoethyl)-6-(diethoxyphosphoryl)-1H-indazole-3-carboxylate (3.98 g, 9.03 mmol) was dissolved in 20 mL of DCM and treated with 5 mL TFA. The mixture was stirred overnight at rt. The volatiles were removed under reduced pressure and the residue was co-evaporated with toluene (10 mL) twice. The dried residue was used directly in the next synthetic step.

2-(6-(Diethoxyphosphoryl)-3-(ethoxycarbonyl)-1H-indazol-1-yl)acetic acid (2.18 g, 4.37 mmol) was mixed with (2S,4R)—N-(3-chloro-2-fluorobenzyl)-4-fluoropyrrolidine-2-carboxamide hydrochloride Int-1 (1.36 g, 4.37 mmol), HATU (1.91 g, 5.02 mmol), and DMF (25 mL). To the resulting solution was added DIEA (4.5 mmol, 0.78 mL) dropwise. The mixture was stirred for 1 h at rt and the volatiles were removed under reduced pressure. The remaining residue was diluted with 10% aqueous sodium carbonate (20 mL) and water (50 mL), and then extracted with ethyl acetate (3x50 mL). The combined organic extracts were washed with water and brine, and then dried over $MgSO_4$. The solution was filtered and the solvent was removed under reduced pressure. The residue was purified by column chromatography to afford ethyl 1-(2-((2S,4R)-2-((3-chloro-2-fluorobenzyl)carbamoyl)-4-fluoropyrrolidin-1-yl)-2-oxoethyl)-6-(diethoxyphosphoryl)-1H-indazole-3-carboxylate 11. $^1H$ NMR (400 MHz, DMSO-$d_6$, 300 K): (major rotamer) δ 1.24 (t, J=7.2 Hz, 6H), 1.39 (t, J=7.2 Hz, 3H), 2.04-2.18 (m, 1H), 2.46-2.57 (m, 1H), 3.92-4.02 (m, 1H), 4.04-4.08 (m, 4H), 4.11-4.36 (m, 2H), 4.38-4.48 (m, 4H), 5.53 (d, J=52.8 Hz, 1H), 5.64-5.98 (m, 2H), 7.0 (t, J=7.6 Hz, 1H), 7.21 (t, J=7.2 Hz, 1H), 7.41 (t, J=7.6 Hz, 1H), 7.59-7.64 (m, 1H), 8.20-8.27 (m, 2H), 8.61 (t, J=6.0, 1H). $^{31}P$ NMR (162 MHz, DMSO-$d_6$, 300 K): (major rotamer) δ 18.07. $^{19}F$ NMR (376 MHz, DMSO-$d_6$, 300 K): (major rotamer) δ −121.83, −176.17. LC (method A): $t_R$=2.15 min. LC/MS (EI) m/z: $[M+H]^+$ 641.

Ethyl 1-(2-((2S,4R)-2-((3-chloro-2-fluorobenzyl)carbamoyl)-4-fluoropyrrolidin-1-yl)-2-oxoethyl)-6-(diethoxyphosphoryl)-1H-indazole-3-carboxylate 11 (692 mg, 1.08 mmol)

was dissolved in co-solvent MeOH-THF-$H_2O$ (3 mL-3 mL-3 mL) and then mixed with LiOH (42 mg, 1.75 mmol). The reaction mixture was stirred overnight at rt. The volatiles were removed under reduced pressure and the residue was acidified with 10% aqueous citric acid (10 mL). The white solid was collected by filtration, washed with water, and dried in vacuo to afford 1-(2-((2S,4R)-2-((3-chloro-2-fluorobenzyl)carbamoyl)-4-fluoropyrrolidin-1-yl)-2-oxoethyl)-6-(diethoxyphosphoryl)-1H-indazole-3-carboxylic acid 12. $^1$H NMR (400 MHz, DMSO-$d_6$, 300 K): (major rotamer) δ 1.23 (t, J=7.2 Hz, 6H), 2.04-2.20 (m, 1H), 2.46-2.57 (m, 1H), 3.87-4.02 (m, 1H), 3.98-4.08 (m, 4H), 4.17-4.38 (m, 2H), 4.40-4.45 (m, 2H), 5.53 (d, J=52.8 Hz, 1H), 5.64- 5.98 (m, 2H), 7.01 (t, J=7.6 Hz, 1H), 7.21 (t, J=7.2 Hz, 1H), 7.41 (t, J=7.6 Hz, 1H), 7.59-7.64 (m, 1H), 8.21-8.27 (m, 2H), 8.61 (t, J=6.0, 1H). $^{31}$P NMR (162 MHz, DMSO-$d_6$, 300K): (major rotamer) δ 18.27. $^{19}$F NMR (376 MHz, DMSO-$d_6$, 300 K): (major rotamer) δ −121.83, −176.18. LC (method A): $t_R$=1.65 min. LC/MS (EI) m/z: $[M+H]^+$ 613.

1-(2-((2S,4R)-2-((3-Chloro-2-fluorobenzyl)carbamoyl)-4-fluoropyrrolidin-1-yl)-2-oxoethyl)-6-(diethoxyphosphoryl)-1H-indazole-3-carboxylic acid 12 (584 mg, 0.95 mmol) was mixed with $NH_4Cl$ (153 mg, 2.85 mmol) in 5 mL DMF. To this solution was added HATU (1.42 mmol), followed by dropwise addition of DIEA (3 mL). The mixture was stirred for 3 h at rt and the volatiles were removed under reduced pressure. The residue was diluted with 10% aqueous sodium carbonate (15 mL) and water (15 mL), and then extracted with ethyl acetate (3×25 mL). The combined organic extracts were washed successively with water and brine, dried over $MgSO_4$, and concentrated under reduced pressure. The remaining residue was purified by column chromatography to afford diethyl (3-carbamoyl-1-(2-((2S,4R)-2-((3-chloro-2-fluorobenzyl)carbamoyl)-4-fluoropyrrolidin-1-yl)-2-oxoethyl)-1H-indazol-6-yl)phosphonate 17 (547 mg). $^1$H NMR (400 MHz, DMSO-$d_6$, 300 K): (major rotamer) δ 1.23 (t, J=7.2 Hz, 6H), 2.02-2.18 (m, 1H), 2.46-2.55 (m, 1H), 3.88-4.02 (m, 1H), 3.98-4.08 (m, 4H), 4.17-4.45 (m, 4H), 5.55 (d, J=52.8 Hz, 1H), 5.64-5.84 (m, 2H), 7.0 (t, J=7.6 Hz, 1H), 7.21 (t, J=7.2 Hz, 1H), 7.41 (t, J=7.6 Hz, 1H), 7.48-7.56 (m, 2H), 7.77 (s, 1H), 8.15 (d, J=15.6 Hz, 1H), 8.33-8.36 (m, 1H), 8.64 (t, J=6.0 Hz, 1H). $^{31}$P NMR (162 MHz, DMSO-$d_6$, 300 K): (major rotamer) δ 18.48. $^{19}$F NMR (376 MHz, DMSO-$d_6$, 300 K): (major rotamer) δ −121.80, −176.12. LC (method A): $t_R$=1.59 min. LC/MS (EI) m/z: $[M+H]^+$ 612.

To a mixture of diethyl (3-carbamoyl-1-(2-((2S,4R)-2-((3-chloro-2-fluorobenzyl)carbamoyl)-4-fluoropyrrolidin-1-yl)-2-oxoethyl)-1H-indazol-6-yl)phosphonate 17 (230 mg, 0.37 mmol) in dichloromethane (30 mL) was added bromotrimethylsilane (0.8 mL) under an atmosphere of argon gas at rt. The resulting solution was stirred overnight, and evaporated to dryness under reduced pressure. The remaining residue was purified by column chromatography (eluted with DCM 10 min, gradient 0-30% MeOH containing 5% AcOH 20 min) and co-evaporated with toluene (20 mL) twice. The residue was rinsed with water, dissolved in 15 mL of $CH_3CN$—$H_2O$ (3:1), and lyophilized to afford 18 (58 mg) as a powder. $^1$H NMR (400 MHz, DMSO-$d_6$, 300 K): (major rotamer) δ 1.92-2.09 (m, 1H), 2.36-2.47 (m, 1H), 3.20 (br, 2H), 3.80-3.90 (m, 1H), 4.11-4.43 (m, 4H), 5.36-5.73 (m, 3H), 6.99 (t, J=8.0 Hz, 1H), 7.16 (t, J=6.4 Hz, 1H), 7.32-7.36 (m, 2H), 7.46-7.51 (m, 1H), 7.64 (s, 1H), 8.98 (d, J=14.8 Hz, 1H), 8.17 (dd, J=2.8, 8.0 Hz, 1H), 8.57 (t, J=5.6 Hz, 1H), 11.20 (br, 2H). $^{31}$P NMR (162 MHz, DMSO-$d_6$, 300K): (major rotamer) δ 12.65. $^{19}$F NMR (376 MHz, DMSO-$d_6$, 300 K): (major rotamer) δ −121.69, −176.06. LC (method A): $t_R$=0.70 min. LC/MS (EI) m/z: $[M+H]^+$ 556.

Example 21. Synthesis of (((3-acetyl-1-(2-((2S,4R)-2-((3-chloro-2-fluorobenzyl)carbamoyl)-4-fluoropyrrolidin-1-yl)-2-oxoethyl)-1H-indol-6-yl)phosphoryl) bis(oxy))bis(methylene) bis(2,2-dimethylpropanoate) (26) and (((3-acetyl-1-(2-((2S,4R)-2-((3-chloro-2-fluorobenzyl)carbamoyl)-4-fluoropyrrolidin-1-yl)-2-oxoethyl)-1H-indol-6-yl)(hydroxy)phosphoryl)oxy)methyl Pivalate (28)

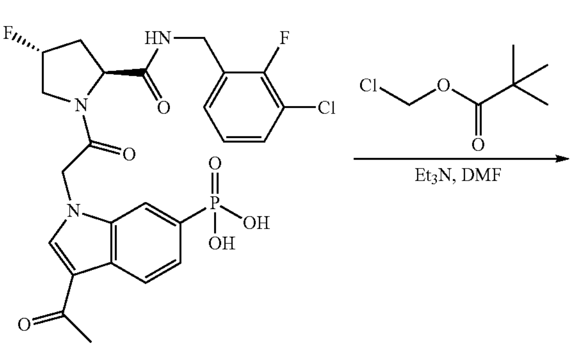

3

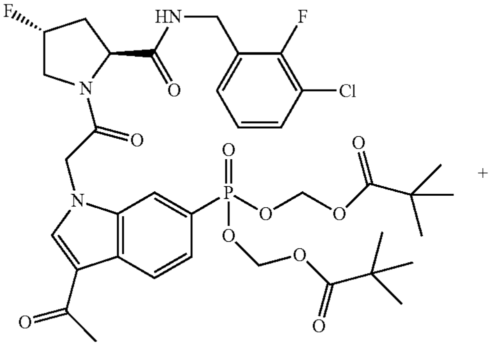

26

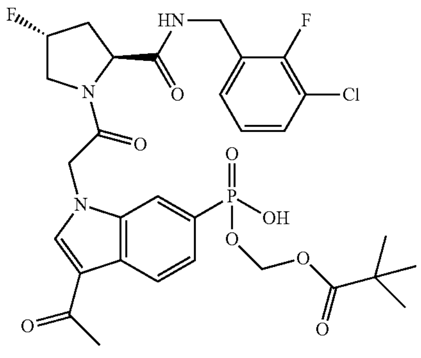

28

A mixture of (3-acetyl-1-(2-((2S,4R)-2-((3-chloro-2-fluorobenzyl)carbamoyl)-4-fluoropyrrolidin-1-yl)-2-oxoethyl)-1H-indol-6-yl)phosphonic acid 3 (128 mg, 0.23 mmol), chloromethyl pivalate (209 mg, 1.4 mmol, 6.0 equiv), and TEA (143 mg, 0.2 mL, 6.0 equiv) in DMF (2.5 mL) was heated in a 55° C. oil bath overnight. Additional chloromethyl pivalate (209 mg, 1.4 mmol, 6.0 equiv) and TEA (143 mg, 0.2 mL, 6.0 equiv) were added and the reaction mixture was stirred at 55° C. for 24 h. The mixture was cooled to rt and the volatiles were removed under reduced pressure. The remaining residue was purified by column chromatography (eluted with DCM/MeOH) to give 26 (89.3 mg) and 28 (18.9 mg). 26: $^{1}H$ NMR (400 MHz, DMSO-$d_6$, 300 K): (major rotamer) δ 1.03 (s, 18H), 2.05-2.20 (m, 1H), 2.46 (s, 3H), 2.50-2.60 (m, 1H), 3.81-3.98 (m, 1H), 4.12-4.47 (m, 4H), 5.29-5.51 (m, 2H), 5.60-5.63 (m, 5H), 7.0 (t, J=8.0 Hz, 1H), 7.24 (t, J=7.2 Hz, 1H), 7.42 (t, J=7.2 Hz, 1H), 7.47-7.52 (m, 1H), 8.01 (d, J=15.6 Hz, 1H), 8.32-8.35 (m), 1H), 8.43 (s, 1H), 8.62 (t, J=6.0 Hz, 1H). $^{31}P$ NMR (162 MHz, DMSO-$d_6$, 300K): (major rotamer) δ 19.97. $^{19}F$ NMR (376 MHz, DMSO-$d_6$, 300 K): (major rotamer) δ −121.77, -176.00. LC (method A): $t_R$=2.41 min. LC/MS (EI) m/z: $[M+H]^+$ 782. 28: $^{1}H$ NMR (400 MHz, DMSO-$d_6$, 300 K): (major rotamer) δ 0.89 (s, 9H), 1.97-2.11 (m, 1H), 2.37 (s, 3H), 2.41-2.44 (m, 1H), 3.78-3.82 (m, 1H), 3.87-3.91 (m, 1H), 4.07-4.65 (m, 3H), 5.19-5.42 (m, 2H), 5.42-5.51 (m, 3H), 6.96 (t, J=7.6 Hz, 1H), 7.17 (t, J=6.8 Hz, 1H), 7.35 (t, J=7.6 Hz, 1H), 7.42-7.47 (m, 1H), 7.87 (d, J=14.8 Hz, 1H), 8.20-8.23 (m, 1H), 8.29 (s, 1H), 8.54 (t, J=5.6 Hz). $^{31}P$ NMR (162 MHz, DMSO-$d_6$, 300K): (major rotamer) δ 16.52. $^{19}F$ NMR (376 MHz, DMSO-$d_6$, 300 K): (major rotamer) 6-121.24, −176.00. LC (method A): $t_R$=1.14 min. LC/MS (EI) m/z: $[M+H]^+$ 668.

Example 22. Synthesis of (3-acetyl-1-(2-((2S,4R)-2-((3-chloro-2-fluorobenzyl)carbamoyl)-4-fluoropyrrolidin-1-yl)-2-oxoethyl)-5-fluoro-1H-indol-6-yl)phosphonic Acid (31)

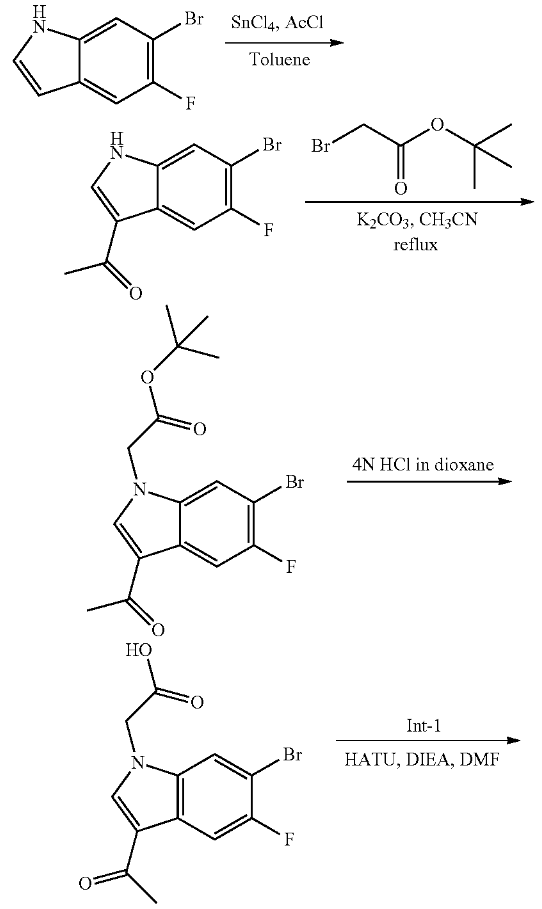

-continued

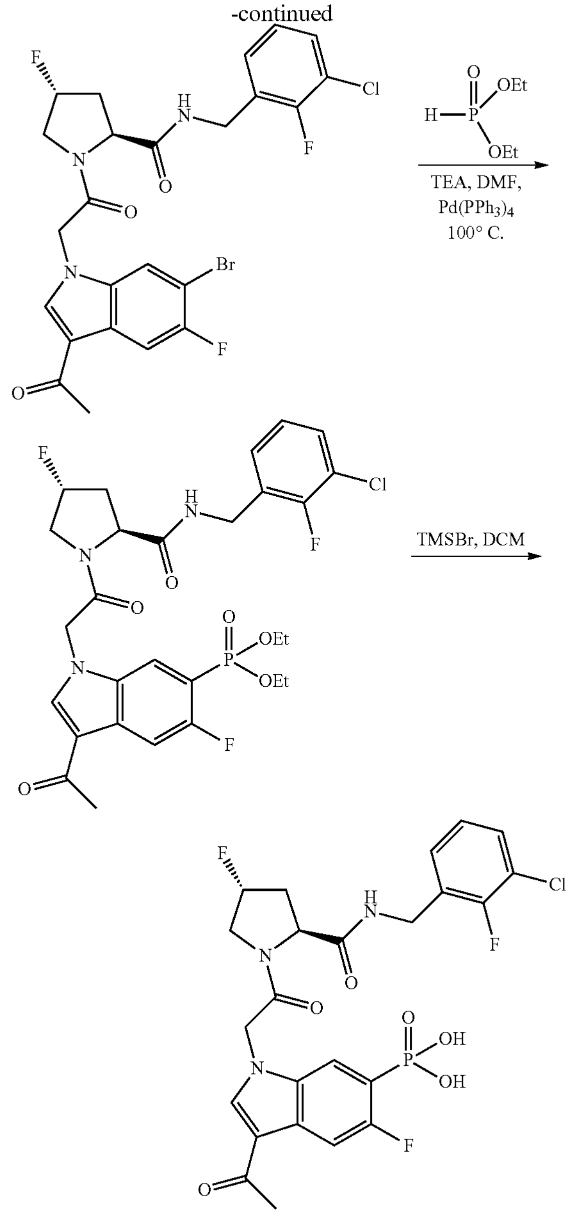

31 tert-Butyl 2-(3-acetyl-6-bromo-5-fluoro-1H-indol-1-yl) acetate (1.28 g), which was prepared from 6-bromo-5-fluoro-1H-indole (1 g) using procedures analogous to those described for the synthesis of tert-butyl 2-(3-acetyl-6-bromo-1H-indol-1-yl)acetate leading to Int-4, was treated with 4 N HCl in 1,4-dioxane (20 mL) at rt for 48 h. The volatiles were removed under reduced pressure to give 2-(3-acetyl-6-bromo-5-fluoro-1H-indol-1-yl)acetic acid that was used directly in the next synthetic step.

A mixture of 2-(3-acetyl-6-bromo-5-fluoro-1H-indol-1-yl)acetic acid and Int-1 (1.07 g) in DMF (30 mL) was treated with HATU (2.63 g) followed by DIEA (2.83 mL) at rt. After stirring overnight at rt, the reaction mixture was poured into 10% aqueous NaCl (300 mL). The resulting precipitate was collected by filtration and purified by column chromatography using MeOH in DCM as eluent to afford (2S,4R)-1-(2-(3-acetyl-6-bromo-5-fluoro-1H-indol-1-yl)acetyl)-N-(3-chloro-2-fluorobenzyl)-4-fluoropyrrolidine-2-carboxamide.

A mixture of (2S,4R)-1-(2-(3-acetyl-6-bromo-5-fluoro-1H-indol-1-yl)acetyl)-N-(3-chloro-2-fluorobenzyl)-4-fluoropyrrolidine-2-carboxamide (0.52 g), TEA (2 equiv), and diethyl phosphite (10 equiv) in DMF (10 mL) was sparged with argon gas for 10 min. Tetrakis(triphenylphosphine) palladium(O) (115 mg) was added and the mixture was stirred at 100° C. under an atmosphere of argon gas overnight. The solvent was removed under reduced pressure and the residue was purified by column chromatography using MeOH in DCM as eluent to give diethyl (3-acetyl-1-(2-((2S, 4R)-2-((3-chloro-2-fluorobenzyl)carbamoyl)-4-fluoropyrrolidin-1-yl)-2-oxoethyl)-5-fluoro-1H-indol-6-yl)phosphonate.

Diethyl (3-acetyl-1-(2-((2S,4R)-2-((3-chloro-2-fluorobenzyl)carbamoyl)-4-fluoropyrrolidin-1-yl)-2-oxoethyl)-5-fluoro-1H-indol-6-yl)phosphonate (100 mg) in DCM (1 mL) was treated with TMSBr (0.5 mL) at rt overnight. After the solvent was removed under reduced pressure, the residue was co-evaporated with 20% MeOH in DCM (20 mL) and washed with EtOAc to give 31 (60 mg). $^1$H NMR (400 MHz, DMSO-$d_6$, 300 K): (major rotamer) δ 2.01-2.18 (m, 1H), 2.42 (s, 3H), 2.38-2.49 (m, 1H), 3.84-4.01 (m, 2H), 4.14-4.45 (m, 4H), 5.26 (d, J=17.1 Hz, 1H), 5.50 (d, J=52.8 Hz, 1H), 5.51 (d, J=17.2 Hz, 1H), 7.06 (t, J=8 Hz, 1H), 7.24 (t, J=8 Hz, 1H), 7.41 (t, J=8 Hz, 1H), 7.83-7.88 (m, 2H), 8.37 (s, 1H), 8.62 (t, J=5.9 Hz, 1H). $^{19}$F NMR (376 MHz, DMSO-$d_6$, 300 K): (major rotamer) δ−177.0 (s, 1F), −121.7 (s, 1F), −114.5 (s, 1F). $^{31}$P NMR (162 MHz, DMSO-$d_6$, 300 K): (major rotamer) δ 8.24 (s). LC-MS (method A): $t_R$ 0.93 min, m/z found 572 ([M+H]$^+$).

Example 23. Synthesis (1-(2-((2S,4R)-2-((3-chloro-2-fluorobenzyl)carbamoyl)-4-fluoropyrrolidin-1-yl)-2-oxoethyl)-3-(2,2,2-trifluoroacetyl)-1H-indol-6-yl) phosphonic Acid (32)

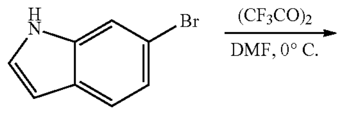

a

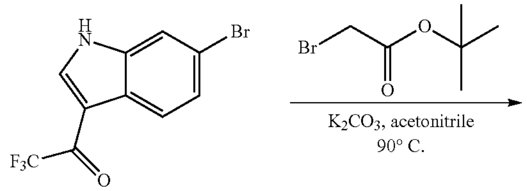

b

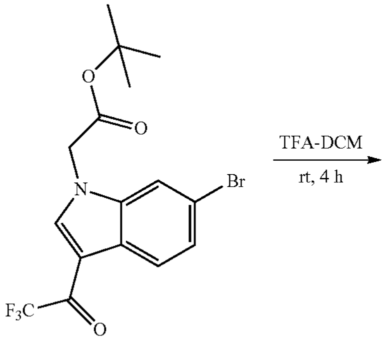

c

-continued

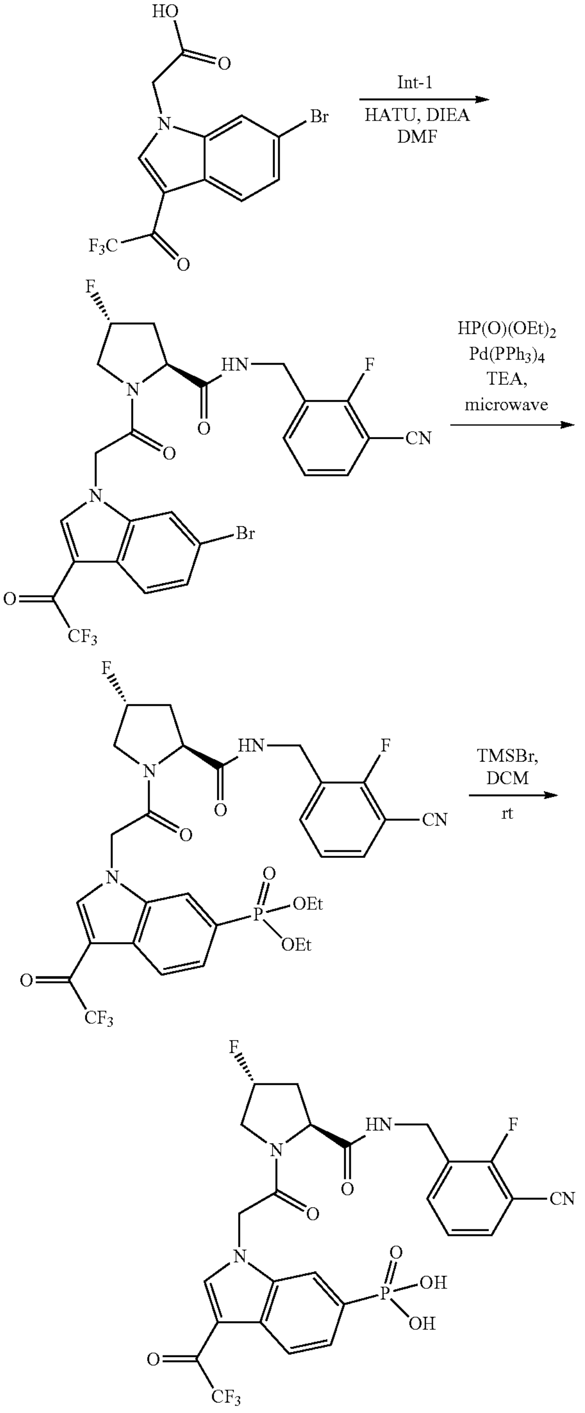

32

6-Bromoindole (1.0 g) was dissolved in DMF (10 mL) and cooled in an ice bath. Trifluoroacetic anhydride (0.85 mL) was added to this ice-cold solution dropwise and stirred for 2.5 h at this temperature. The reaction mixture was then quenched by the addition of 50 mL of water. The precipitate was collected by filtration, washed with water, dissolved in EtOAc, and the solution was washed with a saturated aqueous solution of $NaHCO_3$. The organic layer separated, dried ($Na_2SO_4$), and concentrated to give 1-(6-bromo-1H- indol-3-yl)-2,2,2-trifluoroethanone (1.5 g) as an orange solid, which was used directly in the next synthetic step.

A mixture of 1-(6-bromo-1H-indol-3-yl)-2,2,2-trifluoroethanone (1.45 g), tert-butyl bromoacetate (0.8 mL), and potassium carbonate (0.752 g) in anhydrous acetonitrile (45 mL) was refluxed for 5 h. The reaction mixture was then cooled to rt and the solvent was removed under reduced pressure. The residue was taken in a 1:1 mixture of DCM and water. The two layers were separated and the organic layer was washed with water. Finally, the organic layer was dried ($Na_2SO_4$) and concentrated. The resulting residue was stirred with 15 mL of heptane for 30 min, cooled in an ice bath and filtered, washing the solid with cold heptane (10 mL). The solid was dried under high vacuum to give tert-butyl 2-(6-bromo-3-(2,2,2-trifluoroacetyl)-1H-indol-1-yl)acetate (1.6 g).

tert-Butyl 2-(6-bromo-3-(2,2,2-trifluoroacetyl)-1H-indol-1-yl)acetate (1.5 g) was stirred in 4.0 N HCl in dioxane (15 mL) overnight. The solvent was removed under reduced pressure and the residue was dissolved in DMF (15 mL). Int-1 (1.2 g) was added, followed by of DIEA (3.2 mL). This mixture was cooled in an ice bath and HATU (1.7 g) was added. The cooling bath was then removed and the reaction mixture was stirred at rt for 1 h. The reaction mixture was then poured into water (150 mL) and the resulting solid was collected by filtration, washed with water, and dried under high vacuum to give (2S,4R)-1-(2-(6-bromo-3-(2,2,2-trifluoroacetyl)-1H-indol-1-yl)acetyl)-N-(3-chloro-2-fluorobenzyl)-4-fluoropyrrolidine-2-carboxamide (1.9 g).

A mixture of (2S,4R)-1-(2-(6-bromo-3-(2,2,2-trifluoroacetyl)-1H-indol-1-yl)acetyl)-N-(3-chloro-2-fluorobenzyl)-4-fluoropyrrolidine-2-carboxamide (0.1 μg), diethyl phosphite (0.213 mL), $Pd(PPh_3)_4$ (38 mg), and TEA (46 μL) in DMF (2 mL) was sparged with argon gas. The reaction vessel was then sealed and subjected to microwave irradiation for 30 min at 100° C. The solvent was removed under reduced pressure and the crude product was purified by column chromatography (0-2.5% MeOH in DCM) to give diethyl (1-(2-((2S,4R)-2-((3-chloro-2-fluorobenzyl)carbamoyl)-4-fluoropyrrolidin-1-yl)-2-oxoethyl)-3-(2,2,2-trifluoroacetyl)-1H-indol-6-yl)phosphonate (40 mg) as a light yellow solid.

Diethyl (1-(2-((2 S,4R)-2-((3-chloro-2-fluorobenzyl)carbamoyl)-4-fluoropyrrolidin-1-yl)-2-oxoethyl)-3-(2,2,2-trifluoroacetyl)-1H-indol-6-yl)phosphonate (40 mg) in dichloromethane (1 mL) was treated with TMSBr (1.1 mL) at rt for 2 d. The volatiles were removed under reduced pressure. The residue obtained was evaporated with 10% MeOH in DCM (10 mL). The remaining solid was triturated with tert-butyl methyl ether to give 32 (30 mg) as a light tan solid. $^1$H NMR (400 MHz, DMSO-$d_6$, 300 K): (major rotamer) δ 1.91-2.18 (m, 1H), 2.67-2.89 (m, 1H), 3.87-4.53 (m, 4H), 5.45 (d, J=17.2 Hz, 1H), 5.52 (d, J=55.6 Hz, 1H), 5.67 (d, J=17.2 Hz, 1H), 7.03 (t, J=7.6 Hz, 1H), 7.24 (t, J=7.6 Hz, 1H), 7.41 (t, J=6.8 Hz, 2H), 7.69 (dd, J=12, 8 Hz, 2H), 7.99 (d, J=14.4 Hz, 1H), 8.27 (dd, J=8.4, 3.2 Hz, 1H), 8.58 (s, 1H), 8.62 (t, J=5.6 Hz, 1H). $^{19}$F NMR (376 MHz, DMSO-$d_6$, 300 K): (major rotamer) δ −71.6, −121.7, −175.9. LC (method A): $t_R$=1.54 min. LC/MS (EI) m/z: found, 608 ($[M+H]^+$).

Example 24. Non-Limiting Examples of Compounds of Formula I

Table 1 shows illustrative compounds of Formula I with characterizing data. The assay of Example 25 was used to determine the $IC_{50}$'s of the compounds. Other standard factor D inhibition assays are also available. Three *s are used to denote compounds with an $IC_{50}$ less than 1 micromolar; two s indicate compound with an $IC_{50}$ between 1 micromolar and 10 micromolar, and one * denotes compounds with an $IC_{50}$ greater than 10 micromolar.

TABLE 1

| Cmp No. | Structure | Name | $IC_{50}$ | RT min (Method A or B) | MS (M + 1) |
|---|---|---|---|---|---|
| 1 | 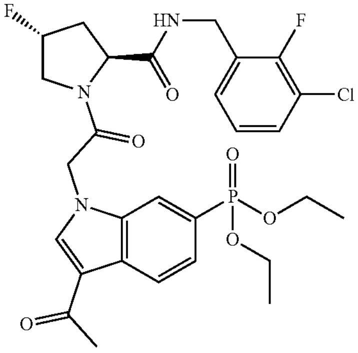 [SMILES: CCOP(=O)(OCC)c1ccc2c(C(C)=O)cn(CC(=O)N3C[C@H](F)C[C@H]3C(=O)NCc3cccc(Cl)c3F)c2c1] | diethyl 3-acetyl-1-(2-((2S,4R)-2-(3-chloro-2-fluorobenzylcarbamoyl)-4-fluoropyrrolidin-1-yl)-2-oxoethyl)-1H-indol-6-ylphosphonate | *** | 1.83 (A) | 610 |

TABLE 1-continued

| Cmp No. | Structure | Name | $IC_{50}$ | RT min (Method A or B) | MS (M + 1) |
|---|---|---|---|---|---|
| 2 | 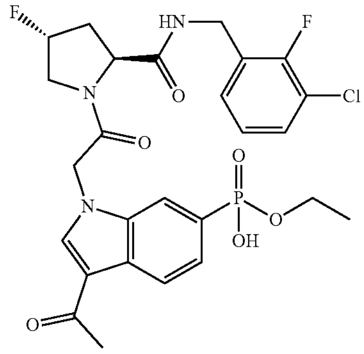 [SMILES: CCOP(=O)(O)c1ccc2c(C(C)=O)cn(CC(=O)N3C[C@H](F)C[C@H]3C(=O)NCc3cccc(Cl)c3F)c2c1] | ethyl hydrogen 3-acetyl-1-(2-((2S,4R)-2-(3-chloro-2-fluorobenzylcarbamoyl)-4-fluoropyrrolidin-1-yl)-2-oxoethyl)-1H-indol-6-ylphosphonate | *** | 1.20 (A) | 582 |
| 3 | 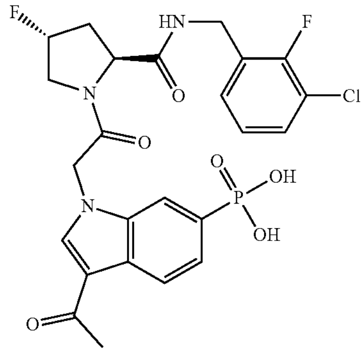 [SMILES: CC(=O)c1cn(CC(=O)N2C[C@H](F)C[C@H]2C(=O)NCc2cccc(Cl)c2F)c2cc(P(=O)(O)O)ccc12] | 3-acetyl-1-(2-((2S,4R)-2-(3-chloro-2-fluorobenzylcarbamoyl)-4-fluoropyrrolidin-1-yl)-2-oxoethyl)-1H-indol-6-ylphosphonic acid | *** | 1.06 (A) | 554 |
| 4 | 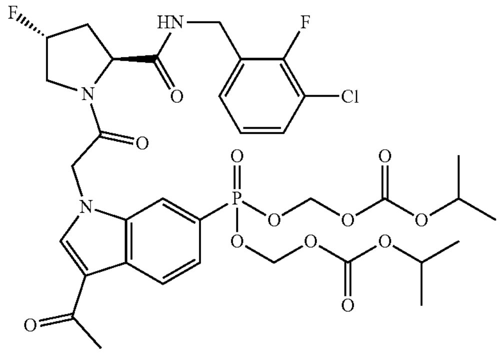 [SMILES: CC(=O)c1cn(CC(=O)N2C[C@H](F)C[C@H]2C(=O)NCc2cccc(Cl)c2F)c2cc(P(=O)(OCOC(=O)OC(C)C)OCOC(=O)OC(C)C)ccc12] | ((3-acetyl-1-(2-((2S,4R)-2-(3-chloro-2-fluorobenzylcarbamoyl)-4-fluoropyrrolidin-1-yl)-2-oxoethyl)-1H-indol-6-yl)phosphoryl)bis(oxy)bis(methylene)isopropyl dicarbonate | *** | 2.31 (A) | 786 |
| 5 | 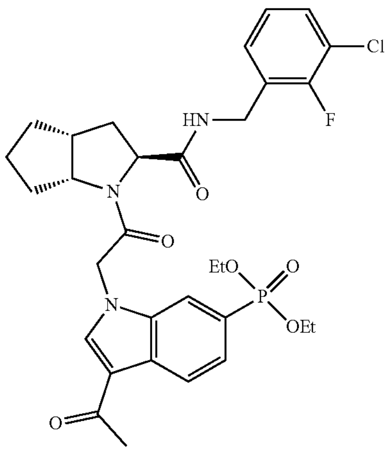 [SMILES: CCOP(=O)(OCC)c1ccc2c(C(C)=O)cn(CC(=O)N3[C@@H]4CCC[C@@H]4C[C@H]3C(=O)NCc3cccc(Cl)c3F)c2c1] | diethyl 3-acetyl-1-(2-((2S,3aR,6aR)-2-(3-chloro-2-fluorobenzylcarbamoyl)hexahydrocyclopenta[b]pyrrol-1(2H)-yl)-2-oxoethyl)-1H-indol-6-ylphosphonate | ** | 2.13 (A) | 632 |

TABLE 1-continued

| Cmp No. | Structure | Name | $IC_{50}$ | RT min (Method A or B) | MS (M + 1) |
|---|---|---|---|---|---|
| 6 | 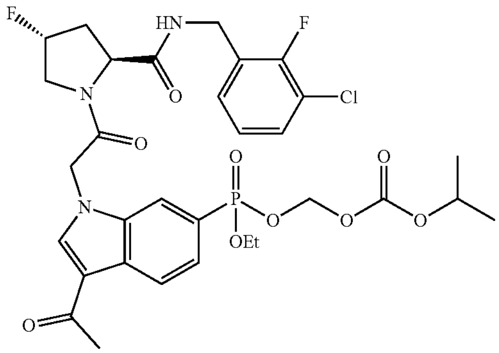 [SMILES: CCOP(=O)(OCOC(=O)OC(C)C)c1ccc2c(C(C)=O)cn(CC(=O)N3C[C@H](F)C[C@H]3C(=O)NCc3cccc(Cl)c3F)c2c1] | ((3-acetyl-1-(2-((2S,4R)-2-(3-chloro-2-fluorobenzylcarbamoyl)-4-fluoropyrrolidin-1-yl)-2-oxoethyl)-1H-indol-6-yl)(ethoxy)phosphoryloxy) methyl isopropyl carbonate | *** | 2.08 (A) | 698 |
| 7 | 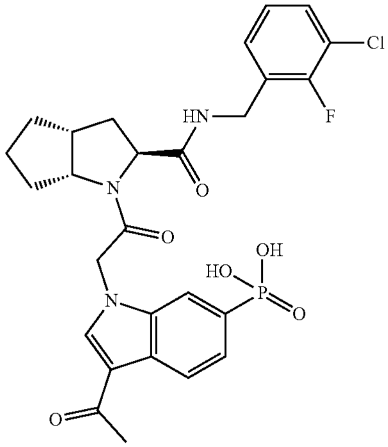 [SMILES: CC(=O)c1cn(CC(=O)N2[C@@H]3CCC[C@@H]3C[C@H]2C(=O)NCc2cccc(Cl)c2F)c2cc(P(=O)(O)O)ccc12] | 3-acetyl-1-(2-((2S,3aR,6aR)-2-(3-chloro-2-fluorobenzylcarbamoyl) hexahydrocyclopenta[b]pyrrol-1(2H)-yl)-2-oxoethyl)-1H-indol-6-ylphosphonic acid | *** | 1.44 (A) | 576 |
| 8 | 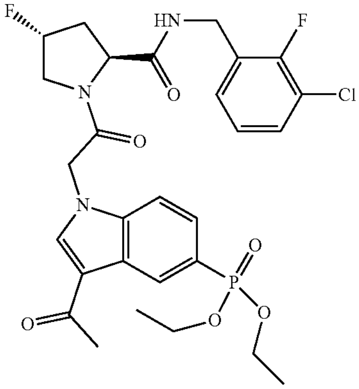 [SMILES: CCOP(=O)(OCC)c1ccc2c(c1)c(C(C)=O)cn2CC(=O)N1C[C@H](F)C[C@H]1C(=O)NCc1cccc(Cl)c1F] | diethyl 3-acetyl-1-(2-((2S,4R)-2-(3-chloro-2-fluorobenzylcarbamoyl)-4-fluoropyrrolidin-1-yl)-2-oxoethyl)-1H-indol-5-ylphosphonate | *** | 1.74 (A) | 610 |
| 9 | 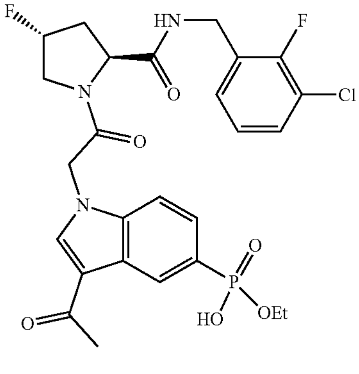 [SMILES: CCOP(=O)(O)c1ccc2c(c1)c(C(C)=O)cn2CC(=O)N1C[C@H](F)C[C@H]1C(=O)NCc1cccc(Cl)c1F] | ethyl hydrogen 3-acetyl-1-(2-((2S,4R)-2-(3-chloro-2-fluorobenxylcarbamoyl)-4-fluoropyrrolidin-1-yl)-2-oxoethyl)-1H-indol-5-ylphosphonate | * | 1.19 (A) | 582 |

TABLE 1-continued

| Cmp No. | Structure | Name | $IC_{50}$ | RT min (Method A or B) | MS (M + 1) |
|---|---|---|---|---|---|
| 10 | 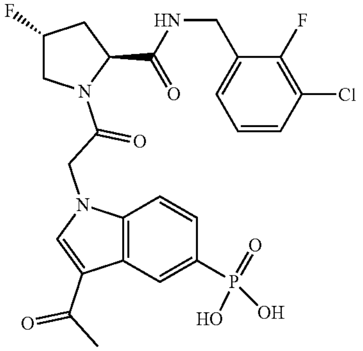 [SMILES: CC(=O)c1cn(CC(=O)N2C[C@H](F)C[C@H]2C(=O)NCc2cccc(Cl)c2F)c2ccc(P(=O)(O)O)cc12] | 3-acetyl-1-(2-((2S,4R)-2-(3-chloro-2-fluorobenzylcarbamoyl)-4-fluoropyrrolidin-1-yl)-2-oxoethyl)-1H-indol-5-ylphosphonic acid | *** | 1.04 (A) | 554 |
| 11 | 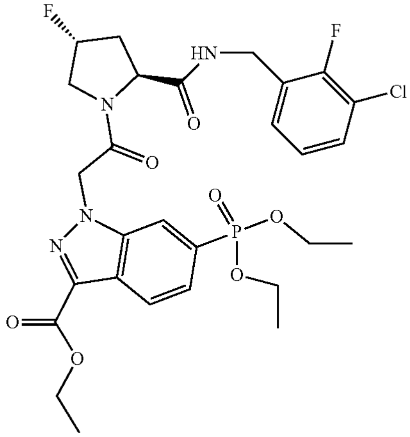 [SMILES: CCOC(=O)c1nn(CC(=O)N2C[C@H](F)C[C@H]2C(=O)NCc2cccc(Cl)c2F)c2cc(P(=O)(OCC)OCC)ccc12] | ethyl 1-(2-((2S,4R)-2-(3-chloro-2-fluorobenzylcarbamoyl)-4-fluoropyrrolidin-1-yl)-2-oxoethyl)-6-(diethoxyphosphoryl)-1H-indazole-3-carboxylate | * | 2.15 (A) | 641 |
| 12 | 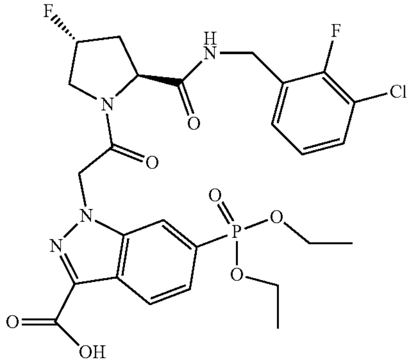 [SMILES: CCOP(=O)(OCC)c1ccc2c(C(=O)O)nn(CC(=O)N3C[C@H](F)C[C@H]3C(=O)NCc3cccc(Cl)c3F)c2c1] | 1-(2-((2S,4R)-2-(3-chloro-2-fluorobenzylcarbamoyl)-4-fluoropyrrolidin-1-yl)-2-oxoethyl)-6-(diethoxyphosphoryl)-1H-indazole-3-carboxylic acid | * | 1.65 (A) | 613 |
| 13 | 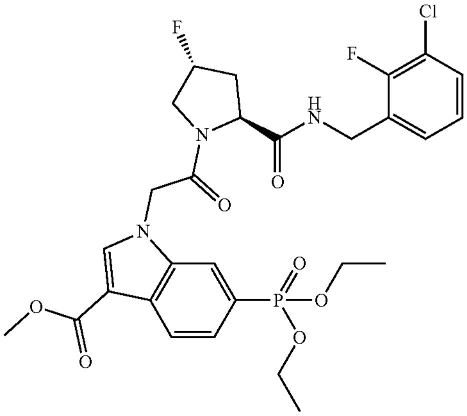 [SMILES: CCOP(=O)(OCC)c1ccc2c(C(=O)OC)cn(CC(=O)N3C[C@H](F)C[C@H]3C(=O)NCc3cccc(Cl)c3F)c2c1] | methyl 1-(2-((2S,4R)-2-(3-chloro-2-fluorobenzylcarbamoyl)-4-fluoropyrrolidin-1-yl)-2-oxoethyl)-6-(diethoxyphosphoryl)-1H-indole-3-carboxylate | *** | 2.03 (A) | 626 |

TABLE 1-continued

| Cmp No. | Structure | Name | $IC_{50}$ | RT min (Method A or B) | MS (M + 1) |
|---|---|---|---|---|---|
| 14 | 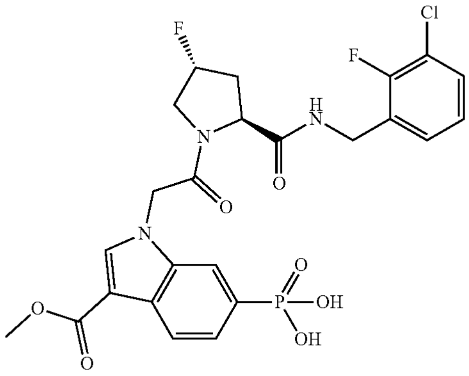 [SMILES: COC(=O)c1cn(CC(=O)N2C[C@H](F)C[C@H]2C(=O)NCc2cccc(Cl)c2F)c2cc(P(=O)(O)O)ccc12] | 1-(2-((2S,4R)-2-(3-chloro-2-fluorobenzylcarbamoyl)-4-fluoropyrrolidin-1-yl)-2-oxoethyl)-3-(methoxycarbonyl)-1H-indol-6-ylphosphonic acid | *** | 1.22 (A) | 570 |
| 15 | 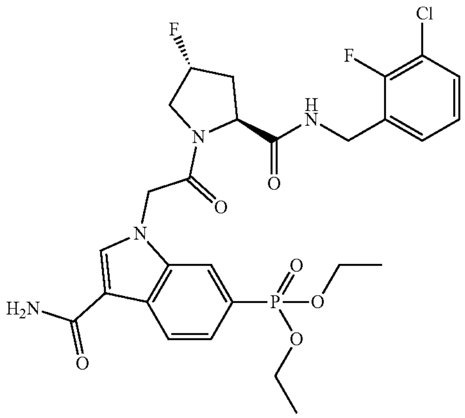 [SMILES: CCOP(=O)(OCC)c1ccc2c(C(N)=O)cn(CC(=O)N3C[C@H](F)C[C@H]3C(=O)NCc3cccc(Cl)c3F)c2c1] | diethyl 3-carbamoyl-1-(2-((2S,4R)-2-(3-chloro-2-fluorobenzylcarbamoyl)-4-fluoropyrrolidin-1-yl)-2-oxoethyl)-1H-indol-6-ylphosphonate | *** | 1.54 (A) | 611 |
| 16 | 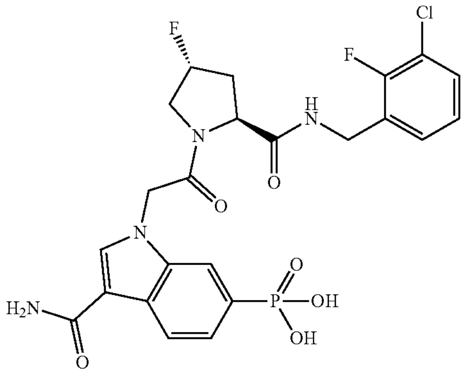 [SMILES: NC(=O)c1cn(CC(=O)N2C[C@H](F)C[C@H]2C(=O)NCc2cccc(Cl)c2F)c2cc(P(=O)(O)O)ccc12] | 3-carbamoyl-1-(2-((2S,4R)-2-(3-chloro-2-fluorobenzylcarbamoyl)-4-fluoropyrrolidin-1-yl)-2-oxoethyl)-1H-indol-6-ylphosphonic acid | *** | 0.72 (A) | 555 |
| 17 | 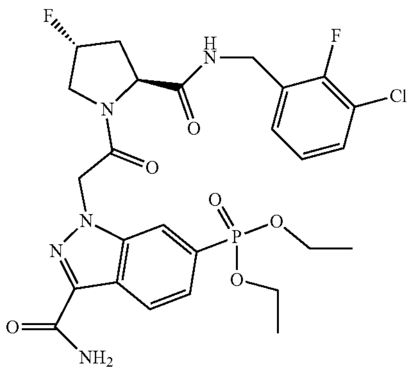 [SMILES: CCOP(=O)(OCC)c1ccc2c(C(N)=O)nn(CC(=O)N3C[C@H](F)C[C@H]3C(=O)NCc3cccc(Cl)c3F)c2c1] | diethyl 3-carbamoyl-1-(2-((2S,4R)-2-(3-chloro-2-fluorobenzylcarbamoyl)-4-fluoropyrrolidin-1-yl)-2-oxoethyl)-1H-indazol-6-ylphosphonate | *** | 1.59 (A) | 612 |

TABLE 1-continued

| Cmp No. | Structure | Name | $IC_{50}$ | RT min (Method A or B) | MS (M + 1) |
|---|---|---|---|---|---|
| 18 | 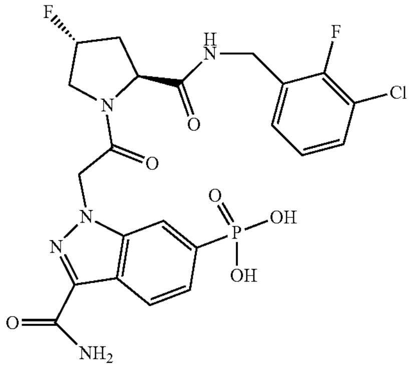 [SMILES: NC(=O)c1nn(CC(=O)N2C[C@H](F)C[C@H]2C(=O)NCc2cccc(Cl)c2F)c2cc(P(=O)(O)O)ccc12] | 3-carbamoyl-1-(2-((2S,4R)-2-(3-chloro-2-fluorobenzylcarbamoyl)-4-fluoropyrrolidin-1-yl)-2-oxoethyl)-1H-indazol-6-ylphosphonic acid | *** | 0.70 (A) | 556 |
| 19 | 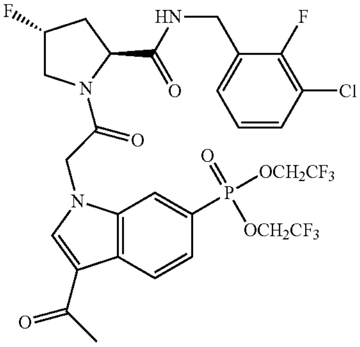 | bis(2,2,2-trifluoroethyl) 3-acetyl-1-(2-((2S,4R)-2-(3-chloro-2-fluorobenzylcarbamoyl)-4-fluoropyrrolidin-1-yl)-2-oxoethyl)-1H-indol-6-ylphosphonate | *** | 2.26 (A) | 718 |
| 20 | 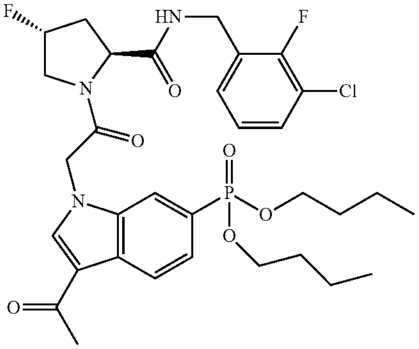 [SMILES: CCCCOP(=O)(OCCCC)c1ccc2c(C(C)=O)cn(CC(=O)N3C[C@H](F)C[C@H]3C(=O)NCc3cccc(Cl)c3F)c2c1] | dibutyl 3-acetyl-1-(2-((2S,4R)-2-(3-chloro-2-fluorobenzylcarbamoyl)-4-fluoropyrrolidin-1-yl)-2-oxoethyl)-1H-indol-6-ylphosphonate | *** | 2.47 (A) | 666 |
| 21 | 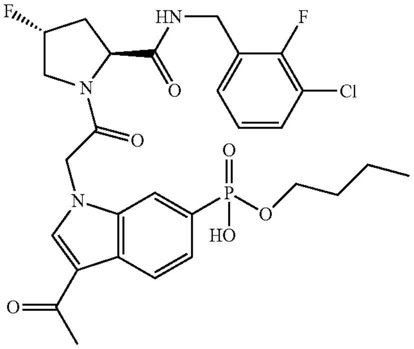 [SMILES: CCCCOP(=O)(O)c1ccc2c(C(C)=O)cn(CC(=O)N3C[C@H](F)C[C@H]3C(=O)NCc3cccc(Cl)c3F)c2c1] | butyl hydrogen 3-acetyl-1-(2-((2S,4R)-2-(3-chloro-2-fluorobenzylcarbamoyl)-4-fluoropyrrolidin-1-yl)-2-oxoethyl)-1H-indol-6-ylphosphonate | *** | 1.49 (A) | 610 |

TABLE 1-continued

| Cmp No. | Structure | Name | $IC_{50}$ | RT min (Method A or B) | MS (M + 1) |
|---|---|---|---|---|---|
| 22 | 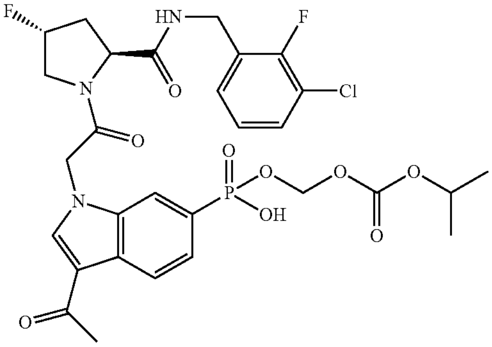 [SMILES: CC(=O)c1cn(CC(=O)N2C[C@H](F)C[C@H]2C(=O)NCc2cccc(Cl)c2F)c2cc(P(=O)(O)OCOC(=O)OC(C)C)ccc12] | ((3-acetyl-1-(2-((2S,4R)-2-(3-chloro-2-fluorobenzylcarbamoyl)-4-fluoropyrrolidin-1-yl)-2-oxoethyl)-1H-indol-6-yl)(hydroxy)phosphoryloxy) methyl isopropyl carbonate | *** | 1.34 (A) | 670 |
| 23 | 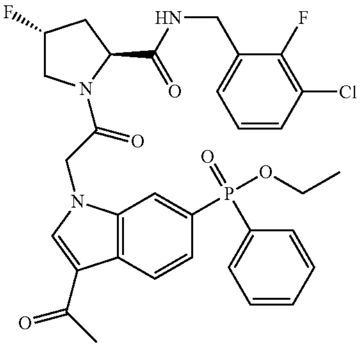 [SMILES: CCOP(=O)(c1ccccc1)c1ccc2c(C(C)=O)cn(CC(=O)N3C[C@H](F)C[C@H]3C(=O)NCc3cccc(Cl)c3F)c2c1] | ethyl 3-acetyl-1-(2-((2S,4R)-2-(3-chloro-2-fluorobenzylcarbamoyl)-4-fluoropyrrolidin-1-yl)-2-oxoethyl)-1H-indol-6-yl(phenyl)phosphinate | *** | 1.97 (A) | 642 |
| 24 | 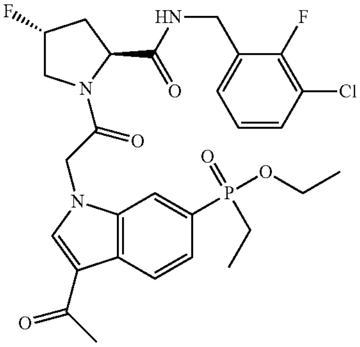 [SMILES: CCOP(=O)(CC)c1ccc2c(C(C)=O)cn(CC(=O)N3C[C@H](F)C[C@H]3C(=O)NCc3cccc(Cl)c3F)c2c1] | ethyl 3-acetyl-1-(2-((2S,4R)-2-(3-chloro-2-fluorobenzylcarbamoyl)-4-fluoropyrrolidin-1-yl)-2-oxoethyl)-1H-indol-6-yl(ethyl)phosphinate | *** | 1.64 (A) | 594 |
| 25 | 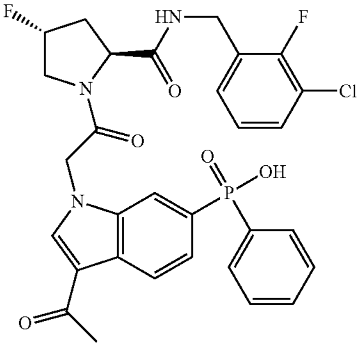 [SMILES: CC(=O)c1cn(CC(=O)N2C[C@H](F)C[C@H]2C(=O)NCc2cccc(Cl)c2F)c2cc(P(=O)(O)c3ccccc3)ccc12] | 3-acetyl-1-(2-((2S,4R)-2-(3-chloro-2-fluorobenzylcarbamoyl)-4-fluoropyrrolidin-1-yl)-2-oxoethyl)-1H-indol-6-yl(phenyl)phosphinic acid | *** | 1.49 (A) | 614 |

TABLE 1-continued

| Cmp No. | Structure | Name | $IC_{50}$ | RT min (Method A or B) | MS (M + 1) |
|---|---|---|---|---|---|
| 26 | 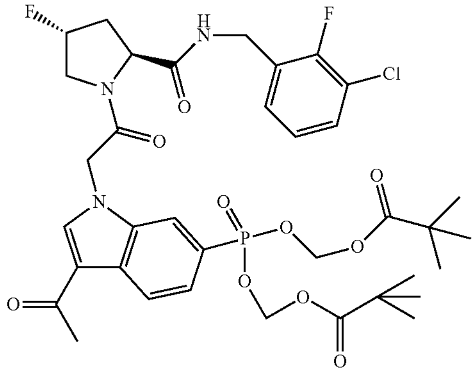 [SMILES: CC(=O)c1cn(CC(=O)N2C[C@H](F)C[C@H]2C(=O)NCc2cccc(Cl)c2F)c2cc(P(=O)(OCOC(=O)C(C)(C)C)OCOC(=O)C(C)(C)C)ccc12] | ((3-acetyl-1-(2-((2S,4R)-2-(3-chloro-2-fluorobenzylcarbamoyl)-4-fluoropyrrolidin-1-yl)-2-oxoethyl)-1H-indol-6-yl)phosphoryl)bis(oxy)bis (methylene) bis(2,2-dimethylpropanoate) | *** | 2.41 (A) | 782 |
| 27 | 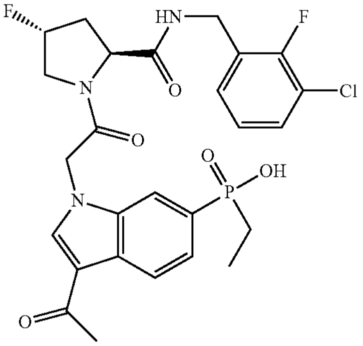 [SMILES: CCP(=O)(O)c1ccc2c(C(C)=O)cn(CC(=O)N3C[C@H](F)C[C@H]3C(=O)NCc3cccc(Cl)c3F)c2c1] | 3-acetyl-1-(2-((2S,4R)-2-(3-chloro-2-fluorobenzylcarbamoyl)-4-fluoropyrrolidin-1-yl)-2-oxoethyl)-1H-indol-6-yl(ethyl)phosphinic acid | *** | 1.24 (A) | 566 |
| 28 | 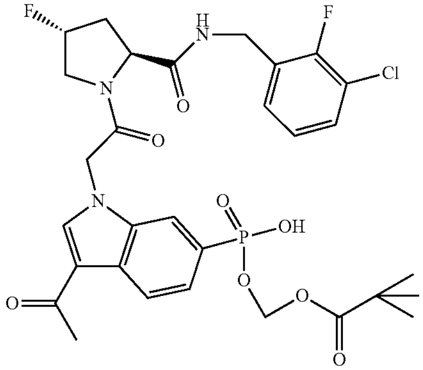 [SMILES: CC(=O)c1cn(CC(=O)N2C[C@H](F)C[C@H]2C(=O)NCc2cccc(Cl)c2F)c2cc(P(=O)(O)OCOC(=O)C(C)(C)C)ccc12] | ((3-acetyl-1-(2-((2S,4R)-2-(3-chloro-2-fluorobenzylcarbamoyl)-4-fluoropyrrolidin-1-yl)-2-oxoethyl)-1H-indol-6-yl)(hydroxy)phosphoryloxy) methyl pivalate | *** | 1.14 (A) | 668 |
| 29 | 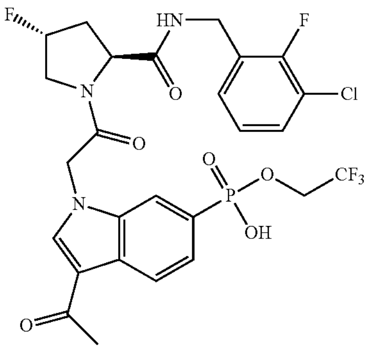 [SMILES: CC(=O)c1cn(CC(=O)N2C[C@H](F)C[C@H]2C(=O)NCc2cccc(Cl)c2F)c2cc(P(=O)(O)OCC(F)(F)F)ccc12] | 2,2,2-trifluoroethyl hydrogen 3-acetyl-1-(2-((2S,4R)-2-(3-chloro-2-fluorobenzylcarbamoyl)-4-fluoropyrrolidin-1-yl)-2-oxoethyl)-1H-indol-6-ylphosphonate | *** | 1.08 (A) | 636 |

TABLE 1-continued

| Cmp No. | Structure | Name | $IC_{50}$ | RT min (Method A or B) | MS (M + 1) |
|---|---|---|---|---|---|
| 30 | 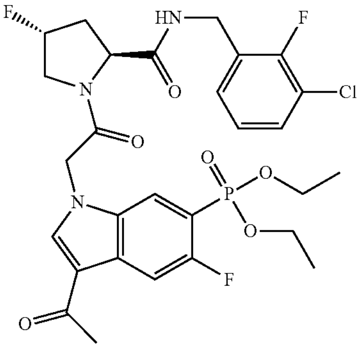 [SMILES: CCOP(=O)(OCC)c1cc2c(cc1F)c(C(C)=O)cn2CC(=O)N1C[C@H](F)C[C@H]1C(=O)NCc1cccc(Cl)c1F] | diethyl 3-acetyl-1-(2-((2S,4R)-2-(3-chloro-2-fluorobenzylcarbamoyl)-4-fluoropyrrolidin-1-yl)-2-oxoethyl)-5-fluoro-1H-indol-6-ylphosphonate | *** | 1.41 (A) | 628 |
| 31 | 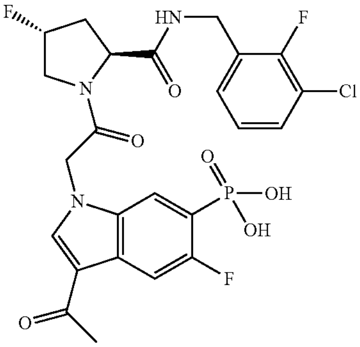 [SMILES: CC(=O)c1cn(CC(=O)N2C[C@H](F)C[C@H]2C(=O)NCc2cccc(Cl)c2F)c2cc(P(=O)(O)O)c(F)cc12] | 3-acetyl-1-(2-((2S,4R)-2-(3-chloro-2-fluorobenzylcarbamoyl)-4-fluoropyrrolidin-1-yl)-2-oxoethyl)-5-fluoro-1H-indol-6-ylphosphonic acid | *** | 0.93 (A) | 572 |
| 32 | 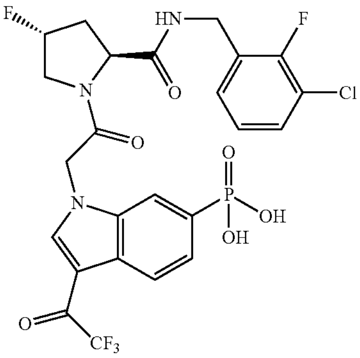 [SMILES: O=C(NCc1cccc(Cl)c1F)[C@@H]1C[C@@H](F)CN1C(=O)Cn1cc(C(=O)C(F)(F)F)c2ccc(P(=O)(O)O)cc21] | 1-(2-((2S,4R)-2-(3-chloro-2-fluorobenzylcarbamoyl)-4-fluoropyrrolidin-1-yl)-2-oxoethyl)-3-(2,2,2-trifluoroacetyl)-1H-indol-6-ylphosphonic acid | *** | 1.54 (A) | 608 |
| 33 | 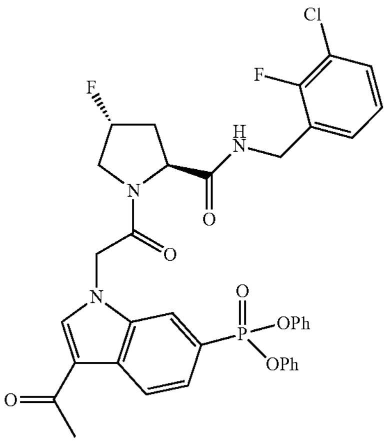 [SMILES: CC(=O)c1cn(CC(=O)N2C[C@H](F)C[C@H]2C(=O)NCc2cccc(Cl)c2F)c2cc(P(=O)(Oc3ccccc3)Oc3ccccc3)ccc12] | diphenyl 3-acetyl-1-(2-((2S,4R)-2-(3-chloro-2-fluorobenzylcarbamoyl)-4-fluoropyrrolidin-1-yl)-2-oxoethyl)-1H-indol-6-ylphosphonate | *** | 2.44 (A) | 707 |

Example 25. Human Factor D Assay

Human factor D (purified from human serum, Complement Technology, Inc.) at 80 nM final concentration is incubated with test compound at various concentrations for 5 minutes at room temperature in 50 mM Tris, 1M NaCl, pH 7.5. A synthetic substrate Z-L-Lys-SBzl and DTNB (Ellman's reagent) are added to final concentrations of 100 μM each. The increase in color is recorded at $OD_{405}$ nm in a microplate in kinetic mode over 30 minutes with 30 second time points in a spectrofluorimeter. $IC_5$o values are calculated by non-linear regression from the percentage of inhibition of complement factor D activity as a function of test compound concentration.

Example 26. Hemolysis Assay

The hemolysis assay was previously described by G. Ruiz-Gomez, et al., J. Med. Chem. (2009) 52: 6042-6052. In the assay red blood cells (RBC), rabbit erythrocyctes (purchased from Complement Technologies), are washed using GVB Buffer (0.1% gelatin, 5 mM Veronal, 145 mM NaCl, 0.025% $NaN_3$, pH 7.3) plus 10 mM final Mg-EGTA. Cells are used at a concentration of $1\times10^8$ cells/mL. Prior to the hemolysis assay, the optimum concentration of Normal Human Serum (NHS) needed to achieve 100% lysis of rabbit erythrocytes is determined by titration. NHS (Complement Technologies) is incubated with inhibitor for 15 min at 37° C., rabbit erythrocytes in buffer were added and incubated for an additional 30 min at 37° C. Positive control (100% lysis) consists of serum and RBC and negative control (0% lysis) of Mg-EGTA buffer and RBC only. Samples are centrifuged at 2000 g for 5 min, and supernatants collected. Optical density of the supernatant is monitored at 405 nm using a UV/visible spectrophotometer. Percentage lysis in each sample is calculated relative to positive control (100% lysis).

This specification has been described with reference to embodiments of the invention. However, one of ordinary skill in the art appreciates that various modifications and changes can be made without departing from the scope of the invention as set forth in the claims below. Accordingly, the specification is to be regarded in an illustrative rather than a restrictive sense, and all such modifications are intended to be included within the scope of invention.

What is claimed is:

1. A method for the treatment of a disorder mediated by complement factor D, comprising administering an effective amount to a host in need thereof a compound of the formula

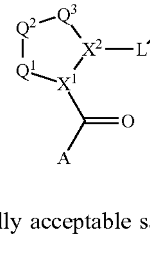

or a pharmaceutically acceptable salt thereof, wherein:

$Q^1$ is $C(R^1R^{1'})$;

$Q^2$ is $C(R^2R^{2'})$;

$Q^3$ is $C(R^3R^{3'})$;

$X^1$ is N and $X^2$ is CH;

$R^1$, $R^{1'}$, $R^2$, $R^{2'}$, $R^3$, and $R^{3'}$ are independently chosen from hydrogen, halogen, hydroxyl, amino, $C_1$-$C_6$alkyl, $C_2$-$C_6$alkenyl, $C_2$-$C_6$alkynyl, $C_1$-$C_6$alkoxy, $C_2$-$C_6$alkynyl, $C_2$-$C_6$alkanoyl, $C_1$-$C_6$thioalkyl, hydroxy$C_1$-$C_6$alkyl, amino$C_1$-$C_6$alkyl, —$C_0$-$C_4$alkylNR$^9$R$^{10}$, —C(O)OR$^9$, —OC(O)R$^9$, —NR$^9$C(O)R$^{10}$, —C(O)NR$^9$R$^{10}$, —OC(O)NR$^9$R$^{10}$, —NR$^9$C(O)OR$^{10}$, $C_1$-$C_2$haloalkyl, and $C_1$-$C_2$haloalkoxy;

or $R^1$ and $R^2$ are linked to form a 3- to 6-membered carbocyclic or aryl ring;

or $R^2$ and $R^3$ are linked to form a 3- to 6-membered carbocyclic ring;

A is a group selected from:

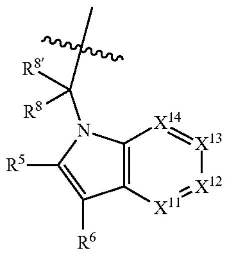

and

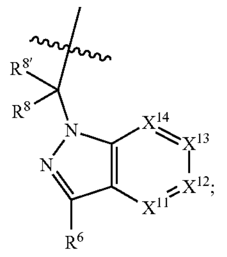

$R^5$ and $R^6$ are independently selected from —C(O)NH$_2$, $C_2$-$C_6$alkanoyl, hydrogen, —COOH, and —C(O)OR$^9$;

$R^8$ and $R^{8'}$ are hydrogen;

$X^{11}$ is N or CR$^{11}$;

$X^{12}$ is CR$^{12}$;

$X^{13}$ is CR$^{13}$;

$X^{14}$ is N or CR$^{14}$;

one of $R^{12}$ and $R^{13}$ is chosen from $R^{31}$ and the other of $R^{12}$ and $R^{13}$ is chosen from $R^{32}$:

$R^{31}$ is chosen from hydrogen, halogen, hydroxyl, amino, —COOH, $C_1$-$C_2$haloalkyl, $C_1$-$C_2$haloalkoxy, $C_1$-$C_6$alkyl, —$C_0$-$C_4$alkyl($C_3$-$C_7$cycloalkyl), $C_2$-$C_6$alkenyl, $C_2$-$C_6$alkanoyl, $C_1$-$C_6$alkoxy, $C_2$-$C_6$alkenyloxy, —C(O)OR$^9$, $C_1$-$C_6$thioalkyl, —$C_0$-$C_4$alkylNR$^9$R$^{10}$, —C(O)NR$^9$R$^{10}$, —SO$_2$R$^9$, —SO$_2$NR$^9$R$^{10}$, —OC(O)R$^9$, and —C(NR$^9$)NR$^9$R$^{10}$;

$R^{32}$ is —P(O)R$^{20}$R$^{20}$;

$R^{20}$ is independently chosen at each occurrence from hydroxyl, $C_1$-$C_6$alkoxy, $C_1$-$C_6$haloalkoxy, $C_1$-$C_6$alkyl, ($C_3$-$C_7$cycloalkyl)$C_0$-$C_4$alkyl-, (aryl)$C_0$-$C_4$alkyl-, —O—$C_0$-$C_4$alkyl(aryl), —O—$C_0$-$C_4$alkyl($C_3$-$C_7$cycloalkyl), (4- to 7-membered heterocycloalkyl)$C_0$-$C_4$alkyl-O— having 1, 2, or 3 heteroatoms independently chosen from N, O, and S; (5- or 6-membered unsaturated or aromatic heterocycle)$C_0$-$C_4$alkyl-O— having 1, 2, or 3 heteroatoms independently chosen from N, O, and S; —O(CH$_2$)$_{2-4}$O(CH$_2$)$_{8-18}$, —OC(R$^{20a}$)$_2$OC(O)OR$^{20b}$, —OC(R$^{20a}$)$_2$OC(O)R$^{20b}$, —NR$^9$R$^{10}$, an N-linked amino acid, and an N-linked amino acid ester;

$R^{20a}$ is independently chosen at each occurrence from hydrogen, $C_1$-$C_8$alkyl, $C_2$-$C_8$alkenyl, $C_2$-$C_8$alkynyl, (aryl)$C_0$-$C_4$alkyl-, (aryl)$C_2$-$C_8$alkenyl-, and (aryl)$C_2$-$C_8$alkynyl-; or two $R^{20a}$ groups can be taken together with the carbon that they are bonded to form a 3-6 membered heterocycloalkyl having 1, 2, or 3 heteroatoms independently chosen from N, O, and S, or a 3-6 membered carbocyclic ring;

$R^{20b}$ is independently chosen at each occurrence from $C_1$-$C_8$alkyl, $C_2$-$C_8$alkenyl, $C_2$-$C_8$alkynyl, (aryl)$C_0$-$C_4$alkyl, (aryl)$C_2$-$C_8$alkenyl, and (aryl)$C_2$-$C_8$alkynyl;

$R^{11}$ and $R^{14}$, are independently chosen at each occurrence from hydrogen, halogen, hydroxyl, nitro, cyano, —$O(PO)(OR^9)_2$, —$(PO)(OR^9)_2$, $C_1$-$C_6$alkyl, $C_2$-$C_6$alkenyl, $C_2$-$C_6$alkynyl, $C_2$-$C_6$alkanoyl, $C_1$-$C_6$alkoxy, $C_1$-$C_6$thioalkyl, —$C_0$-$C_4$alkyl(mono- and di-$C_1$-$C_6$alkylamino), —$C_0$-$C_4$alkyl($C_3$-$C_7$cycloalkyl), —$C_0$-$C_4$alkoxy($C_3$-$C_7$cycloalkyl), $C_1$-$C_2$haloalkyl, and $C_1$-$C_2$haloalkoxy;

$R^{21}$ and $R^{22}$ are independently chosen at each occurrence from hydrogen, hydroxyl, cyano, amino, $C_1$-$C_6$alkyl, $C_1$-$C_6$haloalkyl, $C_1$-$C_6$alkoxy, ($C_3$-$C_7$cycloalkyl)$C_0$-$C_4$alkyl, (phenyl)$C_0$-$C_4$alkyl, —$C_1$-$C_4$alkylOC(O)O$C_1$-$C_6$alkyl, —$C_1$-$C_4$alkylOC(O)$C_1$-$C_6$alkyl, —$C_1$-$C_4$alkylC(O)O$C_1$-$C_6$alkyl, (4- to 7-membered heterocycloalkyl)$C_0$-$C_4$alkyl having 1, 2, or 3 heteroatoms independently chosen from N, O, and S, and (5- or 6-membered unsaturated or aromatic heterocycle) $C_0$-$C_4$alkyl having 1, 2, or 3 heteroatoms independently chosen from N, O, and S;

$R^{23}$ is independently chosen at each occurrence from $C_1$-$C_6$alkyl, $C_1$-$C_6$haloalkyl, (aryl)$C_0$-$C_4$alkyl, ($C_3$-$C_7$cycloalkyl)$C_0$-$C_4$alkyl, (phenyl)$C_0$-$C_4$alkyl, (4- to 7-membered heterocycloalkyl)$C_0$-$C_4$alkyl having 1, 2, or 3 heteroatoms independently chosen from N, O, and S, and (5- or 6-membered unsaturated or aromatic heterocycle)$C_0$-$C_4$alkyl having 1, 2, or 3 heteroatoms independently chosen from N, O, and S;

$R^{24}$ and $R^{25}$ are taken together with the nitrogen to which they are attached to form a 4- to 7-membered monocyclic heterocycloalkyl group, or a 6- to 10-membered bicyclic heterocyclic group having fused, spiro, or bridged rings;

L is

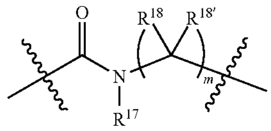

;

$R^{17}$ is hydrogen;

$R^{18}$ and $R^{18'}$ are hydrogen;

m is 0, 1, 2, or 3;

B is a $C_2$-$C_6$alkenyl; $C_2$-$C_6$alkynyl; —($C_0$-$C_4$alkyl)(aryl); —($C_0$-$C_4$alkyl)(heteroaryl); or —($C_0$-$C_4$alkyl)(biphenyl) each of which B is unsubstituted or substituted with one or more substituents independently chosen from $R^{33}$ and $R^{34}$, and 0 or 1 substituents chosen from $R^{35}$ and $R^{36}$;

$R^{33}$ is independently chosen from halogen, hydroxyl, —COOH, cyano, $C_1$-$C_6$alkyl, $C_2$-$C_6$alkanoyl, $C_1$-$C_6$alkoxy, —$C_0$-$C_4$alkyl$NR^9R^{10}$, —$SO_2R^9$, $C_1$-$C_2$haloalkyl, and $C_1$-$C_2$haloalkoxy;

$R^{34}$ is independently chosen from nitro, $C_2$-$C_6$alkenyl, $C_2$-$C_6$alkynyl, $C_1$-$C_6$thioalkyl, -J$C_3$-$C_7$cycloalkyl, —$B(OH)_2$, -JC(O)$NR^9R^{23}$, -$JOSO_2OR^{21}$, —C(O)$(CH_2)_{1-4}S(O)R^{21}$, —$O(CH_2)_{1-4}S(O)NR^{21}R^{22}$, -JOP(O)$(OR^{21})(OR^{22})$, -JP(O)$(OR^{21})(OR^{22})$, -JOP(O)$(OR^{21})R^{22}$, -JP(O)$(OR^{21})R^{22}$, -JOP(O)$R^{21}R^{22}$, -JP(O)$R^{21}R^{22}$, -JSP(O)$(OR^{21})(OR^{22})$, -JSP(O)$(OR^{21})(R^{22})$, -JSP(O)$(R^{21})(R^{22})$, -$JNR^9P(O)(NHR^{21})(NHR^{22})$, -$JNR^9P(O)(OR^{21})(NHR^{22})$ -$JNR^9P(O)(OR^{21})(OR^{22})$, -JC(S)$R^{21}$, -$JNR^{21}SO_2R^{22}$, -$JNR^9S(O)NR^{10}R^{22}$, -$JNR^9SO_2NR^{10}R^{22}$, -$JSO_2NR^9COR^{22}$, -$JSO_2NR^9CONR^{21}R^{22}$, -$JNR^{21}SO_2R^{22}$, -JC(O)$NR^{21}SO_2R^{22}$, -$JC(NH_2)NR^{22}$, -$JC(NH_2)NR^9S(O)_2R^{22}$, -JOC(O)$NR^{21}R^{22}$, -$JNR^{21}C(O)OR^{22}$, -$JNR^{21}OC(O)R^{22}$, —$(CH_2)_{1-4}C(O)NR^{21}R^{22}$, -JC(O)$R^{24}R^{25}$, -$JNR^9C(O)R^{21}$, -JC(O)$R^{21}$, -$JNR^9C(O)NR^{10}R^{22}$, —$CCR^{21}$, —$(CH_2)_{1-4}OC(O)R^{21}$, and -JC(O)$OR^{23}$;

$R^{35}$ is independently chosen from naphthyl, naphthyloxy, indanyl, (4- to 7-membered heterocycloalkyl)$C_0$-$C_4$alkyl containing 1 or 2 heteroatoms chosen from N, O, and S, and bicyclic heterocycle containing 1, 2, or 3 heteroatoms independently chosen from N, O, and S, and containing 4- to 7-ring atoms in each ring; each of which $R^{35}$ is unsubstituted or substituted with one or more substituents independently chosen from halogen, hydroxyl, nitro, cyano, $C_1$-$C_6$alkyl, $C_2$-$C_6$alkenyl, $C_2$-$C_6$alkanoyl, $C_1$-$C_6$alkoxy, (mono- and di-$C_1$-$C_6$alkylamino)$C_0$-$C_4$alkyl, $C_1$-$C_6$alkylester, —$C_0$-$C_4$alkyl($C_3$-$C_7$cycloalkyl), —$SO_2R^9$, $C_1$-$C_2$haloalkyl, and $C_1$-$C_2$haloalkoxy; and $R^{36}$ is independently chosen from tetrazolyl, (phenyl)$C_0$-$C_2$alkyl, (phenyl)$C_1$-$C_2$alkoxy, phenoxy, and 5- or 6-membered heteroaryl containing 1, 2, or 3 heteroatoms independently chosen from N, O, B, and S, each of which $R^{36}$ is unsubstituted or substituted with one or more substituents independently chosen from halogen, hydroxyl, nitro, cyano, $C_1$-$C_6$alkyl, $C_2$-$C_6$alkenyl, $C_2$-$C_6$alkanoyl, $C_1$-$C_6$alkoxy, (mono- and di-$C_1$-$C_6$alkylamino)$C_0$-$C_4$alkyl, $C_1$-$C_6$alkylester, —$C_0$-$C_4$alkyl($C_3$-$C_7$cycloalkyl), —$SO_2R^9$, —$OSi(CH_3)_2C(CH_3)_3$, —$Si(CH_3)_2C(CH_3)_3$, $C_1$-$C_2$haloalkyl, and $C_1$-$C_2$haloalkoxy; and J is independently selected at each occurrence from a covalent bond, $C_1$-$C_4$alkylene, —O$C_1$-$C_4$alkylene, $C_2$-$C_4$alkenylene, and $C_2$-$C_4$alkynylene.

2. The method of claim 1, wherein the host is a human.

3. The method of claim 2, wherein the compound is selected from:

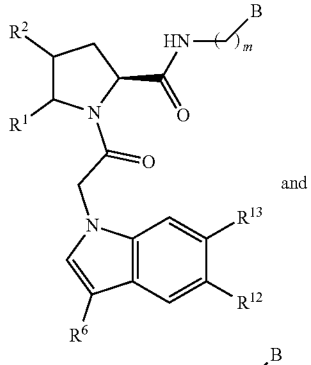

and

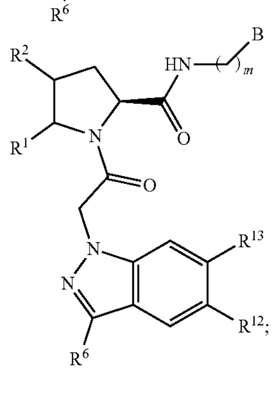

;

or a pharmaceutically acceptable salt thereof.

4. The method of claim 2, wherein the disorder is inflammatory bowel disease.

5. The method of claim 2, wherein the disorder is renal ischemia.

6. The method of claim 3, wherein the disorder is inflammatory bowel disease.

7. The method of claim 3, wherein the disorder is age-related macular degeneration (AMD) or retinal degeneration.

8. The method of claim 3, wherein the disorder multiple sclerosis, arthritis, or COPD.

9. The method of claim 3, wherein the disorder is an ophthalmic disease.

10. The method of claim 3, wherein the disorder is paroxysmal nocturnal hemoglobinuria (PNH).

11. The method of claim 3, wherein the disorder is a respiratory disease.

12. The method of claim 3, wherein the disorder is a cardiovascular disease.

13. The method of claim 3, wherein the disorder is atypical or typical hemolytic uremic syndrome.

14. The method of claim 3, wherein the disorder is rheumatoid arthritis.

15. The method of claim 3, wherein the disorder is C3 glomerulonephritis.

16. The method of claim 3, wherein the disorder is MPGN II.

17. The method of claim 2, wherein the compound is delivered to the intravitreal space of the eye.

18. The method of claim 2, wherein the compound is delivered to the subchoroidal space of the eye.

19. The method of claim 2, wherein the compound is delivered systemically.

20. The method of claim 2, wherein the compound is delivered orally.

* * * * *